US007973044B2

(12) United States Patent
Konradi et al.

(10) Patent No.: US 7,973,044 B2
(45) Date of Patent: Jul. 5, 2011

(54) HETEROARYL, HETEROCYCLIC AND ARYL COMPOUNDS WHICH INHIBIT LEUKOCYTE ADHESION MEDIATED BY VLA-4

(75) Inventors: Andrei W. Konradi, Burlingame, CA (US); Michael A. Pleiss, Sunnyvale, CA (US); Eugene D. Thorsett, Kirkland, WA (US); Susan Ashwell, Plainsboro, NJ (US); Gregory S. Welmaker, Jackson, NJ (US); Anthony Kreft, Langhorne, PA (US); Dimitrios Sarantakis, Newton, PA (US); Darren B. Dressen, San Francisco, CA (US); Francine S. Grant, Mercer Island, WA (US); Christopher Semko, Fremont, CA (US); Ying-Zi Xu, Palo Alto, CA (US)

(73) Assignees: Elan Pharmaceuticals, Inc., S. San Francisco, CA (US); Wyeth, Madison, NJ (US)

( * ) Notice: Subject to any disclaimer, the term of this patent is extended or adjusted under 35 U.S.C. 154(b) by 0 days.

(21) Appl. No.: 12/645,154

(22) Filed: Dec. 22, 2009

(65) Prior Publication Data

US 2010/0160341 A1 Jun. 24, 2010

Related U.S. Application Data

(60) Continuation of application No. 11/582,293, filed on Oct. 16, 2006, now Pat. No. 7,741,328, which is a continuation of application No. 11/033,079, filed on Jan. 10, 2005, now Pat. No. 7,378,529, which is a division of application No. 10/218,366, filed on Aug. 15, 2002, now Pat. No. 6,911,439, which is a division of application No. 09/489,377, filed on Jan. 21, 2000, now Pat. No. 6,492,372.

(60) Provisional application No. 60/116,923, filed on Jan. 22, 1999, provisional application No. 60/160,999, filed on Oct. 21, 1999.

(51) Int. Cl.
*A01N 43/54* (2006.01)
*C07D 239/42* (2006.01)

(52) U.S. Cl. .................... 514/256; 544/224; 544/242

(58) Field of Classification Search .................. 514/256; 544/242, 224
See application file for complete search history.

(56) References Cited

U.S. PATENT DOCUMENTS

| 4,018,913 A | 4/1977 | Okamoto et al. |
| 4,018,915 A | 4/1977 | Okamoto et al. |
| 4,036,955 A | 7/1977 | Okamoto et al. |
| 4,041,156 A | 8/1977 | Okamoto et al. |
| 4,046,876 A | 9/1977 | Okamoto et al. |
| 4,055,636 A | 10/1977 | Okamoto et al. |
| 4,055,651 A | 10/1977 | Okamoto et al. |
| 4,070,457 A | 1/1978 | Okamoto et al. |
| 4,073,914 A | 2/1978 | Kikumoto et al. |
| 4,085,057 A | 4/1978 | Masuda et al. |
| 4,096,255 A | 6/1978 | Kikumoto et al. |
| 4,104,392 A | 8/1978 | Okamoto et al. |
| 4,235,871 A | 11/1980 | Papahadjopoulos et al. |
| 4,438,122 A | 3/1984 | Holmwood et al. |
| 4,501,728 A | 2/1985 | Geho et al. |
| 4,505,910 A | 3/1985 | Bagli |
| 4,518,600 A | 5/1985 | Holmwood et al. |
| 4,544,402 A | 10/1985 | Schnurbusch et al. |
| 4,559,345 A | 12/1985 | Gomarasca et al. |
| 4,672,065 A | 6/1987 | Spatz |
| 4,837,028 A | 6/1989 | Allen et al. |
| 4,908,368 A | 3/1990 | Murase et al. |
| 4,959,364 A | 9/1990 | Mueller et al. |
| 4,992,439 A | 2/1991 | Meanwell |
| 5,011,472 A | 4/1991 | Aebischer et al. |
| 5,023,252 A | 6/1991 | Hseih et al. |
| 5,030,644 A | 7/1991 | Baldwin et al. |
| 5,120,734 A | 6/1992 | Klausener et al. |
| 5,238,934 A | 8/1993 | Knuppel et al. |
| 5,278,184 A | 1/1994 | Artico et al. |
| 5,510,332 A | 4/1996 | Kogan et al. |
| 5,580,868 A | 12/1996 | Lunkenheimer et al. |
| 5,770,573 A | 6/1998 | Arrhenius et al. |
| 5,814,643 A | 9/1998 | Duggan et al. |
| 5,861,429 A | 1/1999 | Sato et al. |
| 5,925,644 A | 7/1999 | Jakobi et al. |
| 5,942,504 A | 8/1999 | Grobelny |
| 5,955,491 A | 9/1999 | Sohda et al. |

(Continued)

FOREIGN PATENT DOCUMENTS

CA 2241149 7/1997

(Continued)

OTHER PUBLICATIONS

Pinedo et al., "Translational Research . . . ", The Oncologist 2000,, 5 (suppl1): 1-2 (www.The Oncologist .com).*
McMahon, Gerald, "VEGF Receptor Signaling in Tumor Angiogenesis", The Oncologist 2000; 5(suppl 1): 3-10 (www.TheOncologist.com).*
U.S. Appl. No. 12/637,719, filed Dec. 14, 2009, Konradi et al.
U.S. Appl. No. 12/579,828, filed Oct. 15, 2009, Semko et al.
Abraham, W.M., et al. "α4-Integrins Mediate Antigen—induced Late Bronchial Responses and Prolonged Airway Hyperresponsiveness in Sheep." *J. Clin. Invest.* 93: 776-787 (1994).

(Continued)

*Primary Examiner* — Paul V. Ward
(74) *Attorney, Agent, or Firm* — Foley & Lardner LLP

(57) ABSTRACT

Disclosed are compounds which bind VLA-4. Certain of these compounds also inhibit leukocyte adhesion and, in particular, leukocyte adhesion mediated by VLA-4. Such compounds are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

19 Claims, No Drawings

U.S. PATENT DOCUMENTS

| | | | |
|---|---|---|---|
| 5,962,479 | A | 10/1999 | Chen |
| 5,972,946 | A | 10/1999 | Murata et al. |
| 6,005,117 | A | 12/1999 | Wehner et al. |
| 6,436,904 | B1 | 8/2002 | Ashwell et al. |
| 6,479,492 | B1 | 11/2002 | Konradi et al. |
| 6,492,372 | B1 | 12/2002 | Konradi et al. |
| 6,544,994 | B2 | 4/2003 | Rabelink et al. |
| 6,545,003 | B1 | 4/2003 | Grant et al. |
| 6,689,781 | B2 | 2/2004 | Konradi et al. |
| 6,794,506 | B2 | 9/2004 | Konradi et al. |
| 6,903,088 | B2 | 6/2005 | Konradi et al. |
| 6,911,439 | B2 | 6/2005 | Konradi et al. |
| 7,005,433 | B2 | 2/2006 | Konradi et al. |
| 7,008,949 | B2 | 3/2006 | Konradi et al. |
| 7,026,328 | B2 | 4/2006 | Konradi et al. |
| 7,049,306 | B2 | 5/2006 | Konradi et al. |
| 7,135,477 | B2 | 11/2006 | Konradi et al. |
| 7,335,663 | B2 | 2/2008 | Konradi et al. |
| 7,378,529 | B2 | 5/2008 | Konradi et al. |
| 7,427,628 | B2 | 9/2008 | Konradi et al. |
| 7,452,912 | B2 | 11/2008 | Grant et al. |
| 2005/0203093 | A1 | 9/2005 | Konradi et al. |
| 2005/0261293 | A1 | 11/2005 | Konradi et al. |
| 2006/0013799 | A1 | 1/2006 | Konradi et al. |
| 2007/0099921 | A1 | 5/2007 | Konradi et al. |
| 2007/0129390 | A1 | 6/2007 | Semko et al. |
| 2007/0142416 | A1 | 6/2007 | Semko et al. |
| 2008/0058357 | A1 | 3/2008 | Smith et al. |

FOREIGN PATENT DOCUMENTS

| | | |
|---|---|---|
| CA | 2259224 | 1/1998 |
| CA | 2359115 | 7/2000 |
| DE | 195 36 891 | 4/1997 |
| DE | 265 56 36 | 6/1997 |
| DE | 195 48 709 A | 7/1997 |
| DE | 196 54 483 A | 1/1998 |
| DE | 197 13 000 | 10/1998 |
| EP | 116494 | 8/1984 |
| EP | 0 147 211 | 7/1985 |
| EP | 0 288 176 | 10/1988 |
| EP | 0 330 506 A2 | 8/1989 |
| EP | 0 526 348 | 2/1993 |
| EP | 0 535 521 | 4/1993 |
| GB | 1500063 | 2/1978 |
| HU | 169926 | 2/1977 |
| JP | 59212480 | 12/1984 |
| WO | WO 91/05038 | 4/1991 |
| WO | WO 92/16549 | 10/1992 |
| WO | WO 93/12809 | 7/1993 |
| WO | WO 93/24154 | 12/1993 |
| WO | WO 96/01644 | 1/1996 |
| WO | WO 96/22966 | 8/1996 |
| WO | WO 96/32383 | 10/1996 |
| WO | WO 97/23451 | 7/1997 |
| WO | WO 79/48726 | 12/1997 |
| WO | WO 98/00395 | 1/1998 |
| WO | WO 98/22430 | 5/1998 |
| WO | WO 98/33783 | 8/1998 |
| WO | WO 98/53814 | 12/1998 |
| WO | WO 98/53817 | 12/1998 |
| WO | WO 99/06390 | 2/1999 |
| WO | WO 99/06391 | 2/1999 |
| WO | WO 99/06431 | 2/1999 |
| WO | WO 99/06432 | 2/1999 |
| WO | WO 99/06433 | 2/1999 |
| WO | WO 99/10312 | 3/1999 |
| WO | WO 99/10313 | 3/1999 |
| WO | WO 99/37605 | 7/1999 |
| WO | WO 99/37618 | 7/1999 |
| WO | WO 99/52898 | 10/1999 |
| WO | WO 00/18759 | 4/2000 |
| WO | WO 00/31067 | 6/2000 |
| WO | WO 00/43369 | 7/2000 |
| WO | WO 00/43371 | 7/2000 |
| WO | WO 00/43372 | 7/2000 |
| WO | WO 02/08201 | 1/2002 |
| WO | WO 03/099231 | 12/2003 |
| WO | WO 03/099809 | 12/2003 |
| WO | WO 2005/111020 | 11/2005 |
| WO | WO 2007/041270 | 4/2007 |
| WO | WO 2007/041324 | 4/2007 |
| WO | WO 2007/101165 | 9/2007 |

OTHER PUBLICATIONS

Abraham, et al., "Blockade of Late-phase Airway Responses and Airway Hyperresponsiveness in allergic Sheep with a Small-molecule Peptide Inhibitor of VLA-4," *Am J Resper Crit Care Med* 156:696-703 (1997).

Advani, S.B., et al. "Potential Antineoplastic Agents: N-(2-Benzoxazolyl)amino Acid Esters." *J. of Pharm. Sci.* 57(10): 1693-1696 (1968).

Anderson, et al., "Acute kidney graft rejection," *APMIS* 102, 23-37 (1994).

Anderson, et al., "Process Development of 5-Fluoro-3-[3-[4-(5-methoxy-4 pyrimidinyl)-1 piperazinyl]propyl]-1$H$-indole Dihydrochloride," *Org Proc Res Devel* 1:300-310 (1997).

Balaban, I., "An Investigation into the Formation of 4(5)-Aminoglyoxalines," *J. chem.. soc.* Part 1:1-268-273 (1930).

Bao, L., et al. "Correlation of VLA-4 integrin expression with metastatic potential in various human tumour cell lines." *Diff.* 52: 239-246 (1993).

Banker, G.S. et al., "Modern Pharmaceutics, 3ed.", Marcel Dekker, New York, pp. 451-596 (1996).

Baron, J.L., et al. "Surface Expression of α4 Integrin by CD4 T Cells is Required for Their Entry into Brain Parenchyma." *J. Exp. Med.* 177: 57-68 (1993).

Baron, J.L., et al. "The Pathogenesis of Adeoptive Murine Autonimmune Diabetes Requires an Interaction between α4-Integrins and Vascular Cell Adhesion Molecule-1." *J. Clin. Invest.* 93: 1700-1708 (1994).

Belka et al., "Radiation induced CNS toxicity—Molecular and cellular mechanism" *Br. J. Cancer* 85:1233-1239 (2001).

Burkly, L.C., et al. "Protection Against Adoptive Transfer of Autoimmune Diabetes Mediated Through Very Late Antigent-4 Integrin." *Diabetes.* 43: 529-534 (1994).

Casanova et al., PubMed Abstract (*Rev Neurol.*) 28(9):909-915 (1999).

Chapman et al. "Time course of allergen-induced leukocyte accumulation in actively sensitized brown Norway rats" Am. J. Resp. Crit. Care Med. 153-154, A219 (1996).

Chapman et al. "Allergen-induced airway hyperreactivity and eosinophil accumulation are temporarily dissociated in actively sensitized brown Norway rats" Am. J. Resp. Crit. Care Med. 154-155, A881 (1997).

Chang et al. "Mechanism underlying the suppression of adjuvant-induced arthritis by 6-mercaptopurine" *Arth. Rheum.* 20; 1135-1141 (1997).

Chen, et al., "Mediation of sperm-egg fusion: evidence that mouse egg $\alpha^6\beta^1$ integrin is the receptor for sperm fertilinβ," *chem. Biol* 6:1-10 (1999).

Coito, et al., "Blockade of Very Late Antigen-4 Integrin Binding to fibronectin in Allograft Recipients," *Transplantation* 65:699-706 (1998).

Cybulsky, M.I., et al. "Endothelial Expression of a Mononuclear Leukocyte Adhesion Molecule During Atherogenesis." *Science.* 251: 788-791 (1991).

Damasio, et al., "Alzheimer's Disease and Related Dementias," *Cecil Textbook of Medicine*, 20th Ed., vol. 2, pp. 1992-1996 (1996).

Elices, M.J., et al. "Expression and Functional Significance of Alternatively Spliced CS1 Fibronecting in Rheumatoid Arthritis Microvasculature." *J. Clin. Invest.* 93: 405-416 (1994).

Elices, M.J., et al. "VCAM-1 on Activated Endothelium Interacts with the Leukocyte Integrin VLA-4 at a Site Distinct from the CLA-4/Fibronectin Binding Site." *Cell.* 60: 577-584 (1990).

Elewaut, et al., "Distinctive Activated Cellular Subsets in Colon fronm Patients with Crohn's Disease and Ulcerative Colitis," *Scand. J. Gastroenterol* 33:743-748 (1998).

Ewenson, et al., "Analogues of substance P containing an α-hydroxy, β-amino acid: synthesis and biological activity," *Eur J Med Chem* 26 435-442 (1991).

Freedman, et al, "Adhesion of Follicular Lymphoma Cells to Lymphoid germinal Centers—A Potential Mechanism of Tumor CellHoming Following Autologous Transplantation," *Leuk and Lymphome* 13:47 (1994).

Georczynski, et al., "Manipulation of skin graft rejection in alloimmune mice by anti-VCAM-1:VLA-4 but not anti-ICAM-1:LFA-1 monoclonal antibodies," *Trans Immunol* 3:55-61 (1995).

Georczynski, et al., "Altered patters of migration of cytokine-producing T lymphocytes in skin-grafted naïve or immune mice following in vivo administration of anti-VCAM-1 or ICAM-1", *Immunology* 87:573-580 (1996).

Giardina, et al., "Selective κ-Opioid Agonists: synthesis and Structure-ActivityFRelationships of Piperidines Incorporating an Oxo-Containing Acyl Group,"*J. Med. Chem.* 37:3482-3491 (1994).

Gonzalez-Amaro et al., Therapeutic anti-integrin (alpha4 and alphaL) monoclonal antibodies: two-edged swords?, *Immunology*, vol. 116, No. 3, pp. 289-296, (2005).

Gordeev, M.F. "Combinatorial Approaches to pharmacophoric Heterocycles: A Solid-Phase Synthesis of 3,1-Benzoxazine-4-ones." *Biotech. and Bioengineering.* 61(1): 13-16 (1998).

Grayson, et al., $\alpha d\beta 2$ Integrin Is Expressed on Human Eosinophils and Functions as an Alternative Ligand for Vascular Cell Adhesion Molecule 1 (VCAM-1) *J. Exp. Med.* 188(11) 2187-2191 (1998).

Hamann, A., et al. "Role of $\alpha 4$-Integrins in Lymphocute Homing to Mucosal Tissues in Vivo." *J. Immunology.* 152: 3283-3292 (1994).

Hartman, et. al., "Synthesis and Activity of Novel Nitropyrazines for use as Hypoxic Cell radiosensitizers," *J Med. Chem.* 27:1634-1639 (1984).

Henke, B.R., et al. "N-(2-Benzoylphenyl)-L-tyrosine :Aryl Agonists. 1. Discovery of a Novel Series of Potent Antihyperglycemic and Antihyperlipidemic Agents." *J. Med. Chem.* 41(25): 5020-5036 (1998).

Hladon, B., et al. In Vitro cytostatic activity of some amino acid 4-N-substituted cytosines. *Arch. Immunol. Ther. Exp.* 40(2): 145-150 (1992). (Abstract).

Hoffman, S., et al. "N-Pyrimidinylamino acids. III. N-(oxopyrimidinyl) derivatives of neutral amino acids." *Z. Chem.* 12(1): 21-22 (1972), Coden: Zeceal (Abstract).

Hoeve, et al., "Chiral Tetraalkylmethanes. Two Syntheses of Optically Active butylethylmethylpropylmethane of Known and High Optical Purity," *J. Org. Chem.* 45:2754-2763 (1980).

Hopewell et al. "Models of CNS radiation damage during space flight" *Adv. Space Res.* 14:433-442 (1994).

Jaeger, et al., "Peptidsynthesen mit-*O*-Carbamoyl-tyrosin Derivaten," *Chem. Ber.* 101:2762-2770 (1968) (English abstract), Only Abstract Considered.

Kawaguchi, S., et al. "VLA-4 Molecules on Tumor Cells Initiate an Adhesive Interaction with VCAM-1 Molecules on Endothelial Cell Surface." *Japanese J. Cancer Res.* 83: 1304-1316 (1992).

Kascheres et al., Chemical Abstract, DN 85:177351, also cited as *J. Org. Chem.* 41/22, 3546-9 (1976).

Keszthelyi, et al., "Evidence for a prolonged role of $\alpha_4$integrin throughout active experimental allergic encephalomyelitis," *Neurology* 47:1053-1059 (1996).

Korom, et al., "Blockade of Very late Angigen-4 Integrin Binding to Fibronectin in Allograft Recipients," *Transplantation* 65:854:859 (1998).

Kroneld, et al., "Expression of the Mucosal Lymphocyte Integrin $\alpha E\beta_7$ and its Ligand E-cadherin in Salivary Glands of Patients with Sjögren's Syndrome," *Scan. J. Rheumatol* 27:215-218 (1998).

Kung et al. "Involvement of IL-5 in a murine model of allergic pulmonary inflammation: prophylactic and therapeutic effect of an anti-IL-5 antibody" *Am J. Respir. Cell. Mol. Biol.* 13:360-365 (1995).

Lauri, D., et al. "Decreased adhesion to endothelial cells and matrix proteins of H-2K$^b$ gene transfected tumour cells." *British J. Cancer.* 68: 862-867 (1993).

Lazer, E.S., et al. "Benzoxazolamines and Benzothiazolamines: Potent, Enantioselective Inhibitors of Leukotriene Biosynthesis with a Novel Mechanism of Action." *J. Med. Chem.* 37(7): 913-923 (1994).

Li, H., et al. "An Atherogenic Diet Rapidly Induces VCAM-1, a Cytokine-Regulatable Mononuclear Leeukocyte Adhesion Molecule, in Rabbit Aortic Endothelium." *Arterioscler. Thromb.* 13(2): 197-204 (1993).

Luque, et al., "Activation Conformations of Very Late Activation Integrins Detected by a Group of Antibodies (HUTS) Specific for a Novel Regulatory Region (355-425) of the Common $\beta 1$ Chain", *J. Biol. Chem.* 271(19) 11067-11075 (1966).

Ma, D., et al., "Accelerating Effect Induced by the Structure of a-Amino Acid in the Copper Catalyzed Coupling Reaction of Aryl Halides with a-Amino Acids. Synthesis of Benzolactam-V8." *J. Am. Chem. Soc.*120(48): 12459-12467 (1998).

Marr-Leisy, et al., Chem. Abstract 105:97885, "The comparative spreading behavior of enantiomeric and racemic tyrosine amphiphiles," *Colloid & Polumer Sci.* 263:791-798 (1985).

Miller, S.D., et al., "Colloquium C15: Comparison of the ability of anti-VLA-4 antibody and a small molecule VLA-4 antagonist to regulate ongoing relapsing EAE," *Journal of Neurochemistry*, C15-02, 85:(Suppl. 1) (2003).

Miller, D.H., "Colloquium C15: Natalizumab (anti0VLA4 antibody) in multiple sclerosis," *Journal of Neurochemistry*, C15-04, 85: (Suppl. 1) (2003).

Mulligan, M.S., et al. "Role of $\beta 1$, $\beta 2$ Integrins and ICAM-1 in Lung Injury after Deposition of IgG and gA Immune Complexes." *J. Immunol.* 150(6): 2407-2417 (1993).

Ohta et al., "Emeheterone: Synthesis and Structural Revision," *Heterocycles* 31(9) 1655-1662 (1990).

Ohta et al., "Conversion of 2,5-Diphenyl- and 2,5-Dibenzyl-pyrazines to 2,5-Diketopiperazines", *Chem.. Pharm. Bull* 27(12):2980-2987 (1979).

Okarhara, H., et al. "Involvement of Very Late Activation Antigen 4 (VLA-4) and Vascular Cell Adhesion Molecule 1(VCAM-1) in Tumor Necrosis Factor $\alpha$ Enhancement of Experimental Metastasis." *Can. Res.* 54: 3233-3236 (1994).

Orosz et al., "Promotion of Experimental Liver Metastasis by Tumor Necrosis Factor," *Int. J. Cancer* 60:867-871 (1995).

Osborne, L. "Leukocyte Adhesion to Endothelium in Inflammation." *Cell.* 62: 3-6 (1990).

Paavonen, T. et al. "In Vivo Evidence of the Role of $\alpha_4\beta_1$-VCAM-1 Interaction in Sarcoma, but not in Carcinoma Extravasation." *Int. J. Can.* 58: 298 (1994).

Palmer, et al., "Sequence and tissue Distribution of the Integrin $\alpha 9$ subnit, a Novel Partner of $\beta 1$ That Is Widely distributed in Epithelia and Muscle, " *J. Cell boil.* 123(5) 1289-1297 (1993).

Pang et al., "UP-Regulation of $\alpha E\beta 7$, A Novel Integrin Adhesion Molecule, on T Cells from Systemic Lupis Erythematosus Patients with Specific Epithelial Involvement," *Arthritis & Reumatism* 41(8):1456-1463 (1998).

Papaioannou, et al., Facile Preparation of the 1-Hydroxybenzotriazolyl Ester of N-Tritypyroglutamic Acid and its Application to the Synthesis of TRH, [D-His$^2$ ]TRH and Analogues Incorporation *cis*- and *rans*-4-Hydroxy-Lproline: *Acta Chemica Scand.* 49:103-114 (1995).

Paul, L.C.,et al. "Monoclonal Antibodies Against LFA-1 and VLA-4 Inhibit Graft Vasculitis inRAt Cardiac Allografts," *Transpl. Proceed.* 25(1): 813-814 (1993).

Paul, et al., "Anti-integrin (LFA,-1, VLA-4, and Mac-1) antibody treatment and acutre cardiac graft rejection in the rat," *Transpl. Int.* 9:420-425 (1996).

Piraino, P.S. et al., "Prolonged reversal of chronic experimental allergic encephalomyelitis using a Small molecule inhibitor of a4 integrin," *Journal of Neuroimmunology*, 131:147-159 (2002).

Postigo, A.A., et al. "Increased Binding of Synovial T Lumphocytes from Rheumatoid Arthritis to Endothelial-Leukocyte Adhesion Molecule-1 (ELAM-1) and Vascular Cell Adhesion Molecule-1 (VCAM-1)." *J. Clin. Invest.* 89: 1445-1452 (1991).

Pretolani, M., et al. "Antibody to Very Late Activation Antigen 4 Prevents Antigen-induced Bronchial Hyperreactivity and Cellular Infiltration in the Guinea Pig Airways." *J. Exp. Med.* 180: 795-805 (1994).

Prusiner, S.B. "Novel proteinaceous infections particles cause scrapie" Science 216:136-144 (1982).

PubMed Abstract 12783578, also cited as *Expert Opinion Ther. Targets*, 7/3, 427-40 (2003).
PubMed Abstract 1287626, also cited as *Mol. Cell Neurosci.*, 23/3, 427-39 (2003).
PubMed Abstract 12877819, also cited as *Pulm. Pharmacol., Ther.*, 16/5, 279-85 (2003).
PubMed Abstract 12876405, also cited as *Int. Arch. Allergy Immunol.*, 31/3, 153-63 (2003).
Sandborn, et al, "Biologic Therapy of Inflammatory Bowel Disease," *Gastroenterology*, 122:1592-1608 (2002).
Sasseville, V.G., et al. "Monocyte Adhesion to Endothelium in Simian Immunodeficiency Virus-Induced AIDS Encephalitis is Mediated by Vascular Cell Adhesion Molecule-1/$\alpha_4\beta_1$ Integrin Interactions." *Am. J. Path.* 144(1): 27-40 (1994).
Schadendorf, D., et al. "Tumour Progression and Metastatic Behaviour in Vivo Correlates with Integrin Expression on Melanocytic Tumours." *J. Path.* 170: 429-434 (1993).
Schlegel, et al., "Inhibition of T Cell Costimulation by VCAM-1 revents Murine Graft-Versus-Host Disease Across Minor Histocompatibility Barriers, "*J. Immunol.* 155:3856-3865 (1995).
Schneider et al., "The role of $\alpha$4 (CD49d) and $\beta$2 (CD18) integrins in eosinophil and neutrophil migration to allergic lung inflammation in the brown Norway rat" *Am. J. Respir. Cell. Mol. Biol.* 20:448-457 (1999).
Simchowitz, et al., "Polyvalent Cations Inhibit Human Neutrophil Chemotaxis by Interfering with the Ploymerization of Actin, "*J. Biol. Chem.* 265(23)13457-13463 (1990).
Sonnenberg, A., "Integrins and Their Ligands," *Current Topics in Microbiology and Immunology* 184:7-35 (1993).
Springer, T.A. "Adhesion receptors of the immune system." *Nature*. 346: 425-434 (1990).
Springer, T.A., "Traffic Signals for Lymphocyte Recirculation and Leukocyte Emigration: The Multistep Paradigm," *Cell* 76:301-314 (1994).
Steinbach et al., "Expression of cell adhesion molecules in an established and characterized new human renal cancer cell line, CCF-RC7" *Urol. Res.* 23:175-183 (1995).
Tarkowski et al., PubMed Abstract (*Int Arch Allergy Immunol.*) 121(1):25-33 (2000).
Teranishi, K., et al. "Synthesis and Chemiluminescence of Coelenterazine (*Oplophorus* Luciferin) Analogues." *Bull. Chem. Soc. Jpn.* 63(11): 3132-3140 (1990).
Tilley et al., "VLA-4 antagonists," *Drugs of the Future*, 26(10):285-998 (2001).
Toniolo, et al., Chemical Abstract DN 77:5775, also cited as *J. Chem. Soc.*, Pekin Transactions, 1, Org. & Bio—org. Chem., 9/10, 1178-81 (1972).
Trollmo et al. "Expression of the mucosal lymphocyte integrin $\alpha^E\beta7$ and its ligand E-cadherin in the synovium of patients with rheumatoid arthritis" Scand. J. Immunol. 44:293-298 (1996).
Van Dinther-Janssen, A.C.H.M., et al. "Role of the CS1 adhesion motif of fibronectin in T cell adhesion to synovial membrane and peripheral lymph node endothelium." *Annals. Rheumatic Dis.* 52: 672-676 (1993).
Van Dinther-Janssen, A.C.H.M., et al. "The VLA-4/VCAM-1 Pathway is Involved in Lymphocyte Adhesion to Endothelium in Rheumatoid Synovium." *J. Immunology.* 147(12): 4207-4210 (1991).
Vedder, N.B., et al. "Role of neutrophils in generalized reperfusion injury associated with resuscitation from shock." *Surgery*. 106: 509-516 (1989).

Verhoef, et al., "Transport of peptide and protein drugs across biological membranes, "*Eur. J. Drug Metab. Pharmacokietics* 15(2):83-93 (1990).
Wen, et al., "The Chemistry of 1,2,3-Thiadiazoles. II. 3,4-Disubstituted Derivatives of 1,2,5-Thiadiazole 1,1-Dioxide," *J. Org. Chem.* 40(19):2743-2748 (1975).
Wen et al., "1,2,5-Thiadiazolid-3,4-Dione-1-Oxide", *Org. Prep. Proceed.* 1(4):255-258 (1969).
Whittaker, N., "A New Synthesis and the Chemical Properties of 5-Aminopyrimidine," *Chem.. Society* 354:1565-1570 (1951).
Wolft, M., "Burger's Medicinal Chemistry, 5ed, Part 1", John Wiley & Sons, (1995), pp. 975-977.
Wyzsza et al., Chemical Abstract DN 70:96568, also cited as Roczniki Chemii, 42/10, 1647-60 (1968) (English translation not provided).
Yamamoto et al. "Total synthesis of ($\pm$)-Celacinnine, ($\pm$)-celallocinnine, ($\pm$)-celafurine, ($\pm$)-celabenzine" *J. Am. Chem. Soc.* 103:6133-6136 (1981).
Yang, C-D., et al. "Inhibition of insultitis and prevention of diabetes in nonobese diabetic mice by blocking L-selecting and very late antigen 4 adhesion receptors." *Proc. Natl. Acad. Sci., USA.* 10494-10498 (1993).
Yang, et al., "Prolongation of Rate Islet Allograft Survival by Treatment with Monoclonal Antibodies Against VLA-4 and LFA-1," *Transplantation* 60:71-76 (1995).
Yednock, T.A., et al., "Prevention of experimental autoimmune encephalomyelitis by antibodies agains $\alpha_4\beta_1$ integrin." *Nature*. 356: 63 (1992).
Yednock, et al., "$\alpha4\beta^1$ Inegrin-dependent Cell Adhesion Is Regulated by a Low Affinity Receptor Pool That is Conformationally Responsive to Ligand," *J. Biol. Chem.*, 270: 28740 (1965).
Yokosaki, et al., "The Integrin$\alpha9\beta1$ Mediates Cell Attachmetn to a Non-RGD Site in the Third Fibronection Type III Repeast of Tenascin," *J. Biol. Chem.* 269:26691-26696 (1994).
Zhu, et al., "The Direct Formation of Funcationalized Alky(aryl)zinc Halides by Oxidative Addition of Highly Reactive Zinc with Organic Halides and Their Reactions with Acid Chlorides, $\alpha\beta$-Unsaturated Ketones, and Allylic, Aryl, and Vinyl Halides," *J. Org. Chem.* 5:1445-1453 (1991).
Chem. Abstract 130:52724 structures for WO 9853814 dated Dec. 1998.
Chem. Abstract 69:676 structures for Jaeger et al., *Chem. Berichte* 101/8, 2762-70 (1968).
Chem. Abstract 105:97885 for structure, Marr-Leisy et al., *Coloid and Polymer Sc.* 263/10,79-8 (1985).
Chem Abstract 102:149279 for structure of JP 59212480 dated Dec. 1984.
Chem. Abstract 102:24642 for structures of EP 116494 dated Aug. 1984.
Chem. Abstract 125:89348 also cited as HCAPLUS, JP 08100141; Hiroshi et al., (1996).
Chem. Abstract 114:101454-1991:101454, also cited as Ohta et al., *Heterocycles*, 31/9, 166-62 (1990).
Chem. Abstract 113:130558-1990:530558, also cited as Simchowitz et al., *J. Biol. Chem.*, 265/23, 13457-63 (1990).
Chem. Abstract 93:46584-1980:446584, also cited as Ohta et al., *Chem. & Pharmaceutical Bulletin*, 27/12, 2980-7 (1979).

* cited by examiner

HETEROARYL, HETEROCYCLIC AND ARYL COMPOUNDS WHICH INHIBIT LEUKOCYTE ADHESION MEDIATED BY VLA-4

CROSS-REFERENCE TO RELATED APPLICATIONS

This application is a continuation of U.S. application Ser. No. 11/582,293, filed Oct. 16, 2006, which is a continuation of U.S. application Ser. No. 11/033,079, filed Jan. 10, 2005, now U.S. Pat. No. 7,378,529, issued on May 27, 2008, which is a division of U.S. application Ser. No. 10/218,366, filed Aug. 15, 2002, now U.S. Pat. No. 6,911,439, issued on Jun. 28, 2005, which is a division of U.S. application Ser. No. 09/489,377, filed on Jan. 21, 2000, now U.S. Pat. No. 6,492,372, issued Dec. 10, 2002, which claims the benefit under 35 U.S.C. §119(e) of U.S. Application No. 60/116,923, filed Jan. 22, 1999, and U.S. Application No. 60/160,999, filed Oct. 21, 1999; the disclosures of which are incorporated herein by reference in their entirety.

BACKGROUND OF THE INVENTION

Field of the Invention

This invention relates to compounds which inhibit leukocyte adhesion and, in particular, leukocyte adhesion mediated by VLA-4.

REFERENCES

The following publications, patents and patent applications are cited in this application as superscript numbers:
1 Hemler and Takada, European Patent Application Publication No. 330,506, published Aug. 30, 1989
2 Elices, et al., *Cell,* 60:577-584 (1990)
3 Springer, *Nature,* 346:425-434 (1990)
4 Osborn, *Cell,* 62:3-6 (1990)
5 Vedder, et al., *Surgery,* 106:509 (1989)
6 Pretolani, et al., *J. Exp. Med.,* 180:795 (1994)
7 Abraham, et al., *J. Clin. Invest.,* 93:776 (1994)
8 Mulligan, et al., *J. Immunology,* 150:2407 (1993)
9 Cybulslcy, et al., *Science,* 251:788 (1991)
10 Li, et al., *Arterioscler. Thromb.,* 13:197 (1993)
11 Sasseville, et al., *Am. J. Path.,* 144:27 (1994)
12 Yang, et al., *Proc. Nat. Acad. Science (USA),* 90:10494 (1993)
13 Buddy, et al., *Diabetes,* 43:529 (1994)
14 Baron, et al, *J. Clin. Invest.,* 93:1700 (1994)
15 Hamann, et al., *J. Immunology,* 152:3238 (1994)
16 Yednock, et al., *Nature,* 356:63 (1992)
17 Baron, et al., *J. Exp. Med.,* 177:57 (1993)
18 van Dinther-Janssen, et al., *J. Immunology,* 147:4207 (1991)
19 van Dinther-Janssen, et al., *Annals. Rheumatic Dis.,* 52:672 (1993)
20 Elices, et al., *J. Clin. Invest.,* 93:405 (1994)
21 Postigo, et al., *J. Clin. Invest.,* 89:1445 (1991)
22 Paul, et al., *Transpl. Proceed.,* 25:813 (1993)
23 Okarhara, et al., *Can. Res.,* 54:3233 (1994)
24 Paavonen, et al., *Int. J. Can.,* 58:298 (1994)
25 Schadendorf, et al., *J. Path.,* 170:429 (1993)
26 Bao, et al., *Diff.,* 52:239 (1993)
27 Lauri, et al., *British J. Cancer,* 68:862 (1993)
28 Kawaguchi, et al., *Japanese J. Cancer Res.,* 83:1304 (1992)
29 Kogan, et al., U.S. Pat. No. 5,510,332, issued Apr. 23, 1996
30 International Patent Appl. Publication No. WO 96/01644

All of the above publications, patents and patent applications are herein incorporated by reference in their entirety to the same extent as if each individual publication, patent or patent application was specifically and individually indicated to be incorporated by reference in its entirety.

STATE OF THE ART

VLA-4 (also referred to as $\alpha_4\beta_1$ integrin and CD49d/CD29), first identified by Hemler and Takada[1] is a member of the β1 integrin family of cell surface receptors, each of which comprises two subunits, an α chain and a β chain. VLA-4 contains an α4 chain and a β1 chain. There are at least nine β1 integrins, all sharing the same β1 chain and each having a distinct a chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

Intercellular adhesion mediated by VLA-4 and other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.[5]). Other inflammatory or medical conditions mediated by an adhesion mechanism include, by way of example, asthmas[6-8], Alzheimer's disease, atherosclerosis[9-10], AIDS dementia[11], diabetes[12-14] (including acute juvenile onset diabetes), inflammatory bowel disease[15] (including ulcerative colitis and Crohn's disease), multiple sclerosis[16-17], rheumatoid arthritis[18-21], tissue transplantation[22], tumor metastasis[23-28], meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

In view of the above, assays for determining the VLA-4 level in a biological sample containing VLA-4 would be useful, for example, to diagnosis VLA-4 mediated conditions. Additionally, despite these advances in the understanding of leukocyte adhesion, the art has only recently addressed the use of inhibitors of adhesion in the treatment of inflammatory brain diseases and other inflammatory conditions[29-30]. The present invention addresses these and other needs.

SUMMARY OF THE INVENTION

This invention provides compounds which bind to VLA-4. Such compounds can be used, for example, to assay for the presence of VLA-4 in a sample and in pharmaceutical compositions to inhibit cellular adhesion mediated by VLA-4, for example, binding of VCAM-1 to VLA-4. The compounds of this invention have a binding affinity to VLA-4 as expressed by an $IC_{50}$ of about 15 µM or less (as measured using the procedures described in Example A below).

Accordingly, in one of its method aspects, this invention is directed to a method for treating a disease mediated by VLA-4 in a patient, which method comprises administering a pharmaceutical composition comprising a pharmaceutically acceptable carrier and a therapeutically effective amount of a compound of formula Ia and/or Ib:

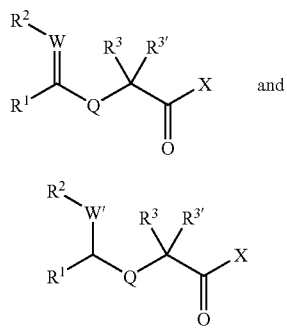

wherein, in formula Ia, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in formula Ib, $R^1$ and $R^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case of the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of formula Ia or Ib is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted-thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-allyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, —N[S(O)$_2$—R']$_2$ and —N[S(O)$_2$—NR']$_2$ where each R' is independently selected from the group consisting of alkyl, substituted alkyl, aryl, substituted aryl, heteroaryl, substituted heteroaryl, heterocyclic and substituted heterocyclic;

$R^3$ and $R^{3'}$ are independently selected from the group consisting of hydrogen, isopropyl, —CH$_2$Z where Z is selected from the group consisting of hydrogen, hydroxyl, acylamino, alkyl, alkoxy, aryloxy, aryl, aryloxyaryl, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted alkyl, substituted alkoxy, substituted aryl, substituted aryloxy, substituted aryloxyaryl, substituted cycloalkyl, heteroaryl, substituted heteroaryl, heterocyclic and substituted heterocyclic, and where $R^3$ and $R^{3'}$ are joined to form a substituent selected from the group consisting of =CHZ where Z is defined above provided that Z is not hydroxyl or thiol, cycloalkyl, substituted cycloalkyl, cycloalkenyl, substituted cycloalkenyl, heterocyclic and substituted heterocyclic;

Q is selected from the group consisting of —O—, —S—, —S(O)—, —S(O)$_2$, and —NR$^4$—;

$R^4$ is selected from the group consisting of hydrogen, alkyl, substituted alkyl, alkenyl, substituted alkenyl, cycloalkyl, substituted cycloalkyl, cycloalkenyl, substituted cycloalkenyl, aryl, substituted aryl, heteroaryl, substituted heteroaryl, heterocyclic and substituted heterocyclic or, optionally, $R^4$ and $R^1$ or $R^4$ and $R^2$, together with the atoms to which they are bound, are joined to form a heteroaryl, a substituted heteroaryl, a heterocyclic or a substituted heterocyclic group;

W is selected from the group consisting of nitrogen and carbon; and

W' is selected from the group consisting of nitrogen, carbon, oxygen, sulfur, S(O), and S(O)$_2$;

X is selected from the group consisting of hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and —NR"R" where each R" is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic and substituted heterocyclic;

and enantiomers, diastereomers and pharmaceutically acceptable salts thereof;

and further wherein the compound of formula Ia and/or Ib has a binding affinity to VLA-4 as expressed by an $IC_{50}$ of about 15 µM or less.

Preferably, in the above method, $R^3$ is —$(CH_2)_x$—Ar—$R^9$, where Ar is aryl, substituted aryl, heteroaryl and substituted heteroaryl; $R^9$ is selected from the group consisting of acyl, acylamino, acyloxy, aminoacyl, aminocarbonylamino, aminothiocarbonylamino, aminocarbonyloxy, oxythiocarbonylamino, thioamidino, thiocarbonylamino, aminosulfonylamino, aminosulfonyloxy, aminosulfonyl, oxysulfonylamino and oxysulfonyl; and x is an integer from 0 to 4. $R^{3'}$ is preferably alkyl or hydrogen; more preferably, $R^{3'}$ is hydrogen.

More preferably, $R^3$ is a group of the formula:

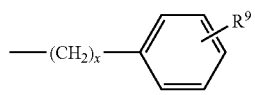

wherein $R^9$ and x are as defined herein. Preferably, $R^9$ is in the para position of the phenyl ring; and x is an integer of from 1 to 4, more preferably, x is 1.

In a preferred embodiment, $R^9$ is selected from —O—Z—$NR^{11}R^{11'}$ and —O—Z—$R^{12}$ wherein $R^{11}$ and $R^{11'}$ are independently selected from the group consisting of hydrogen, alkyl, substituted alkyl, cycloalkyl, substituted cycloalkyl, cycloalkenyl, substituted cycloalkenyl, heterocyclic, substituted heterocyclic, and where $R^{11}$ and $R^{11'}$ are joined to form a heterocycle or a substituted heterocycle, $R^{12}$ is selected from the group consisting of heterocycle and substituted heterocycle, and Z is selected from the group consisting of —C(O)— and —$SO_2$—. More preferably, $R^9$ is —OC(O)$NR^{11}R^{11'}$, wherein $R^{11}$ and $R^{11'}$ are as defined herein.

In the above method, Z is preferably —C(O)—. Preferably, Q is —$NR^4$—.

In a preferred embodiment, the above method employs a compound of formula IIa or IIb:

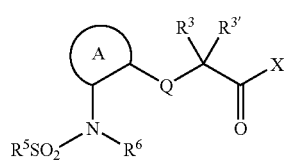

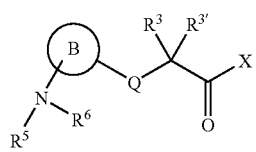

wherein $R^3$, $R^{3'}$ and X are as defined herein;

ring A and ring B independently form a heteroaryl or substituted heteroaryl group having two nitrogen atoms in the heteroaryl ring;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

or optionally, one of, $R^4$ and ring A, $R^4$ and $R^5$, $R^4$ and $R^6$, or $R^5$ and $R^6$, together with the atoms to which they are bound, can be joined to form a heterocyclic or substituted heterocyclic ring;

and enantiomers, diastereomers and pharmaceutically acceptable salts thereof; and provided that ring B does not form a 6-amino or substituted amino pyrimidin-4-yl group.

Preferably, ring A forms a pyridazine, pyrimidine or pyrazine ring; more preferably, a pyrimidine or pyrazine ring; wherein the pyridazine, pyrimidine or pyrazine ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

Preferably, ring B forms a pyridazine, pyrimidine, pyrazine, 1-oxo-1,2,5-thiadiazole or a 1,1-dioxo-1,2,5-thiadiazole ring; more preferably, a pyrimidine, pyrazine, 1-oxo-1,2,5-thiadiazole or a 1,1-dioxo-1,2,5-thiadiazole ring; wherein the pyridazine, pyrimidine or pyrazine ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

In another preferred embodiment, the method employs a compound of formula IIIa, IIIc, IIId, IIIe or IIIf:

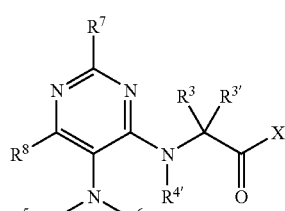

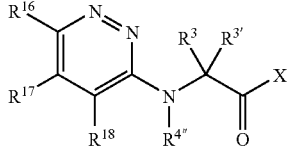

IIId

[Chemical structure: pyrimidine ring with R16, R20, R18 substituents and N(R4″)-C(R3)(R3′)-C(=O)-X sidechain]

IIIe

[Chemical structure: pyrazine ring with R16, R17, R21 substituents and N(R4″)-C(R3)(R3′)-C(=O)-X sidechain]

IIIf

[Chemical structure: thiadiazole ring with S(O)b, R5-N(R6)-, and N(R4″)-C(R3)(R3′)-C(=O)-X sidechain]

wherein $R^3$, $R^{3'}$ and X are as defined herein;

$R^{4'}$ is selected from the group consisting of hydrogen and alkyl or, optionally, one of, $R^{4'}$ and $R^5$, $R^{4'}$ and $R^6$, $R^5$ and $R^6$, $R^5$ and $R^8$, or $R^6$ and $R^8$, together with the atoms to which they are bound, are joined to form a heterocyclic, a substituted heterocyclic, a heteroaryl or substituted heteroaryl group optionally containing from 1 to 3 additional hetero ring atoms selected from the group consisting of oxygen, nitrogen and sulfur;

$R^{4''}$ is selected from the group consisting of hydrogen and alkyl;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

$R^7$ and $R^8$ are independently selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and halogen;

$R^{16}$ and $R^{17}$ are independently selected from the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen; and $R^{18}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

$R^{20}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

$R^{21}$ is selected from the group consisting of alkyl, substituted alkyl, alkoxy, substituted alkoxy, amino, substituted amino, cycloalkyl, substituted cycloalkyl, aryl, substituted aryl, heterocyclic and substituted heterocyclic;

b is 1 or 2;

and enantiomers, diastereomers and pharmaceutically acceptable salts thereof.

Preferably, the method employs a compound of formula IIId, IIIe or IIIf.

In another of its method aspects, this invention is directed to a method for treating a disease mediated by VLA-4 in a patient, which method comprises administering a pharmaceutical composition comprising a pharmaceutically acceptable carrier and a therapeutically effective amount of a compound of formula IVa and/or IVb:

IVa

[Chemical structure: R2-W=C(R1)-N(R13)-C(R14)(R15)-X']

and

IVb

[Chemical structure: R2-W'-CH(R1)-N(R13)-C(R14)(R15)-X']

wherein, in formula IVa, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in formula IVb, $R^1$ and $R^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of formula IVa or IVb is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, —N[S(O)$_2$—R']$_2$ and —N[S(O)$_2$—NR']$_2$ where each R' is independently selected from the group consisting of alkyl, substituted alkyl, aryl, substituted aryl, heteroaryl, substituted heteroaryl, heterocyclic and substituted heterocyclic;

$R^{13}$ is selected from the group consisting of hydrogen, $C_{1-10}$ alkyl, Cy, and Cy-$C_{1-10}$ alkyl, wherein alkyl is optionally substituted with one to four substituents independently selected from $R^a$; and Cy is optionally substituted with one to four substituents independently selected from $R^b$;

$R^{14}$ is selected from the group consisting of hydrogen, $C_{1-10}$ alkyl, $C_{2-10}$ alkenyl, $C_{2-10}$ alkynyl, Cy, Cy-$C_{1-10}$ alkyl, Cy-$C_{2-10}$ alkenyl and Cy-$C_{2-10}$ alkynyl, wherein alkyl, alkenyl, and alkynyl are optionally substituted with one to four substituents selected from phenyl and $R^x$, and Cy is optionally substituted with one to four substituents independently selected from $R^y$;

or $R^{13}$, $R^{14}$ and the atoms to which they are attached together form a mono- or bicyclic ring containing 0-2 additional heteroatoms selected from N, O and S;

$R^{15}$ is selected from the group consisting of $C_{1-10}$ alkyl, $C_{2-10}$ alkenyl, $C_{2-10}$ alkynyl, aryl, aryl-$C_{1-10}$ alkyl, heteroaryl, heteroaryl-$C_{1-10}$ alkyl, wherein alkyl, alkenyl and alkynyl are optionally substituted with one to four substituents selected from $R^x$, and aryl and heteroaryl are optionally substituted with one to four substituents independently selected from $R^y$;

or $R^{14}$, $R^{15}$ and the carbon to which they are attached form a 3-7 membered mono- or bicyclic ring containing 0-2 heteroatoms selected from N, O and S;

$R^a$ is selected from the group consisting of Cy and a group selected from $R^x$, wherein Cy is optionally substituted with one to four substituents independently selected from $R^c$:

$R^b$ is selected from the group consisting of $R^a$, $C_{1-10}$ alkyl, $C_{2-10}$ alkenyl, $C_{2-10}$ alkynyl, aryl $C_{1-10}$alkyl, heteroaryl $C_{1-10}$ alkyl, wherein alkyl, alkenyl, alkynyl, aryl, heteroaryl are optionally substituted with a group independently selected from $R^c$;

$R^c$ is selected from the group consisting of halogen, NO$_2$, C(O)OR$^f$, $C_{1-4}$ alkyl, $C_{1-4}$ alkoxy, aryl, aryl $C_{1-4}$ alkyl, aryloxy, heteroaryl, NR$^f$R$^g$, R$^f$C(O)R$^g$, NR$^f$C(O)NR$^f$R$^g$, and CN;

$R^d$ and $R^e$ are independently selected from hydrogen, $C_{1-10}$ alkyl, $C_{2-10}$ alkenyl, $C_{2-10}$ alkynyl, Cy and Cy $C_{1-10}$alkyl, wherein alkyl, alkenyl, alkynyl and Cy are optionally substituted with one to four substituents independently selected from $R^c$;

or $R^d$ and $R^e$ together with the atoms to which they are attached form a heterocyclic ring of 5 to 7 members containing 0-2 additional heteroatoms independently selected from oxygen, sulfur and nitrogen;

$R^f$ and $R^g$ are independently selected from hydrogen, $C_{1-10}$ alkyl, Cy and Cy-$C_{1-10}$ alkyl wherein Cy is optionally substituted with $C_{1-10}$ alkyl; or $R^f$ and $R^g$ together with the carbon to which they are attached form a ring of 5 to 7 members containing 0-2 heteroatoms independently selected from oxygen, sulfur and nitrogen;

$R^h$ is selected from the group consisting of hydrogen, $C_{1-10}$alkyl, $C_{2-10}$ alkenyl, $C_{2-10}$ alkynyl, cyano, aryl, aryl $C_{1-10}$ alkyl, heteroaryl, heteroaryl $C_{1-10}$ alkyl, and —SO$_2$R$^1$; wherein alkyl, alkenyl, and alkynyl are optionally substituted with one to four substitutents independently selected from $R^a$; and aryl and heteroaryl are each optionally substituted with one to four substituents independently selected from $R^b$;

$R^i$ is selected from the group consisting of $C_{1-10}$ alkyl, $C_{2-10}$ alkenyl, $C_{2-10}$ alkynyl, and aryl; wherein alkyl, alkenyl, alkynyl and aryl are each optionally substituted with one to four substituents independently selected from $R^e$;

$R^x$ is selected from the group consisting of —OR$^d$, —NO$_2$, halogen, —S(O)$_m$R$^d$, —SR$^d$, —S(O)$_2$OR$^d$, —S(O)NR$^d$R$^e$, —NR$^d$R$^e$, —O(CR$^f$R$^g$)$_n$NR$^d$R$^e$, —C(O)R$^d$, —CO$_2$R$^d$, —CO$_2$(CR$^f$R$^g$)$_n$CONR$^d$R$^e$, —OC(O)R$^d$, —CN, —C(O)NR$^d$R$^e$, —NR$^d$C(O)R$^e$, —OC(O)NR$^d$R$^e$, —NR$^d$C(O)OR$^e$, —NR$^d$C(O)NR$^d$R$^e$, —CR$^d$(N—OR$^e$), CF$_3$, oxo, NR$^d$C(O)NR$^d$SO$_2$R$^1$, NR$^d$S(O)$_m$R$^e$, —OS(O)$_2$OR$^d$, and —OP(O)(OR$^d$)$_2$;

$R^y$ is selected from the group consisting of $R^x$, $C_{1-10}$ alkyl, $C_{2-10}$ alkenyl, $C_{2-10}$ alkynyl, aryl $C_{1-10}$alkyl, heteroaryl $C_{1-10}$ alkyl, cycloalkyl, heterocyclyl; wherein alkyl, alkenyl, alkynyl and aryl are each optionally substituted with one to four substitutents independently selected from $R^x$;

Cy is cycloalkyl, heterocyclyl, aryl, or heteroaryl;

m is an integer from 1 to 2;

n is an integer from 1 to 10;

W is selected from the group consisting of carbon and nitrogen;

W' is selected from the group consisting of carbon, nitrogen, oxygen, sulfur, S(O) and S(O)$_2$;

X' is selected from the group consisting of —C(O)OR$^d$, —P(O)(OR$^d$)(OR$^e$), —P(O)(R$^d$)(OR$^e$), —S(O)$_m$OR$^d$, —C(O)NR$^d$R$^h$, and -5-tetrazolyl;

and enantiomers, diastereomers and pharmaceutically acceptable salts thereof;

and further wherein the compound of formula IVa and/or IVb has a binding affinity to VLA-4 as expressed by an IC$_{50}$ of about 15 μM or less.

Preferably, in the above method, $R^1$ and $R^2$, together with the carbon atom and W to which they are bound respectively, are joined to form a heteroaryl or substituted heteroaryl group having two nitrogen atoms in the heteroaryl ring. Optionally, the heteroaryl ring may contain other heteroatoms such as oxygen or sulfur. More preferably, $R^1$ and $R^2$, together with the carbon atom and W to which they are bound respectively, are joined to form a pyridazine, pyrimidine, pyrazine, 1-oxo-1,2,5-thiadiazole or 1,1-dioxo-1,2,5-thiadiazole ring; more preferably, a pyrimidine, pyrazine, 1-oxo-1,2,5-thiadiazole or 1,1-dioxo-1,2,5-thiadiazole ring; wherein the pyridazine, pyrimidine, pyrazine, 1-oxo-1,2,5-thiadiazole or 1,1-dioxo-1,2,5-thiadiazole ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

Preferably, X' is —C(O)OR$^d$.

In a preferred embodiment, the above method employs a compound of formula Va, Vc, Vd, Ve or Vf:

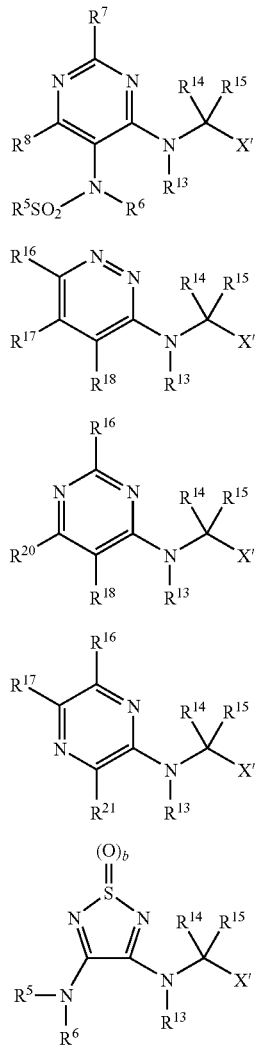

wherein R$^{13}$, R$^{14}$, R$^{15}$ and X' are as defined herein;

R$^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocyclic, heteroaryl and substituted heteroaryl;

R$^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —SO$_2$R$^{10}$ where R$^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl; and R$^7$ and R$^8$ are independently selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and halogen;

R$^{16}$ and R$^{17}$ are independently selected from the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen; and R$^{18}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

R$^{20}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

R$^{21}$ is selected from the group consisting of alkyl, substituted alkyl, alkoxy, substituted alkoxy, amino, substituted amino, cycloalkyl, substituted cycloalkyl, aryl, substituted aryl, heterocyclic and substituted heterocyclic;

b is 1 or 2;

and enantiomers, diastereomers and pharmaceutically acceptable salts thereof.

More preferably, the above method employs a compound of formula Vd, Ve or Vf.

In yet another of its method aspects, this invention is directed to a method for treating a disease mediated by VLA-4 in a patient, which method comprises administering a pharmaceutical composition comprising a pharmaceutically acceptable carrier and a therapeutically effective amount of a compound of formula VIa and/or VIb:

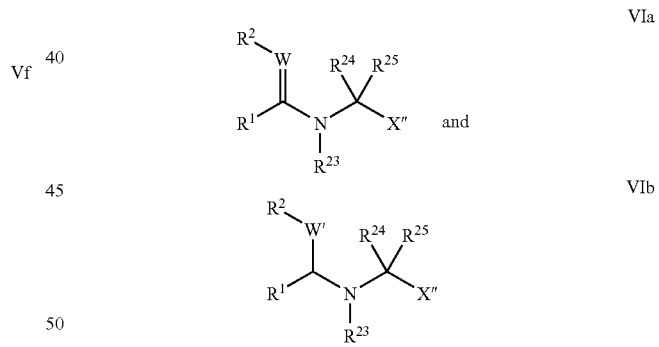

wherein, in formula VIa, R$^1$ and R$^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in formula VIb, R$^1$ and R$^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case of the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of formula VIa or VIb is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O), —NR-heterocyclic, —NRS(O)$_2$—NR-substituted heterocyclic where R is hydrogen or alkyl, —N[S(O)$_2$—R']$_2$ and —N[S(O)$_2$—NR']$_2$ where each R' is independently selected from the group consisting of alkyl, substituted alkyl, aryl, substituted aryl, heteroaryl, substituted heteroaryl, heterocyclic and substituted heterocyclic;

$R^{23}$ is selected from the group consisting of hydrogen, $C_{1-10}$ alkyl optionally substituted with one to four substituents independently selected from $R^{a'}$ and Cy optionally substituted with one to four substituents independently selected from $R^{b'}$;

$R^{24}$ is selected from the group consisting of $Ar^1$—$Ar^2$—$C_{1-10}$ alkyl, $Ar^1$—$Ar^2$—$C_{2-10}$ alkenyl, —$Ar^1$—$Ar^2$—$C_{2-10}$ alkynyl, wherein $Ar^1$ and $Ar^2$ are independently aryl or heteroaryl each of which is optionally substituted with one to four substituents independently selected from $R^{b'}$; alkyl, alkenyl and alkynyl are optionally substituted with one to four substituents independently selected from $R^{a'}$;

$R^{25}$ is selected from the group consisting of hydrogen, $C_{1-10}$ alkyl, $C_{2-10}$ alkenyl, $C_{2-10}$ alkynyl, aryl, aryl $C_{1-10}$alkyl, heteroaryl, and heteroaryl $C_{1-10}$ alkyl, wherein alkyl, alkenyl and alkynyl are optionally substituted with one to four substituents selected from $R^{a'}$, and aryl and heteroaryl are optionally substituted with one to four substituents independently selected from $R^{b'}$;

$R^{a'}$ is selected from the group consisting of Cy, —OR$^{d'}$, —NO$_2$, halogen —S(O)$_m$R$^{d'}$, —SR$^{d'}$, —S(O)$_2$OR$^{d'}$, —S(O)$_m$NR$^{d'}$R$^{e'}$, —NR$^{d'}$R$^{e'}$, —O(CR$^{f'}$R$^{g'}$)$_n$NR$^{d'}$R$^{e'}$, —C(O)R$^{d'}$, —CO$_2$R$^{d'}$, —CO$_2$(CR$^{f'}$R$^{g'}$)$_n$CONR$^{d'}$R$^{e'}$, —OC(O)R$^{d'}$, —CN, —C(O)NR$^{d'}$R$^{e'}$, —NR$^{d'}$C(O)R$^{e'}$, —OC(O)NR$^{d'}$R$^{e'}$, —NR$^{d'}$C(O)OR$^{e'}$, —NR$^{d'}$C(O)NR$^{d'}$R$^{e'}$, —CR$^{d'}$(N—OR$^{e'}$), CF$_3$, and —OCF$_3$;

wherein Cy is optionally substituted with one to four substituents independently selected from R$^{c'}$;

$R^{b'}$ is selected from the group consisting of R$^{a'}$, $C_{1-10}$ alkyl, $C_{2-10}$ alkenyl, $C_{2-10}$ alkynyl, aryl $C_{1-10}$ alkyl, heteroaryl $C_{1-10}$alkyl, wherein alkyl, alkenyl, aryl, heteroaryl are optionally substituted with a group independently selected from R$^{c'}$;

R$^{c'}$ is selected from the group consisting of halogen, amino, carboxy, $C_{1-4}$ alkyl, $C_{1-4}$ alkoxy, aryl, aryl $C_{1-4}$alkyl, hydroxy, CF$_3$, and aryloxy;

$R^{d'}$ and $R^{e'}$ are independently selected from hydrogen, $C_{1-10}$ alkyl, $C_{2-10}$ alkenyl, $C_{2-10}$ alkynyl, Cy and Cy $C_{1-10}$alkyl, wherein alkyl, alkenyl, alkynyl and Cy are optionally substituted with one to four substituents independently selected from R$^{e'}$; or $R^{d'}$ and $R^{e'}$ together with the atoms to which they are attached form a heterocyclic ring of 5 to 7 members containing 0-2 additional heteroatoms independently selected from oxygen, sulfur and nitrogen;

$R^{f'}$ and $R^{g'}$ are independently selected from hydrogen, $C_{1-10}$ alkyl, Cy and Cy-$C_{1-10}$ alkyl; or $R^{f'}$ and $R^{g'}$ together with the carbon to which they are attached form a ring of 5 to 7 members containing 0-2 heteroatoms independently selected from oxygen, sulfur and nitrogen;

$R^{h'}$ is selected from the group consisting of hydrogen, $C_{1-10}$ alkyl, $C_{2-10}$ alkenyl, $C_{2-10}$ alkynyl, cyano, aryl, aryl $C_{1-10}$ alkyl, heteroaryl, heteroaryl $C_{1-10}$ alkyl, or —SO$_2$R$^{i'}$;

wherein alkyl, alkenyl, and alkynyl are optionally substituted with one to four substituents independently selected from R$^{a'}$; and aryl and heteroaryl are each optionally substituted with one to four substituents independently selected from R$^{b'}$;

$R^{i'}$ is selected from the group consisting of $C_{1-10}$ alkyl, $C_{2-10}$ alkenyl, $C_{2-10}$ alkynyl, and aryl;

wherein alkyl, alkenyl, alkynyl and aryl are each optionally substituted with one to four substituents independently selected from R$^{c'}$;

Cy is cycloalkyl, heterocyclyl, aryl, or heteroaryl;

X" is selected from the group consisting of —C(O)OR$^{d'}$, —P(O)(OR$^{d'}$)(OR$^{e'}$), —P(O)(R$^{d'}$)(OR$^{e'}$), —S(O)$_m$OR$^{d'}$, —C(O)NR$^{d'}$R$^{h'}$, and -5-tetrazolyl;

m is an integer from 1 to 2;

n is an integer from 1 to 10;

and enantiomers, diastereomers and pharmaceutically acceptable salts thereof;

and further wherein the compound of formula VIa and/or VIb has a binding affinity to VLA-4 as expressed by an IC$_{50}$ of about 15 μM or less.

Preferably, in the above method, R$^1$ and R$^2$, together with the carbon atom and W to which they are bound respectively, are joined to form a heteroaryl or substituted heteroaryl group having two nitrogen atoms in the heteroaryl ring. Optionally, the heteroaryl ring may contain other heteroatoms such as oxygen or sulfur. More preferably, R$^1$ and R$^2$, together with the carbon atom and W to which they are bound respectively, are joined to form a pyridazine, pyrimidine, pyrazine, 1-oxo-1,2,5-thiadiazole or 1,1-dioxo-1,2,5-thiadiazole, ring; more preferably, a pyrimidine, pyrazine, 1-oxo-1,2,5-thiadiazole or 1,1-dioxo-1,2,5-thiadiazole ring; wherein the pyridazine, pyrimidine, pyrazine, 1-oxo-1,2,5-thiadiazole or 1,1-dioxo-1,2,5-thiadiazole ring, is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

Preferably, in the above method, X" is —C(O)OR$^{d'}$.

Preferably, R$^{24}$ is —CH$_2$—Ar$^2$—Ar$^1$ and R$^{25}$ is hydrogen.

In a preferred embodiment, the above method employs a compound of formula VIIa, VIIc, VIId, VIIe or VIIf:

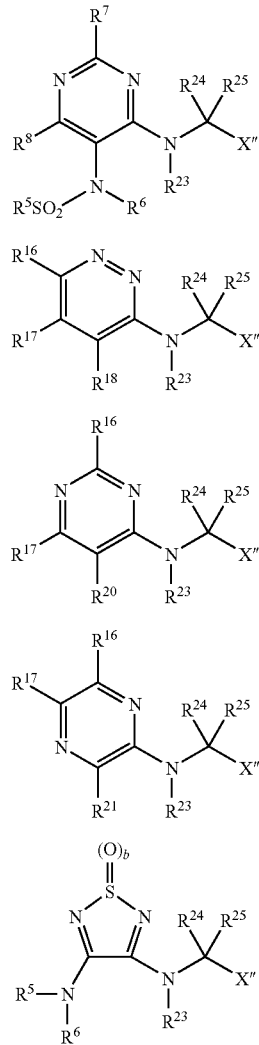

wherein $R^{23}$, $R^{24}$, $R^{25}$ and X″ are as defined herein;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —SO$_2$R$^{10}$ where R$^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl; and $R^7$ and $R^8$ are independently selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and halogen;

$R^{16}$ and $R^{17}$ are independently selected from the group consisting of hydrogen, alkyl, substituted alkyl, alkoxy, substituted alkoxy, amino, substituted amino, cycloalkyl, substituted cycloalkyl, aryl, substituted aryl; heteroaryl, substituted heteroaryl, heterocyclic, substituted heterocyclic and halogen; and $R^{18}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

$R^{20}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

$R^{21}$ is selected from the group consisting of alkyl, substituted alkyl, alkoxy, substituted alkoxy, amino, substituted amino, cycloalkyl, substituted cycloalkyl, aryl, substituted aryl, heterocyclic and substituted heterocyclic;

b is 1 or 2;

and enantiomers, diastereomers and pharmaceutically acceptable salts thereof.

Preferably, the compound employed in the above method is selected from formula VIId, VIIe or VIIf.

The compounds and pharmaceutical compositions of this invention are useful for treating disease conditions mediated by VLA-4 or leucocyte adhesion. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis; rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Other disease conditions include, but are not limited to, inflammatory conditions such as erythema nodosum, allergic conjunctivitis, optic neuritis, uveitis, allergic rhinitis, Ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

In a preferred, embodiment, the disease condition mediated by VLA-4 is an inflammatory disease.

The present invention is also directed to novel compounds useful for treating a disease condition mediated by VLA-4 or leucocyte adhesion. Accordingly, in one of its composition aspects, this invention is directed to a compound of formula Ia and/or Ib:

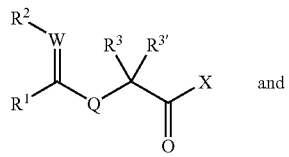

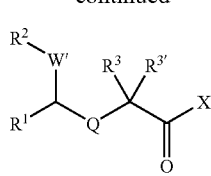

wherein, in formula Ia, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in formula Ib, $R^1$ and $R^2$, together with the carbon atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case of the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of formula Ia or Ib is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where each R is independently hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O), —NR-alkyl, —NRS(O)$_2$—NR-substituted alkyl, —NRS(O)$_2$—NR-aryl, —NRS(O), —NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, —N[S(O)$_2$—R']$_2$ and —N[S(O)$_2$—NR'], where each R' is independently selected from the group consisting of alkyl, substituted alkyl, aryl, substituted aryl, heteroaryl, substituted heteroaryl, heterocyclic and substituted heterocyclic;

$R^3$ is —(CH$_2$)$_x$—Ar—R$^9$, where Ar is aryl, substituted aryl, heteroaryl and substituted heteroaryl; R$^9$ is selected from the group consisting of acyl, acylamino, acyloxy, aminoacyl, aminocarbonylamino, aminothiocarbonylamino, aminocarbonyloxy, oxycarbonylamino, oxythiocarbonylamino, thioamidino, thiocarbonylamino, aminosulfonylamino, aminosulfonyloxy, aminosulfonyl, oxysulfonylamino and oxysulfonyl; x is an integer from 0 to 4;

$R^{3'}$ is selected from the group consisting of hydrogen, isopropyl, —CH$_2$Z where Z is selected from the group consisting of hydrogen, hydroxyl, acylamino, alkyl, alkoxy, aryloxy, aryl, aryloxyaryl, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted alkyl, substituted alkoxy, substituted aryl, substituted aryloxy, substituted aryloxyaryl, substituted cycloalkyl, heteroaryl, substituted heteroaryl, heterocyclic and substituted heterocyclic;

Q is selected from the group consisting of —O—, —S—, —S(O)—, —S(O)$_2$, and —NR$^4$—;

$R^4$ is selected from the group consisting of hydrogen, alkyl, substituted alkyl, alkenyl, substituted alkenyl, cycloalkyl, substituted cycloalkyl, cycloalkenyl, substituted cycloalkenyl, aryl, substituted aryl, heteroaryl, substituted heteroaryl, heterocyclic and substituted heterocyclic or, optionally, $R^4$ and $R^1$ or $R^4$ and $R^2$, together with the atoms to which they are bound, are joined to form a heteroaryl, a substituted heteroaryl, a heterocyclic or a substituted heterocyclic group;

W is selected from the group consisting of nitrogen and carbon; and

W' is selected from the group consisting of nitrogen, carbon, oxygen, sulfur, S(O), and S(O)$_2$;

X is selected from the group consisting of hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and —NR"R" where each R" is independently selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic and substituted heterocyclic;

and enantiomers, diastereomers and pharmaceutically acceptable salts thereof;

and further wherein the compound of formula Ia and/or Ib has a binding affinity to VLA-4 as expressed by an IC$_{50}$ of about 15 µM or less.

More preferably, $R^3$ is a group of the formula:

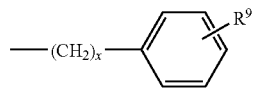

wherein $R^9$ and x are as defined herein. Preferably, $R^9$ is in the para position of the phenyl ring; and x is an integer of from 1 to 4, more preferably, x is 1.

Preferably, $R^{3'}$ is hydrogen.

In a preferred embodiment, $R^9$ is selected from the group consisting of —O—Z—NR$^{11}$R$^{11'}$ and —O—Z—R$^{12}$ wherein $R^{11}$ and $R^{11'}$ are independently selected from the group consisting of hydrogen, alkyl, substituted alkyl, cycloalkyl, substituted cycloalkyl, cycloalkenyl, substituted cycloalkenyl, heterocyclic, substituted heterocyclic, and where $R^{11}$ and $R^{11'}$ are joined to form a heterocycle or a substituted heterocycle, $R^{12}$ is selected from the group consisting of heterocycle and substituted heterocycle, and Z is selected from the group consisting of —C(O)— and —SO$_2$—. More preferably, R$^9$ is –OC(O)NR$^{11}$R$^{11'}$, wherein R$^{11}$ and R$^{11'}$ are as defined herein.

Preferably, in the above compounds, Z is —C(O)— and Q is preferably —NR$^4$—.

In a preferred embodiment, this invention is directed to compounds of formula IIa or IIb:

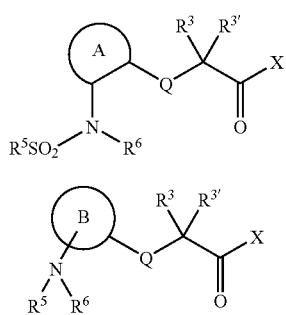

wherein X is as defined herein;

R$^3$ is —(CH$_2$)$_x$—Ar—R$^9$, where Ar is aryl, substituted aryl, heteroaryl and substituted heteroaryl; R$^9$ is selected from the group consisting of acyl, acylamino, acyloxy, aminoacyl, aminocarbonylamino, aminothiocarbonylamino, aminocarbonyloxy, oxycarbonylamino, oxythiocarbonylamino, thioamidino, thiocarbonylamino, aminosulfonylamino, aminosulfonyloxy, aminosulfonyl, oxysulfonylamino and oxysulfonyl; x is an integer from 0 to 4;

R$^{3'}$ is selected from the group consisting of hydrogen, isopropyl, —CH$_2$Z where Z is selected from the group consisting of hydrogen, hydroxyl, acylamino, alkyl, alkoxy, aryloxy, aryl, aryloxyaryl, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted alkyl, substituted alkoxy, substituted aryl, substituted aryloxy, substituted aryloxyaryl, substituted cycloalkyl, heteroaryl, substituted heteroaryl, heterocyclic and substituted heterocyclic;

ring A and ring B independently form a heteroaryl or substituted heteroaryl group having two nitrogen atoms in the heteroaryl ring;

R$^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

R$^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —SO$_2$R$^{10}$ where R$^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

or optionally, one of, R$^4$ and ring A, R$^4$ and R$^5$, R$^4$ and R$^6$, or R$^5$ and R$^6$, together with the atoms to which they are bound, can be joined to form a heterocyclic or substituted heterocyclic ring;

and enantiomers, diastereomers and pharmaceutically acceptable salts thereof; and provided that ring B does not form a 6-amino or substituted amino pyrimidin-4-yl group.

R$^{3'}$ is preferably hydrogen. Preferably, x is an integer from 1 to 4; more preferably, x is 1.

Preferably, ring A forms a pyridazine, pyrimidine or pyrazine ring; more preferably, a pyrimidine or pyrazine ring; wherein the pyridazine, pyrimidine or pyrazine ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

Preferably, ring B forms a pyridazine, pyrimidine, pyrazine, 1-oxo-1,2,5-thiadiazole or a 1,1-dioxo-1,2,5-thiadiazole ring; more preferably, a pyrimidine, pyrazine, 1-oxo-1,2, 5-thiadiazole or a 1,1-dioxo-1,2,5-thiadiazole ring; wherein the pyridazine, pyrimidine or pyrazine ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

In another preferred embodiment, this invention is directed to compounds of formula IIIa, IIIc, IIId, IIIe or IIIf:

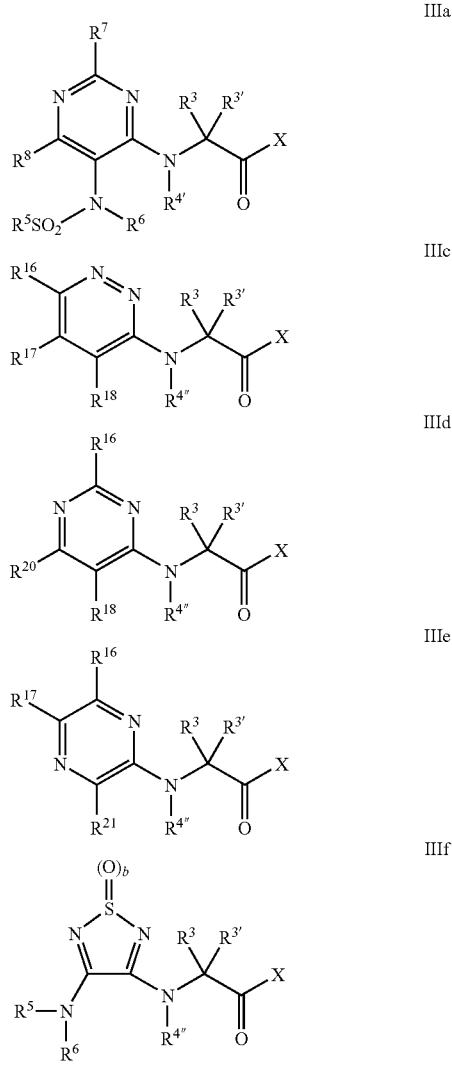

wherein X is as defined herein;

$R^3$ is —$(CH_2)_x$—Ar—$R^9$, where Ar is aryl, substituted aryl, heteroaryl and substituted heteroaryl; $R^9$ is selected from the group consisting of acyl, acylamino, acyloxy, aminoacyl, aminocarbonylamino, aminothiocarbonylamino, aminocarbonyloxy, oxycarbonylamino, oxythiocarbonylamino, thioamidino, thiocarbonylamino, aminosulfonylamino, aminosulfonyloxy, aminosulfonyl, oxysulfonylamino and oxysulfonyl; x is an integer from 0 to 4;

$R^{3'}$ is selected from the group consisting of hydrogen, isopropyl, —$CH_2Z$ where Z is selected from the group consisting of hydrogen, hydroxyl, acylamino, alkyl, alkoxy, aryloxy, aryl, aryloxyaryl, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted alkyl, substituted alkoxy, substituted aryl, substituted aryloxy, substituted aryloxyaryl, substituted cycloalkyl, heteroaryl, substituted heteroaryl, heterocyclic and substituted heterocyclic;

$R^{4'}$ is selected from the group consisting of hydrogen and, alkyl or, optionally; one of, $R^{4'}$ and $R^5$, and $R^6$, $R^5$ and $R^6$, $R^5$ and $R^8$, or $R^6$ and $R^8$, together with the atoms to which they are bound, are joined to form a heterocyclic, a substituted heterocyclic, a heteroaryl or substituted heteroaryl group optionally containing from 1 to 3 additional hetero ring atoms selected from the group consisting of oxygen, nitrogen and sulfur;

$R^{4''}$ is selected from the group consisting of hydrogen and alkyl;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl;

$R^7$ and $R^8$ are independently selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and halogen;

$R^{16}$ and $R^{17}$ are independently selected from the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen; and $R^{18}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

$R^{20}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

$R^{21}$ is selected from the group consisting of alkyl, substituted alkyl, alkoxy, substituted alkoxy, amino, substituted amino, cycloalkyl, substituted cycloalkyl, aryl, substituted aryl; heterocyclic and substituted heterocyclic;

b is 1 or 2;

and enantiomers, diastereomers and pharmaceutically acceptable salts thereof.

In the above compounds, $R^{3'}$ is preferably hydrogen. Preferably, x is an integer from 1 to 4; more preferably, x is 1.

Preferably, the compound is selected from formula IIId, IIIe or IIIf.

In another of its composition aspects, this invention is directed to a compound of formula IVa:

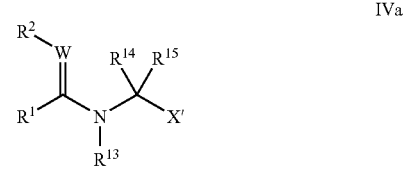

IVa wherein $R^1$ and $R^2$, together with the carbon atom and W to which they are bound respectively, are joined to form a heteroaryl group having two nitrogen atoms in the heteroaryl ring;

and further wherein said heteroaryl group is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS($O)_2$-alkyl, —OS($O)_2$-substituted alkyl, —OS($O)_2$-aryl, —OS($O)_2$-substituted aryl, —OS($O)_2$-heteroaryl, —OS($O)_2$- ubstituted heteroaryl, —OS($O)_2$-heterocyclic, —OS($O)_2$-substituted heterocyclic, —$OSO_2$—NRR where each R is independently hydrogen or alkyl, —NRS($O)_2$-alkyl, —NRS($O)_2$-substituted alkyl, —NRS($O)_2$-aryl, —NRS($O)_2$-substituted aryl, —NRS($O)_2$-heteroaryl, —NRS($O)_2$-substituted heteroaryl, —NRS($O)_2$-heterocyclic, —NRS($O)_2$-substituted heterocyclic, —NRS($O)_2$—NR-alkyl, —NRS(O), —NR-substituted alkyl, —NRS($O)_2$—NR-aryl, —NRS($O)_2$—NR-substituted aryl, —NRS($O)_2$—NR-heteroaryl, —NRS($O)_2$—NR-substituted heteroaryl, —NRS($O)_2$—NR-heterocyclic, —NRS($O)_2$—NR-substituted heterocyclic where R is hydrogen or alkyl, —N[S($O)_2$—R']$_2$ and —N[S($O)_2$—NR']$_2$ where each R' is independently selected from the group consisting of alkyl, substituted alkyl, aryl, substituted aryl, heteroaryl, substituted heteroaryl, heterocyclic and substituted heterocyclic;

$R^{13}$ is selected from the group consisting of hydrogen, $C_{1-10}$ alkyl, Cy, and Cy-$C_{1-10}$ alkyl, wherein alkyl is optionally substituted with one to four substituents independently selected from $R^a$; and Cy is optionally substituted with one to four substituents independently selected from $R^b$;

$R^{14}$ is selected from the group consisting of hydrogen, $C_{1-10}$ alkyl, $C_{2-10}$ alkenyl, $C_{2-10}$ alkynyl, Cy, Cy-$C_{1-10}$ alkyl, Cy-$C_{2-10}$ alkenyl and Cy-$C_{2-10}$ alkynyl, wherein alkyl, alkenyl, and alkynyl are optionally substituted with one to four substituents selected from phenyl and $R^x$, and Cy is optionally substituted with one to four substituents independently selected from $R^y$;

or $R^{13}$, $R^{14}$ and the atoms to which they are attached together form a mono- or bicyclic ring containing 0-2 additional heteroatoms selected from N, O and S;

$R^{15}$ is selected from the group consisting of $C_{1-10}$ alkyl, $C_{2-10}$ alkenyl, $C_{2-10}$ alkynyl, aryl, aryl-$C_{1-10}$ alkyl, heteroaryl, heteroaryl-$C_{1-10}$ alkyl, wherein alkyl, alkenyl and alkynyl are optionally substituted with one to four substituents selected from $R^x$, and aryl and heteroaryl are optionally substituted with one to four substituents independently selected from $R^y$;

or $R^{14}$, $R^{15}$ and the carbon to which they are attached form a 3-7 membered mono- or bicyclic ring containing 0-2 heteroatoms selected from N, O and S;

$R^a$ is selected from the group consisting of Cy and a group selected from $R^x$, wherein Cy is optionally substituted with one to four substituents independently selected from $R^c$;

$R^b$ is selected from the group consisting of $R^a$, $C_{1-10}$ alkyl, $C_{2-10}$ alkenyl, $C_{2-10}$ alkynyl, aryl $C_{1-10}$ alkyl, heteroaryl $C_{1-10}$ alkyl, wherein alkyl, alkenyl, alkynyl, aryl, heteroaryl are optionally substituted with a group independently selected from $R^c$;

$R^c$ is selected from the group consisting of halogen, $NO_2$, $C(O)OR^f$, $C_{1-4}$ alkyl, $C_{1-4}$ alkoxy, aryl, aryl $C_{1-4}$ alkyl, aryloxy, heteroaryl, $NR^fR^g$, $R^fC(O)R^g$, $NR^fC(O)NR^fR^g$, and CN;

$R^d$ and $R^e$ are independently selected from hydrogen, $C_{1-10}$ alkyl, $C_{2-10}$ alkenyl, $C_{2-10}$ alkynyl, Cy and Cy $C_{1-10}$alkyl, wherein alkyl, alkenyl, alkynyl and Cy are optionally substituted with one to four substituents independently, selected from $R^c$;

or $R^d$ and $R^e$ together with the atoms to which they are attached form a heterocyclic ring of 5 to 7 members containing 0-2 additional heteroatoms independently selected from oxygen, sulfur and nitrogen;

$R^f$ and $R^g$ are independently selected from hydrogen, $C_{1-10}$ alkyl, Cy and Cy-$C_{1-10}$ alkyl wherein Cy is optionally substituted with $C_{1-10}$ alkyl; or $R^f$ and $R^g$ together with the carbon to which they are attached form a ring of 5 to 7 members containing 0-2 heteroatoms independently selected from oxygen, sulfur and nitrogen;

$R^h$ is selected from the group consisting of hydrogen, $C_{1-10}$ alkyl, $C_{2-10}$ alkenyl, $C_{2-10}$ alkynyl, cyano, aryl, aryl $C_{1-10}$ alkyl, heteroaryl, heteroaryl $C_{1-10}$ alkyl, and —$SO_2R^i$; wherein alkyl, alkenyl, and alkynyl are optionally substituted with one to four substitutents independently selected from $R^a$; and aryl and heteroaryl are each optionally substituted with one to four substituents independently selected from $R^b$;

$R^i$ is selected from the group consisting of $C_{1-10}$ alkyl, $C_{2-10}$ alkenyl, $C_{2-10}$ alkynyl, and aryl; wherein alkyl, alkenyl, alkynyl and aryl are each optionally substituted with one to four substituents independently selected from $R^c$;

$R^x$ is selected from the group consisting of —$OR^d$, —$NO_2$, halogen, —$S(O)_mR^d$, —$SR^d$, —$S(O)_2OR^d$, —$S(O)_mNR^dR^e$, —$NR^dR^e$, —$O(CR^fR^g)_nNR^dR^e$, —$C(O)R^d$, —$CO_2R^d$, —$CO_2(CR^fR^g)_nCONR^dR^e$, —$OC(O)R^d$, —$CN$, —$C(O)NR^dR^e$, —$NR^dC(O)R^e$, —$OC(O)NR^dR^e$, —$NR^dC(O)OR^e$, —$NR^dC(O)NR^dR^e$, —$CR^d(N—OR^e)$, $CF_3$, oxo, $NR^dC(O)NR^dSO_2R^i$, $NR^dS(O)_mR^e$, —$OS(O)_2OR^d$, and —$OP(O)(OR^d)_2$;

$R^y$ is selected from the group consisting of $R^x$, $C_{1-10}$ alkyl, $C_{2-10}$ alkenyl, $C_{2-10}$ alkynyl, aryl $C_{1-10}$alkyl, heteroaryl $C_{1-10}$ alkyl, cycloalkyl, heterocyclyl; wherein alkyl, alkenyl, alkynyl and aryl are each optionally substituted with one to four substitutents independently selected from $R^x$;

Cy is cycloalkyl, heterocyclyl, aryl, or heteroaryl;

m is an integer from 1 to 2;

n is an integer from 1 to 10;

W is selected from the group consisting of carbon and nitrogen;

W' is selected from the group consisting of carbon, nitrogen, oxygen, sulfur, S(O) and S(O)$_2$;

X' is selected from the group consisting of —$C(O)OR^d$, —$P(O)(OR^d)(OR^e)$, —$P(O)(R^d)(OR^e)$, —$S(O)_mOR^d$, —$C(O)NR^dR^h$, and -5-tetrazolyl;

and enantiomers, diastereomers and pharmaceutically acceptable salts thereof;

and further wherein the compound of formula IV has a binding affinity to VLA-4 as expressed by an $IC_{50}$ of about 15 μM or less;

and provided that when $R^1$ and $R^2$, together with the carbon atom and W to which they are bound respectively, are joined to form a 2-arylpyrimidin-4-yl group and $R^{14}$ is hydrogen, then $R^{15}$ is not alkyl of from 1 to 6 carbon atoms optionally substituted with hydroxyl; and when $R^1$ and $R^2$, together with the carbon atom and W to which they are bound respectively, are joined to form a 5-arylpyrazin-2-yl group and $R^{14}$ is hydrogen, then $R^{15}$ is not 4-hydroxybenzyl.

In the above compounds, $R^1$ and $R^2$ are preferably joined to form art pyridazine, pyrimidine, pyrazine, 1-oxo-1,2,5-thiadiazole or 1,1-dioxo-1,2,5-thiadiazole ring; more preferably, a pyrimidine, pyrazine, 1-oxo-1,2,5-thiadiazole or 1,1-dioxo-1,2,5-thiadiazole ring; wherein the pyridazine, pyrimidine, pyrazine, 1-oxo-1,2,5-thiadiazole or 1,1-dioxo-1,2,5-thiadiazole ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

Preferably, in the above compounds, X' is —$C(O)OR^d$.

In a preferred embodiment, this invention is directed to compounds of formula Va, Vc, Vd, Ve or Vf:

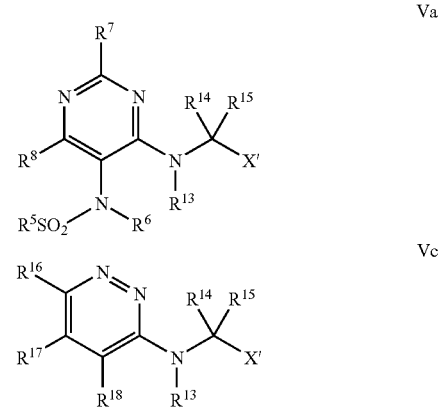

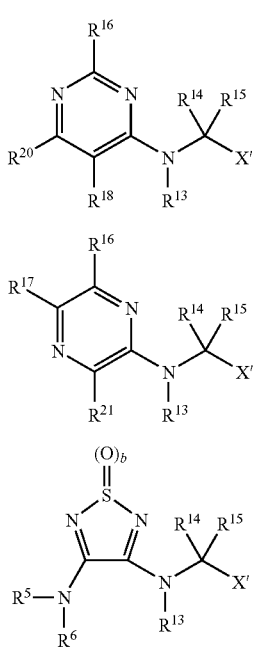

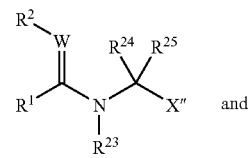

wherein $R^{13}$, $R^{14}$, $R^{15}$ and X' are as defined herein;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and —$SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl; and $R^7$ and $R^8$ are independently selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and halogen;

$R^{16}$ and $R^{17}$ are independently selected from the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen; and $R^{18}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

$R^{20}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

$R^{21}$ is selected from the group consisting of alkyl, substituted alkyl, alkoxy, substituted alkoxy, amino, substituted amino, cycloalkyl, substituted cycloalkyl, aryl, substituted aryl, heterocyclic and substituted heterocyclic;

b is 1 or 2;

and enantiomers, diastereomers and pharmaceutically acceptable salts thereof.

More preferably, the compound is selected from formula Vd, Ve or Vf.

In yet another of its composition aspects, this invention is directed to a compound of formula VIa and/or VIb:

wherein, in formula VIa, $R^1$ and $R^2$, together with the carbon atom and W to which they are bound respectively, are joined to form an aryl, cycloalkenyl, heteroaryl or heterocyclic group having at least five atoms in the aryl, cycloalkenyl, heteroaryl or heterocyclic group and optionally containing or additionally containing in the case of heteroaryl and heterocyclic groups 1 to 3 heteroatoms selected from the group consisting of oxygen, nitrogen and sulfur, and wherein the heteroaryl or heterocyclic group is mono-cyclic;

in formula VIb, $R^1$ and $R^2$, together with the carbon, atom and W' to which they are bound respectively, are joined to form a cycloalkyl, cycloalkenyl or heterocyclic group having at least five atoms in the cycloalkyl, cycloalkenyl or heterocyclic group and optionally containing or additionally containing in the case of the heterocyclic group 1 to 3 heteroatoms selected from the group consisting of oxygen, nitrogen and sulfur, and wherein the heterocyclic group is mono-cyclic;

and further wherein said aryl, cycloalkyl, cycloalkenyl, heteroaryl or heterocyclic group of formula VIa or VIb is optionally substituted, on any ring atom capable of substitution, with 1-3 substituents selected from the group consisting of alkyl, substituted alkyl, alkoxy, substituted alkoxy, acyl, acylamino, thiocarbonylamino, acyloxy, amino, substituted amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, carboxyl, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —OSO₂—NRR where each R is independently hydrogen or alkyl, —NRS(O)₂-alkyl, —NRS(O)₂-substituted alkyl, —NRS(O)₂-aryl, —NRS(O)₂-substituted aryl, —NRS(O)₂-heteroaryl, —NRS(O)₂-substituted heteroaryl, —NRS(O)₂-heterocyclic, —NRS(O)₂-substituted heterocyclic, —NRS(O)₂—NR-alkyl, —NRS(O)₂—NR-substituted alkyl, —NRS(O)₂—NR-aryl, —NRS(O)₂NR-substituted aryl, —NRS(O)₂—NR-heteroaryl, —NRS(O)₂—NR-substituted heteroaryl, —NRS(O)₂—NR-heterocyclic, —NRS(O)₂—NR-substituted heterocyclic where R is hydrogen or alkyl, —N[S(O)₂—R']₂ and —N[S(O)₂—NR']₂ where each R' is independently selected from the group consisting of alkyl, substituted alkyl, aryl, substituted aryl, heteroaryl, substituted heteroaryl, heterocyclic and substituted heterocyclic;

$R^{23}$ is selected from the group consisting of hydrogen, $C_{1-10}$ alkyl optionally substituted with one to four substituents independently selected from $R^{a'}$ and Cy optionally substituted with one to four substituents independently selected from $R^{b'}$;

$R^{24}$ is selected from the group consisting of $Ar^1$—$Ar^2$—$C_{1-10}$ alkyl, $Ar^1$—$Ar^2$—$C_{2-10}$ alkenyl, $Ar^1$—$Ar^2$—$C_{2-10}$ alkynyl, wherein $Ar^1$ and $Ar^2$ are independently aryl or heteroaryl each of which is optionally substituted with one to four substituents independently selected from $R^{b'}$; alkyl, alkenyl and alkynyl are optionally substituted with one to four substituents independently selected from $R^{a'}$;

$R^{25}$ is selected from the group consisting of hydrogen, $C_{1-10}$ alkyl, $C_{2-10}$ alkenyl, $C_{2-10}$ alkynyl, aryl, aryl $C_{1-10}$alkyl, heteroaryl, and heteroaryl $C_{1-10}$ alkyl, wherein alkyl, alkenyl and alkynyl are optionally substituted with one to four substituents selected from $R^{a'}$, and aryl and heteroaryl are optionally substituted with one to four substituents independently selected from $R^{b'}$;

$R^{a'}$ is selected from the group consisting of Cy, —$OR^{d'}$, —$NO_2$, halogen —$S(O)_mR^{d'}$, —$SR^{d'}$, —$S(O)_2OR^{d'}$, —$S(O)_mNR^{d'}R^{e'}$, —$O(CR^{f'}R^{g'})_nNR^{d'}R^{e'}$, —$C(O)R^{d'}$, —$CO_2R^{d'}$, —$CO_2(CR^{f'}R^{g'})_nCONR^{d'}R^{e'}$, —$OC(O)R^{d'}$, —CN, —$C(O)NR^{d'}R^{e'}$, —$NR^{d'}C(O)R^{e'}$, —$OC(O)NR^{d'}R^{e'}$, —$NR^{d'}C(O)OR^{e'}$, —$Nr^{d'}C(O)NR^{d'}R^{e'}$, —$CR^{d'}(N-OR^{e'})$, $CF_3$, and —$OCF_3$;

wherein Cy is optionally substituted with one to four substituents independently selected from $R^{c'}$;

$R^{b'}$ is selected from the group consisting of $R^{a'}$, $C_{1-10}$ alkyl, $C_{2-10}$ alkenyl, $C_{2-10}$ alkynyl, aryl $C_{1-10}$ alkyl, heteroaryl $C_{1-10}$ alkyl, wherein alkyl, alkenyl, aryl, heteroaryl are optionally substituted with a group independently selected from $R^{c'}$;

$R^{c'}$ is selected from the group consisting of halogen, amino, carboxy, $C_{1-4}$ alkyl, $C_{1-4}$ alkoxy, aryl, aryl $C_{1-4}$alkyl, hydroxy, $CF_3$, and aryloxy;

$R^{d'}$ and $R^{e'}$ are independently selected from hydrogen, $C_{1-10}$ alkyl, $C_{2-10}$ alkenyl, $C_{2-10}$ alkynyl, Cy and Cy $C_{1-10}$alkyl, wherein alkyl, alkenyl, alkynyl and Cy are optionally substituted with one to four substituents independently selected from $R^{c'}$; or $R^{d'}$ and $R^{e'}$ together with the atoms to which they are attached form a heterocyclic ring of 5 to 7 members containing 0-2 additional heteroatoms independently selected from oxygen, sulfur and nitrogen;

$R^{f'}$ and $R^{g'}$ are independently selected from hydrogen, $C_{1-10}$ alkyl, Cy and Cy-$C_{1-10}$ alkyl; or $R^{f'}$ and $R^{g'}$ together with the carbon to which they are attached form a ring of 5 to 7 members containing 0-2 heteroatoms independently selected from oxygen, sulfur and nitrogen;

$R^{h'}$ is selected from the group consisting of hydrogen, $C_{1-10}$ alkyl, $C_{2-10}$ alkenyl, $C_{2-40}$ alkynyl, cyano, aryl, aryl $C_{1-10}$ alkyl, heteroaryl, heteroaryl $C_{1-10}$ alkyl, or —$SO_2R^{i'}$;

wherein alkyl, alkenyl, and alkynyl are optionally substituted with one to four substituents independently selected from $R^{a'}$; and aryl and heteroaryl are each optionally substituted with one to four substituents independently selected from $R^{b'}$;

$R^{i'}$ is selected from the group consisting of $C_{1-10}$ alkyl, $C_{2-10}$ alkenyl, alkynyl, and aryl;

wherein alkyl, alkenyl, alkynyl and aryl are each optionally substituted with one to four substituents independently selected from $R^{c'}$;

Cy is cycloalkyl, heterocyclyl, aryl, or heteroaryl;

X" is selected from the group consisting of —$C(O)OR^{d'}$, —$P(O)(OR^{d'})(OR^{e'})$, —$P(O)(R^{d'})(OR^{e'})$, —$S(O)_mOR^{d'}$, —$C(O)NR^{d'}R^{h'}$, and -5-tetrazolyl;

m is an integer from 1 to 2;

n is an integer from 1 to 10;

and enantiomers, diastereomers and pharmaceutically acceptable salts thereof;

and further wherein the compounds of formula VIa and/or VIb have a binding affinity to VLA-4 as expressed by an $IC_{50}$ of about 15 μM or less.

In the above compounds, $R^1$ and $R^2$ are preferably joined to form a heteroaryl or substituted heteroaryl group having two nitrogen atoms in the heteroaryl ring. More preferably, $R^1$ and $R^2$ are joined to form a pyridazine, pyrimidine, pyrazine, 1-oxo-1,2,5-thiadiazole or 1,1-dioxo-1,2,5-thiadiazole ring; more preferably, a pyrimidine, pyrazine, 1-oxo-1,2,5-thiadiazole or 1,1-dioxo-1,2,5-thiadiazole ring; wherein the pyridazine, pyrimidine, pyrazine, 1-oxo-1,2,5-thiadiazole or 1,1-dioxo-1,2,5-thiadiazole ring is optionally substituted with 1 to 3 substituents selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen.

Preferably, X" is —$C(O)OR^{d'}$.

In the above compounds, $R^{24}$ is preferably —$CH_2$—$Ar^2$—$Ar^1$ and $R^{25}$ is preferably hydrogen.

In a preferred embodiment, this invention is directed to compounds of formula VIIa, VIIc, VIId, VIIe or VIIf:

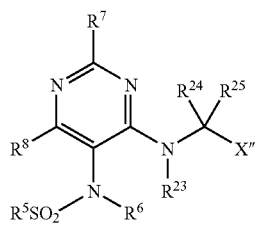

VIIa

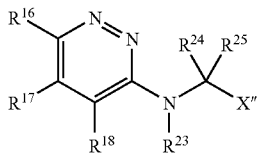

VIIc

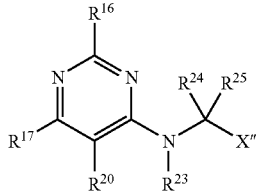

VIId

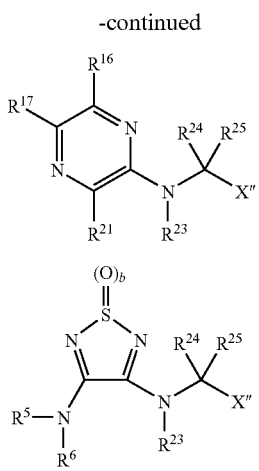

wherein $R^{24}$, $R^{25}$ and $X''$ are as defined herein;

$R^5$ is selected from the group consisting of alkyl, substituted alkyl, alkenyl, substituted alkenyl, aryl, substituted aryl, cycloalkyl, substituted cycloalkyl, cycloalkenyl, substituted cycloalkenyl, heterocyclic, substituted heterocylic, heteroaryl and substituted heteroaryl;

$R^6$ is selected from the group consisting of hydrogen, alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl, and $-SO_2R^{10}$ where $R^{10}$ is selected from the group consisting of alkyl, substituted alkyl, cycloalkyl, substituted cycloalkyl, cycloalkenyl, substituted cycloalkenyl, heterocyclic, substituted heterocyclic, aryl, substituted aryl, heteroaryl, substituted heteroaryl; and $R^7$ and $R^8$ are independently selected from the group consisting of hydrogen, alkyl, substituted alkyl, cycloalkyl, substituted cycloalkyl, aryl, substituted aryl, heteroaryl, substituted heteroaryl, heterocyclic, substituted heterocyclic and halogen;

$R^{16}$ and $R^{17}$ are independently selected from the group consisting of hydrogen, alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic, substituted heterocyclic and halogen; and $R^{18}$ is selected from the group consisting of alkyl, substituted alkyl, alkoxy, substituted alkoxy, amino, substituted amino, cycloalkyl, substituted cycloalkyl, aryl, substituted aryl, heteroaryl, substituted heteroaryl, heterocyclic and substituted heterocyclic;

$R^{20}$ is selected from the group consisting of hydrogen, alkyl, substituted alkyl, alkoxy, substituted alkoxy, cycloalkyl, substituted cycloalkyl, aryl, substituted aryl, heteroaryl, substituted heteroaryl, heterocyclic, substituted heterocyclic and halogen;

$R^{21}$ is selected from the group consisting of alkyl, substituted alkyl; alkoxy, substituted alkoxy, amino, substituted amino, cycloalkyl, substituted cycloalkyl, aryl, substituted aryl, heterocyclic and substituted heterocyclic;

b is 1 or 2;

and enantiomers, diastereomers and pharmaceutically acceptable salts thereof.

Preferably, the compound is selected from formula VIId, VIIe or VIIf.

This invention also provides pharmaceutical compositions comprising a pharmaceutically acceptable carrier and a therapeutically effective amount of the compounds defined herein.

In the above compounds, when X is other than —OH or pharmaceutical salts thereof, X is preferably a substituent which will convert (e.g., hydrolyze, metabolize, etc.) in vivo to a compound where X is —OH or a salt thereof. Accordingly, suitable X groups are any art recognized pharmaceutically acceptable groups which will hydrolyze or otherwise convert in vivo to a hydroxyl group or a salt thereof including, by way of example, esters (X is alkoxy, substituted alkoxy, cycloalkoxy, substituted cycloalkoxy, alkenoxy, substituted alkenoxy, cycloalkenoxy, substituted cycloalkenoxy, aryloxy, substituted aryloxy, heteroaryloxy, substituted heteroaryloxy, heterocyclooxy, substituted heterocyclooxy, and the like).

Unless otherwise defined, $R^3$ and $R^{15}$ in the above compounds are preferably selected from all possible isomers arising by substitution with the following groups:
4-methylbenzyl,
4-hydroxybenzyl,
4-methoxybenzyl,
4-t-butoxybenzyl,
4-benzyloxybenzyl,
4-[φ-CH(CH$_3$)O-]benzyl,
4-[φ-CH(COOH)O-]benzyl,
4-[BocNHCH$_2$C(O)NH-]benzyl,
4-chlorobenzyl,
4-[NH$_2$CH$_2$C(O)NH-]benzyl,
4-carboxybenzyl,
4-[CbzNHCH$_2$CH$_2$NH-]benzyl,
3-hydroxy-4-(φ-OC(O)NH—)benzyl,
4-[HOOCCH$_2$CH$_2$C(O)NH-]benzyl,
benzyl,
4-[2'-carboxylphenoxy-]benzyl,
4-[φ—C(O)NH-]benzyl,
3-carboxybenzyl,
4-iodobenzyl,
4-hydroxy-3,5-diiodobenzyl,
4-hydroxy-3-iodobenzyl,
4-[2'-carboxyphenyl-]benzyl,
φ-CH$_2$CH$_2$—,
4-nitrobenzyl,
2-carboxybenzyl,
4-[dibenzylamino]-benzyl,
4-[(1'-cyclopropylpiperidin-4'-yl)C(O)NH-]benzyl,
4-[-NHC(O)CH$_2$NHBoc]benzyl,
4-carboxybenzyl,
4-hydroxy-3-nitrobenzyl,
4-[-NHC(O)CH(CH$_3$)NHBoc]benzyl,
4-[-NHC(O)CH(CH$_2$φ)NHBoc]benzyl,
isobutyl,
methyl,
4-[CH$_3$C(O)NH-]benzyl,
—CH$_2$-(3-indolyl),
n-butyl,
t-butyl-OC(O)CH$_2$—,
t-butyl-OC(O)CH$_2$CH$_2$—,
H$_2$NC(O)CH$_2$—,
H$_2$NC(O)CH$_2$CH$_2$—,
BocNH—(CH$_2$)$_4$—,
t-butyl-OC(O)—(CH$_2$)$_2$—,
HOOCCH$_2$—,
HOOC(CH$_2$)$_2$—,
H$_2$N(CH$_2$)$_4$—,
isopropyl,
(1-naphthyl)-CH$_2$—,
(2-naphthyl)-CH$_2$—,
(2-thiophenyl)-CH$_2$—,
(φ-CH$_2$—OC(O)NH—(CH$_2$)$_4$—,
cyclohexyl-CH$_2$—, benzyloxy-CH$_2$—,
HOCH$_2$—,
5-(3-N-benzyl)imidazolyl-CH$_2$—,
2-pyridyl-CH$_2$—,
3-pyridyl-CH$_2$—,
4-pyridyl-CH$_2$—,
5-(3-N-methyl)imidazolyl-CH$_2$—,
N-benzylpiperid-4-yl-CH$_2$—,
N-Boc-piperidin-4-yl-CH$_2$—,
N-(phenyl-carbonyl)piperidin-4-yl-CH$_2$—,
H$_3$CSCH$_2$CH$_2$—,
1-N-benzylimidazol-4-yl-CH$_2$—,
iso-propyl-C(O)NH—(CH$_2$)$_4$—,
iso-butyl-C(O)NH—(CH$_2$)$_4$—,
phenyl-C(O)NH—(CH$_2$)$_4$—,
benzyl-C(O)NH—(CH$_2$)$_4$—,
allyl-C(O)NH—(CH$_2$)$_4$—,
4-(3-N-methylimidazolyl)-CH$_2$—,
4-imidazolyl,
4-[(CH$_3$)$_2$NCH$_2$CH$_2$CH$_2$—O-]benzyl,
4-[(benzyl)$_2$N—]-benzyl,
4-aminobenzyl,
allyloxy-C(O)NH(CH$_2$)$_4$—,
allyloxy-C(O)NH(CH$_2$)$_3$—,
allyloxy-C(O)NH(CH$_2$)$_2$—,
NH$_2$C(O)CH$_2$—,
φ-CH=,
2-pyridyl-C(O)NH—(CH$_2$)$_4$—,
4-methylpyrid-3-yl-C(O)NH—(CH$_2$)$_4$—,
3-methylthien-2-yl-C(O)NH—(CH$_2$)$_4$—,
2-pyrrolyl-C(O)NH—(CH$_2$)$_4$—,
2-furanyl-C(O)NH—(CH$_2$)$_4$—,
4-methylphenyl-SO$_2$—N(CH$_3$)CH$_2$C(O)NH(CH$_2$)$_4$—,
4-[cyclopentylacetylenyl]-benzyl,
4-[-NHC(O)—(N-Boc)-pyrrolidin-2-yl)]-benzyl-,
1-N-methylimidazol-4-yl-CH$_2$—,
imidazol-5-yl-CH$_2$—,
6-methylpyrid-3-yl-C(O)NH—(CH$_2$)$_4$—,
4-[2'-carboxymethylphenyl]-benzyl,
4-[-NHC(O)NHCH$_2$CH$_2$CH$_2$-φ]-benzyl,
4-[-NHC(O)NHCH$_2$CH$_2$-φ]-benzyl,
—CH$_2$C(O)NH(CH$_2$)$_4$φ,
4-[φ(CH$_2$)$_4$O—]-benzyl,
4-[—C≡C-φ-4'φ]-benzyl,
4-[—C≡C—CH$_2$—O—S(O)$_2$-4'-CH$_3$-φ]-benzyl,
4-[—C≡C—CH$_2$NHC(O)NH$_2$]-benzyl,    4-[—C≡C—CH$_2$—O-4'-COOCH$_2$CH$_3$-φ]-benzyl,
4-[—C≡C—CH(NH$_2$)-cyclohexyl]-benzyl,
—(CH$_2$)$_4$NHC(O)CH$_2$-3-indolyl,
—(CH$_2$)$_4$NHC(O)CH$_2$CH$_2$-3-indolyl,
—(CH$_2$)$_4$NHC(O)-3-(5-methoxyindolyl),
—(CH$_2$)$_4$NHC(O)-3-(1-methylindolyl),
—(CH$_2$)$_4$NHC(O)-4-(—SO$_2$(CH$_3$)-φ),
—(CH$_2$)$_4$NHC(O)-4-(C(O)CH$_3$)-phenyl,
—(CH$_2$)$_4$NHC(O)-4-fluorophenyl,
—(CH$_2$)$_4$NHC(O)CH$_2$O-4-fluorophenyl,
4-[—C≡C-(2-pyridyl)]benzyl,
4-[—C≡C—CH$_2$—O-phenyl]benzyl,
4-[—C≡C—CH$_2$OCH$_3$]benzyl,
4-[—C≡C-(3-hydroxyphenyl)]benzyl,
4-[—C≡C—CH$_2$—O-4'-(—C(O)OC$_2$H$_5$)phenyl]benzyl,
4-[—C≡C—CH$_2$CH(C(O)OCH$_3$)$_2$]benzyl,
4-[—C≡C—CH$_2$NH-(4,5-dihydro-4-oxo-5-phenyl-oxazol-2-yl),
3-aminobenzyl,
4-[—C≡C—CH$_2$CH(NHC(O)CH$_3$)C(O)OH]-benzyl,
—CH$_2$C(O)NHCH(CH$_3$)φ,
—CH$_2$C(O)NHCH$_2$-(4-dimethylamino)-φ,
—CH$_2$C(O)NHCH$_2$-4-nitrophenyl,
—CH$_2$CH$_2$C(O)N(CH$_3$)CH$_2$-φ,
—CH$_2$CH$_2$C(O)NHCH$_2$CH$_2$—(N-methyl)-2-pyrrolyl,
—CH$_2$CH$_2$C(O)NHCH$_2$CH$_2$CH$_2$CH$_3$,
—CH$_2$CH$_2$C(O)NHCH$_2$CH$_2$-3-indolyl,
—CH$_2$C(O)N(CH$_3$)CH$_2$-phenyl,
—CH$_2$C(O)NH(CH$_2$)$_2$—(N-methyl)-2-pyrrolyl,
—CH$_2$C(O)NHCH$_2$CH$_2$CH$_2$CH$_3$,
—CH$_2$C(O)NHCH$_2$CH$_2$-3-indolyl,
—(CH$_2$)$_2$C(O)NHCH(CH$_3$)φ,
—(CH$_2$)$_2$C(O)NHCH$_2$-4-dimethylaminophenyl,
—(CH$_2$)$_2$C(O)NHCH$_1$-4-nitrophenyl,
—CH$_2$C(O)NH-4-[-NHC(O)CH$_3$-phenyl],
—CH$_2$C(O)NH-4-pyridyl,
—CH$_2$C(O)NH-4-[dimethylaminophenyl],
—CH$_2$C(O)NH-3-methoxyphenyl,
—CH$_2$CH$_2$C(O)NH-4-chlorophenyl,
—CH$_2$CH$_2$C(O)NH-2-pyridyl,
—CH$_2$CH$_2$C(O)NH-4-methoxyphenyl,
—CH$_2$CH$_2$C(O)NH-3-pyridyl,
4-[(CH$_3$)$_2$NCH$_2$CH$_2$O-]benzyl,
—(CH$_2$)$_3$NHC(NH)NH—SO$_2$-4-methylphenyl,
4-[(CH$_3$)$_2$NCH$_2$CH$_2$O-]benzyl,
—(CH$_2$)$_4$NHC(O)NHCH$_2$CH$_3$,
—(CH$_2$)$_4$NHC(O)NH-phenyl,
—(CH$_2$)$_4$NHC(O)NH-4-methoxyphenyl,
4-[4'-pyridyl-C(O)NH-]benzyl,
4-[3'-pyridyl-C(O)NH-]benzyl,
4-[-NHC(O)NH-3'-methylphenyl]benzyl,
4-[-NHC(O)CH$_2$NHC(O)NH-3'-methylphenyl]benzyl,
4-[-NHC(O)-(2',3'-dihydroindol-2-yl)]benzyl,
4-[-NHC(O)-(2',3'-dihydro-N-Boc-indol-2-yl)]benzyl,
p-[—OCH$_2$CH$_2$-1'-(4'-pyrimidinyl)-piperazinyl]benzyl,
4-[—OCH$_2$CH$_2$-(1'-piperidinyl)benzyl,
4-[—OCH$_2$CH$_2$-(1'-pyrrolidinyl)]benzyl,
4-[—OCH$_2$CH$_2$CH$_2$-(1'-piperidinyl)]benzyl-,
—CH$_2$-3-(1,2,4-triazolyl),
4-[—OCH$_2$CH$_2$CH$_2$-4-(3'-chlorophenyl)-piperazin-1-yl]benzyl,
4-[—OCH$_2$CH$_2$N(φ)CH$_2$CH$_3$]benzyl,
4-[—OCH$_2$-3'-(N-Boc)-piperidinyl]benzyl,
4-[di-n-pentylamino]benzyl,
4-[n-pentylamino]benzyl,
4-[di-iso-propylamino-CH$_2$CH$_2$O-]benzyl,
4-[—OCH$_2$CH$_2$—(N-Morpholinyl)]benzyl,
4-[—O-(3'-(N-Boc)-piperidinyl]benzyl,
4-[—OCH$_2$CH(NHBoc)CH$_2$cyclohexyl]benzyl,
p-[OCH$_2$CH$_2$—(N-piperidinyl)]benzyl,
4-[—OCH$_2$CH$_2$CH$_2$-(4-m-chlorophenyl)-piperazin-1-yl]benzyl,
4-[—OCH$_2$CH$_2$—(N-homopiperidinyl)benzyl,
4-[-NHC(O)-3-(N-Boc)-piperidinyl]benzyl,
4-[—OCH$_2$CH$_2$N(benzyl)$_2$]benzyl,
—CH$_2$-2-thiazolyl,
3-hydroxybenzyl,
4-[—OCH$_2$CH$_2$CH$_2$N(CH$_3$)$_2$]benzyl,
4-[-NHC(S)NHCH$_2$CH$_2$—(N-morpholino)]benzyl,
4-[—OCH$_2$CH$_2$N(C$_2$H$_5$)$_2$]benzyl,
4-[—OCH$_2$CH$_2$CH$_2$N(C$_2$H$_5$)$_2$]benzyl,
4-[CH$_3$(CH$_2$)$_4$NH-]benzyl,
4-[N-n-butyl,N-n-pentylamino]benzyl,
4-[-NHC(O)-4'-piperidinyl]benzyl,
4-[-NHC(O)NHBoc)(CH$_2$)$_4$NHCbz)benzyl,
4-[-NHC(O)-(1',2',3',4'-tetrahydro-N-Boc-isoquinolin-1'-yl)benzyl,
p-[—OCH$_2$CH$_2$CH$_2$-1'-(4'-methyl)-piperazinyl]benzyl, —(CH₂)₄NH-Boc,
3-[—OCH₂CH₂CH₂N(CH₃)₂]benzyl,
4-[—OCH₂CH₂CH₂N(CH₃)₂]benzyl,
3-[—OCH₂CH₂-(1'-pyrrolidinyl)]benzyl,
4-[—OCH₂CH₂CH₂N(CH₃)benzyl]benzyl,
4-[-NHC(S)NHCH₂CH₂CH₂—(N-morpholino)]benzyl,
4-[—OCH₂CH₂—(N-morpholino)]benzyl,
4-[-NHCH₂-(4'-chlorophenyl)]benzyl,
4-[-NHC(O)NH-(4'-cyanophenyl)]benzyl,
4-[—OCH₂COOH]benzyl,
4-[—OCH₂COO-t-butyl]benzyl,
4-[-NHC(O)-5'-fluoroindol-2-yl]benzyl,
4-[-NHC(S)NH(CH₂)₂-1-piperidinyl]benzyl,
4-[-N(SO₂CH₃)(CH₂)₃—N(CH₃)₂]benzyl,
4-[-NHC(O)CH₂CH(C(O)OCH₂φ)—NHCbz]benzyl,
4-[-NHS(O)₂CF₃]benzyl,
3-[—O—(N-methylpiperidin-4'-yl]benzyl,
4-[—C(=NH)NH₂]benzyl,
4-[-NHSO₂—CH₂Cl]benzyl,
4-[-NHC(O)-(1',2', 3',4'-tetrahydroisoquinolin-2'-yl]benzyl,
4-[-NHC(S)NH(CH₂)₃—N-morpholino]benzyl,
4-[-NHC(O)CH(CH₂CH₂CH₂CH₂NH₂)NHBoc]benzyl,
4-[—C(O)NH₂]benzyl,
4-[-NHC(O)NH-3'-methoxyphenyl]benzyl,
4-[—OCH₂CH₂-indol-3'-yl]benzyl,
4-[—OCH₂C(O)NH-benzyl]benzyl,
4-[—OCH₂C(O)O-benzyl]benzyl,
4-[—OCH₂C(O)OH]benzyl,
4-[—OCH₂-2'-(4',5'-dihydro)imidazolyl]benzyl,
—CH₂C(O)NHCH₂-(4-dimethylamino)phenyl,
—CH₂C(O)NHCH₂-(4-dimethylamino)phenyl,
4-[-NHC(O)-L-2'-pyrrolidinyl-N—SO₂-4'-methylphenyl]benzyl,
4-[-NHC(O)NHCH₂CH₂CH₃]benzyl,
4-aminobenzyl]benzyl,
4-[—OCH₂CH₂-1-(4-hydroxy-4-(3-methoxypyrrol-2-yl)-piperazinyl]benzyl,
4-[—O—(N-methylpiperidin-4'-yl)]benzyl,
3-methoxybenzyl,
4-[-NHC(O)-piperidin-3'-yl]benzyl,
4-[-NHC(O)-pyridin-2'-yl]benzyl,
4-[-NHCH₂-(4'-chlorophenyl)]benzyl,
4-[-NHC(O)—(N-(4'-CH3-φ-SO₂)-L-pyrrolidin-2'-yl)]benzyl,
4-[-NHC(O)NHCH₂CH₂-φ]benzyl,
4-[—OCH₂C(O)NH₂]benzyl,
4-[—OCH₂C(O)NH-t-butyl]benzyl,
4-[—OCH₂CH₂-1-(4-hydroxy-4-phenyl)-piperidinyl]benzyl,
4-[-NHSO₂—CH=CH₂]benzyl,
4-[-NHSO₂—CH₂CH₂Cl]benzyl,
—CH₂C(O)NHCH₂CH₂N(CH₃)₂,
4-[(1'-Cbz-piperidin-4'-yl)C(O)NH-]benzyl,
4-[(1'-Boc-piperidin-4'-yl)C(O)NH-]benzyl,
4-[(2'-bromophenyl)C(O)NH-]benzyl,
4-[-NHC(O)-pyridin-4'-yl]benzyl,
4-[(4'-(CH₃)₂NC(O)O-)phenyl]-C(O)NH-]benzyl,
4-[-NHC(O)-1'-methylpiperidin-4'-yl-]benzyl,
4-(dimethylamino)benzyl,
4-[-NHC(O)-(1'-N-Boc)-piperidin-2'-yl]benzyl,
3-[-NHC(O)-pyridin-4'-yl]benzyl,
4-[(tert-butyl-O(O)CCH₂—O-benzyl)-NH-]benzyl,
[BocNHCH₂C(O)NH-]butyl,
4-benzylbenzyl,
2-hydroxyethyl,
4-[(Et)₂NCH₂CH₂CH₂NHC(S)NH-]benzyl,
4-[(1'-Boc-4'-hydroxypyrrolidin-2'-yl)C(O)NH-]benzyl,
4-[φCH₂CH₂CH₂NHC(S)NH-]benzyl,
4-[(perhydroindolin-2'-yl)C(O)NH-]benzyl,
2-[4-hydroxy-4-(3-methoxythien-2-yl)piperidin-1-yl]ethyl,
4-[(1'-Boc-perhydroindolin-2'-yl)-C(O)NH-]benzyl,
4-[N-3-methylbutyl-N-trifluoromethanesulfonyl)amino]benzyl,
4-[N-vinylsulfonyl)amino]benzyl,
4-[2-(2-azabicyclo[3.2.2]octan-2-yl)ethyl-O-]benzyl,
4-[4'-hydroxypyrrolidin-2'-yl)C(O)NH-]benzyl,
4-(φNHC(S)NH)benzyl,
4-(EtNHC(S)NH)benzyl,
4-(4)CH₂NHC(S)NH)benzyl,
3-[(1'-Boc-piperidin-2'-yl)C(O)NH-]benzyl,
3-[piperidin-2'-yl-C(O)NH-]benzyl,
4-[(3'-Boc-thiazolidin-4'-yl)C(O)NH-]benzyl,
4-(pyridin-3'-yl-NHC(S)NH)benzyl,
4-(CH₃—NHC(S)NH)benzyl,
4-(H₂NCH₂CH₂CH₂C(O)NH)benzyl,
4-(BocHNCH₂CH₂CH₂C(O)NH)benzyl,
4-(pyridin-4'-yl-CH₂NH)benzyl,
4-[(N,N-di(4-N,N-dimethylamino)benzyl)amino]benzyl,
4-[(1-Cbz-piperidin-4-yl)C(O)NH-]butyl,
4-[φCH₂OCH₂(BocHN)CHC(O)NH]benzyl,
4-[(piperidin-4'-yl)C(O)NH-]benzyl,
4-[(pyrrolidin-2'-yl)C(O)NH-]benzyl,
4-(pyridin-3'-yl-C(O)NH)butyl,
4-(pyridin-4'-yl-C(O)NH)butyl,
4-(pyridin-3'-yl-C(O)NH)benzyl,
4-[CH₃NHCH₂CH₂CH₂C(O)NH-]benzyl,
4-[CH₃N(Boc)CH₂CH₂CH₂C(O)NH-]benzyl,
4-(aminomethyl)benzyl,
4-[φCH₂OCH₂(H₂N)CHC(O)NH]benzyl,
4-[(1',4'-di(Boc)piperazin-2'-yl)-C(O)NH-]benzyl,
4-[(piperazin-2'-yl)-C(O)NH-]benzyl,
4-[(N-toluenesulfonylpyrrolidin-2'-yl)C(O)NH-]butyl,
4-[-NHC(O)-4'-piperidinyl]butyl,
4-[-NHC(O)-1'-N-Boc-piperidin-2'-yl]benzyl,
4-[-NHC(O)-piperidin-2'-yl]benzyl,
4-[(1'-N-Boc-2',3'-dihydroindolin-2'-yl)-C(O)NH]benzyl,
4-(pyridin-3'-yl-CH₂NH)benzyl,
4-[(piperidin-1'-yl)C(O)CH₂—O-]benzyl,
4-[((CH₃)₂CH)₂NC(O)CH₂—O-]benzyl,
4-[HO(O)C(Cbz-NH)CHCH₂CH₂—C(O)NH-]benzyl,
4-[φCH₂O(O)C(Cbz-NH)CHCH₂CH₂—C(O)NH-]benzyl,
4-[-NHC(O)-2'-methoxyphenyl]benzyl,
4-[(pyrazin-2'-yl)C(O)NH-]benzyl,
4-[HO(O)C(NH₂)CHCH₂CH₂—C(O)NH-]benzyl,
4-(2'-formyl-1',2',3',4'-tetrahydroisoquinolin-3'-yl-CH₂NH—)benzyl,
N-Cbz-NHCH₂—,
4-[(4'-methylpiperazin-1'-yl)C(O)O-]benzyl,
4-[CH₃(N-Boc)NCH₂C(O)NH-]benzyl,
4-[-NHC(O)-(1',2',3',4'-tetrahydro-N-Boc-isoquinolin-3'-yl]-benzyl,
4-[CH₃NHCH₂C(O)NH-]benzyl,
(CH₃)₂NC(O)CH₂—,
4-(N-methylacetamido)benzyl,
4-(1',2',3',4'-tetrahydroisoquinolin-3'-yl-CH₂NH—)benzyl,
4-[(CH₃)₂NHCH₂C(O)NH-]benzyl,
(1-toluenesulfonylimidizol-4-yl)methyl,
4-[(1'-Boc-piperidin-4'-yl)C(O)NH-]benzyl,
4-trifluoromethylbenzyl,
4-[(2'-bromophenyl)C(O)NH-]benzyl,
4-[(CH₃)₂NC(O)NH-]benzyl,
4-[CH₃OC(O)NH-]benzyl,
4-[(CH₃)₂NC(O)O-]benzyl
4-[(CH₃)₂NC(O)N(CH₃)-]benzyl, 4-[CH₃OC(O)N(CH₃)-]benzyl,
4-(N-methyltrifluoroacetamido)benzyl,
4-[(1'-methoxycarbonylpiperidin-4'-yl)C(O)NH-]benzyl,
4-[(4-phenylpiperidin-4'-yl)C(O)NH-]benzyl,
4-[(4'-phenyl-1'-Boc-piperidin-4'-yl)-C(O)NH-]benzyl,
4-[(piperidin-4'-yl)C(O)O-]benzyl, 4-[(1'-methylpiperidin-4'-yl)-O-]benzyl,
4-[(1'-methylpiperidin-4'-yl)C(O)O-]benzyl,
4-[(4'-methylpiperazin-1'-yl)C(O)NH-]benzyl,
3-[(CH₃)₂NC(O)O-]benzyl,
4-[(4'-phenyl-1'-Boc-piperidin-4'-yl)-C(O)O-]benzyl,
4-(N-toluenesulfonylamino)benzyl,
4-[(CH₃)₃CC(O)NH-]benzyl,
4-[(morpholin-4'-yl)C(O)NH-]benzyl,
4-[(CH₃CH₂)₂NC(O)NH-]benzyl,
4-[—C(O)NH-(4'-piperidinyl)]benzyl,
4-[(2'-trifluoromethylphenyl)C(O)NH-]benzyl,
4-[(2'-methylphenyl)C(O)NH-]benzyl,
4-[(CH₃)₂NS(O)₂O-]benzyl,
4-[(pyrrolidin-2'-yl)C(O)NH-]benzyl,
4-[-NHC(O)-piperidin-1'-yl]benzyl,
4-[(thiomorpholin-4'-yl)C(O)NH-]benzyl,
4-[(thiomorpholin-4'-yl sulfone)-C(O)NH-]benzyl,
4-[(morpholin-4'-yl)C(O)O-]benzyl,
3-nitro-4-(CH₃OC(O)CH₂O-)benzyl,
(2-benzoxazolinon-6-yl)methyl-,
(2H-1,4-benzoxazin-3(4H)-one-7-yl)methyl-,
4-[(CH₃)₂NS(O)₂NH-]benzyl,
4-[(CH₃)₂NS(O)₂N(CH₃)-]benzyl,
4-[(thiomorpholin-4'-yl)C(O)O-]benzyl,
4-[(thiomorpholin-4'-yl sulfone)-C(O)O-]benzyl,
4-[(piperidin-1'-yl)C(O)O-]benzyl,
4-[(pyrrolidin-1'-yl)C(O)O-]benzyl,
4-[(4'-methylpiperazin-1'-yl)C(O)O-]benzyl,
4-[(2'-methylpyrrolidin-1'-yl)-,
(pyridin-4-yl)methyl-,
4-[(piperazin-4'-yl)-C(O)O-]benzyl,
4-[(1'-Boc-piperazin-4'-yl)-C(O)O-]benzyl,
4-[(4'-acetylpiperazin-1'-yl)C(O)O-]benzyl,
p-[(4'-methanesulfonylpiperazin-1'-yl)-benzyl,
3-nitro-4-[(morpholin-4'-yl)-C(O)O-]benzyl,
4-{[(CH₃)₂NC(S)]₂N-}benzyl,
N-Boc-2-aminoethyl-,
4-[(1,1-dioxothiomorpholin-4-yl)-C(O)O-]benzyl,
4-[(CH₃)₂NS(O)₂-]benzyl,
4-(imidazolid-2'-one-1'-yl)benzyl,
4-[(piperidin-1'-yl)C(O)O-]benzyl,
1-N-benzyl-imidazol-4-yl-CH₂—,
3,4-dioxyethylenebenzyl (i.e., 3,4-ethylenedioxybenzyl),
3,4-dioxymethylenebenzyl (i.e., 3,4-methylenedioxybenzyl),
4-[-N(SO₂)(CH₃)CH₂CH₂CH₂N(CH₃)₂]benzyl,
4-(3'-formylimidazolid-2'-one-1'-yl)benzyl,
4-[NHC(O)CH(CH₂CH₂CH₂NH₂)NHBoc]benzyl,
[2'-[4''-hydroxy-4''-(3'''-methoxythien-2'''-yl)piperidin-2''-yl]ethoxy]benzyl, and
p-[(CH₃)₂NCH₂CH₂N(CH₃)C(O)O-]benzyl.

Preferably, $R^5$ in the above compounds is selected from the group consisting of alkyl, substituted alkyl, aryl, substituted aryl, heterocyclic, substituted heterocylic, heteroaryl and substituted heteroaryl. Even more preferably $R^5$ is selected from the group consisting of 4-methylphenyl, methyl, benzyl, n-butyl, n-hexyl, 4-chlorophenyl, 1-naphthyl, 2-naphthyl, 4-methoxyphenyl, phenyl, 2,4,6-trimethylphenyl, 2-(methoxycarbonyl)phenyl, 2-carboxyphenyl, 3,5-dichlorophenyl, 4-trifluoromethylphenyl, 3,4-dichlorophenyl, 3,4-dimethoxyphenyl, 4-(CH₃C(O)NH—)phenyl, 4-trifluoromethoxyphenyl, 4-cyanophenyl, isopropyl, 3,5-di-(trifluoromethyl)phenyl, 4-t-butylphenyl, 4-t-butoxyphenyl, 4-nitrophenyl, 2-thienyl, 1-N-methyl-3-methyl-5-chloropyrazol-4-yl, phenethyl, 1-N-methylimidazol-4-yl, 4-bromophenyl, 4-amidinophenyl, 4-methylamidinophenyl, 4-[CH₃SC(=NH)]phenyl, 5-chloro-2-thienyl, 2,5-dichloro-4-thienyl, 1-N-methyl-4-pyrazolyl, 2-thiazolyl, 5-methyl-1,3,4-thiadiazol-2-yl, 4-[H₂NC(S)]phenyl, 4-aminophenyl, 4-fluorophenyl, 2-fluorophenyl, 3-fluorophenyl, 3,5-difluorophenyl, pyridin-3-yl, pyrimidin-2-yl, 4-(3'-dimethylamino-n-propoxy)-phenyl, and 1-methylpyrazol-4-yl.

Preferably, $R^{13}$ in the above compounds is selected from hydrogen or $C_{1-6}$ alkyl; more preferably, hydrogen or $C_{1-3}$ alkyl; and still more preferably, hydrogen or methyl.

In a preferred embodiment, $R^{14}$ in the above compounds is preferably hydrogen and $R^{15}$ is preferably $C_{1-10}$ alkyl or Cy-$C_{1-10}$ alkyl, wherein allyl is optionally substituted with one to four substituents selected from phenyl and $R^x$, and Cy is optionally substituted with one to four substituents independently selected from $R^y$, or $R^{14}$ and $R^{15}$ and the carbon to which they are attached together from a 3-7 membered mono- or bicyclic carbon only ring. For the purpose of $R^{15}$, Cy is preferably aryl, more preferably phenyl. In a preferred embodiment, $R^{15}$ is phenyl-$C_{1-3}$ alkyl, wherein phenyl is optionally substituted with one or two groups selected from $R^y$. Additional preferred embodiments for $R^{14}$ and $R^{15}$ are disclosed in International Patent Application Publication No. WO 98/53814, which application is incorporated herein by reference in its entirety.

In a preferred embodiment of the above compounds, $R^{16}$ is substituted amino; $R^{17}$ and/or $R^{20}$ are hydrogen; and $R^{18}$ and/or $R^{21}$ are alkyl, substituted alkyl, aryl or substituted aryl.

In a preferred embodiment, $R^{23}$ in the above compounds is hydrogen. Preferably, $R^{24}$ in the above compounds is $Ar^1$—$Ar^2$—$C_{1-10}$ alkyl wherein $Ar^1$ and $Ar^2$ are optionally substituted with from 1 to 4 groups independently selected from $R^b$ and $R^{25}$ is hydrogen. More preferably, $R^{24}$ is $Ar^1$—$Ar^2$—$C_{1-3}$ alkyl wherein $Ar^1$ and $Ar^2$ are optionally substituted with from 1 to 4 groups independently selected from $R^b$; still more preferably, $R^{24}$ is —CH₂—$Ar^2$—$Ar^1$ and $R^{25}$ is hydrogen. Additional preferred embodiments are disclosed in International Patent Application Publication No. WO 98/53817, which application is incorporated herein by reference in its entirety.

Preferably, $R^3$ and $R^{3'}$, or $R^{14}$ and $R^{15}$, or $R^{24}$ and $R^{25}$ are derived from L-amino acids or other similarly configured starting materials. Alternatively, racemic mixtures can be used.

Preferably, x in the above compounds is an integer from 1 to 4.

This invention also provides methods for binding VLA-4 in a biological sample which method comprises contacting the biological sample with a compound of this invention under conditions wherein said compound binds to VLA-4.

The pharmaceutical compositions may be used to treat disease conditions mediated by VLA-4 or leucocyte adhesion. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Other disease conditions include, but are not limited to, inflammatory conditions such as erythema nodosum, allergic conjunctivitis, optic neuritis, uveitis, allergic rhinitis, ankylosing spondylitis, psoriatic arthritis, vasculitis, Reiter's syndrome, systemic lupus erythematosus, progressive systemic sclerosis; polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

Preferred compounds of this invention include those set forth in the Tables below:

TABLE I

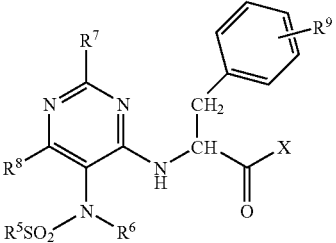

| $R^5$ | $R^6$ | $R^7$ | $R^8$ | $R^9$ | X |
|---|---|---|---|---|---|
| 4-CH$_3$-Ph- | H— | H— | H— | 4-(CH$_3$)$_2$NC(O)O— | —OC(CH$_3$)$_3$ |
| 4-CH$_3$-Ph- | H— | H— | H— | 4-(CH$_3$)$_2$NC(O)O— | —OH |
| 4-CH$_3$-Ph- | CH$_3$— | H— | H— | 4-(CH$_3$)$_2$NC(O)O— | —OC(CH$_3$)$_3$ |
| 4-CH$_3$-Ph- | CH$_3$- | H— | H— | 4-(CH$_3$)$_2$NC(O)O— | —OH |
| 4-CH$_3$-Ph- | 4-CH$_3$-Ph- | H— | H— | 4-(CH$_3$)$_2$NC(O)O— | —OH |
| 1-CH$_3$-pyrazol-4-yl- | CH$_3$— | H— | H— | 4-(CH$_3$)$_2$NC(O)O— | —OH |
| 4-CH$_3$-Ph- | CH$_3$— | H— | H— | 4-(CH$_3$)$_2$NC(O)O— | —OCH(CH$_3$)$_2$ |
| 3-pyridyl- | CH$_3$— | H— | H— | 4-(CH$_3$)$_2$NC(O)O— | —OC(CH$_3$)$_3$ |
| 1-(n-C$_4$H$_9$)-pyrazol-4-yl- | CH$_3$— | H— | H— | 4-(CH$_3$)$_2$NC(O)O— | —OC(CH$_3$)$_3$ |
| 4-CH$_3$-Ph- | CH$_3$— | H— | H— | H— | —OH |
| 1-(n-C$_4$H$_9$)-pyrazol-4-yl- | CH$_3$— | H— | H— | 4-(CH$_3$)$_2$NC(O)O— | —OH |
| 3-pyridyl- | CH$_3$— | H— | H— | 4-(CH$_3$)$_2$NC(O)O— | —OH |
| 4-CH$_3$-Ph- | CH$_3$— | (CH$_3$)$_2$N— | H— | H— | —OH |
| 1-CH$_3$-pyrazol-4-yl- | CH$_3$— | H— | H— | 4-(CH$_3$)$_2$NC(O)O— | —OCH(CH$_3$)$_2$ |
| 3-pyridyl- | CH$_3$— | H— | H— | 4-(1-CH$_3$-piperazin-4-yl)C(O)O— | —OCH(CH$_3$)$_2$ |
| 3-pyridyl- | CH$_3$— | H— | H— | 4-(1-CH$_3$-piperazin-4-yl)C(O)O— | —OC(CH$_3$)$_3$ |
| 3-pyridyl- | CH$_3$— | H— | H— | 4-(1-CH$_3$-piperazin-4-yl)-C(O)O— | —OH |

Ph = phenyl

TABLE II

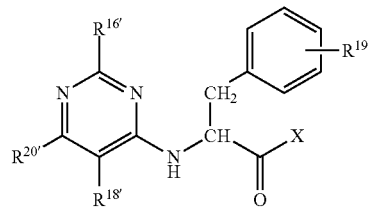

| $R^{16'}$ | $R^{20'}$ | $R^{18'}$ | $R^{19}$ | X |
|---|---|---|---|---|
| Cl— | H— | NO$_2$— | 4-(CH$_3$)$_2$NC(O)O— | —OH |
| H— | H— | PhCH$_2$O— | H— | —OH |
| H— | H— | PhCH$_2$O— | 4-(CH$_3$)$_2$NC(O)O— | —OH |
| H— | H— | Ph- | 4-(CH$_3$)$_2$NC(O)O— | —OH |
| H | H | 3-NO$_2$-Ph- | 4-(CH$_3$)$_2$NC(O)O— | —OH |
| H— | H— | 3-pyridyl- | 4-(CH$_3$)$_2$NC(O)O— | —OH |
| H— | H— | 2-PhCH$_2$CH$_2$— | 4-(CH$_3$)$_2$NC(O)O— | —OH |

TABLE II-continued

| $R^{16'}$ | $R^{20'}$ | $R^{18'}$ | $R^{19}$ | X |
|---|---|---|---|---|
| H— | H— | 2-CH$_3$-Ph- | 4-(CH$_3$)$_2$NC(O)O— | —OH |
| H— | H— | (CH$_3$)$_2$NC(O)—(CH$_2$)$_2$— | 4-(CH$_3$)$_2$NC(O)O— | —OH |
| H— | Ph- | H— | 4-(CH$_3$)$_2$NC(O)O— | —OH |
| H— | 2-CF$_3$-Ph- | H— | 4-(CH$_3$)$_2$NC(O)O— | —OH |
| H— | 2-HOCH$_2$Ph- | H— | 4-(CH$_3$)$_2$NC(O)O— | —OH |
| H— | H— | CF$_3$CH$_2$— | 4-(CH$_3$)$_2$NC(O)O— | —OH |
| H— | H— | PhCH$_2$— | 4-(CH$_3$)$_2$NC(O)O— | —OH |
| H— | H— | 2-CH$_3$-Ph- | 4-(CH$_3$)$_2$NC(O)O— | —OCH(CH$_3$)$_2$ |
| H— | H— | 2-PhCH$_2$CH$_2$— | 4-(CH$_3$)$_2$NC(O)O— | —OCH(CH$_3$)$_2$ |
| H— | H— | 2-PhCH$_2$CH$_2$— | H— | —OCH(CH$_3$)$_2$ |
| cyclohexyl-(CH$_3$)N— | H— | H— | 4-(CH$_3$)$_2$NC(O)O— | —OH |
| H— | H— | CH$_3$CH$_2$CH$_2$— | 4-(CH$_3$)$_2$NC(O)O— | —OH |
| H— | H— | 2-CH$_3$O-Ph- | 4-(CH$_3$)$_2$NC(O)O— | —OH |
| H— | H— | 2-F-Ph- | 4-(CH$_3$)$_2$NC(O)O— | —OH |
| (CH$_3$)$_2$CH—(CH$_3$)N— | H— | 2-CH$_3$-Ph- | 4-(CH$_3$)$_2$NC(O)O— | —OH |
| (CH$_3$)$_2$CH—NH— | H— | 2-CH$_3$-Ph- | 4-(CH$_3$)$_2$NC(O)O— | —OH |
| (CH$_3$)$_2$CHCH$_2$—(CH$_3$)N— | H— | 2-CH$_3$-Ph- | 4-(CH$_3$)$_2$NC(O)O— | —OH |
| CH$_3$CH$_2$—(CH$_3$)N— | H— | 2-CH$_3$-Ph- | 4-(CH$_3$)$_2$NC(O)O— | —OH |
| (CH$_3$)$_2$N— | H— | 2-CH$_3$-Ph- | 4-(CH$_3$)$_2$NC(O)O— | —OH |
| cyclohexyl-(CH$_3$)N— | H— | 3-pyridyl- | 4-(CH$_3$)$_2$NC(O)O— | —OH |
| H— | H— | 2-PhCF$_2$CH$_2$— | 4-(CH$_3$)$_2$NC(O)O— | —OH |
| H— | Cl— | 2-PhCF$_2$CH$_2$— | 4-(CH$_3$)$_2$NC(O)O— | —OH |
| (HOCH$_2$CH$_2$)$_2$N— | H— | H— | 4-(CH$_3$)$_2$NC(O)O— | —OH |
| (HOCH$_2$CH$_2$)$_2$N— | H— | 2-CH$_3$-Ph- | 4-(CH$_3$)$_2$NC(O)O— | —OH |
| Ph(CH$_3$)N— | H— | 2-CH$_3$-Ph- | 4-(CH$_3$)$_2$NC(O)O— | —OH |
| (CH$_3$)$_2$CHO— | H— | 2-CH$_3$-Ph- | 4-(CH$_3$)$_2$NC(O)O— | —OH |
| (CH$_3$)$_2$CHCH$_2$—CH$_2$(CH$_3$)N— | H— | 2-CH$_3$-Ph- | 4-(CH$_3$)$_2$NC(O)O— | —OH |
| CH$_3$NH— | H— | 2-CH$_3$-Ph- | 4-(CH$_3$)$_2$NC(O)O— | —OH |
| 2-CH$_3$-Ph- | H— | 2-CH$_3$-Ph- | 4-(CH$_3$)$_2$NC(O)O— | —OH |
| HOCH$_2$CH$_2$—(CH$_3$)N— | H— | 2-CH$_3$-Ph- | 4-(CH$_3$)$_2$NC(O)O— | —OH |
| cyclohexyl-NH— | H— | 2-CH$_3$-Ph- | 4-(CH$_3$)$_2$NC(O)O— | —OH |
| 1-CH$_3$-piperidin-4-yl-(CH$_3$)N— | H— | 2-CH$_3$-Ph- | 4-(CH$_3$)$_2$NC(O)O— | —OH |
| (CH$_3$)$_2$CH—(CH$_3$CH$_2$—)N— | H— | 2-CH$_3$-Ph- | 4-(CH$_3$)$_2$NC(O)O— | —OH |
| H— | H— | 2,4,6-tri-CH$_3$-Ph- | 4-(CH$_3$)$_2$NC(O)O— | —OH |
| H— | H— | (CH$_3$)$_2$CH— | 4-(CH$_3$)$_2$NC(O)O— | —OH |
| CH$_3$(CH$_2$)$_3$—(CH$_3$)N— | H— | 2-CH$_3$-Ph- | 4-(CH$_3$)$_2$NC(O)O— | —OH |
| CH$_3$CH$_2$CH$_2$—(CH$_3$CH$_2$—)N— | H— | 2-CH$_3$-Ph- | 4-(CH$_3$)$_2$NC(O)O— | —OH |
| (CH$_3$CH$_2$)$_2$N— | H— | 2-CH$_3$-Ph- | 4-(CH$_3$)$_2$NC(O)O— | —OH |
| CH$_3$CH$_2$—(CH$_3$)N— | H— | 2-CH$_3$-Ph- | 4-(CH$_3$)$_2$NC(O)O— | —OH |
| H— | H— | cyclohexyl- | 4-(CH$_3$)$_2$NC(O)O— | —OH |
| (furan-2-yl)CH$_2$—(CH$_3$)N— | H— | 2-CH$_3$-Ph- | 4-(CH$_3$)$_2$NC(O)O— | —OH |
| 4-Cl-Ph-(CH$_3$)N— | H— | 2-CH$_3$-Ph- | 4-(CH$_3$)$_2$NC(O)O— | —OH |
| H— | H— | thien-3-yl- | 4-(CH$_3$)$_2$NC(O)O— | —OH |
| H— | H— | thien-2-yl- | 4-(CH$_3$)$_2$NC(O)O— | —OH |
| HOCH$_2$CH$_2$—(CH$_3$)N— | H— | 2-F-Ph- | 4-(CH$_3$)$_2$NC(O)O— | —OH |
| H— | H— | piperidin-1-yl- | 4-(CH$_3$)$_2$NC(O)O— | —OH |
| H— | H— | (CH$_3$CH$_2$CH$_2$)$_2$—CH— | 4-(CH$_3$)$_2$NC(O)O— | —OH |
| cyclobutyl-(CH$_3$)N— | H— | 2-CH$_3$-Ph- | 4-(CH$_3$)$_2$NC(O)O— | —OH |
| H— | H— | 2-HOCH$_2$-Ph- | 4-(CH$_3$)$_2$NC(O)O— | —OH |
| H— | H— | 2,6-di-F-Ph- | 4-(CH$_3$)$_2$NC(O)O— | —OH |
| H— | H— | 2,4-di-CH$_3$O-pyrimidin-5-yl | 4-(CH$_3$)$_2$NC(O)O— | —OH |
| cyclohexyl-(CH$_3$N— | H— | 2-CH$_3$-Ph- | 4-(CH$_3$)$_2$NC(O)O— | —OH |
| H— | H— | 2-CF$_3$-Ph- | 4-(CH$_3$)$_2$NC(O)O— | —OH |
| cyclohexyl-(CH$_3$)N— | H— | 2-CH$_3$O-Ph- | 2,6-di-CH$_3$O-Ph- | —OH |
| (CH$_3$)$_2$CH—(CH$_3$)N— | H— | 2-F-Ph- | 2,6-di-CH$_3$O-Ph- | —OH |
| (CH$_3$)$_2$CH—(CH$_3$)N— | H— | 2-F-Ph- | 2-CH$_3$O-Ph- | —OH |
| cyclohexyl-(CH$_3$)N— | H— | 2,6-di-F-Ph- | 2,6-di-F-Ph- | —OH |

TABLE II-continued

| R16' | R20' | R18' | R19 | X |
|---|---|---|---|---|
| cyclohexyl-(CH₃)N— | H— | 2-HOCH₂-Ph- | 2,6-di-CH₃O-Ph- | —OH |
| (HOCH₂CH₂)₂N— | H— | 2,4,6-tri-CH₃-Ph- | 2,6-di-CH₃O-Ph- | —OH |
| cyclohexyl-(CH₃)N— | H— | 2-CF₃-Ph- | 2-NC-Ph- | —OH |
| cyclohexyl-(CH₃)N— | H— | thien-3-yl- | 2,6-di-CH₃O-Ph- | —OH |
| cyclohexyl-(CH₃)N— | H— | thien-2-yl- | 4-CF₃-Ph- | —OH |
| cyclohexyl-(CH₃)N— | H— | 3-pyridyl- | 2,6-di-CH₃O-Ph- | —OH |
| cyclohexyl-(CH₃)N— | H— | 3-NO₂-Ph- | 2,6-di-CH₃O-Ph- | —OH |
| cyclohexyl-(CH₃)N— | H— | 2,6-di-Cl-Ph- | 2,6-di-CH₃O-Ph- | —OH |
| cyclohexyl-(CH₃)N— | H— | 4-pyridyl- | 3-HOCH₂-Ph- | —OH |
| (CH₃)₂CH—(CH₃CH₂—)N— | H— | 2,6-di-CH₃O-Ph- | 2,6-di-CH₃O-Ph- | —OH |
| cyclohexyl-(CH₃)N— | H— | 2,3-di-Cl-Ph- | 2,6-di-CH₃O-Ph- | —OH |
| CH₃CH₂—(CH₃)N— | H— | 2,4,6,-tri-CH₃-Ph- | 2-NC-Ph- | —OH |
| (CH₃)₂CH—(CH₃)N— | H— | 2,4,6-tri-CH₃-Ph- | 3-pyridyl- | —OH |
| (HOCH₂CH₂)₂N— | H— | 2,4,6-tri-CH₃-Ph- | 2-NC-Ph- | —OH |
| 1-CH₃-piperidin-4-yl-(CH₃)N— | H— | 2-NC-Ph- | 2,6-di-F-Ph- | —OH |
| (CH₃)₂CH—(CH₃CH₂—)N— | H— | 2,4,6-tri-CH₃-Ph- | 2-CH₃-Ph- | —OH |
| 4-Cl-Ph-(CH₃)N— | H— | 2,4,6-tri-CH₃-Ph- | 2,6-di-CH₃O-Ph- | —OH |
| H— | H— | PhCH₂CH₂—(CH₃)N— | 4-(CH₃)₂NC(O)O— | —OH |
| H— | H— | CH₃(CH₂)₅—(CH₃)N— | 4-(CH₃)₂NC(O)O— | —OH |
| H— | H— | (CH₃)₂CH—(CH₃)N— | 4-(CH₃)₂NC(O)O— | —OH |
| H— | H— | (CH₃)₃C—(CH₃)N— | 4-(CH₃)₂NC(O)O— | —OH |
| H— | H— | (CH₃)₂CH—(CH₃CH₂—)N— | 4-(CH₃)₂NC(O)O— | —OH |
| H— | H— | 4-pyridyl-CH₂CH₂—(CH₃)N— | 4-(CH₃)₂NC(O)O— | —OH |
| H— | H— | PhCH₂CH₂—(CH₃)N— | 2,6-di-CH₃O-Ph- | —OH |
| H— | H— | CH₃(CH₂)₅—(CH₃)N— | 2,6-di-CH₃O-Ph- | —OH |
| H— | H— | (CH₃)₂CH—(CH₃)N— | 2,6-di-CH₃O-Ph- | —OH |
| H— | H— | (CH₃)₃C—(CH₃)N— | 2,6-di-CH₃O-Ph- | —OH |
| H— | H— | (CH₃)₂CH—(CH₃CH₂—)N— | 2,6-di-CH₃O-Ph- | —OH |
| H— | H— | 4-pyridyl-CH₂CH₂—(CH₃)N— | 2,6-di-CH₃O-Ph- | —OH |
| cyclohexyl-(CH₃)N— | H— | CH₃CH₂— | 4-(CH₃)₂NC(O)O— | —OH |
| H— | H— | CF₃CH₂— | 2,6-di-CH₃O-Ph- | —OH |
| cyclohexyl-(CH₃)N— | H— | 2-CH₃-Ph- | 2,6-di-CH₃O-Ph- | —OH |
| H— | H— | 2-F-Ph- | 2,6-di-CH₃O-Ph- | —OH |
| CH₃CH₂CH₂—(CH₃)N— | H— | 2-CH₃-Ph- | 2,6-di-CH₃O-Ph- | —OH |

Ph = phenyl

TABLE III

| R⁵ | R⁶ | R⁷' | R⁸' | R⁹' | X |
|---|---|---|---|---|---|
| 4-CH₃-Ph- | CH₃— | H— | H— | 4-(CH₃)₂NC(O)O— | —OH |
| 4-CH₃-Ph- | CH₃— | H— | H— | 4-(CH₃)₂NC(O)O— | —OCH(CH₃)₂ |

Ph = phenyl

TABLE IV

| R⁵ | R⁶ | b | R⁹' | X |
|---|---|---|---|---|
| CH₃(CH₂)₅— | CH₃(CH₂)₅— | 2 | 4-HO— | —OH |
| CH₃(CH₂)₅— | CH₃(CH₂)₅— | 2 | 4-(CH₃)₂NC(O)O— | —OH |
| CH₃— | CH₃— | 1 | 4-(CH₃)₂NC(O)O— | —OC(CH₃)₃ |
| 3-CH₃-PhNH—C(O)NH(CH₂)₂— | H— | 2 | 4-(CH₃)₂NC(O)O— | —OH |
| CH₃(CH₂)₅— | CH₃(CH₂)₅— | 2 | 4-(1-CH₃-piperazin-4-yl)C(O)O— | —OH |

Ph = phenyl

Accordingly, this invention is also directed to each of the following compounds:

N-(2-chloro-5-nitropyrimidin-4-yl)-L-4-(N,N-dimethylcarbamyloxy)phenylalanine,
N-[5-(N-4-toluenesulfonylamino)pyrimidin-4-yl]-L-4-(N,N-dimethylcarbamyloxy)phenylalanine tert-butyl ester,
N-[5-(N-4-toluenesulfonylamino)pyrimidin-4-yl]-L-4-(N,N-dimethylcarbamyloxy)phenylalanine,
N-[5-(N-methyl-N-4-toluenesulfonylamino)pyrimidin-4-yl]-L-4-(N,N-dimethylcarbamyloxy)phenylalanine tert-butyl ester,
N-[5-(N-methyl-N-4-toluenesulfonylamino)pyrimidin-4-yl]-L-4-(N,N-dimethylcarbamyloxy)phenylalanine,
N-[5-(N,N-di-4-toluenesulfonylamino)pyrimidin-4-yl]-L-4-(N,N-dimethylcarbamyloxy)phenylalanine,
N-[5-[N-(1-N'-methylpyrazol-4-ylsulfonyl)-N-methylamino]pyrimidin-4-yl]-L-4-(N,N-dimethylcarbamyloxy)phenylalanine,
N-[5-(N-methyl-N-4-toluenesulfonylamino)pyrimidin-4-yl]-L-4-(N,N-dimethylcarbamyloxy)phenylalanine isopropyl ester,
N-[5-(N-methyl-N-3-pyridylsulfonylamino)pyrimidin-4-yl]-L-4-(N,N-dimethylcarbamyloxy)phenylalanine tert-butyl ester,
N-(5-(N-methyl-N-(1-butylpyrazol-4-yl)sulfonylamino)pyrimidin-4-yl)-L-4-(N,N-dimethylcarbamyloxy)phenylalanine,
N-(5-(2,4-dimethoxypyrimidin-5-yl)pyrimidin-4-yl)-L-4-(N,N-dimethylcarbamyloxy)phenylalanine,
N-(5-(2,6-difluorophenyl)pyrimidin-4-yl)-L-4-(N,N-dimethylcarbamyloxy)phenylalanine,
N-(5-(2-hydroxymethylphenyl)pyrimidin-4-yl)-L-4-(N,N-dimethylcarbamyloxy)phenylalanine,
N-(2-(N-cyclohexylamino)-5-(2-tolyl)pyrimidin-4-yl)-L-4-(N,N-dimethylcarbamyloxy)phenylalanine,
N-(2-(N-methyl-N-(1-methylpiperidin-4-yl)amino)-5-(2-tolyl)pyrimidin-4-yl)-L-4-(N,N-dimethylcarbamyloxy)phenylalanine,
N-(2-(N-ethyl-N-isopropylamino)-5-(2-tolyl)pyrimidin-4-yl)-L-4-(N,N-dimethylcarbamyloxy)phenylalanine,
N-(5-(2, 4-6-trimethylphenyl)pyrimidin-4-yl)-L-4-(N,N-dimethylcarbamyloxy)phenylalanine,
N-(5-isopropylpyrimidin-4-yl)-L-4-(N,N-dimethylcarbamyloxy)phenylalanine,
N-(2-(N-methyl-N-butylamino)-5-(2-tolyl)pyrimidin-4-yl)-L-4-(N,N-dimethylcarbamyloxy)phenylalanine,
N-(2-(N-ethyl-N-propylamino)-5-(2-tolyl)pyrimidin-4-yl)-L-4-(N,N-dimethylcarbamyloxy)phenylalanine,
N-(2-(N,N-diethylamino)-5-(2-tolyl)pyrimidin-4-yl)-L-4-(N,N-dimethylcarbamyloxy)phenylalanine,
N-(2-(N-methyl-N-ethylamino)-5-(2-tolyl)pyrimidin-4-yl)-L-4-(N,N-dimethylcarbamyloxy)phenylalanine,
N-(5-benzyloxypyrimidin-4-yl)-L-phenylalanine,
N-(5-benzyloxypyrimidin-4-yl)-L-4-(N,N-dimethylcarbamyloxy)phenylalanine,
N-(5-(N-methyl-N-4-toluenesulfonylamino)pyrimidin-4-yl)-L-phenylalanine,
N-(5-(N-methyl-N-3-pyridinesulfonylamino)pyrimidin-4-yl)-L-4-(N,N-dimethylcarbamyloxy)phenylalanine,
N-(5-phenylpyrimidin-4-yl)-L-4-(N,N-dimethylcarbamyloxy)phenylalanine,
N-(3-(N-methyl-N-4-toluenesulfonylamino)pyrazin-2-yl)-L-4-(N,N-dimethylcarbamyloxy)phenylalanine,
N-(5-(2,2,2-trifluoroethyl)pyrimidin-4-yl)-L-4-(N,N-dimethylcarbamyloxy)phenylalanine,
N-(5-(N-methyl-N-3-pyridinesulfonylamino)pyrimidin-4-yl)-L-4-(4-methylpiperazin-1-ylcarbonyloxy)phenylalanine isopropyl ester,
N-(5-benzylpyrimidin-4-yl)-L-4-(N,N-dimethylcarbamyloxy)phenylalanine,
N-(5-(N-methyl-N-3-pyridinesulfonylamino)pyrimidin-4-yl)-L-4-(4-methylpiperazin-1-ylcarbonyloxy)phenylalanine tert-butyl ester, N-(5-(2-trifluoromethylphenyl)pyrimidin-4-yl)-L-4-(N,N-dimethylcarbamyloxy)phenylalanine,
N-(5-(2-N,N-dimethylcarbamylethyl)pyrimidin-4-yl)-L-4-(N,N-dimethylcarbamyloxy)phenylalanine,
N-(5-(N-methyl-N-3-(1-methylpyrazole)sulfonylamino)pyrimidin-4-yl)-L-4-(N,N-dimethylcarbamyloxy)phenylalanine isopropyl ester,
N-(6-phenylpyrimidin-4-yl)-L-4-(N,N-dimethylcarbamyloxy)phenylalanine,
N-(6-(2-trifluoromethylphenyl)pyrimidin-4-yl)-L-4-(N,N-dimethylcarbamyloxy)phenylalanine,
N-(6-(2-hydroxymethylphenyl)pyrimidin-4-yl)-L-4-(N,N-dimethylcarbamyloxy)phenylalanine,
N-(5-cyclohexylpyrimidin-4-yl)-L-4-(N,N-dimethylcarbamyloxy)phenylalanine,
N-(2-(N-methyl-N-2-furanmethylamino)-5-(2-tolyl)pyrimidin-4-yl)-L-4-(N,N-dimethylcarbamyloxy)phenylalanine,
N-(2-(N-methyl-N-4-chlorophenylamino)-5-(2-tolyl)pyrimidin-4-yl)-L-4-(N,N-dimethylcarbamyloxy)phenylalanine,
N-(5-(3-thienyl)pyrimidin-4-yl)-L-4-(N,N-dimethylcarbamyloxy)phenylalanine,
N-(5-(2-thienyl)pyrimidin-4-yl)-L-4-(N,N-dimethylcarbamyloxy)phenylalanine,
N-(2-(N-methyl-N-2-hydroxyethylamino)-542-fluorophenyl)pyrimidin-4-yl)-L-4-(N,N-dimethylcarbamyloxy)phenylalanine,
N-(5-(piperidin-1-yl)pyrimidin-4-yl)-L-4-(N,N-dimethylcarbamyloxy)phenylalanine,
N-(5-(1-propylbutyl)pyrimidin-4-yl)-L-4-(N,N-dimethylcarbamyloxy)phenylalanine,
N-(2-(N-methyl-N-cyclobutylamino)-5-(2-tolyl)pyrimidin-4-yl)-L-4-(N,N-dimethylcarbamyloxy)phenylalanine,
N-(2-(N,N-bis-(2-hydroxyethyl)amino)pyrimidin-4-yl)-L-4-(N,N-dimethylcarbamyloxy)phenylalanine,
N-(2-(N,N-bis-(2-hydroxyethyl)amino)-5-(2-tolyl)pyrimidin-4-yl)-L-4-(N,N-dimethylcarbamyloxy)phenylalanine;
N-(2-(N-methyl-N-phenylamino)-5-(2-tolyl)pyrimidin-4-yl)-L-4-(N,N-dimethylcarbamyloxy)phenylalanine,
N-(2-(isopropoxy)-5-(2-tolyl)pyrimidin-4-yl)-L-4-(N,N-dimethylcarbamyloxy)phenylalanine,
N-(2-(N-methyl-N-3-methylbutylamino)-5-(2-tolyl)pyrimidin-4-yl)-L-4-(N,N-dimethylcarbamyloxy)phenylalanine,
N-(2-(N-methylamino)-5-(2-tolyl)pyrimidin-4-yl)-L-4-(N,N-dimethylcarbamyloxy)phenylalanine,
N-(2-(2-tolyl)-5-(2-tolyl)pyrimidin-4-yl)-L-4-(N,N-dimethylcarbamyloxy)phenylalanine,
N-(2-(N-methyl-N-2-hydroxyethylamino)-5-(2-tolyl)pyrimidin-4-yl)-L-4-(N,N-dimethylcarbamyloxy)phenylalanine,
N-(2-(N-methyl-N-2-methylpropylamino)-5-(2-tolyl)pyrimidin-4-yl)-L-4-(N,N-dimethylcarbamyloxy)phenylalanine,
N-(2-(N-methyl-N-propylamino)-5-(2-tolyl)pyrimidin-4-yl)-L-4-(N,N-dimethylcarbamyloxy)phenylalanine,
N-(2-(N,N-dimethylamino)-5-(2-tolyl)pyrimidin-4-yl)-L-4-(N,N-dimethylcarbamyloxy)phenylalanine,
N-(2-(N-methyl-N-cyclohexylamino)-5-(3-pyridyl)pyrimidin-4-yl)-L-4-(N,N-dimethylcarbamyloxy)phenylalanine,
N-(5-(2-phenyl-2,2-difluoroethyl)pyrimidin-4-yl)-L-4-(N,N-dimethylcarbamyloxy)phenylalanine,
N-(5-(2-phenyl-2,2-difluoroethyl)-6-chloropyrimidin-4-yl)-L-4-(N,N-dimethylcarbamyloxy)phenylalanine,
N-(5-(2-phenylethyl)pyrimidin-4-yl)-L-4-(N,N-dimethylcarbamyloxy)phenylalanine,
N-(2-(N-methyl-N-cyclohexylamino)pyrimidin-4-yl)-L-4-(N,N-dimethylcarbamyloxy)phenylalanine,
N-(5-propylpyrimidin-4-yl)-L-4-(N,N-dimethylcarbamyloxy)phenylalanine,
N-(5-(2-methoxyphenyl)pyrimidin-4-yl)-L-4-(N,N-dimethylcarbamyloxy)phenylalanine,
N-(5-(2-fluorophenyl)pyrimidin-4-yl)-L-4-(N,N-dimethylcarbamyloxy)phenylalanine,
N-(2-(N-Methyl-N-isopropylamino)-5-(2-tolyl)pyrimidin-4-yl)-L-4-(N,N-dimethylcarbamyloxy)phenylalanine,
N-(2-(N-isopropylamino)-5-(2-tolyl)pyrimidin-4-yl)-L-4-(N,N-dimethylcarbamyloxy)phenylalanine,
N-(5-(2-phenylethyl)pyrimidin-4-yl)-L-4-(N,N-dimethylcarbamyloxy)phenylalanine isopropyl ester,
N-(3-(N-methyl-N-4-toluenesulfonylamino)pyrazin-2-yl)-L-phenylalanine isopropyl ester,
N-(5-(2-phenylethyl)pyrimidin-4-yl)-L-phenylalanine isopropyl ester,
N-(5-(N-methyl-N-3-pyridinesulfonylamino)pyrimidin-4-yl)-L-4-(4-methylpiperazin-1-ylcarbonyloxy)phenylalanine,
N-(2-(N-methyl-N-cyclohexylamino)-5-(2-tolyl)pyrimidin-4-yl)-L-4-(N,N-dimethylcarbamyloxy)phenylalanine,
N-(2-(N-methyl-N-cyclohexylamino)-5-ethylpyrimidin-4-yl)-L-4-(N,N-dimethylcarbamyloxy)phenylalanine,
N-(5-(2-tolyl)pyrimidin-4-yl)-L-4-(N,N-dimethylcarbamyloxy)phenylalanine isopropyl ester,
N-(5-(3-nitrophenyl)pyrimidin-4-yl)-L-4-(N,N-dimethylcarbamyloxy)phenylalanine,
N-(5-(3-pyridyl)pyrimidin-4-yl)-L-4-(N,N-dimethylcarbamyloxy)phenylalanine,
N-(5-(2-phenylethyl)pyrimidin-4-yl)-L-4-(N,N-dimethylcarbamyloxy)phenylalanine,
N-(2-N,N-dimethylamino-5-(N-methyl-N-4-toluenesulfonylamino)pyrimidin-4-yl)-L-phenylalanine,
N-(5-(2-tolyl)pyrimidin-4-yl)-L-4-(N,N-dimethylcarbamyloxy)phenylalanine,
N-(2-(N-methyl-N-cyclohexylamino)-5-(2-methoxyphenyl)pyrimidin-4-yl)-L-4-(2,6-dimethoxyphenyl)phenylalanine,
N-(2-(N-methyl-N-isopropylamino)-5-(2-fluorophenyl)pyrimidin-4-yl)-L-4-(2,6-dimethoxyphenyl)phenylalanine,
N-(2-(N-methyl-N-isopropylamino)-5-(2-fluorophenyl)pyrimidin-4-yl)-L-4-(2-methoxyphenyl)phenylalanine,
N-(2-(N-methyl-N-cyclohexylamino)-5-(2,6-difluorophenyl)pyrimidin-4-yl)-L-4-(2,6-difluorophenyl)phenylalanine,
N-(2-(N-methyl-N-cyclohexylamino)-5-(2-hydroxymethylphenyl)pyrimidin-4-yl)-L-4-(2,6-dimethoxyphenyl)phenylalanine,
N-(2-(N,N-bis-(2-hydroxyethyl)amino)-5-(2,4,6-trimethylphenyl)pyrimidin-4-yl)-L-4-(2,6-dimethoxyphenyl)phenylalanine,
N-(2-(N-methyl-N-cyclohexylamino)-5-(2-trifluoromethylphenyl)pyrimidin-4-yl)-L-4-(2-cyanophenyl)phenylalanine,
N-(2-(N-methyl-N-cyclohexylamino)-5-(3-thienyl)pyrimidin-4-yl)-L-4-(2,6-dimethoxyphenyl)phenylalanine,
N-(2-(N-methyl-N-cyclohexylamino)-5-(2-thienyl)pyrimidin-4-yl)-L-4-(4-trifluoromethylphenyl)phenylalanine,
N-(2-(N-methyl-N-cyclohexylamino)-5-(3-pyridyl)pyrimidin-4-yl)-L-4-(2,6-dimethoxyphenyl)phenylalanine,
N-(2-(N-methyl-N-cyclohexylamino)-5-(3-nitrophenyl)pyrimidin-4-yl)-L-4-(2,6-dimethoxyphenyl)phenylalanine,
N-(2-(N-methyl-N-cyclohexylamino)-5-(2,6-dichlorophenyl)pyrimidin-4-yl)-L-4-(2,6-dimethoxyphenyl)phenylalanine,
N-(2-(N-methyl-N-cyclohexylamino)-5-(4-pyridyl)pyrimidin-4-yl)-L-4-(3-hydroxymethylphenyl)phenylalanine, N-(2-(N-ethyl-N-isopropylamino)-5-(2,6-dimethoxyphenyl)pyrimidin-4-yl)-L-4-(2,6-dimethoxyphenyl)phenylalanine, N-(2-(N-methyl-N-cyclohexylamino)-5-(2,3-dichlorophenyl)pyrimidin-4-yl)-L-4-(2,6-dimethoxyphenyl)phenylalanine, N-(2-(N-methyl-N-ethylamino)-5-(2,4,6-trimethylphenyl)pyrimidin-4-yl)-L-4-(2-cyanophenyl)phenylalanine, N-(2-(N-methyl-N-isopropylamino)-5-(2,4,6-trimethylphenyl)pyrimidin-4-yl)-L-4-(3-pyridyl)phenylalanine, N-(2-(N,N-bis-(2-hydroxyethyl)amino)-5-(2,4,6-trimethylphenyl)pyrimidin-4-yl)-L-4-(2-cyanophenyl)phenylalanine, N-(2-(N-methyl-N-(1-methylpiperidin-4-yl)amino)-5-(2-cyanophenyl)pyrimidin-4-yl)-L-4-(2,6-difluorophenyl)phenylalanine, N-(2-(N-ethyl-N-isopropylamino)-5-(2,4,6-trimethylphenyl)pyrimidin-4-yl)-L-4-(o-tolyl)phenylalanine, N-(2-(N-methyl-N-4-chlorophenylamino)-5-(2,4,6-trimethylphenyl)pyrimidin-4-yl)-L-4-(2,6-dimethoxyphenyl)phenylalanine, N-(5-(N-methyl-N-2-(phenyl)ethylamino)pyrimidin-4-yl)-L-4-(N,N-dimethylcarbamyloxy)phenylalanine, N-(5-(N-methyl-N-hexylamino)pyrimidin-4-yl)-L-4-(N,N-dimethylcarbamyloxy)phenylalanine, N-(5-(N-methyl-N-isopropylamino)pyrimidin-4-yl)-L-4-(N,N-dimethylcarbamyloxy)phenylalanine, N-(5-(N-methyl-N-tert-butylamino)pyrimidin-4-yl)-L-4-(N,N-dimethylcarbamyloxy)phenylalanine, N-(5-(N-ethyl-N-isopropylamino)pyrimidin-4-yl)-L-4-(N,N-dimethylcarbamyloxy)phenylalanine, N-(5-(N-methyl-N-2-(4-pyridyl)ethyl-pyrimidin-4-yl)-L-4-(N,N-dimethylcarbamyloxy)phenylalanine, N-(5-(N-methyl-N-2-(phenyl)ethylamino)pyrimidin-4-yl)-L-4-(4-(2,6-dimethoxyphenyl)phenylalanine, N-(5-(N-methyl-N-hexylamino)pyrimidin-4-yl)-L-4-(2,6-dimethoxyphenyl)phenylalanine, N-(5-(N-methyl-N-isopropylamino)pyrimidin-4-yl)-L-4-(2,6-dimethoxyphenyl)phenylalanine, N-(5-(N-methyl-N-tert-butylamino)pyrimidin-4-yl)-L-4-(2,6-dimethoxyphenyl)phenylalanine, N-(5-(N-ethyl-N-isopropylamino)pyrimidin-4-yl)-L-4-(2,6-dimethoxyphenyl)phenylalanine, N-(5-(N-methyl-N-2-(4-pyridyl)ethyl-pyrimidin-4-yl)-L-4-(2,6-dimethoxyphenyl)phenylalanine, N-(2-(N-methyl-N-cyclohexylamino)-5-ethylpyrimidin-4-yl)-L-4-(N,N-dimethylcarbamyloxy)phenylalanine, N-(4-(N,N-di-n-hexylamino)-1,1-dioxo-1,2,5-thiadiazol-3-yl)-L-tyrosine, N-(4-(N,N-di-n-hexylamino)-1,1-dioxo-1,2,5-thiadiazol-3-yl)-L-4-(N,N-dimethylcarbamyloxy)phenylalanine, N-(4-(N,N-dimethylamino)-1-oxo-1,2,5-thiadiazol-3-yl)-L-4-(N,N-dimethylcarbamyloxy)phenylalanine tert-butyl ester, N-[4-(2-(3-methylphenylaminocarbonylamino)eth-1-ylamino)-1,1-dioxo-1,2,5-thiadiazol-3-yl]-4-(N,N-dimethylcarbamyloxy)phenylalanine N-(4-(N,N-di-n-hexylamino)-1,1-dioxo-1,2,5-thiadiazol-3-yl)-L-4-(4-methylpiperazin-1-ylcarbonyloxy)phenylalanine, N-(5-(2,2,2-trifluoroethyl)pyrimidin-4-yl)-L-4-(2,6-dimethoxyphenyl)phenylalanine, N-(2-(N-cyclohexyl-N-methyl)-5-(2-tolyl)pyrimidin-4-yl)-L-4-(2,6-dimethoxyphenyl)phenylalanine, N-(5-(2-fluorophenyl)pyrimidin-4-yl)-L-4-(2,6-dimethoxyphenyl)phenylalanine, N-(2-(N-methyl-N-propyl)-5-(2-tolyl)pyrimidin-4-yl)-L-4-(2,6-dimethoxyphenyl)phenylalanine, N-(3-chloropyrazin-2-yl)-L-4-[1-(tert-butoxycarbonyl)piperidin-4-ylcarbonylamino]phenylalanine ethyl ester, and pharmaceutically acceptable salts thereof.

DETAILED DESCRIPTION OF THE INVENTION

As above, this invention relates to compounds which inhibit leukocyte adhesion and, in particular, leukocyte adhesion mediated by VLA-4. However, prior to describing this invention in further detail, the following terms will first be defined.

DEFINITIONS

As used herein, "alkyl" refers to alkyl groups preferably having from 1 to 10 carbon atoms and more preferably 1 to 6 carbon atoms. This term is exemplified by groups such as methyl, t-butyl, n-heptyl, octyl and the like.

"Substituted alkyl" refers to an alkyl group, preferably of from 1 to 10 carbon atoms, having from 1 to 5 substituents selected from the group consisting of alkoxy, substituted alkoxy, acyl, acylamino, thiocarbonylamino, acyloxy, amino, amidino, alkyl amidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy; heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O), —NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkyl groups having amino groups blocked by conventional blocking groups such as Boc, Cbz, formyl, and the like or alkyl/substituted alkyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O—".

"Alkenoxy" refers to the group "alkenyl-O—".

"Substituted alkenoxy" refers to the group "substituted alkenyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acylamino" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" refers to the group —C(S)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form, together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxysulfonyl" refers to the groups alkyl-SO$_2$O—, substituted alkyl-SO$_2$O—, alkenyl-SO$_2$O—, substituted alkenyl-SO$_2$O—, alkynyl-SO$_2$O—, substituted alkynyl-SO$_2$O—, aryl-SO$_2$O—, substituted aryl-SO$_2$O—, cycloalkyl-SO$_2$O—, substituted cycloalkyl-SO$_2$O—, heteroaryl-SO$_2$O—, substituted heteroaryl-SO$_2$O—, heterocyclic-SO$_2$O—, and substituted heterocyclic-SO$_2$O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation.

"Substituted alkenyl" refers to alkenyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkenyl groups having amino groups blocked by conventional blocking groups such as Boc, Cbz, formyl, and the like or alkenyl/substituted alkenyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Alkynyl" refers to alkynyl group preferably having from 2 to 10 carbon atoms and more preferably 3 to 6 carbon atoms and having at least 1 and preferably from 1-2 sites of alkynyl unsaturation.

"Substituted alkynyl" refers to alkynyl groups having from 1 to 5 substituents selected from the group consisting of alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl; carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O), —NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkylamino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

"Amidino" refers to the group H$_2$NC(=NH)— and the term "alkylamidino" refers to compounds having 1 to 3 alkyl groups (e.g., alkylHNC(=NH)—).

"Thioamidino" refers to the group RSC(=NH)— where R is hydrogen or alkyl.

"Amino" refers to the group —NH$_2$.

"Substituted amino" refers to the group —NRR, where each R group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, provided that both R groups are not hydrogen; or the R groups can be joined together with the nitrogen atom to form a heterocyclic or substituted heterocyclic ring.

"Aminoacyl" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the groups —NRSO$_2$alkyl, —NRSO$_2$substituted alkyl, —NRSO$_2$cycloalkyl, —NRSO$_2$substituted cycloalkyl, —NRSO$_2$alkenyl, —NRSO$_2$substituted alkenyl, —NRSO$_2$alkynyl, —NRSO$_2$substituted alkynyl, —NRSO$_2$aryl, —NRSO$_2$substituted aryl, —NRSO$_2$heteroaryl, —NRSO$_2$substituted heteroaryl, —NRSO$_2$heterocyclic, and —NRSO$_2$substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the groups —NRC(O)O-alkyl, —NRC(O)O-substituted alkyl, —NRC(O)O-alkenyl, —NRC(O)O-substituted alkenyl, —NRC(O)O-alkynyl, —NRC(O)O-substituted alkynyl, —NRC(O)0-cycloalkyl, —NRC(O)O-substituted cycloalkyl, —NRC(O)O-aryl, —NRC(O)O-substituted aryl, —NRC(O)O-heteroaryl, —NRC(O)O-substituted heteroaryl, —NRC(O)O-heterocyclic, and —NRC(O)O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the groups —NRSO$_2$O-alkyl, —NRSO$_2$O-substituted alkyl, —NRSO$_2$O-alkenyl, —NRSO$_2$O-substituted alkenyl, —NRSO$_2$O-alkynyl, —NRSO$_2$O-substituted alkynyl, —NRSO$_2$O-cycloalkyl, —NRSO$_2$O-substituted cycloalkyl, —NRSO$_2$O-aryl, —NRSO$_2$O-substituted aryl, —NRSO$_2$O-heteroaryl, —NRSO$_2$O-substituted heteroaryl, —NRSO$_2$O-heterocyclic, and —NRSO$_2$O-substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" refers to the groups —OC(O)NH$_2$, —OC(O)NRR, —OC(O)NR-alkyl, —OC(O)NR-substituted alkyl, —OC(O)NR-alkenyl, —OC(O)NR-substituted alkenyl, —OC(O)NR-alkynyl, —OC(O)NR-substituted alkynyl, —OC(O)NR-cycloalkyl, —OC(O)NR-substituted cycloalkyl, —OC(O)NR-aryl, —OC(O)NR-substituted aryl, —OC(O)NR-heteroaryl, —OC(O)NR-substituted heteroaryl, —OC(O)NR-heterocyclic, and —OC(O)NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl; cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NH$_2$, —OC(S)NRR, —OC(S)NR-alkyl, —OC(S)NR-substituted alkyl, —OC(S)NR-alkenyl, —OC(S)NR-substituted alkenyl, —OC(S)NR-alkynyl, —OC(S)NR-substituted alkynyl, —OC(S)NR-cycloalkyl, —OC(S)NR-substituted cycloalkyl, —OC(S)NR-aryl, —OC(S)NR-substituted aryl, —OC(S)NR-heteroaryl, —OC(S)NR-substituted heteroaryl, —OC(S)NR-heterocyclic, and —OC(S)NR-substituted heterocyclic where R is hydrogen, alkyl or where each R is joined to form together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxysulfonylamino" refers to the groups —OSO$_2$NH$_2$, —OSO$_2$NRR, —OSO$_2$NR-alkyl, —OSO$_2$NR-substituted alkyl, —OSO$_2$NR-alkenyl, —OSO$_2$NR-substituted alkenyl, —OSO$_2$NR-alkynyl, —OSO$_2$NR-substituted alkynyl, —OSO$_2$NR-cycloalkyl, —OSO$_2$NR-substituted cycloalkyl, —OSO$_2$NR-aryl, —OSO$_2$NR-substituted aryl, —OSO$_2$NR-heteroaryl, —OSO$_2$NR-substituted heteroaryl, —OSO$_2$NR-heterocyclic, and —OSO$_2$NR-substituted heterocyclic where R is hydrogen, alkyl or where each R is joined to form, together with the nitrogen atom a heterocyclic or substituted heterocyclic ring and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the groups —NRC(O)NRR, —NRC(O)NR-alkyl, —NRC(O)NR-substituted alkyl, —NRC(O)NR-alkenyl, —NRC(O)NR-substituted alkenyl, —NRC(O)NR-alkynyl, —NRC(O)NR-substituted alkynyl, —NRC(O)NR-aryl, —NRC(O)NR-substituted aryl, —NRC(O)NR-cycloalkyl, —NRC(O)NR-substituted cycloalkyl, —NRC(O)NR-heteroaryl, and —NRC(O)NR-substituted heteroaryl, —NRC(O)NR-heterocyclic, and —NRC(O)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the groups —NRC(S)NRR, —NRC(S)NR-alkyl, —NRC(S)NR-substituted alkyl, —NRC(S)NR-alkenyl, —NRC(S)NR-substituted alkenyl, —NRC(S)NR-alkynyl, —NRC(S)NR-substituted alkynyl, —NRC(S)NR-aryl, —NRC(S)NR-substituted aryl, —NRC(S)NR-cycloalkyl, —NRC(S)NR-substituted cycloalkyl, —NRC(S)NR-heteroaryl, and —NRC(S)NR-substituted heteroaryl, —NRC(S)NR-heterocyclic, and —NRC(S)NR-substituted heterocyclic where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the groups —NRSO$_2$NRR, —NRSO$_2$NR-alkyl, —NRSO$_2$NR-substituted alkyl, —NRSO$_2$NR-alkenyl, —NRSO$_2$NR-substituted alkenyl, —NRSO$_2$NR-alkynyl, —NRSO$_2$NR-substituted alkynyl, —NRSO$_4$NR-aryl, —NRSO$_2$NR-substituted aryl, —NRSO$_2$NR-cycloalkyl, —NRSO$_2$NR-substituted cycloalkyl, —NRSO$_2$NR-heteroaryl, and —NRSO$_2$NR-substituted heteroaryl, —NRSO$_2$NR-heterocyclic, and —NRSO$_2$NR-substituted heterocyclic, where each R is independently hydrogen, alkyl or where each R is joined to form together with the nitrogen atom a heterocyclic or substituted heterocyclic ring as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7yl, and the like). Preferred aryls include phenyl and naphthyl.

Substituted aryl refers to aryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-allyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, =NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, monoand di-alkylamino, mono- and di-(substituted alkylamino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2NRR$ where R is hydrogen or alkyl.

"Aryloxy" refers to the group aryl-O— which includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic; cycloalkoxy, substituted cycloalkoxy, heteroaryloxy, substituted heteroaryloxy, heterocyclyloxy, substituted heterocyclyloxy, oxycarbonylamino, oxythiocarbonylamino, —$S(O)_2$-alkyl, —$S(O)_2$-substituted alkyl, —$S(O)_2$-cycloalkyl, —$S(O)_2$-substituted cycloalkyl, —$S(O)_2$-alkenyl, —$S(O)_2$-substituted alkenyl, —$S(O)_2$-aryl, —$S(O)_2$-substituted aryl, —$S(O)_2$-heteroaryl, —$S(O)_2$-substituted heteroaryl, —$S(O)_2$-heterocyclic, —$S(O)_2$-substituted heterocyclic, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl; —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)_2$—NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —$SO_2NRR$ where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclohexyl, cyclooctyl and the like. Excluded from this definition are multi-ring alkyl groups such as adamantanyl, etc.

"Cycloalkenyl" refers to cyclic alkenyl groups of from 3 to 8 carbon atoms having single or multiple unsaturation but which are not aromatic.

"Substituted cycloalkyl" and "substituted cycloalkenyl" refer to a cycloalkyl and cycloalkenyl groups, preferably of from 3 to 8 carbon atoms, having from 1 to 5 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, —$OSO_2$—NRR where R is hydrogen or alkyl, —$NRS(O)_2$-alkyl, —$NRS(O)_2$-substituted alkyl, —$NRS(O)_2$-aryl, —$NRS(O)_2$-substituted aryl, —$NRS(O)_2$-heteroaryl, —$NRS(O)_2$-substituted heteroaryl, —$NRS(O)_2$-heterocyclic, —$NRS(O)_2$-substituted heterocyclic, —$NRS(O)_2$—NR-alkyl, —$NRS(O)_2$—NR-substituted alkyl, —$NRS(O)_2$—NR-aryl, —$NRS(O)$, —NR-substituted aryl, —$NRS(O)_2$—NR-heteroaryl, —$NRS(O)_2$—NR-substituted heteroaryl, —$NRS(O)_2$—NR-heterocyclic, —$NRS(O)_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic and —$SO_2NRR$ where R is hydrogen or alkyl.

"Cycloalkoxy" refers to —O-cycloalkyl groups.

"Substituted cycloalkoxy" refers to —O-substituted cycloalkyl groups.

"Cycloalkenoxy" refers to —O-cycloalkenyl groups.

"Substituted cycloalkenoxy" refers to —O-substituted cycloalkenyl groups.

"Guanidino" refers to the groups —NRC(=NR)NRR, —NRC(=NR)NR-alkyl, —NRC(=NR)NR-substituted alkyl, —NRC(=NR)NR-alkenyl, —NRC(=NR)NR-substituted alkenyl, —NRC(=NR)NR-alkynyl, —NRC(=NR)NR-substituted alkynyl, —NRC(=NR)NR-aryl, —NRC(=NR)NR-substituted aryl, —NRC(=NR)NR-cycloalkyl, —NRC(=NR)NR-heteroaryl, —NRC(=NR)NR-substituted heteroaryl, —NRC(=NR)NR-heterocyclic, and —NRC(=NR)NR-substituted heterocyclic where each R is independently hydrogen and alkyl as well as where one of the amino groups is blocked by conventional blocking groups such as Boc, Cbz, formyl, and the like and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NRC(=NR)NRSO$_2$-alkyl, —NRC(=NR)NRSO$_2$-substituted alkyl, —NRC(=NR)NRSO$_2$-alkenyl, —NRC(=NR)NRSO$_2$-substituted alkenyl, —NRC(=NR)NRSO$_2$-alkynyl, —NRC(=NR)NRSO$_2$-substituted alkynyl, —NRC(=NR)NRSO$_2$-aryl, —NRC(=NR)NRSO$_2$-substituted aryl, —NRC(=NR)NRSO$_2$-cycloalkyl, —NRC(=NR)NRSO$_2$-substituted cycloalkyl, —NRC(=NR)NRSO$_2$-heteroaryl, and —NRC(=NR)NRSO$_2$-substituted heteroaryl, —NRC(=NR)NRSO$_2$ heterocyclic, and —NRC(=NR)NRSO$_2$-substituted heterocyclic where each R is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or bromo.

"Heteroaryl" refers to an aromatic carbocyclic group of from 2 to 10 carbon atoms and 1 to 4 heteroatoms selected from oxygen, nitrogen and sulfur within the ring or oxides thereof. Such heteroaryl groups can have a single ring (e.g., pyridyl or furyl) or multiple condensed rings (e.g., indolizinyl or benzothienyl). Additionally, the heteroatoms of the heteroaryl group may be oxidized, i.e., to form pyridine N-oxides or 1,1-dioxo-1,2,5-thiadiazoles and the like. Preferred heteroaryls include pyridyl, pyrrolyl, indolyl, furyl, pyridazinyl, pyrimidinyl, pyrazinyl, 1-oxo-1,2,5-thiadiazolyl and 1,1-dioxo-1,2,5-thiadiazolyl. The term "heteroaryl having two nitrogen atoms in the heteroaryl ring" refers to a heteroaryl group having two, and only two, nitrogen atoms in the heteroaryl ring and optionally containing 1 or 2 other heteroatoms in the heteroaryl ring, such as oxygen or sulfur "Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy; alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from nitrogen, sulfur or oxygen within the ring wherein, in fused ring systems, one or more of the rings can be aryl or heteroaryl.

"Substituted heterocyclic" refers to heterocycle groups which are substituted with from 1 to 3 substituents selected from the group consisting of oxo (=O), thioxo (=S), alkoxy, substituted alkoxy, acyl, acylamino, thiocarbonylamino, acyloxy, amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, halogen, hydroxyl, cyano, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, substituted cycloalkyl, guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O), —NR-aryl, —NRS(O)$_2$—NR-substituted aryl, —NRS(O)$_2$—NR-heteroaryl, —NRS(O)$_2$—NR-substituted heteroaryl, —NRS(O), —NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents selected from alkyl, substituted alkyl, aryl, substituted aryl, heteroaryl, substituted heteroaryl, heterocyclic and substituted heterocyclic and substituted alkynyl groups having amino groups blocked by conventional blocking groups such as Boc, Cbz, formyl, and the like or alkynyl/substituted alkynyl groups substituted with —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic and —SO$_2$NRR where R is hydrogen or alkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Thiol" refers to the group —SH.

"Thioalkyl" refers to the groups —S-alkyl

"Substituted thioalkyl" refers to the group —S-substituted alkyl.

"Thiocycloalkyl" refers to the groups —S-cycloalkyl.

"Substituted thiocycloalkyl" refers to the group —S-substituted cycloalkyl.

"Thioaryl" refers to the group —S-aryl and "substituted thioaryl" refers to the group —S-substituted aryl.

"Thioheteroaryl" refers to the group —S-heteroaryl and "substituted thioheteroaryl" refers to the group —S-substituted heteroaryl.

"Thioheterocyclic" refers to the group —S-heterocyclic and "substituted thioheterocyclic" refers to the group —S-substituted heterocyclic.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second. Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

In a preferred method of synthesis, the compounds of this invention are prepared by coupling an amino acid derivative of the formula:

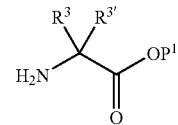

where $R^3$ and $R^{3'}$ are as defined herein and $P^1$ is a carboxylic acid protecting group (such as an alkyl group, i.e. methyl, ethyl and the like), with a suitably functionalized heteroaryl or heterocyclic intermediate. For example, such coupling reactions may be performed by displacing a leaving group, such as chloro, bromo, iodo, tosyl and the like, from the heteroaryl or heterocyclic intermediate with the amino group of the amino acid derivative; or by reductive alkylation of the amino group of amino acid derivative with a carbonyl-functionalized intermediate. Such coupling reactions are well-known to those skilled in the art.

By way of illustration, the synthesis of a representative compound of formula I is shown in Scheme 1.

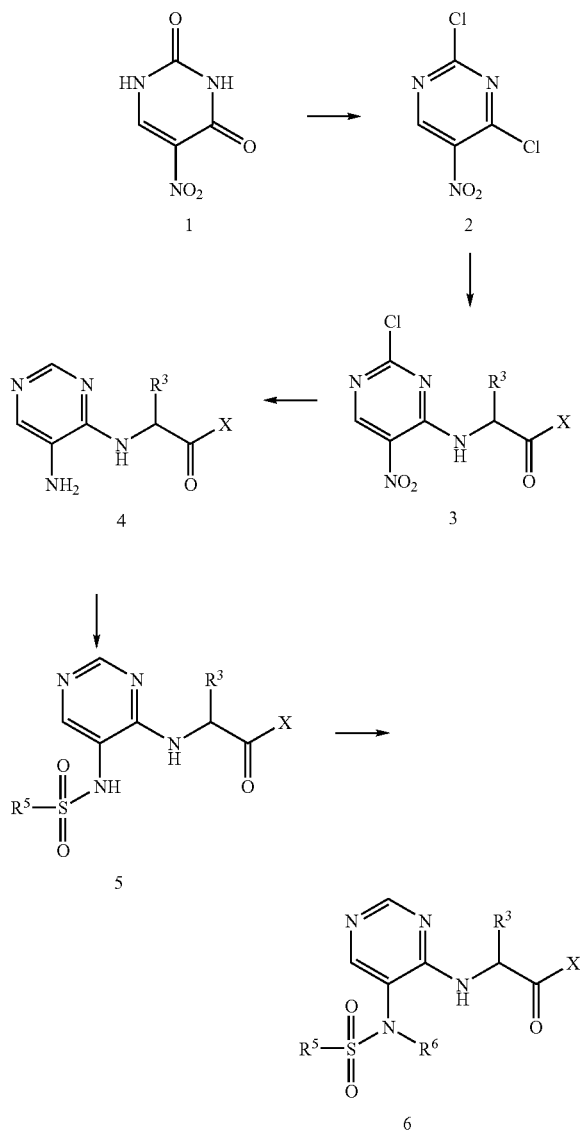

As shown in Scheme 1, 5-nitrouracil, 1, (commercially available from Aldrich Chemical Company, Milwaukee, Wis. USA) is treated with phosphorus oxychloride and N,N-dimethylaniline according to the procedure described in Whittaker, *J. Chem. Soc.* 1951, 1565 to give 1,3-dichloro-4-nitropyrimidine, 2.

1,3-Dichloro-4-nitropyrimidine, 2, is then reacted with about one molar equivalent of an amino acid derivative of the formula: $H_2N-CH(R^3)C(O)X$ where $R^3$ and X are as defined herein or X is $-OP^1$ where $P^1$ is a carboxylic acid protecting group, in the presence of a trialkylamine, such as diisopropylethylamine (DIEA). Typically, this reaction is conducted in an inert diluent, such as dichloromethane, at a temperature ranging from about 0° C. to about 10° C. for about 5 min. to about 6 hours to afford intermediate 3.

The nitro group of intermediate 3 is then reduced using a conventional reducing agent, such as hydrogen and a palladium on carbon catalyst. When hydrogen and palladium on carbon are employed as the reducing agent, the chloro group of intermediate 3 is also removed. This reaction is typically conducted by contacting 3 with a Degussa-type palladium on carbon catalyst (typically 20%) and excess sodium bicarbonate in an inert diluent, such as methanol, under hydrogen (typically about 55 psi) for about 12 to 36 hours at ambient temperature to afford amino intermediate 4.

Amino intermediate 4 is then reacted with a sulfonyl chloride of the formula: $R^5-S(O)_2-Cl$, where $R^5$ is as defined herein, to provide sulfonamide intermediate 5. This reaction is typically conducted by reacting the amino intermediate 4 with at least one equivalent, preferably about 1.1 to about 2 equivalents, of the sulfonyl chloride in an inert diluent such as dichloromethane and the like. Generally, the reaction is conducted at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like, as the base. Upon completion of the reaction, the resulting sulfonamide 5 is recovered by conventional methods including neutralization, extraction, precipitation, chromatography, filtration, and the like.

Other heteroaryl intermediates may also be employed in the above described reactions including, but not limited to, 2-chloro-3-nitropyrazine (*J. Med. Chem.* 1984, 27, 1634); 4-chloro-5-nitroimidazole (*J. Chem. Soc.* 1930, 268); and the like.

The amino acid derivatives employed in the above reactions are either known compounds or compounds that can be prepared from known compounds by conventional synthetic procedures. For example, amino acid derivatives can be prepared by C-alkylating commercially available diethyl 2-acetamidomalonate (Aldrich, Milwaukee, Wis., USA) with an alkyl or substituted alkyl halide. This reaction is typically conducted by treating the diethyl 2-acetamidomalonate with at least one equivalent of sodium ethoxide and at least one equivalent of an alkyl or substituted alkyl halide in refluxing ethanol for about 6 to about 12 hours. The resulting C-alkylated malonate is then deacetylated, hydrolyzed and decarboxylated by heating in aqueous hydrochloric acid at reflux for about 6 to about 12 hours to provide the amino acid, typically as the hydrochloride salt.

Examples of amino acid derivatives suitable for use in the above reactions include, but are not limited to, L-alanine methyl ester, L-isoleucine methyl ester, L-leucine methyl ester, L-valine methyl ester, p-tert-butyl-L-aspartic acid methyl ester, L-asparagine tert-butyl ester, ε-Boc-L-lysine methyl ester, ε-Cbz-L-lysine methyl ester, γ-tert-butyl-L-glutamic acid methyl ester, L-glutamine tert-butyl ester, L-(N-methyl)histidine methyl ester, L-(N-benzyl)histidine methyl ester, L-methionine methyl ester, L-(O-benzyl)serine methyl ester, L-tryptophan methyl ester, L-phenylalanine methyl ester, L-phenylalanine isopropyl ester, L-phenylalanine benzyl ester, L-phenylalaninamide, N-methyl-L-phenylalanine benzyl ester, 3-carboxy-D,L-phenylalanine methyl ester, 4-carboxy-D,L-phenylalanine methyl ester, L-4-chlorophenylalanine methyl ester, L-4-(3-dimethylaminopropyloxy)-phenylalanine methyl ester, L-4-iodophenylalanine methyl ester, L-3,4-methylenedioxyphenylalanine methyl ester, L-3,4-ethylenedioxyphenylalanine methyl ester, L-4-nitrophenylalanine methyl ester, L-tyrosine methyl ester, D,L-homophenylalanine methyl ester, L-(O-methyl)tyrosine methyl ester, L-(O-tert-butyl)tyrosine methyl ester, L-(O-benzyl)tyrosine methyl ester, L-3,5-diiodotyrosine methyl ester, L-3-iodotyrosine methyl ester, β-(1-naphthyl)-L-alanine methyl ester, β-(2-naphthyl)-L-alanine methyl ester, (3-(2-thienyl)-L-alanine methyl ester, β-cyclohexyl-L-alanine methyl ester, β-(2-pyridyl)-L-alanine methyl ester, β-(3-pyridyl)-L-alanine methyl ester, β-(4-pyridyl)-L-alanine methyl ester, β-(2-thiazolyl)-D,L-alanine methyl ester, β-(1,2,4-triazol-3-yl)-D,L-alanine methyl ester, and the like. If desired, of course, other esters or amides of the above-described compounds may also be employed.

Additionally, α-hydroxy and α-thio carboxylic acids may also be employed in the above-described reactions. Such compounds are well-known in the art and are either commercially available or may be prepared from commercially available starting materials using conventional reagents and reaction conditions.

The sulfonyl chlorides employed in the above reaction are also either known compounds or compounds that can be prepared from known compounds by conventional synthetic procedures. Such compounds are typically prepared from the corresponding sulfonic acid, i.e., from compounds of the formula $R^5$—$SO_3$1-1 where $R^5$ is as defined above, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the sulfonyl chloride can be prepared from the corresponding thiol compound, i.e., from compounds of the formula $R^5$—SH where $R^5$ is as defined herein, by treating the thiol with chlorine ($Cl_2$) and water under conventional reaction conditions.

Examples of sulfonyl chlorides suitable for use in this invention include, but are not limited to, methanesulfonyl chloride, 2-propanesulfonyl chloride, 1-butanesulfonyl chloride, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reaction to form the sulfonamide intermediate 5.

If desired, sulfonamide intermediate 5 can be alkylated at the sulfonamide nitrogen atom to provide compound 6. For example, 5 can be contacted with excess diazomethane (generated, for example, using 1-methyl-3-nitro-1-nitrosoguanidine and sodium hydroxide) to afford 6 where $R^6$ is methyl. Other conventional alkylation procedures and reagents may also be employed to prepare various compounds of this invention.

In another preferred embodiment, compounds of this invention may be prepared by displacement of a leaving group as shown in Scheme 2:

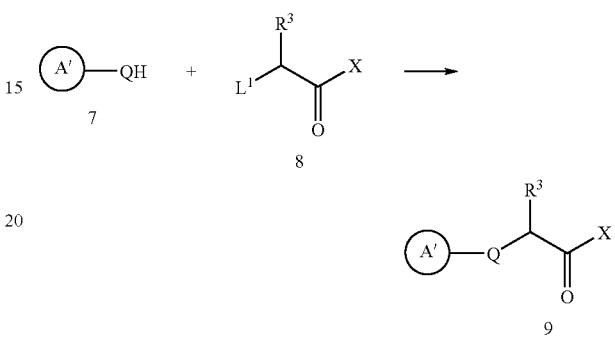

where $R^3$, Q and X are as defined herein; A' is heteroaryl, substituted heteroaryl, heterocyclic or substituted heterocyclic containing two nitrogen atoms in the heteroaryl or heterocyclic ring; and $L^1$ is a leaving group, such as chloro, bromo, iodo, sulfonate ester and the like.

Typically, this reaction is conducted by combining approximately stoichiometric equivalents of 7 and 8 in a suitable inert diluent such as water, dimethylsulfoxide (DMSO) and the like, with an excess of a suitable base such as sodium bicarbonate, sodium hydroxide, etc. to scavenge the acid generated by the reaction. The reaction is preferably conducted at from about 25° C. to about 100° C. until reaction completion which typically occurs within 1 to about 24 hours. This reaction is further described in U.S. Pat. No. 3,598,859, which is incorporated herein by reference in its entirety. Upon reaction completion, the product 9 is recovered by conventional methods including precipitation, chromatography, filtration and the like.

In still another alternative embodiment, compounds of this invention in which Q is $NR^4$ can be prepared by reductive amination of a suitable 2-oxocarboxylic acid ester, 10, such as a pyruvate ester, as shown in Scheme 3:

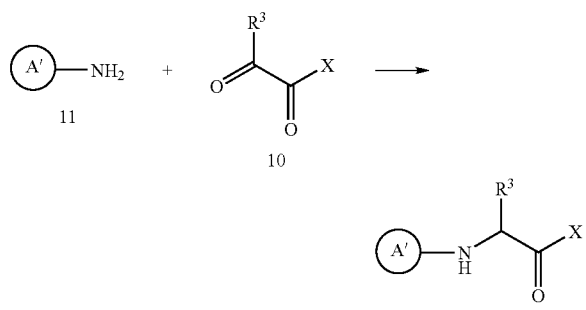

where A', $R^3$ and X are as defined herein.

Generally, this reaction is conducted by combining equamolar amounts of 10 and 11 in an inert diluent such as methanol, ethanol and the like under conditions which provide for imine formation (not shown). The imine formed is then reduced under conventional conditions by a suitable reducing agent such as sodium cyanoborohydride, $H_2$/palladium on carbon and the like to form the product 12. In a particularly preferred embodiment, the reducing agent is $H_2$/palladium on carbon which is incorporated into the initial reaction medium thereby permitting imine reduction in situ in a one pot procedure to provide 12. The reaction is preferably conducted at from about 20° C. to about 80° C. at a pressure of from 1 to 10 atmospheres until reaction completion which typically occurs within 1 to about 24 hours. Upon reaction completion, the product 12 is recovered by conventional methods including chromatography, filtration and the like.

Alternatively, certain compounds of this invention can be prepared via a rhodium-catalyzed insertion reaction as shown in Scheme 4:

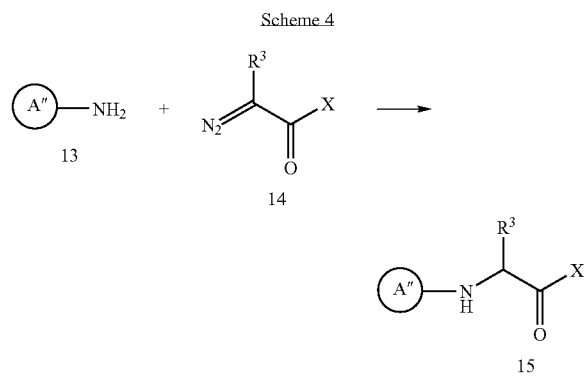

where A" is heteroaryl or substituted heteroaryl containing two nitrogen atoms in the heteroaryl ring, and $R^3$ and X (preferably alkoxy) are as defined herein. Typically, this reaction is conducted using rhodium acetate dimer, $Rh_2(OAc)_4$, in an inert diluent such as toluene at a temperature ranging from about 25° C. to about 80° C. for about 1 to 12 hours to afford 15. This reaction is described further in B. R. Henke et. al., *J. Med. Chem.* 1998, 41, 5020-5036 and references cited therein.

Similarly, certain compounds of this invention can be prepared by the copper-catalyzed coupling reaction shown in Scheme 5:

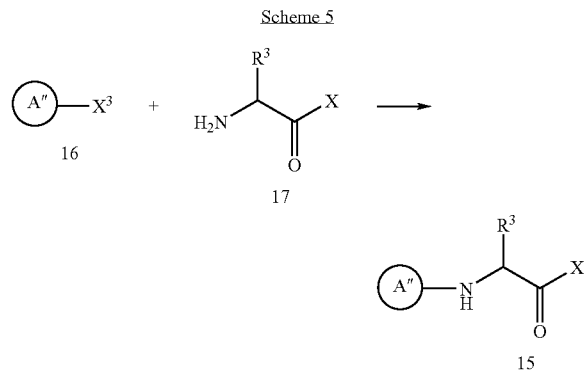

where A" is as defined herein, $X^3$ is halogen, such as chloro, bromo or iodo (preferably iodo), and $R^3$ and X (preferably alkoxy) are as defined herein. Typically, this reaction is conducted using copper iodide (CuI) and potassium carbonate in an inert diluent such as N,N-dimethyl acetamide (DMA) at a temperature ranging from about 60° C. to about 120° C. for about 12 to 36 hours to afford 15. This reaction is described further in D. Ma et. al., *J. Am. Chem. Soc.* 1998, 120, 12459-12467 and references cited therein.

For ease of synthesis, the compounds of this invention are typically prepared as an ester, i.e., where X is an alkoxy or substituted alkoxy group and the like. If desired, the ester group can be hydrolysed using conventional conditions and reagents to provide the corresponding carboxylic acid. Typically, this reaction is conducted by treating the ester with at least one equivalent of an alkali metal hydroxide, such as lithium, sodium or potassium hydroxide, in an inert diluent, such as methanol or mixtures of methanol and water, at a temperature ranging about 0° C. to about 24° C. for about 1 to about 12 hours. Alternatively, benzyl esters may be removed by hydrogenolysis using a palladium catalyst, such as palladium on carbon, and tert-butyl esters can be removed using formic acid to afford the corresponding carboxylic acid.

As will be apparent to those skilled in the art, other functional groups present on any of the substituents of the compounds of formulas I-VII can be readily modified or derivatized either before or after the above-described synthetic reactions using well-known synthetic procedures. For example, a nitro group present on a substituent of a compound of formula I-VII or an intermediate thereof may be readily reduced by hydrogenation in the presence of a palladium catalyst, such as palladium on carbon, to provide the corresponding amino group. This reaction is typically conducted at a temperature of from about 20° C. to about 50° C. for about 6 to about 24 hours in an inert diluent, such as methanol. Compounds having a nitro group on the $R^3$ and/or $R^{3'}$ substituent can be prepared, for example, by using a 4-nitrophenylalanine derivative and the like in the above-described coupling reactions.

Similarly, a pyridyl group can be hydrogenated in the presence of a platinum catalyst, such as platinum oxide, in an acidic diluent to provide the corresponding piperidinyl analogue. Generally, this reaction is conducted by treating the pyridine compound with hydrogen at a pressure ranging from about 20 psi to about 60 psi, preferably about 40 psi, in the presence of the catalyst at a temperature of about 20° C. to about 50° C. for about 2 to about 24 hours in an acidic diluent, such as a mixture of methanol and aqueous hydrochloric acid.

Additionally, when the $R^3$ and/or $R^{3'}$ substituent of a compound of formula I-VII or an intermediate thereof contains a primary or secondary amino group, such amino groups can be further derivatized either before or after the above coupling reactions to provide, by way of example, amides, sulfonamides, ureas, thioureas, carbamates, secondary or tertiary amines and the like. Compounds having a primary amino group on the $R^3$ and/or $R^{3'}$ substituent may be prepared, for example, by reduction of the corresponding nitro compound as described above.

By way of illustration, a compound of formula I-VII or an intermediate thereof having a substituent containing a primary or secondary amino group, such as where $R^3$ is a (4-aminophenyl)methyl group, can be readily N-acylated using conventional acylating reagents and conditions to provide the corresponding amide. This acylation reaction is typically conducted by treating the amino compound with at least one equivalent, preferably about 1.1 to about 1.2 equivalents, of a carboxylic acid in the presence of a coupling reagent such as a carbodiimide, BOP reagent (benzotriazol-1-yloxy-tris(dimethylamino)phosphonium hexafluorophosphonate) and the like, in an inert diluent, such as dichloromethane, chloroform, acetonitrile, tetrahydrofuran, N,N-dimethylformamide and the like, at a temperature ranging from about 0° C. to about 37° C. for about 4 to about 24 hours. Preferably, a promoter, such as N-hydroxysuccinimide, 1-hydroxy-benzotriazole and the like, is used to facilitate the acylation reaction. Examples of carboxylic acids suitable for use in this reaction include, but are not limited to, N-tert-butyloxycarbonylglycine N-tert-butyloxycarbonyl-L-phenylalanine, N-tert-butyloxycarbonyl-L-aspartic acid benzyl ester, benzoic acid, N-tert-butyloxycarbonylisonipecotic acid, N-methylisonipecotic acid, N-tert-butyloxycarbonylnipecotic acid, N-tert-butyloxycarbonyl-L-tetrahydroisoquinoline-3-carboxylic acid, N-(toluene-4-sulfonyl)-L-proline and the like.

Alternatively, a compound of formula I-VII or an intermediate thereof containing a primary or secondary amino group can be N-acylated using an acyl halide or a carboxylic acid anhydride to form the corresponding amide. This reaction is typically conducted by contacting the amino compound with at least one equivalent, preferably about 1.1 to about 1.2 equivalents, of the acyl halide or carboxylic acid anhydride in an inert diluent, such as dichloromethane, at a temperature ranging from about −70° C. to about 40° C. for about 1 to about 24 hours. If desired, an acylation catalyst such as 4-(N,N-dimethylamino)pyridine may be used to promote the acylation reaction. The acylation reaction is preferably conducted in the presence of a suitable base to scavenge the acid generated during the reaction. Suitable bases include, by way of example, tertiary amines, such as triethylamine, diisopropylethylamine, N-methylmorpholine and the like. Alternatively, the reaction can be conducted under Schotten-Baumann-type conditions using aqueous alkali, such as sodium hydroxide and the like.

Examples of acyl halides and carboxylic acid anhydrides suitable for use in this reaction include, but are not limited to, 2-methylpropionyl chloride, trimethylacetyl chloride, phenylacetyl chloride, benzoyl chloride, 2-bromobenzoyl chloride, 2-methylbenzoyl chloride, 2-trifluoro-methylbenzoyl chloride, isonicotinoyl chloride, nicotinoyl chloride, picolinoyl chloride, acetic anhydride, succinic anhydride, and the like. Carbamyl chlorides, such as N,N-dimethylcarbamyl chloride, N,N-diethylcarbamyl chloride and the like, can also be used in this reaction to provide ureas. Similarly, dicarbonates, such as di-tert-butyl dicarbonate, may be employed to provide carbamates.

In a similar manner, a compound of formula I-VII or an intermediate thereof containing a primary or secondary amino group may be N-sulfonated to form a sulfonamide using a sulfonyl halide or a sulfonic acid anhydride. Sulfonyl halides and sulfonic acid anhydrides suitable for use in this reaction include, but are not limited to, methanesulfonyl chloride, chloromethanesulfonyl chloride, p-toluenesulfonyl chloride, trifluoromethanesulfonic anhydride, and the like. Similarly, sulfamoyl chlorides, such as dimethylsulfamoyl chloride, can be used to provide sulfamides (e.g., >N—SO₂—N<).

Additionally, a primary and secondary amino group present on a substituent of a compound of formula I-VII or an intermediate thereof can be reacted with an isocyanate or a thioisocyanate to give a urea or thiourea, respectively. This reaction is typically conducted by contacting the amino compound with at least one equivalent, preferably about 1.1 to about 1.2 equivalents, of the isocyanate or thioisocyanate in an inert diluent, such as toluene and the like, at a temperature ranging from about 24° C. to about 37° C. for about 12 to about 24 hours. The isocyanates and thioisocyanates used in this reaction are commercially available or can be prepared from commercially available compounds using well-known synthetic procedures. For example, isocyanates and thioisocyanates are readily prepared by reacting the appropriate amine with phosgene or thiophosgene. Examples of isocyanates and thioisocyanates suitable for use in this reaction include, but are not limited to, ethyl isocyanate, n-propyl isocyanate, 4-cyanophenyl isocyanate, 3-methoxyphenyl isocyanate, 2-phenylethyl isocyanate, methyl thioisocyanate, ethyl thioisocyanate, 2-phenylethyl thioisocyanate, 3-phenylpropyl thioisocyanate, 3-(N,N-diethylamino)propyl thioisocyanate, phenyl thioisocyanate, benzyl thioisocyanate, 3-pyridyl thioisocyanate; fluorescein isothiocyanate (isomer I) and the like.

Furthermore, when a compound of formula I-VII or an intermediate thereof contains a primary or secondary amino group, the amino group can be reductively alkylated using aldehydes or ketones to form a secondary or tertiary amino group. This reaction is typically conducted by contacting the amino compound with at least one equivalent, preferably about 1.1 to about 1.5 equivalents, of an aldehyde or ketone and at least one equivalent based on the amino compound of a metal hydride reducing agent, such as sodium cyanoborohydride, in an inert diluent, such as methanol, tetrahydrofuran, mixtures thereof and the like, at a temperature ranging from about 0° C. to about 50° C. for about 1 to about 72 hours. Aldehydes and ketones suitable for use in this reaction include, by way of example, benzaldehyde, 4-chlorobenzaldehyde, valeraldehyde and the like.

In a similar manner, when a compound of formula I-VII or an intermediate thereof has a substituent containing a hydroxyl group, the hydroxyl group can be further modified or derivatized either before or after the above coupling reactions to provide, by way of example, ethers, carbamates and the like. Compounds having a hydroxyl group on the $R^3$ substituent, for example, can be prepared using an amino acid derivative derived from tyrosine and the like in the above-described reactions.

By way of example, a compound of formula I-VII or an intermediate thereof having a substituent containing a hydroxyl group, such as where $R^3$ is a (4-hydroxyphenyl) methyl group, can be readily O-alkylated to form ethers. This O-alkylation reaction is typically conducted by contacting the hydroxy compound with a suitable alkali or alkaline earth metal base, such as potassium carbonate, in an inert diluent, such as acetone, 2-butanone and the like, to form the alkali or alkaline earth metal salt of the hydroxyl group. This salt is generally not isolated, but is reacted in situ with at least one equivalent of an alkyl or substituted alkyl halide or sulfonate, such as an alkyl chloride, bromide, iodide, mesylate or tosylate, to afford the ether. Generally, this reaction is conducted at a temperature ranging from about 60° C. to about 150° C. for about 24 to about 72 hours. Preferably, a catalytic amount of sodium or potassium iodide is added to the reaction mixture when an alkyl chloride or bromide is employed in the reaction.

Examples of alkyl or substituted alkyl halides and sulfonates suitable for use in this reaction include, but are not limited to, tert-butyl bromoacetate, N-tert-butyl chloroacetamide, 1-bromoethylbenzene, ethyl α-bromophenylacetate, 2-(N-ethyl-N-phenylamino)ethyl chloride, 2-(N,N-ethylamino)ethyl chloride, 2-(N,N-diisopropylamino)ethyl chloride, 2-(N,N-dibenzylamino)ethyl chloride, 3-(N,N-ethylamino)propyl chloride, 3-(N-benzyl-N-methylamino)propyl chloride, N-(2-chloroethyl)morpholine, 2-(hexamethyleneimino)ethyl chloride; 3-(N-methylpiperazine)propyl chloride, 1-(3-chlorophenyl)-4-(3-chloropropyl) piperazine, 2-(4-hydroxy-4-phenylpiperidine)ethyl chloride, N-tert-butyloxycarbonyl-3-piperidinemethyl tosylate, and the like.

Alternatively, a hydroxyl group present on a substituent of a compound of formula I-VII or an intermediate thereof can be O-alkylating using the Mitsunobu reaction. In this reaction, an alcohol, such as 3-(N,N-dimethylamino)-1-propanol and the like, is reacted with about 1.0 to about 1.3 equivalents of triphenylphosphine and about 1.0 to about 1.3 equivalents of diethyl azodicarboxylate in an inert diluent, such as tetrahydrofuran, at a temperature ranging from about −10° C. to about 5° C. for about 0.25 to about 1 hour. About 1.0 to about 1.3 equivalents of a hydroxy compound, such as N-tert-butyltyrosine methyl ester, is then added and the reaction mixture is stirred at a temperature of about 0° C. to about 30° C. for about 2 to about 48 hours to provide the O-alkylated product.

In a similar manner, a compound of formula I-VII or an intermediate thereof containing an aryl hydroxy group can be reacted with an aryl iodide to provide a diaryl ether. Generally, this reaction is conducted by forming the alkali metal salt of the hydroxyl group using a suitable base, such as sodium hydride, in an inert diluent such as xylenes at a temperature of about −25° C. to about 10° C. The salt is then treated with about 1.1 to about 1.5 equivalents of cuprous bromide dimethyl sulfide complex at a temperature ranging from about 10° C. to about 30° C. for about 0.5 to about 2.0 hours, followed by about 1.1 to about 1.5 equivalents of an aryl iodide, such as sodium 2-iodobenzoate and the like. The reaction is then heated to about 70° C. to about 150° C. for about 2 to about 24 hours to provide the diaryl ether.

Additionally, a hydroxy-containing compound can also be readily derivatized to form a carbamate. In one method for preparing such carbamates, a hydroxy compound of formula I-VII or an intermediate thereof is contacted with about 1.0 to about 1.2 equivalents of 4-nitrophenyl chloroformate in an inert diluent, such as dichloromethane, at a temperature ranging from about −25° C. to about 0° C. for about 0.5 to about 2.0 hours. Treatment of the resulting carbonate with an excess, preferably about 2 to about 5 equivalents, of a trialkylamine, such as triethylamine, for about 0.5 to 2 hours, followed by about 1.0 to about 1.5 equivalents of a primary or secondary amine provides the carbamate. Examples of amines suitable for using in this reaction include, but are not limited to, piperazine, 1-methylpiperazine, 1-acetylpiperazine, morpholine, thiomorpholine, pyrrolidine, piperidine and the like.

Alternatively, in another method for preparing carbamates, a hydroxy-containing compound is contacted with about 1.0 to about 1.5 equivalents of a carbamyl chloride in an inert diluent, such as dichloromethane, at a temperature ranging from about 25° C. to about 70° C. for about 2 to about 72 hours. Typically, this reaction is conducted in the presence of a suitable base to scavenge the acid generated during the reaction. Suitable bases include, by way of example, tertiary amines, such as triethylamine, diisopropylethylamine, N-methylmorpholine and the like. Additionally, at least one equivalent (based on the hydroxy compound) of 4-(N,N-dimethylamino)pyridine is preferably added to the reaction mixture to facilitate the reaction. Examples of carbamyl chlorides suitable for use in this reaction include, by way of example, dimethylcarbamyl chloride, diethylcarbamyl chloride and the like.

Likewise, when a compound of formula I-VII or an intermediate thereof contains a primary or secondary hydroxyl group, such hydroxyl groups can be readily converted into a leaving group and displaced to form, for example, amines, sulfides and fluorides. Generally, when a chiral compound is employed in these reactions, the stereochemistry at the carbon atom attached to the derivatized hydroxyl group is typically inverted.

These reactions are typically conducted by first converting the hydroxyl group into a leaving group, such as a tosylate, by treatment of the hydroxy compound with at least one equivalent of a sulfonyl halide, such as p-toluenesulfonyl chloride and the like, in pyridine. This reaction is generally conducted at a temperature of from about 0° C. to about 70° C. for about 1 to about 48 hours. The resulting tosylate can then be readily displaced with sodium azide, for example, by contacting the tosylate with at least one equivalent of sodium azide in an inert diluent, such as a mixture of N,N-dimethylformamide and water, at a temperature ranging from about 0° C. to about 37° C. for about 1 to about 12 hours to provide the corresponding azido compound. The azido group can then be reduced by, for example, hydrogenation using a palladium on carbon catalyst to provide the amino ($-NH_2$) compound.

Similarly, a tosylate group can be readily displaced by a thiol to form a sulfide. This reaction is typically conducted by contacting the tosylate with at least one equivalent of a thiol, such as thiophenol, in the presence of a suitable base, such as 1,8-diazabicyclo[5.4.0]undec-7-ene (DBU), in an inert diluent, such as N,N-dimethylformamide, at a temperature of from about 0° C. to about 37° C. for about 1 to about 12 hours to provide the sulfide. Additionally, treatment of a tosylate with morpholinosulfur trifluoride in an inert diluent, such as dichloromethane, at a temperature ranging from about 0° C. to about 37° C. for about 12 to about 24 hours affords the corresponding fluoro compound.

Furthermore, a compound of formula I-VII or an intermediate thereof having a substituent containing an iodoaryl group, for example, when $R^3$ is a (4-iodophenyl)methyl group, can be readily converted either before or after the above coupling reactions into a biaryl compound. Typically, this reaction is conducted by treating the iodoaryl compound with about 1.1 to about 2 equivalents of an arylzinc iodide, such as 2-(methoxycarbonyl)phenylzinc iodide, in the presence of a palladium catalyst, such as palladium tetra(triphenylphosphine), in an inert diluent, such as tetrahydrofuran, at a temperature ranging from about 24° C. to about 30'C until reaction completion. This reaction is further described, for example, in Rieke, *J. Org. Chem.* 1991, 56, 1445. Additional methods for preparing biaryl derivatives are disclosed in International Publication Number WO 98/53817, published Dec. 3, 1998, the disclosure of which is incorporated herein by reference in its entirety.

In some cases, the compounds of formula I-VII or intermediates thereof may contain substituents having one or more sulfur atoms. When present, such sulfur atoms can be oxidized either before or after the above coupling reactions to provide a sulfoxide or sulfone compound using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. The oxidation reaction is typically conducted by contacting the sulfide compound with about 0.95 to about 1.1 equivalents of the oxidizing reagent in an inert diluent, such as dichloromethane, at a temperature ranging from about −50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent. Such reactions are described further in March, "*Advanced Organic Chemistry*", 4th Ed., pp. 1201-1202, Wiley Publisher, 1992.

Other procedures and reaction conditions for preparing the compounds of this invention are described in the examples set forth below. Additionally, other procedures for preparing compounds useful in certain aspects of this invention are disclosed in U.S. Ser. No. 11/145,489, filed on June 2, 2005 even date herewith, entitled "Compounds Which Inhibit Leucocyte Adhesion Mediated by VLA-4" (Attorney Docket No. 002010-525); the disclosure of which is incorporated herein by reference in its entirety.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I-VII above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated M a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

Formulation Example 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
|---|---|
| Active Ingredient | 250.0 mg |
| Isotonic saline | 1000 ml |

Formulation Example 10

A topical formulation may be prepared as follows:

| Ingredient | Quantity |
|---|---|
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See. e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Utility

The compounds of this invention can be employed to bind VLA-4 ($\alpha_4\beta_1$ integrin) in biological samples, i.e., the compounds bind VLA-4 with an $IC_{50}$ of 15 µM or less in a competitive binding assay as described herein. Accordingly, these compounds have utility in, for example, assaying such samples for VLA-4. In such assays, the compounds can be bound to a solid support and the VLA-4 sample added thereto. The amount of VLA-4 in the sample can be determined by conventional methods such as use of a sandwich ELISA assay. Alternatively, labeled VLA-4 can be used in a competitive assay to measure for the presence of VLA-4 in the sample. Other suitable assays are well known in the art.

In addition, certain of the compounds of this invention inhibit, in vivo, adhesion of leukocytes to endothelial cells mediated by VLA-4 by competitive binding to VLA-4. Accordingly, the compounds of this invention can be used in the treatment of diseases mediated by VLA-4 or leucocyte adhesion. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis; rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The biological activity of the compounds identified above may be assayed in a variety of systems. For example, a compound can be immobilized on a solid surface and adhesion of cells expressing VLA-4 can be measured. Using such formats, large numbers of compounds can be screened. Cells suitable for this assay include any leukocytes known to express VLA-4 such as T cells, B cells, monocytes, eosinophils, and basophils. A number of leukocyte cell lines can also be used, examples include Jurkat and U937.

The test compounds can also be tested for the ability to competitively inhibit binding between VLA-4 and VCAM-1, or between VLA-4 and a labeled compound known to bind VLA-4 such as a compound of this invention or antibodies to VLA-4. In these assays, the VCAM-1 can be immobilized on a solid surface. VCAM-1 may also be expressed as a recombinant fusion protein having an Ig tail (e.g., IgG) so that binding to VLA-4 may be detected in an immunoassay. Alternatively, VCAM-1 expressing cells, such as activated endothelial cells or VCAM-1 transfected fibroblasts can be used. For assays to measure the ability to block adhesion to brain endothelial cells, the assays described in International Patent Application Publication No. WO 91/05038 are particularly preferred. This application is incorporated herein by reference in its entirety.

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3$H, $^{125}$I, $^{35}$S, $^{14}$C, or $^{32}$P labelled compounds or the like. Non-radioactive labels include ligands which bind to labelled antibodies, fluorophores, chemiluminescent agents, enzymes and antibodies which can serve as specific binding pair members for a labelled ligand. The choice of label depends on sensitivity required, ease of conjugation with the compound, stability requirements, and available instrumentation.

Appropriate in vivo models for demonstrating efficacy in treating inflammatory responses include EAE (experimental autoimmune encephalomyelitis) in mice, rats, guinea pigs or primates, as well as other inflammatory models dependent upon α4 integrins.

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83-93).

For diagnostic purposes, a wide variety of labels may be linked to the compounds, which may provide, directly or indirectly, a detectable signal. Thus, the compounds of the subject invention may be modified in a variety of ways for a variety of end purposes while still retaining biological activity. In addition, various reactive sites may be introduced at the terminus for linking to particles, solid substrates, macromolecules, or the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications such as monitoring inflammatory responses by detecting the presence of leukocytes expressing VLA-4. The compounds of this invention can also be used for isolating or labeling such cells. In addition, as mentioned above, the compounds of the invention can be used to assay for potential inhibitors of VLA-4/VCAM-1 interactions.

For in vivo diagnostic imaging to identify, e.g., sites of inflammation, radioisotopes are typically used in accordance with well known techniques. The radioisotopes may be bound, to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which are well known. In general, any conventional method for visualizing diagnostic imaging can be used. Usually gamma- and positron-emitting radioisotopes are used for camera imaging and paramagnetic isotopes are used for MRI. Thus, the compounds can be used to monitor the course of amelioration of an inflammatory response in an individual. By measuring the increase or decrease in lymphocytes expressing VLA-4 it is possible to determine whether a particular therapeutic regimen aimed at ameliorating the disease is effective.

The pharmaceutical compositions of the present invention can be used to block or inhibit cellular adhesion associated with a number of diseases and disorders. For instance, a number of inflammatory disorders are associated with integrins or leukocytes. Treatable disorders include, e.g., transplantation rejection (e.g., allograft rejection), Alzheimer's disease, atherosclerosis, AIDS dementia, diabetes (including acute juvenile onset diabetes), retinitis, cancer metastases, rheumatoid arthritis, acute leukocyte-mediated lung injury (e.g., adult respiratory distress syndrome), asthma, nephritis, and acute and chronic inflammation, including atopic dermatitis, psoriasis, myocardial ischemia, and inflammatory bowel disease (including Crohn's disease and ulcerative colitis). In preferred embodiments the pharmaceutical compositions are used to treat inflammatory brain disorders, such as multiple sclerosis (MS), viral meningitis and encephalitis.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology* (3d ed., Raven Press, 1993).

Another indication for the compounds of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. $CD8^+$ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420-425 (1996); Georczynski et al., *Immunology* 87, 573-580 (1996); Georczynski et al., *Transplant. Immunol.* 3, 55-61 (1995); Yang et al., *Transplantation* 60, 71-76 (1995); Anderson et al., *APMIS* 102, 23-27 (1994).

A related use for compounds of this invention which bind to VLA-4 is in modulating the immune response involved in "graft versus host" disease (GVHD). See e.g., Schlegel et al., *J. Immunol.* 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is inhibiting tumor metastasis. Several tumor cells have been reported to express VLA-4 and compounds which bind VLA-4 block adhesion of such cells to endothelial cells. Steinback et al., *Urol. Res.* 23, 175-83 (1995); Orosz et al., *Int. J. Cancer* 60, 867-71 (1995); Freedman et al., *Leuk. Lymphoma* 13, 47-52 (1994); Okahara et al., *Cancer Res.* 54, 3233-6 (1994).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems. Suitable formulations for use in the present invention are found in *Remington's Pharmaceutical Sciences*, Mace Publishing. Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 µg to about 500 µg per kilogram body weight, preferably about 100 µg to about 300 µg per kilogram body weight. Suitable dosage ranges for intranasal administration are generally about 0.1 µg to 1 mg per kilogram body weight. Effective doses can be extrapolated from dose-response curves derived from in vitro or animal model test systems.

Compounds of this invention are also capable of binding or antagonizing the actions of $\alpha_6\beta_1$, $\alpha_9\beta_1$, $\alpha_4\beta_7$, $\alpha_d\beta_2$, $\alpha_e\beta_7$ integrins (although $\alpha_4\beta_1$ and $\alpha_9\beta_1$ are preferred in this invention). Accordingly, compounds of this invention are also useful for preventing or reversing the symptoms, disorders or diseases induced by the binding of these integrins to their respective ligands.

For example, International Publication Number WO 98/53817, published Dec. 3, 1998 (the disclosure of which is incorporated herein by reference in its entirety) and references cited therein describe disorders mediated by $\alpha_4\beta_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., *J. Exp. Med.* 1998, 188(11) 2187-2191. Compounds that bind $\alpha_e\beta_7$ integrin are also useful for the treatment of systemic lupus erythematosus (see, for example, M. Pang et al., *Arthritis Rheum.* 1998, 41(8), 1456-1463); Crohn's disease, ulcerative colitis and infammatory bowel disease (IBD) (see, for example, D. Elewaut et al., *Scand J. Gastroenterol* 1998, 33(7) 743-748); Sjogren's syndrome (see, for example, U. Kroneld et al., *Scand J. Gastroenterol* 1998, 27(3), 215-218); and rheumatoid arthritis (see, for example, *Scand J. Gastro-* enterol 1996, 44(3), 293-298). And compounds that bind $\alpha_6\beta_1$ may be useful in preventing fertilization (see, for example, H. Chen et al., *Chem. Biol.* 1999, 6, 1-10).

Certain of the compounds within the generic formulas described herein are also useful as synthetic intermediates for other compounds of this invention as illustrated in the examples herein.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| aq or aq. = | aqueous |
| AcOH | acetic acid |
| bd = | broad doublet |
| bm = | broad multiplet |
| bs = | broad singlet |
| Bn = | benzyl |
| Boc = | N-tert-butoxylcarbonyl |
| Boc$_2$O = | di-tert-butyl dicarbonate |
| BOP = | belizotriazol-1-yloxy-tris(dimethylamino)phosphonium hexafluorophosphate |
| Cbz = | carbobenzyloxy |
| CHCl$_3$ = | chloroform |
| CH$_2$Cl$_2$ = | dichloromethane |
| (COCl)$_2$ = | oxalyl chloride |
| d = | doublet |
| dd = | doublet of doublets |
| dt = | doublet of triplets |
| DBU = | 1,8-diazabicyclo[5.4.0]undec-7-ene |
| DCC = | 1,3-dicyclohexylcarbodiimide |
| DMAP = | 4-N,N-dimethylaminopyridine |
| DME = | ethylene glycol dimethyl ether |
| DMF = | N,N-dimethylformamide |
| DMSO = | dimethylsulfoxide |
| EDC = | 1-(3-dimethylaminopropyl)-3-ethylcarbodiimide hydrochloride |
| Et$_3$N = | triethylamine |
| Et$_2$O = | diethyl ether |
| EtOAc = | ethyl acetate |
| EtOH = | ethanol |
| eq or eq. = | equivalent |
| Fmoc = | N-(9-fluorenylmethoxycarbonyl) |
| FmocONSu = | N-(9-fluorenylmethoxycarbonyl)-succinimide |
| g = | grams |
| h = | hour |
| H$_2$O = | water |
| HBr = | hydrobromic acid |
| HCl = | hydrochloric acid |
| HOBT = | 1-hydroxybenzotriazole hydrate |
| hr = | hour |
| K$_2$CO$_3$ = | potassium carbonate |
| L = | liter |
| m = | multiplet |
| MeOH = | methanol |
| mg = | milligram |
| MgSO$_4$ = | magnesium sulfate |
| mL = | milliliter |
| mm = | millimeter |
| mM = | millimolar |
| mmol = | millimol |
| mp = | melting point |
| N = | normal |
| NaCl = | sodium chloride |
| Na$_2$CO$_3$ = | sodium carbonate |
| NaHCO$_3$ = | sodium bicarbonate |
| NaOEt = | sodium ethoxide |
| NaOH = | sodium hydroxide |
| NH$_4$Cl = | ammonium chloride |

-continued

| | |
|---|---|
| NMM = | N-methylmorpholine |
| Phe = | L-phenylalanine |
| Pro = | L-proline |
| psi = | pounds per square inch |
| PtO$_2$ = | platinum oxide |
| q = | quartet |
| quint. = | quintet |
| rt = | room temperature |
| s = | singlet |
| sat = | saturated |
| t = | triplet |
| t-BuOH = | tert-butanol |
| TFA = | trifluoroacetic acid |
| THF = | tetrahydrofuran |
| TLC or tlc = | thin layer chromatography |
| Ts = | tosyl |
| TsCl = | tosyl chloride |
| TsOH = | tosylate |
| µL = | microliter |

The following Methods may be used to prepare the compounds of this invention.

Method A

Methyl Ester Preparation Procedure

Amino acid methyl esters can be prepared using the method of Brenner and Huber. *Helv. Chim. Acta* 1953, 36, 1109.

Method B

BOP Coupling Procedure

The desired dipeptide ester was prepared by the reaction of a carboxylic acid (1 equivalent) with the appropriate amino acid ester or amino acid ester hydrochloride (1 equivalent), benzotriazol-1-yloxy-tris(dimethylamino)phosphonium hexafluorophosphate [BOP] (2.0 equivalent), triethylamine (1.1 equivalent), and DMF. The reaction mixture was stirred at room temperature overnight. The crude product is purified flash chromatography to afford the dipeptide ester.

Method C

Hydrogenation Procedure I

Hydrogenation was performed using 10% palladium on carbon (10% by weight) in methanol at 30 psi overnight. The mixture was filtered through a pad of Celite and the filtrate concentrated to yield the desired compound.

Method D

Hydrolysis Procedure I

To a chilled (0° C.) THF/H$_2$O solution (2:1, 5-10 mL) of the appropriate ester was added LiOH (or NaOH) (0.95 equivalents). The temperature was maintained at 0° C. and the reaction was complete in 1-3 hours. The reaction mixture was extracted with ethyl acetate and the aqueous phase was lyophilized resulting in the desired carboxylate salt.

Method E

Ester Hydrolysis Procedure II

To a chilled (0° C.) THF/H$_2$O solution (2:1, 5-10 mL) of the appropriate ester was added LiOH (1.1 equivalents). The temperature was maintained at 0° C. and the reaction was complete in 1-3 hours. The reaction mixture was concentrated and the residue was taken up into H$_2$O and the pH adjusted to 2-3 with aqueous HCl. The product was extracted with ethyl acetate and the combined organic phase was washed with brine, dried over MgSO$_4$, filtered and concentrated to yield the desired acid.

Method F

Ester Hydrolysis Procedure III

The appropriate ester was dissolved in dioxane/H$_2$O (1:1) and 0.9 equivalents of 0.5 N NaOH was added. The reaction was stirred for 3-16 hours and then concentrated. The resulting residue was dissolved in H$_2$O and extracted with ethyl acetate. The aqueous phase was lyophilized to yield the desired carboxylate sodium salt.

Method G

BOC Removal Procedure

Anhydrous hydrochloride (HCl) gas was bubbled through a methanolic solution of the appropriate Boc-amino acid ester at 0° C. for 15 minutes and the reaction mixture was stirred for three hours. The solution was concentrated to a syrup and dissolved in Et$_2$O and reconcentrated. This procedure was repeated and the resulting solid was placed under high vacuum overnight.

Method H tert-Butyl Ester Hydrolysis Procedure I

The tert-butyl ester was dissolved in CH$_2$Cl$_2$ and treated with TFA. The reaction was complete in 1-3 hr at which time the reaction mixture was concentrated and the residue dissolved in H$_2$O and lyophilized to yield the desired acid.

Method I

EDC Coupling Procedure I

To a CH$_2$Cl$_2$ solution (5-20 mL) of a carboxylic acid (1 equivalent), the appropriate amino acid ester hydrochloride (1 equivalent), N-(1.1-2.2 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was poured into H$_2$O and the organic phase was washed with sat. NaHCO$_3$, brine, dried (MgSO$_4$ or Na$_2$SO$_4$), filtered and concentrated. The crude product was purified by column chromatography.

Method J

EDC Coupling Procedure II

To a DMF solution (5-20 mL) of a carboxylic acid (1 equivalent), the appropriated amino acid ester hydrochloride (1 equivalent); Et$_3$N (1.1 equivalents) and 1-hydroxybenzotriazole (2 equivalents) were mixed, placed in an ice bath and 1-(3-dimethylaminopropyl)-3-ethyl carbodiimide (1.1 equivalents) added. The reaction was allowed to rise to room temperature and stirred overnight. The reaction mixture was partitioned between EtOAc and H$_2$O and the organic phase washed with 0.2 N citric acid, H$_2$O, sat. NaHCO$_3$, brine, dried (MgSO$_4$ or Na$_2$SO$_4$), filtered and concentrated. The crude product was purified by column chromatography or preparative TLC.

Method K tert-Butyl Ester Hydrolysis Procedure II

The tert-butyl ester was dissolved in CH$_2$Cl$_2$ (5 mL) and treated with TFA (5 mL). The reaction was complete in 1-3 hours at which time the reaction mixture was concentrated and the residue dissolved in H$_2$O and concentrated. The residue was redissolved in H$_2$O and lyophilized to yield the desired product.

Method L

Carbamate Formation Procedure I

Into a reaction vial were combined 15.2 mmol, 1.0 eq. of the starting hydroxy compound (typically a tyrosine derivative) and 1.86 g (15.2 mmol, 1.0 eq) DMAP. Methylene chloride (50 mL), triethylamine (2.12 mL, 1.54 g, 15.2 mmol, 1.0 eq), and dimethylcarbamyl chloride (1.68 mL, 1.96 g, 18.2 mmol, 1.2 eq) were then added. The vial was capped tightly, and the reaction solution swirled to obtain a homogeneous solution. The reaction solution was then heated to 40° C. After 48 h, TLC of the resulting colorless solution indicated complete conversion. The work-up of the reaction solution was as follows: 50 mL EtOAc and 50 mL hexanes was added to the reaction mixture, and the resulting mixture was washed with 0.5 M citric acid (3×50 mL), water (2×50 mL), 10% K$_2$CO$_3$(2×50 mL), and sat. NaCl (1×50 mL); dried with MgSO$_4$, filtered and evaporated to afford the desired compound.

Method M

Carbamate Formation Procedure II

Into a reaction vial were combined 84.34 mmol (1.0 eq) of the starting hydroxy compound (typically a tyrosine derivative) and 17.0 g (84.34 mmol, 1.0 eq) 4-nitrophenyl chloroformate. Methylene chloride (700 mL) was added and the vial was capped with a septum. A nitrogen line was attached and the vial was immersed in a 4:1 water/ethanol dry ice slurry with stirring to cool to −15° C. Triethylamine (29.38 mL, 21.33 g, 210.81 mmol, 2.5 eq) was added over five minutes with stirring and the stirring was continued at −10 to −15° C. for 1 h. N-Methyl piperazine (9.35 mL, 8.45 g, 84.34 mmol, 1.0 eq) was added over three minutes with stirring and stirring was continued overnight while warming to room temperature. The reaction mixture was diluted with 700 mL hexanes and the resulting mixture was washed repeatedly with 10% K$_2$CO$_3$, until no yellow color (from 4-nitrophenol) is observed in the aqueous layer. The mixture was then washed with sat. NaCl, dried over anhydrous MgSO$_4$, filtered and evaporated. The residue was dissolved in 500 mL of ethanol and evaporated to remove triethylamine. The residue was again dissolved in 500 mL of ethanol and evaporated to remove triethylamine. The residue was then dissolved in 400 mL of ethanol and 600 mL of water was added with stirring to precipitate a solid or oil. If an oil if formed, the oil is stirred vigorously to induce it to solidify. The solid is then isolated by filtration. Dissolution, precipitation, and filtration are repeated once and the resulting solid is rinsed with water to remove traces of yellow color. The solid is then subjected to high vacuum until the mass remains constant thereby affording the desired carbamyloxy compound.

Method N Preparation of 5-Iodo-4(3H)-pyrimidinone The procedure of Sakamoto et. al. (Chem. Pharm. Bull. 1986, 34(7), 2719-2724) was used to convert 4(3H)-pyrimidinone into 5-iodo-4(3H)-pyrimidinone, which was of sufficient purity for conversion to 4-chloro-5-iodopyrimidine.

Method O

Preparation of 4-Chloro-5-iodopyrimidine

5-Iodo-4(3H)-pyrimidinone (1 eq.) was suspended in toluene to which was added $POCl_3$ (2.0 eq.). The reaction mixture was heated to reflux for 3 hours, and then cooled and concentrated. The residue was suspended in water, adjusted to pH=7 by addition of 4N sodium hydroxide, and extracted with ethyl acetate. The organic extracts were washed with brine, dried ($MgSO_4$), filtered and stripped to give a red oil. The crude product was dissolved in methanol and silica gel was added. Following concentration, the coated silica gel was loaded onto a plug of silica gel and elution with ethyl acetate/hexanes yielded the title compound.

Method P

Preparation of N-(5-Iodopyrimidin-4-yl)-L-4-(N,N-dimethylcarbamyloxy)phenylalanine tert-Butyl Ester A solution 4-chloro-5-iodopyrimidine (1.0 eq.), L-4-(N,N-dimethylcarbamyloxy)-phenylalanine tert-butyl ester (1.0 eq), and N,N-diisoproylethyl amine (2.0 eq) in tetrahydrofuran was heated at reflux for 16 hours. The reaction mixture was then cooled and diluted with water and ethyl acetate. The organic phase was washed with 0.2 N citric acid, water, saturated $NaHCO_3$, brine, dried ($MgSO_4$), filtered and concentrated. The residue was purified by silica gel chromatography using ethyl acetate/hexanes to afford the title compound.

Method Q

Suzuki Coupling Procedure I

To an ethyleneglycol dimethyl ether solution of tetrakis(triphenylphosphine)palladium (0.04 eq) was added N-(5-iodopyrimidin-4-yl)-L-4-(N,N-dimethylcarbamyloxy)phenylalanine tert-butyl ester (1.0 eq.). After stirring for approximately ten minutes a boronic acid or ester (1.2 eq) and 2M $Na_2CO_3$ (2.0 eq) were added, and the reaction flask was evacuated and then flushed with nitrogen gas. The reaction was heated at reflux from three to sixteen hours. The reaction mixture was then cooled, diluted with water and ethyl acetate, and the organic phase was washed with 0.2 N citric acid, water, saturated $NaHCO_3$, brine, dried ($MgSO_4$), filtered and concentrated. Alternatively, the cooled reaction mixture was diluted with ethyl acetate and washed with water, saturated $NaHCO_3$, dried ($MgSO_4$), filtered and concentrated. Either column chromatography or preparative thin layer chromatography on silica gel using ethyl acetate/hexanes afforded the desired product.

Method R

Suzuki Coupling Procedure II

To a dimethylformamide solution of tetrakis(triphenylphosphine)-palladium (0.02-0.05 eq) was added N-(5-iodopyrimidin-4-yl)-L-4-(N,N dimethylcarbamyloxy)phenylalanine tert-butyl ester (1.0 eq.). After stirring for approximately ten minutes, the boronic acid (1.1-4.0 eq) and $K_3PO_4$ (1.5-2.0 eq) were added, and the reaction was heated at 100° C. for three to sixteen hours. The reaction mixture was then cooled, diluted with water and ethyl acetate, and the organic phase was washed with 0.2 N citric acid, water, saturated $NaHCO_3$, brine, dried ($MgSO_4$), filtered and concentrated. Either column chromatography or preparative thin layer chromatography on silica gel using ethyl acetate/hexanes afforded the desired product.

Method S

Suzuki Coupling Procedure III

An ethyleneglycol dimethyl ether/2M $Na_2CO_3$ (1:1 by volume) solution of tetrakis(triphenylphosphine)palladium (0.04 eq), N-(5-iodopyrimidin-4-yl)-L-4-(N,N-dimethylcarbamyloxy)phenylalanine tert-butyl ester (1.0 eq.), the boronic acid (1.1 eq) and lithium chloride (3.0 eq) was heated to reflux for approximately six hours. The cooled reaction mixture was diluted with ethyl acetate and washed with water, brine, dried ($MgSO_4$), filtered and concentrated. The residue was purified by silica gel column chromatography using ethyl acetate/hexanes to afford the desired product.

Method T

Suzuki Coupling Procedure IV

An ethyleneglycol dimethyl ether/2M $Na_2CO_3$, (1:1 by volume) solution of tetrakis(triphenylphosphine)palladium (0.05 eq), N-(5-iodopyrimidin-4-yl)-L-4-(N,N-dimethylcarbamyloxy)phenylalanine tert-butyl ester (1.0 eq.), the boronic acid (1.5 eq) and tri-o-tolylphosphine (0.1 eq) was heated to reflux for approximately three hours. The cooled reaction mixture was diluted with ethyl acetate and water and washed with water, brine, dried ($MgSO_4$), filtered and concentrated. The residue was purified by preparative thin layer chromatography on silica gel using ethyl acetate/hexanes to afford the desired product.

Method U

Heck Reaction Procedure I

A dimethylformamide solution of N-(5-iodopyrimidin-4-yl)-L-4-(N,N-dimethylcarbamyloxy)phenylalanine tert-butyl ester (1.0 eq.), N,N-dimethylacrylamide (2.0 eq), and triethylamine (6.0 eq) was degassed with nitrogen and then dichlorobis-(triphenylphosphine)palladium was added. The reaction was warmed to 90° C. under a stream of nitrogen for 16 hours. The cooled reaction mixture was diluted with ethyl acetate and water and washed with water, brine, dried ($MgSO_4$), filtered and concentrated. The residue was purified by column chromatography on silica gel using ethyl acetate/hexanes followed by preparative thin layer chromatography on silica gel using ethyl acetate/hexanes to afford the desired product.

Method V

Hydrogenation Procedure II

N-(5-(2-N,N-dimethylcarbamylethyl)pyrimidin-4-yl)-L-4-(N,N-dimethylcarbamyloxy)-phenylalanine tert-butyl ester was dissolved in ethanol to which was added 10% palladium on carbon. The reaction mixture was hydrogenated at 35 psi hydrogen for approximately five hours. The reaction mixture was filtered through a pad of Celite, and the filtrate was concentrated. The residue was purified by preparative thin layer chromatography on silica gel using methanol/dichloromethane to afford the desired product.

Method W

Heck Reaction Procedure II

To a tetrahydrofuran solution of N-(5-iodopyrimidin-4-yl)-L-4-(N,N-dimethylcarbamyloxy)phenylalanine tert-butyl ester (1.0 eq) dichlorobis(triphenylphosphine)palladium, triethylamine (0.05 eq) and triphenylphosphine (0.025 eq) was added phenylacetylene (1.5 eq) and triethylamine (1.5 eq). After twenty minutes, copper (I) iodide (0.012 eq) was added, and the resulting mixture was stirred overnight at room temperature. The reaction mixture was then diluted with ethyl acetate and water and washed with 0.2 N citric acid, water, saturated NaHCO$_3$, brine, dried (MgSO$_4$), filtered and concentrated. The residue was chromatographed on a silica gel column using ethyl acetate/hexanes. $^1$H NMR analysis showed that the desired product to be contaminated with the iodopyrimidine starting material. However, the product was used without further purification.

Method X

Hydrogenation Procedure III

Crude N-(5-(2-phenylethynyl)pyrimidin-4-yl)-L-4-(N,N-dimethylcarbamyloxy)phenylalanine tert-butyl ester was dissolved in ethanol to which was added 10% palladium on carbon and sodium acetate (3.0 eq). The reaction mixture was hydrogenated at 40 psi hydrogen for approximately three hours, then filtered through a pad of Celite, and the filtrate concentrated. The residue was washed with 0.2 N citric acid, water, saturated NaHCO$_3$, brine, dried (MgSO$_4$), filtered and concentrated. Silica gel column chromatography using ethyl acetate/hexanes yielded the desired product.

Method Y

Preparation of N-6-Chloropyrimidin-4-yl)-L-4-(N,N-dimethylcarbamyloxy)phenylalanine tert-Butyl Ester A solution 4,6-dichloropyrimidine (1.2 eq), L-4-(N,N-dimethylcarbamyloxy)-phenylalanine tert-butyl ester (1.0 eq), and triethylamine (1.05 eq) in ethanol was heated at reflux for 16 hours. The reaction mixture was cooled and concentrated, and the residue was taken-up in water and ethyl acetate. The organic phase was washed with 0.2 N citric acid, water, saturated NaHCO$_3$, brine, dried (MgSO$_4$), filtered and concentrated. The residue was purified by silica gel Chromatography using ethyl acetate/hexanes to afford the title compound.

Method Z

Suzuki Coupling Procedure V

An ethyleneglycol dimethyl ether solution of tetrakis (triphenylphosphine)palladium (0.12 eq), N-(6-chloropyrimidin-4-yl)-L-4-(N,N-dimethylcarbamyloxy)phenylalanine tort-butyl ester (1.0 eq.) and triphenylphosphine (0.05 eq) was stirred for approximately ten minutes. The boronic acid or ester (1.2-2.5 eq) and 2M Na$_2$CO$_3$ (2.0 eq) were added, and the reaction was heated at 90° C. for 16 to 72 hours. The reaction mixture was cooled and concentrated, and the residue was taken up in water and ethyl acetate. The organic phase was washed with 0.2 N citric acid, water, saturated NaHCO$_3$, brine, dried (MgSO$_4$), filtered and concentrated. The residue was purified by preparative thin layer chromatography on silica gel using ethyl acetate/hexanes to afford the desired product.

Method AA

Preparation of N-(6-(N-Alkylamino)pyrimidin-4-yl)-L-4-(N,N-dimethylcarbamyloxy)phenylalanine tert-Butyl Ester A mixture of N-(6-chloropyrimidin-4-yl)-L-4-(N,N-dimethylcarbamyloxy)phenylalanine tert-butyl ester (1.0 eq) and an alkylamine (10.0 eq) was heated in a sealed tube at 120° C. for 16 hours. The reaction mixture was cooled and diluted with ethyl acetate. The organic portion was washed with 0.2 N citric acid, water, saturated NaHCO$_3$, brine, dried (MgSO$_4$), filtered and concentrated. The residue was purified by silica gel chromatography using ethyl acetate/hexanes to afford the desired compound.

Method BB

Preparation of 4-N-Alkylamino-5-bromo-2-chloropyrimidine

A methanol solution of 5-bromo-2,4-dichloropyrimidine (1.0 eq), the alkylamine (1.05 eq, typically L-4-(N,N-dimethylcarbamyloxy)phenylalanine tert-butyl ester), and N,N-diisoproylethylamine (5.0 eq) was heated to 40° C. for 16 hours. The reaction mixture was then concentrated, and the residue was taken up in ethyl acetate. The organic portion was washed with 0.2 N citric acid, water, saturated NaHCO$_3$, brine, dried (MgSO$_4$), filtered and concentrated. The crude material was purified by silica gel chromatography using ethyl acetate/hexanes to afford the desired compound.

Method CC

Preparation of 4-N-Alkylamino-5-bromo-2-N-alkylaminopyrimidine

An isopropanol solution of the 4-N-alkylamino-5-bromo-2-chloropyrimidine (1.0 eq) and an alkylamine (5.0 eq) was heated in sealed tube at 130° C. for 3-5 hours. The reaction mixture was then cooled and washed with 0.2 N citric acid, water, saturated NaHCO$_3$, brine, dried (MgSO$_4$), filtered and concentrated. The crude material was purified by silica gel chromatography using ethyl acetate/hexanes to afford the desired compound.

Method DD

4-N-Alkylamino-5-bromo-2-N-alkylaminopyrimidine Suzuki Coupling Procedure

To an ethyleneglycol dimethyl ether solution of tetrakis (triphenylphosphine)palladium (0.04 eq) was added an 4-N-alkylamino-5-bromo-2-N-alkylaminopyrimidine (1.0 eq.). After stirring for approximately ten minutes, the boronic acid or ester (1.2 eq) and 2M $Na_2CO_3$ (2.0 eq) was added, and the reaction flask was evacuated and then flushed with nitrogen gas. The reaction was heated at reflux for three to four hours. The reaction mixture was then cooled and diluted with water and ethyl acetate, and the organic phase was washed with 0.2 N citric acid, water, saturated $NaHCO_3$, brine, dried ($MgSO_4$), filtered and concentrated. The residue was purified by either silica gel column or preparative thin layer chromatography using ethyl acetate/hexanes to afford the desired product.

Method EE

Preparation of N-tert-Butoxycarbonyl-4-Iodo-L-phenyalanine Methyl Ester

The title compound was prepared from 4-iodo-L-phenylalanine by standard conditions described by Bodanszky and Bodanszky in *The Practice of Peptide Synthesis*; Springer-Verlag: Berlin, 1984.

Method FF

Preparation of N-tert-Butoxycarbonyl-4-(2,6-dimethoxyphenyl)-L-phenyalanine Methyl Ester To a dimethylformamide solution of tetrakis(triphenylphosphine)palladium (0.02-0.05 eq) was added N-tert-butoxycarbonyl-4-(2,6-dimethoxyphenyl)-L-phenyalanine methyl ester (1.0 eq.). After stirring for approximately ten minutes, 2,6-dimethoxyphenyl boronic acid (1.1 eq) and $K_3PO_4$ (2.0 eq) were added, and the reaction was heated at 100° C. for sixteen hours. The reaction mixture was then cooled, diluted with water and ethyl acetate, and the organic phase was washed with 0.2 N citric acid, water, saturated $NaHCO_3$, brine, dried ($MgSO_4$), filtered and concentrated. Column chromatography on silica gel using ethyl acetate/hexanes afforded the desired product.

Method GG

Preparation of 4-(2,6-Dimethoxyphenyl)-L-phenyalanine Methyl Ester Trifluoroacetic Acid Salt A methylene chloride solution of N-tert-butoxycarbonyl-4-(2,6-dimethoxyphenyl)-L-phenyalanine methyl ester was treated with trifluoroacetic acid for six hours at room temperature. Concentration of the volatiles yielded the title compound.

Method HH tert-Butyl Ester Cleavage Procedure III

A methylene chloride solution of the appropriate tert-butyl ester was treated with trifluoroacetic acid at room temperature. After 2-3 hours the volatiles were evaporated, and the residue was treated again with methylene chloride and trifluoroacetic acid. After 2-3 hours the volatiles were evaporated again to yield the desired compound.

Method II

Preparation of N-(5-Allylpyrimidin-4-yl)-L-4-(N,N-dimethyl-carbamyloxy)phenylalanine tert-Butyl Ester N-(5-Iodo-pyrimidin-4-yl)-L-4-(N,N-dimethyl-carbamyloxy)phenylalanine test-butyl ester (1.0 eq) was dissolved in dry DMF, with allyltributylstannane (1.1 eq), bis(triphenylphosphine)palladium dichloride (0.03 eq) and LiCl (3.0 eq). The reaction mixture was flushed under nitrogen, and heated to 90° C. for 2 hours. EtOAc was added, and the organic layer was washed with water and brine, and dried over $MgSO_4$. After filtration and evaporation of the solvent under reduced pressure, the crude material was purified by column chromatography (silica gel) eluting with EtOAc/hexanes 1:3. The title material was isolated in good yields.

Method JJ

Preparation of N-[5-propylpyrimidin-4-yl]-L-4-(N,N-dimethyl-carbamyloxy)phenylalanine tert-Butyl Ester N-(5-Allylpyrimidin-4-yl)-L-4-(N,N-dimethylcarbamyloxy)phenylalanine tert-butyl ester was dissolved in methanol and treated with a catalytic amount of 10% palladium on carbon. The mixture was shaken under 10 psi hydrogen gas for 3 hours. Upon filtration though a pad of Celite, and evaporation of the solvent under reduced pressure, the desired material was isolated as a foam.

Method KK

Preparation of N-(5-propylpyrimidin-4-yl)-L-4-(N,N-dimethyl-carbamyloxy)phenylalanine N-(5-Propylpyrimidin-4-yl)-L-4-(N,N-dimethylcarbamyloxy)phenylalanine tert-butyl ester was treated with neat trifluoroacetic acid, and the mixture was stirred for 5 h at room temperature. Upon evaporation of the solvent under reduced pressure, the desired material was isolated as a foam.

Method LL

Preparation of Dimethyl 2-Alkylmalonate

To a suspension of sodium hydride 60% dispersion in mineral oil (1.1 eq) in anhydrous THF was added slowly with stirring dimethyl malonate (1.1 eq), causing the evolution of gas. To the resulting solution was added a bromoalkane, iodoalkane, or trifluoromethanesulfonyloxyalkane (1.0 eq), and the mixture was heated to 50° C. for 48 h, at which point TLC indicated consumption of the bromoalkane, iodoalkane, or trifluoromethanesulfonyloxyalkane. The mixture was diluted with diethyl ether and washed with 70% saturated sodium chloride. The organic extracts were treated with anhydrous magnesium sulfate, filtered, and evaporated to afford a dimethyl 2-alkylmalonate of sufficient purity for immediate conversion to a 5-alkyl-4,6-dihydroxypyrimidine.

Method MM

Preparation of Diethyl 2-Alkylidenylmalonate

Procedure B (p. 2759) of Houve and Winberg (J. Org. Chem. 1980, 45(14), 2754-2763) was employed to react diethyl malonate with a ketone or an aldehyde to afford a diethyl 2-alkylidenylmalonate of sufficient purity for immediate conversion to a diethyl 2-alkylmalonate.

Method NN

Preparation of Diethyl 2-Alkylmalonate

A diethyl 2-alkylidenylmalonate and an equal mass 10% palladium on carbon were suspended in ethanol. The mixture was shaken under 55 psi hydrogen gas for 24 h, at which point TLC indicated consumption of the diethyl 2-alkylidenylmalonate. The mixture was filtered through Celite and evaporated to afford a diethyl 2-alkylmalonate of sufficient purity for immediate conversion to a 5-alkyl-4,6-dihydroxypyrimidine.

Method OO

Preparation of 5-Alkyl-4,6-dihydroxypyrimidine

To a diethyl 2-alkylmalonate or a dimethyl 2-alkylmalonate (1.0 eq) was added formamidine acetate (1.0 eq) and 25% sodium methoxide in methanol (3.3 eq). The resulting slurry was stirred vigorously and heated to 60° C. for 4 h, and then allowed to cool. The slurry was diluted with water, and acidified to pH=2 by addition of HCl. The resulting precipitate was collected by filtration, washed with water, and dried under vacuum, to afford a 5-alkyl-4,6-dihydroxypyrimidine of sufficient purity for immediate conversion to a 5-alkyl-4,6-dichloropyrimidine.

Method PP

Preparation of 5-Alkoxy-4-hydroxypyrimidine

The method (p. 308) of Anderson et al. (Org. Proc. Res. Devel. 1997, 1, 300-310) was employed to react a methyl alkoxyacetate, sodium methoxide, ethyl formate, and formamidine acetate to afford a 5-alkoxy-4-hydroxypyrimidine of sufficient purity for immediate conversion to a 5-alkoxy-4-chloropyrimidine.

Method QQ

Preparation of 5-Alkyl-4,6-dichloropyrimidine or 5-Alkoxy-4-chloropyrimidine To a 5-alkyl-4,6-dihydroxypyrimidine or a 5-alkoxy-4-hydroxypyrimidine (1.0 eq) were added phosphorus oxychloride (15.0 eq) and N,N-dimethylaniline (1.0 eq), and the mixture was heated to 100° C. for 3 h, and then allowed to cool. The resulting solution was poured onto ice, and the mixture was extracted with dichloromethane. The organic extracts were treated with anhydrous magnesium sulfate, filtered, and evaporated to afford a 5-alkyl-4,6-dichloropyrimidine or a 5-alkoxy-4-chloropyrimidine of sufficient purity for immediate conversion to a 5-alkyl-4-N-alkylamino-6-chloropyrimidine or a 5-alkoxy-4-N-alkylaminopyrimidine.

Method RR

Preparation of 5-Alkyl-4-N-alkylamino-6-chloropyrimidine or 5-Alkoxy-4-N-alkylaminopyrimidine To a solution of a 5-alkyl-4,6-dichloropyrimidine or a 5-alkoxy-4-chloropyrimidine (1.0 eq) in ethanol were added an alkyl amine (1.2 eq, typically L-4-(N,N-dimethylcarbamyloxy)-phenylalanine tert-butyl ester) and diisopropylethylamine (2.0 eq). The mixture was sealed in a pressure tube and heated to 120° C. for 48 h, at which point TLC indicated consumption of the 5-alkyl-4,6-dichloropyrimidine or the 5-alkoxy-4-chloropyrimidine. The mixture was evaporated, and the residue was partitioned between ethyl acetate and pH=4.5 citrate buffer. The organic extracts were washed with saturated sodium chloride, treated with anhydrous magnesium sulfate, filtered, and evaporated. The residue was purified by chromatography on silica gel using ethyl acetate and hexanes to afford a pure 5-alkyl-4-N-alkylamino-6-chloropyrimidine or 5-alkoxy-4-N-alkylaminopyrimidine.

Method SS

Preparation of 5-Alkyl-4-N-alkylaminopyrimidine (Procedure I)

A suspension of 5-alkyl-4-N-alkylamino-6-chloropyrimidine (1.0 eq), and an equal mass 10% palladium on carbon, and sodium bicarbonate (5.0 eq) in methanol was shaken under 55 psi hydrogen gas for 16 h, at which point TLC indicated consumption of the 5-alkyl-4-N-alkylamino-6-chloropyrimidine. The mixture was filtered through Celite and evaporated to give a residue, which was partitioned between ethyl acetate and 70% saturated sodium chloride. The organic extracts were treated with anhydrous magnesium sulfate, filtered, and evaporated. The residue was purified by chromatography on silica gel using ethyl acetate and hexanes to afford a pure 5-alkyl-4-N-alkylaminopyrimidine.

Method TT

Preparation of 5-Alkyl-4-N-alkylaminopyrimidine (Procedure II)

A suspension of 5-alkyl-4-N-alkylamino-6-chloropyrimidine (1.0 eq), sodium acetate (10.0 eq), and zinc powder (20.0 eq) in a 9:1 mixture of acetic acid and water was stirred vigorously at 40° C. for 72 h, at which point TLC indicated partial consumption of the 5-alkyl-4-N-alkylamino-6-chloropyrimidine. The supernatant solution was decanted from remaining zinc and evaporated. The residue was partitioned between ethyl acetate and saturated sodium bicarbonate, and the organic extracts were treated with anhydrous magnesium sulfate, filtered, and evaporated. The residue was purified by chromatography on silica gel using ethyl acetate and hexanes to afford a pure 5-alkyl-4-N-alkylaminopyrimidine.

Method UU

Preparation of N-Benzyloxycarbonyl-L-Tyrosine tert-Butyl Ester

To a 0° C. suspension of L-tyrosine tert-butyl ester (Bachem, 1.0 eq) and sodium bicarbonate (2.0 eq) in a 1:1 mixture of THF and water was added slowly with stirring benzyl chloroformate (1.1 eq). After the addition, the mixture was stirred at 0° C. for 3 h and at room temperature for 24 h. The mixture was diluted with diethyl ether, and the aqueous layer was separated. The organic extracts were washed with saturated sodium chloride, treated with anhydrous magnesium sulfate, filtered, and evaporated to afford N-benzyloxycarbonyl-L-tyrosine tert-butyl ester of sufficient purity for immediate conversion of the tyrosine hydroxyl into a carbamate.

Method VV

Preparation of N-Benzyloxycarbonyl-L-4-(N,N-Dimethylcarbamyloxy)phenylalanine tert-Butyl Ester A mixture of N-benzyloxycarbonyl-L-tyrosine tert-butyl ester (1.0 eq), 4-dimethylaminopyridine (1.0 eq), triethylamine (1.5 eq), dimethylcarbamylchloride (1.2 eq), and dichloromethane was heated to 37° C. for 16 h. The mixture was diluted with additional dichloromethane and washed sequentially with 1.0 M potassium bisulfate, water, saturated sodium bicarbonate, and saturated sodium chloride. The organic extracts were treated with anhydrous magnesium sulfate, filtered, and evaporated to afford N-benzyloxycarbonyl-L-4-(N,N-dimethylcarbamyloxy)phenylalanine tert-butyl ester as a white solid of sufficient purity for immediate conversion to L-4-(N,N-dimethylcarbamyloxy)phenylalanine tert-butyl ester.

Method WW

Preparation of L-4-(N,N-Dimethylcarbamyloxy)phenylalanine tert-Butyl Ester

A suspension of N-benzyloxycarbonyl-L-4-(N,N-tert-butyl ester and an equal mass of 10% palladium on carbon in methanol was shaken under 55 psi hydrogen gas for 1 h, at which point TLC indicated consumption of the N-benzyloxy carbonyl-L-4-(N,N-dimethylcarbamyloxy)phenylalanine tert-butyl ester. The mixture was filtered through Celite and evaporated to afford L-4-(N,N-dimethylcarbamyloxy)-phenylalanine tert-butyl ester of sufficient purity for immediate use in reactions with chloropyrimidines.

Method XX

Preparation of N-Benzyloxycarbonyl-L-4-(4-methylpiperazin-1-ylcarbonyloxy)phenylalanine tert-Butyl Ester To a stirred solution maintained at 0° C. of N-benzyloxycarbonyl-L-tyrosine tert-butyl ester (1.0 eq) and triethylamine (2.5 eq) in dichloromethane was added 4-nitrophenyl chloroformate (1.0 eq). The mixture was stirred for 30 min at 0° C., and then 1-methylpiperazine (1.5 eq) was added, and then the mixture was stirred for 2 h while warming to room temperature. The mixture was diluted with ethyl acetate and washed five times with 10% potassium carbonate and once with saturated sodium chloride. The organic extracts were treated with anhydrous magnesium sulfate, filtered, and evaporated to afford N-benzyloxycarbonyl-L-4-(4-methylpiperazin-1-ylcarbonyloxy)phenylalanine, tert-butyl ester of sufficient purity for immediate conversion to L-4-(4-methylpiperazin-1-ylcarbonyloxy)phenylalanine tert-butyl ester.

Method YY

Preparation of L-4-(4-Methylpiperazin-1-ylcarbonyloxy)phenylalanine tert-Butyl Ester A suspension of N-benzyloxycarbonyl-L-4-(4-methylpiperazin-1-ylcarbonyloxy)-phenylalanine tert-butyl ester and an equal mass of 10% palladium on carbon in methanol was shaken under 55 psi hydrogen gas for 1 h, at which point TLC indicated consumption of N-benzyloxycarbonyl-L-4-(4-methylpiperazin-1-ylcarbonyloxy)phenylalanine tert-butyl ester. The mixture was filtered through Celite and evaporated to afford L-4-(4-methylpiperazin-1-ylcarbonyloxy)phenylalanine tert-butyl ester of sufficient purity for immediate use in reactions with chloropyrimidines.

Method ZZ tert-Butyl Ester Cleavage Procedure IV

The tert-butyl ester was dissolved in 96% formic acid and heated to 40° C. for 16 h, at which point TLC indicated consumption of the tert-butyl ester. The mixture was evaporated under a stream of air to give a residue, which was stored under high vacuum for 72 h to afford the pure carboxylic acid.

Method AAA

Preparation of 2,4-Dichloro-5-nitropyrimidine

5-Nitrouracil was treated with phosphorus oxychloride and N,N-dimethylaniline, according to the procedure of Whittaker (J. Chem. Soc. 1951, 1565), to give 2,4-dichloro-5-nitropyrimidine as an orange oil, which was used without distillation immediately in the next step.

Method BBB

Preparation of N-(2-Chloro-5-nitropyrimidin-4-yl)-L-4-(N,N-dimethylcarbamyloxy)phenylalanine tert-Butyl Ester To a stirred solution of L-4-(N,N-dimethylcarbamyloxy)phenylalanine tert-butyl ester (6.38 g, 20.69 mmol) and N,N-diisopropylethylamine (5.40 mL, 4.01 g, 31.03 mmol) in 70 mL $CH_2Cl_2$ at 0° C., was added a solution of 2,4-dichloro-5-nitropyrimidine (3.25 g, 20.69 mmol) in 70 mL of $CH_2Cl_2$, at such a rate the temperature did not exceed 10° C. After the addition, the mixture was stirred at 0-10° C. for 15 minutes, at which point TLC indicated conversion of 2,4-dichloro-5-nitropyrimidine. To the mixture were added 100 mL 1 M $KHSO_4$ and 200 mL diethyl ether. The organic layer was separated, washed ($H_2O$, sat. $NaHCO_3$, and sat. NaCl), dried ($MgSO_4$), filtered, and evaporated to give N-(2-chloro-5-nitropyrimidin-4-yl)-L-4-(N,N-dimethylcarbamyloxy)phenylalanine tert-butyl ester (9.52 g, 20.45 mmol, 99%) as an orange oil, which was used immediately in the next step.

Method CCC

Preparation of N-(5-Aminopyrimidin-4-yl)-L-4-(N,N-dimethylcarbamyloxy)phenylalanine tert-Butyl Ester A mixture of N-(2-chloro-5-nitropyrimidin-4-yl)-L-4-(N,N-dimethylcarbamyloxy)-phenylalanine tert-butyl ester (9.52 g, 20.45 mmol), Degussa-type 20% palladium on carbon (9.5.2 g), NaHCO₃ (8.59 g, 102.2 mmol), and 165 mL MeOH was shaken under 55 Psi H₂ for 16 h, at which point TLC indicated conversion of N-(2-chloro-5-nitropyrimidin-4-yl)-L-4-(N,N-dimethylcarbamyloxy)phenylalanine tert-butyl ester into a single product. The mixture was filtered through Celite, and the filtrate was evaporated to give a residue, which was dissolved by addition of 150 mL EtOAc and 75 mL H₂O. The organic layer was separated, washed (sat. NaCl), dried (MgSO₄), filtered, and evaporated to give N-(5-aminopyrimidin-4-yl)-L-4-(N,N-dimethylcarbamyloxy) phenylalanine tert-butyl ester (7.14 g, 17.79 mmol, 87%) as an orange solid, which was used immediately in the next step.

Method DDD

Preparation of N-(5-(N-4-Toluenesulfonylamino) pyrimidin-4-yl)-L-4-(N,N-dimethylcarbamyloxy) phenylalanine tert-Butyl Ester To a stirred solution of N-(5-aminopyrimidin-4-yl)-L-4-(N,N-dimethylcarbamyloxy)-phenylalanine tert-butyl ester (1.00 g, 2.49 mmol) in 10 mL anhydrous pyridine at 0° C.; was added in portions 4-toluenesulfonylchloride (0.474 g, 2.49 mmol). After the addition, the resulting red solution was stirred at 0° C. for 3 h, at which point TLC indicated nearly complete conversion of N-(5-aminopyrimidin-4-yl)-L-4-(N,N-dimethylcarbamyloxy)phenylalanine tert-butyl ester. To the mixture was added 3-dimethylaminopropylamine (0.325 mL, 0.264 g, 2.49 mmol), and the mixture was stirred for 30 min while warming to room temperature. The mixture was poured into 100 mL 1 M KHSO₄, and extracted with 150 mL EtOAc. The organic layer was washed (2×1 M KHSO₄, H₂O, sat. NaHCO₃, sat. NaCl), dried (MgSO₄), filtered, and evaporated to give a brown residue, which was purified by flash chromatography using EtOAc/hexanes on silica gel, to give N-(5-(N-4-toluenesulfonylamino)pyrimidin-4-yl)-L-4-(N,N-dimethylcarbamyloxy)phenylalanine tert-butyl ester (1.01 g, 1.81 mmol, 73%) as a clear oil.

Method EEE

Preparation of N-(5-(N-Methyl-N-4-toluenesulfonylamino)pyrimidin-4-yl)-L-4-(N,N-dimethylcarbamyloxy)phenylalanine tert-Butyl Ester To a stirred two-phase mixture of 45 mL 1 M NaOH and 25 mL diethyl ether at 0° C., was added in portions 1-methyl-3-nitro-1-nitrosoguanidine (1.33 g, 9.05 mmol). After stirring for 25 min, at which point evolution of N₂ had subsided, the bright yellow solution of diazomethane in diethyl ether was transferred by pipette to a stirred solution of N-(5-(N-4-toluenesulfonylamino)pyrimidin-4-yl)-L-4-(N,N-dimethylcarbamyloxy)phenylalanine tert-butyl ester (1.01 g, 1.81 mmol) in 15 mL diethyl ether and 15 mL CH₂Cl₂ at 0° C. After stirring for 15 min, at which point TLC indicated complete conversion of N-(5-(N-4-toluenesulfonylamino)pyrimidin-4-yl)-L-4-(N,N-dimethylcarbamyloxy)phenylalanine tert-butyl ester, excess AcOH was added to destroy unreacted diazomethane. The mixture was diluted with 100 mL diethyl ether, washed (2×sat. NaHCO₃, sat. NaCl), dried (MgSO₄), filtered and evaporated to give a yellow residue, which was purified by flash chromatography using EtOAc/hexanes on silica gel, to give N-(5-(N-methyl-N-4-toluenesulfonylamino)pyrimidin-4-yl)-L-4-(N,N-dimethylcarbamyloxy) phenylalanine tert-butyl ester (0.846 g, 1.48 mmol, 82%) as a clear oil.

Method FFF

Preparation of Diethyl 2-(N,N-Dialkylamino)malonate

The appropriate amine (1.0 eq) was added to a 0° C. solution of diethyl bromomalonate (1.0 eq) and N,N-diisopropylethyl amine (1.1 eq) in ethanol. The mixture was stirred and allowed to warm room temperature. After 16 hours, the reaction mixture was concentrated and the residue was suspended in ethyl acetate and sat. NaHCO₃. The organic portion was washed with sat NaHCO₃, brine, dried (MgSO₄) filtered and concentrated to yield the diethyl 2-(N,N-dialkylamino)malonate, of sufficient purity for immediate conversion to a 5-(N,N-dialkylamino)-4,6-dihydroxypyrimidine Method GGG Preparation of 5-(N,N-Dialkylamino)-4,6-dihydroxypyrimidine A suspension of a diethyl 2-(N,N-dialkylamino)malonate (1.0 eq), formamidine acetate (1.10 eq.) and 25% sodium methoxide in methanol (3.3 eq) was heated to 65° C. for 3.5 hours. The reaction mixture was cooled and diluted with water. The mixture was acidified to pH=4.5 by addition of dilute HCl. The resulting precipitate was collected by filtration, washed with water, and dried under vacuum to afford a 5-(N,N-dialkylamino)-4,6-dihydroxypyrimidine of sufficient purity for immediate conversion to a 5-(N,N-dialkylamino)-4,6-dichloropyrimidine. Alternatively, the acidified solution was evaporated to give a solid residue, which was extracted with boiling ethanol. The ethanol extracts were filtered and concentrated to give a residue, which was recrystallized from isopropyl alcohol to afford a 5-(N,N-dialkylamino)-4,6-dihydroxypyrimidine of sufficient purity for immediate conversion to a 5-(N,N-dialkylamino)-4,6-dichloropyrimidine.

Method HHH

Preparation of 5-(N,N-Dialkylamino)-4,6-dichloropyrimidine

A 5-(N,N-dialkylamino)-4,6-dihydroxypyrimidine (1.0 eq) was suspended in POCl₃ (15.0 eq), and the mixture was heated to reflux for 16 hours. Then the mixture was cooled and carefully poured into a suspension of ethyl ether and aqueous K₂CO₃. The organic portion was washed with brine, dried (MgSO₄), filtered and concentrated to yield a 5-(N,N-dialkylamino)-4,6-dichloro-pyrimidine of sufficient purity for immediate reaction with alkylamines.

Method III

Preparation of 4-(N-Alkylamino)-5-(N,N-dialkylamino)-6-chloropyrimidine

A 5-(N,N-dialkylamino)-4,6-dichloropyrimidine (1.0 eq), L-4-(N,N-dimethylcarbamyloxy)phenylalanine tert-butyl ester (1.5 eq) and N,N-diisopropyl ethylamine (1.5 eq) were dissolved in ethanol and heated to 120° C. in a sealed tube for 72 h. The cooled reaction mixture was concentrated, and the residue dissolved in ethyl acetate. The ethyl acetate solution was washed with 0.2 N citric acid, water, saturated NaHCO$_3$, brine, dried (MgSO$_4$), filtered and concentrated. The residue was purified by silica gel chromatography using ethyl acetate/hexanes to afford the 4-(N-alkylamino)-5-(N,N-dialkylamino)-6-chloropyrimidine.

Method JJJ

Preparation of 4-(N-Alkylamino)-5-(N,N-dialkylamino)pyrimidine

A 4-(N-Alkylamino)-5-(N,N-dialkylamino)-6-chloropyrimidine (1.0 eq), an equal mass of 10% palladium on carbon and NaHCO$_3$ (5.0 eq) were suspended in methanol. The reaction mixture was hydrogenated at 45 psi hydrogen for 16 hours and then filtered through a pad of Celite. The filtrate was concentrated, and the residue was dissolved in ethyl acetate. The ethyl acetate solution was washed with water, brine, dried (MgSO$_4$), filtered and concentrated to yield an oil. The oil was purified by column chromatography on silica gel using ethyl acetate and hexanes to afford a pure 4-(N-alkylamino)-5-(N,N-dialkylamino)pyrimidine.

Method KKK

Suzuki Coupling Procedure V

To an ethyleneglycol dimethyl ether solution of tetrakis(triphenylphosphine) palladium (0.04 eq) was added N-(5-bromo-2-chloro-pyrimidin-4-yl)-L-4-(N,N-dimethylcarbamyloxy)phenylalanine tert-butyl ester (1:5 eq.). After stirring for approximately ten minutes o-tolylboronic acid (1.5 eq) and 2M Na$_2$CO$_3$ (2.0 eq) were added, and the reaction flask was evacuated and flushed with nitrogen gas. The reaction was heated tp reflux for four hours. The reaction mixture was then cooled and diluted with water and methylene chloride. The organic phase was separated and washed with brine, dried (MgSO$_4$), filtered and concentrated. The residue was purified by silica gel chromatography using ethyl acetate/hexanes to afford the desired product.

Method LLL

Preparation of L-Phenylalanine Isopropyl Ester Hydrochloride or L-Tyrosine Isopropyl Ester Hydrochloride Excess HCl gas was added with stirring to a suspension of L-phenylalanine or L-tyrosine in excess isopropanol. The mixture was heated to reflux for 16 h, and then the volatiles were evaporated under vacuum to give L-phenylalanine isopropyl ester hydrochloride or L-tyrosine isopropyl ester hydrochloride of sufficient purity for immediate use.

Method MMM

Bromopyrimidine Debromination Procedure

The bromopyrimidine was dissolved in isopropyl alcohol to which was added 10% palladium on carbon. The reaction was hydrogenated at 45 psi hydrogen. Filtration and concentration of the filtrate yielded the desired dehalogenated pyrimidine.

Method NNN

Preparation of 2-Isopropropoxypyrimidine

A 2-chloropyrimidine was dissolved in isopropyl alcohol to which was added diisopropylamine. The reaction was heated in a sealed tube for ten days at 130° C. The cooled reaction mixture was concentrated, and the product purified via silica gel column chromatography to yield the 2-isopropoxypyrimidine.

Method OOO

Heck Reaction Procedure III

To a dioxane/triethylamine (1:1 by volume) solution of the N-(5-iodopyridin-4-yl)-L-4-(N,N-dimethylcarbamyloxy) phenylalanine isopropyl ester (1.0 eq), triphenylphosphine (0.05 eq), copper (I) iodide (0.2 eq) was added phenylacetylene (4.0 eq). After flushing the solution for ten minutes with nitrogen gas, dichlorobis(triphenylphosphine)palladium (0.10 eq) was added, and the resulting reaction mixture heated to 50° C. for 16 hours. The reaction mixture was then diluted with ethyl acetate and water, and the organic portion was washed with 0.2 N citric acid, water, saturated NaHCO$_3$, brine, dried (MgSO$_4$), filtered and concentrated. The residue was chromatographed on a silica gel column using ethyl acetate/hexanes to afford the desired product.

Method PPP

Preparation of N-[5-(Phenyl)pyrimidin-4-yl]-L-4-(N,N-dimethylcarbamyloxy)phenylalanine tert-Butyl Ester N-[5-iodopyrimidin-4-yl]-L-4-(N,N-dimethylcarbamyloxy)phenylalanine tert-butyl ester (123 mg, 0.2 mmol) was diluted in dry DMF (5 mL) under nitrogen with KOAc (3.0 eq, 73 mg), bis(pinacolato)diboron (1.1 eq, 63 mg), and a catalytic amount of [1,1'-bis(diphenylphosphino)ferrocene]dichloropalladium (II) complex with dichloromethane (1:1). The reaction was heated for 2 hours at 100° C.: To this was added, K3PO4 (2.0 eq, 105 mg), iodobenzene (2.0 eq, 0.056 mL) and an additional catalytic amount of [1,1'-bis(diphenylphosphino)-ferrocene]dichloropalladium (II) complex with dichloromethane (1:1). The reaction mixture was stirred overnight at 100° C. EtOAc was added and the organic layer washed with brine, dried over MgSO$_4$. Upon filtration, and evaporation of the solvent under reduced pressure, the crude material was eluted on column chromatography (silica gel) with EtOAc/hexanes 1:1. The desired material was isolated in good yields.

Method QQQ

Preparation of 2-Amino-3-Chloropyrazine

A mixture of 2,3-dichloropyrazine (Lancaster) and ammonium hydroxide was heated in a sealed tube at 100° C. for 24 h resulting in a white precipitate. The precipitate was collected by filtration and dried under vacuum to afford 2-amino-3-chloropyrazine of sufficient purity for immediate conversion to 2-chloro-3-nitropyrazine.

Method RRR

Preparation of 2-Chloro-3-Nitropyrazine

The method (p. 1638) of Hartman et al. (J. Med. Chem. 1984, 27(12), 1634-1639) was employed to convert 2-amino-3-chloropyrazine into 2-chloro-3-nitropyrazine of sufficient purity for immediate use.

Method SSS

Preparation of 4-Alkylamino-2-dialkylamino-5-nitropyrimidine

A solution of 1.0 eq 4-alkylamino-2-chloro-5-nitropyrimidine and 5.0 eq dialkylamine in THF was allowed to stand for 16 h. The mixture was diluted with ethyl acetate and then washed with pH=4.5 citrate buffer and saturated sodium chloride. The organic extracts were treated with anhydrous magnesium sulfate, filtered, and evaporated to give a residue, which was purified by chromatography on silica gel using ethyl acetate, and hexanes.

Method TTT

Preparation of L-4-(26-Dimethoxyphenyl)phenylalanine Methyl Ester

To a stirred solution (DMF, 66 mL) of N-Boc-L-(p-iodo) phenylalanine methyl ester (13.2 g, 32.7 mmol) prepared according to the procedure of Schwabacher et al., J. Org. Chem. 1994, 59, 4206-4210) was added Pd(PPh$_3$)$_4$ (0.03 eq, 1.13 g, 1 mmol). The solution was stirred for 10 min and then 2,6-dimethoxyboronic acid (1.2 eq, 7.1 g, 39 mmol) and K$_3$PO$_4$ (1.5 eq, 10.4 g, 49 mmol) were added. The reaction flask was evacuated and flushed with nitrogen. This process was repeated twice and the reaction mixture was then heated to 100° C. under a stream of nitrogen for about 3.5 h at which time TLC showed the reaction to be complete (4.5:1 hexanes:EtOAc, R$_f$=0.2, UV active). The reaction mixture was cooled and partitioned between water and ethyl acetate (200 mL each). The organic portion was washed with 0.2N citric acid (3×100 mL), brine (1×100 mL), dried (MgSO$_4$), filtered and stripped to a thick reddish oil, about 13 g. The resulting product was chromatographed on silica gel eluting with 4.5:1 hexanes/EtOAc, R$_f$=0.2. The combined fractions were stripped and treated with methanol saturated with HCl to yield the title intermediate as the hydrochloride salt.

Example 1

Synthesis of N-(2-Chloro-5-nitropyrimidin-4-yl)-L-4-(N,N-dimethylcarbamyloxy)phenylalanine

Step A—Preparation of 2,4-Dichloro-5-nitropyrimidine

5-Nitrouracil (Aldrich Chemical Company) was treated with phosphorous oxychloride and N,N-dimethylaniline according to the procedure described in Whittaker, J. Chem. Soc. 1951, 1565, to give 2,4-dichloro-5-nitropyrimidine as an orange oil which was used without distillation immediately in the next step.

Step B—Preparation of N-(2-Chloro-5-nitropyrimidin-4-1-L-4-(N,N-dimethylcarbamyloxy)phenylalanine tert-Butyl Ester To a stirred solution of L-4-(N,N-dimethylcarbamyloxy) phenylalanine tert-butyl ester (6.38 g, 2069 mol) and N,N-diisopropylethylamine (5.40 mL, 4.01 g, 31.03 mol.) in 70 mL CH$_2$Cl$_2$ at 0° C., was added a solution of 2,4-dichloro-5-nitropyrimidine (3.25 g, 20.69 mol.) in 70 mL CH$_2$Cl$_2$ at such a rate that the temperature did not exceed 10° C. After the addition, the mixture was stirred at 0-10° C. for 15 minutes, at which point TLC indicated conversion of the starting materials. To the mixture were added 100 mL 1 M KHSO$_4$ and 200 mL diethyl ether. The organic layer was separated, washed (H$_2$O, sat. NaHCO$_3$, and sat. NaCl), dried (MgSO$_4$), filtered, and evaporated to give the title compound (9.52 g, 2045 mol., 99%) as an orange oil.

Step C—Preparation of N-(2-Chloro-5-nitropyrimidin-4-yl)-L-4-(N,N-dimethylcarbamyloxy)phenylalanine The title compound was prepared by hydrolysis of the product from Step B using the procedure of Example 5.

Example 2

Synthesis of N-[5-(N-4-Toluenesulfonylamino)pyrimidin-4-yl]-L-4-(N,N-dimethylcarbamyloxy)phenylalanine tert-Butyl Ester

Step A—Preparation of N-(5-Aminopyrimidin-4-yl)-L-4-(N,N-dimethylcarbamyloxy)phenylalanine tert-Butyl Ester A mixture of N-(2-chloro-5-nitropyrimidin-4-yl)-L-4-(N,N-dimethylcarbamyloxy)phenylalanine tert-butyl ester (9.52 g, 20.45 mol), Degussa-type 20% palladium on carbon (9.52 g), NaHCO$_3$ (8.59 g, 102.2 mol), and 165 mL MeOH was shaken under 55 psi for 16 h, at which point TLC indicated conversion of the starting material into a single product. The mixture was filtered through Celite, and the filtrate was evaporated to give a residue, which was dissolved by addition of 150 mL EtOAc and 75 mL H$_2$O. The organic layer was separated, washed (sat. NaCl), dried (MgSO$_4$), filtered, and evaporated to give the title intermediate (7.14 g, 17.79 mol, 87%) as an orange solid, which was used immediately in the next-step.

Step B—Preparation of N-[5-(N-4-Toluenesulfonylamino)pyrimidin-4-yl]-L-4-(N,N-dimethylcarbamyloxy)phenylalanine tert-Butyl Ester To a stirred solution of the product from Step A (100 g, 2.49 mol) in 10 ml., anhydrous pyridine at 0° C., was added in portions 4-toluenesulfonyl chloride (0.474 g, 2.49 mol). After the addition, the resulting red solution was stirred at 0° C. for 3 h, at which point TLC indicated nearly complete conversion of the starting material. To the mixture was added 3-dimethylaminopropylamine (0.325 mL, 0.264 g, 2.49 mol), and the mixture was stirred for 30 min while warming to room temperature. The mixture was poured into 100 mL 1 M KHSO$_4$, and extracted with 150 mL EtOAc. The organic layer was washed (2×1 M KHSO$_4$, H$_2$O, sat. NaHCO$_3$, sat. NaCl), dried (MgSO$_4$), filtered, and evaporated to give a brown residue, which was purified by flash chromatography using EtOAc/hexanes on silica gel, to give the title compound (1.01 g, 1.81 mol., 73%) as a clear oil.

Example 3

Synthesis of N-[5-(N-4-Toluenesulfonylamino)pyrimidin-4-yl]-L-4-(N,N-dimethylcarbamyloxy)phenylalanine The title compound was prepared by hydrolysis of N-[5-(N-4-toluenesulfonylamino)pyrimidin-4-yl]-L-4-(N,N-dimethylcarbamyloxy)phenylalanine tert-butyl ester using the procedure of Example 5.

Example 4

Synthesis of N-[5-(N-Methyl-N-4-toluenesulfonylamino)pyrimidin-4-yl]-L-4-(N,N-dimethylcarbamyloxy)phenylalanine tert-Butyl Ester To a stirred two-phase mixture of 45 mL 1 M NaOH and 25 mL diethyl ether at 0° C., was added in portions 1-methyl-3-nitro-1-nitrosoguanidine (1.33 g, 9.05 mol). After stirring for 25 min, at which point evolution of $N_2$ had subsided, the bright yellow solution of diazomethane in diethyl ether was transferred by pipette to a stirred solution of the product of Example 2 (1.01 g, 1.81 mol) in 15 mL diethyl ether and 15 mL $CH_2Cl_2$ at 0° C. After stirring for 15 min, at which point TLC indicated complete conversion of the starting material, excess AcOH was added to destroy unreacted diazomethane. The mixture was diluted with 100 mL diethyl ether, washed (2×sat. $NaHCO_3$, sat. NaCl), dried ($MgSO_4$), filtered and evaporated to give a yellow residue, which was purified by flash chromatography using EtOAc/hexanes on silica gel, to give the title compound (0.846 g, 1.48 mol, 82%) as a clear oil.

Example 5

Synthesis of N-[5-(N-Methyl-N-4-toluenesulfonylamino)pyrimidin-4-yl]-L-4-(N,N-dimethylcarbamyloxy)phenylalanine The product of Example 4 (0.400 g, 0.700 mol) was dissolved in 8 mL 96% formic acid, and the mixture was heated to 40° C. for 16 h, at which point TLC indicated conversion of the starting material. Most of the formic acid was evaporated under a stream of $N_2$, and then the residue was placed under high vacuum for 48 h to give the title compound (0.382 g, 0.700 mol, 100%) as a clear oil.

Physical data were as follows:

$^1$H NMR ($CD_3OD$): δ=8.33 (bs, 1H), 8.07 (bs, 1H), 7.64 (d, J=8.1 Hz, 2H), 7.42 (d, J=8.1 Hz, 2H), 7.36 (bs, 1H), 7.29 (bs, 2H), 6.99 (d, J=7.5 Hz, 2H), 5.07-4.96 (m, 1H), 3.42-3.31 (m, 1H), 3.25-3.15 (m, 1H), 3.08 (s, 3H), 3.05 (bs, 3H), 2.96 (s, 3H), 2.44 (s, 3H).

$^{13}$C NMR ($CD_3OD$): δ=174.7, 174.6, 164.6, 157.8, 156.8, 152.9, 152.1, 146.5, 135.4, 135.1, 131.7, 131.3, 129.4, 123.2, 122.9, 55.8, 38.2, 37.1, 36.8, 36.7, 21.5.

Using the appropriate starting materials and reagents, the following additional compounds were prepared:

N-[5-(N,N-Di-4-toluenesulfonylamino)pyrimidin-4-yl]-L-4-(N,N-dimethylcarbamyloxy)phenylalanine (Example 6);

N-[5-[N-(1-N'-Methylpyrazol-4-ylsulfonyl)-N-methylamino]pyrimidin-4-yl]-L-4-(N,N-dimethylcarbamyloxy)phenylalanine (Example 7);

N-[5-(N-Methyl-N-4-toluenesulfonylamino)pyrimidin-4-yl]-L-4-(N,N-dimethylcarbamyloxy)phenylalanine isopropyl ester (Example 8);

N-[5-(N-Methyl-N-3-pyridylsulfonylamino)pyrimidin-4-yl]-L-4-(N,N-dimethylcarbamyloxy)phenylalanine tert-butyl ester (Example 9); and

Example 10

Synthesis of N-(5-(N-Methyl-N-(1-butylpyrazol-4-yl)sulfonylamino)pyrimidin-4-yl)-L-4-(N,N-dimethylcarbamyloxy)phenylalanine L-Tyrosine tert-butyl ester (Bachem) was, sequentially converted via Methods UU, VV and WW into L-4-(N,N-dimethylcarbamyloxy)-phenylalanine tert-butyl ester. 5-Nitrouracil (Aldrich) was converted via Method AAA into 2,4-dichloro-5-nitropyrimidine. L-4-(N,N-Dimethylcarbamyloxy)-phenylalanine tert-butyl ester and 2,4-dichloro-5-nitropyrimidine were coupled via Method BBB, and the product of this coupling was sequentially converted via Methods CCC, DDD (using 1-butyl-4-chlorosulfonylpyrazole), EEE and ZZ to give the title compound.

Physical data were as follows:

$^1$H NMR ($CD_3OD$): δ=8.35 (s, 1H), 8.14 (s, 1H), 7.76 (s, 1H), 7.61 (bs, 1H), 7.23 (bs, 2H), 6.98 (d, 2H), 5.01-4.94 (m, 1H), 4.19 (t, 2H), 3.40-3.28 (m, 1H), 3.26-3.14 (m, 1H), 3.09 (s, 3H), 3.06 (bs, 3H), 2.96 (s, 3H), 1.84 (pent., 2H), 1.29 (sext., 2H), 0.945 (t, 3H).

Example 11

Synthesis of N-(5-(2,4-Dimethoxypyrimidin-5-yl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-pyrimidinone (Aldrich) was sequentially converted via Methods N and O into 4-chloro-5-iodopyrimidine. L-4-(N,N-dimethylcarbamyloxy)phenylalanine tert-butyl ester and 4-chloro-5-iodopyrimidine were coupled via Method P, and the coupled product was reacted with 2,4-dimethoxypyrimidin-5-yl boronic acid (Frontier Scientific, Inc.) via Method S. The product of this coupling was converted via Method KK to give the title compound.

Example 12

Synthesis of N-(5-(2,6-Difluorophenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P, and the coupled product was reacted with 2,6-difluorophenyl boronic acid (Lancaster Synthesis) via Method R. The product of this coupling was converted via Method HH to give the title compound.

Example 13

Synthesis of N-(5-(2-Hydroxymethylphenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-dimethylcarbamyloxy)phenylalanine tert-butyl ester and 4-chloro-5-iodopyrimidine were coupled via Method P, and the coupled product was reacted with 2-(hydroxymethyl)phenyl boronic acid (Lancaster Synthesis) via Method Q. The product of this coupling was converted via Method HH to give the title compound.

Example 14

Synthesis of N-(2-(N-Cyclohexylamino)-5-(2-tolyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with cyclohexylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=9.68 (s, 1H), 7.3-6.8 (m, 9H), 6.35 (m, 1H), 4.73 (m, 1H), 3.81 (bs, 1H), 3.6-3.0 (m, 2H), 3.09 (s, 3H), 3.0 (s, 3H), 2.18 (s, 1.5H), 1.94 (s, 1.5H), 2.1-1.1 (m, 10H).
$^{13}$C NMR (CDCl$_3$): δ=176.11, 175.94, 160.05, 159.79, 154.76, 153.58, 150.05, 150.01, 139.26, 137.84, 137.63, 134.29, 134.15, 130.66, 130.36, 130.11, 129.14, 126.70, 126.41, 121.25, 109.57, 109.39, 56.84, 56.35, 50.15, 36.55, 36.32, 32.34, 31.99, 25.41, 24.86, 19.48, 19.27.

Example 15

Synthesis of N-(2-(N-Methyl-N-(1-methylpiperidin-4-yl)amino)-5-(2-tolyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with 1-methyl-4-(N-methylamino)piperidine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=8.82 (s, 2H), 8.43 (s, 1H), 7.62 (s, 1H), 7.30-6.90 (m, 8H), 5.42 (br, 1H), 4.66 (br, 2H), 3.60-2.8 (m, 15H), 2.66 (bs, 3H), 2.32 (br, 2H), 2.18 (s, 1.5H), 1.82 (brs, 3.5H).

Example 16

Synthesis of N-(2-(N-Ethyl-N-isopropylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-ethyl-N-isopropylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=8.0-6.5 (br, 1H), 7.66 (s, 0.5H), 7.62 (s, 0.5H), 7.3-6.8 (m, 8H), 6.2 (m, 1H), 4.86 (br, 1H), 4.70 (m, 1H), 3.70-3.08 (m, 4H), 3.09 (s, 3H), 3.0 (s, 3H), 2.14 (bs, 1.5H), 1.92 (bs, 1.5H), 1.4-0.9 (br, 9H).
$^{13}$C NMR (CDCl$_3$): δ=174.38, 174.19, 159.44, 159.16, 155.24, 154.68, 152.39, 150.02, 141.63, 137.77, 137.56, 134.30, 134.09, 130.79, 130.66, 130.54, 130.46, 130.41, 130.33, 130.08, 129.07, 126.54, 126.45, 126.38, 121.21, 121.16, 110.27, 110.01, 56.77, 56.36, 47.59, 36.80, 36.55, 36.32, 20.27, 20.18, 19.57, 19.38, 14.51.

Example 17

Synthesis of N-(5-(2, 4-6-Trimethylphenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P, and the coupled product was reacted with 2,4,6-trimethylphenyl boronic acid (Frontier Scientific, Inc) via Method R. The product of this coupling was converted via Method HH to give the title compound.

Physical data were as follows:
$^1$H NMR (CD$_3$OD): δ=8.68 (d, 1H), 7.95 (d, 1H), 7.10 (d, 2H), 7.09-6.95 (m, 2H), 6.94-6.91 (m, 2H), 5.32-5.27 (m, 1H), 3.42-3.36 (m, 1H), 3.15-3.09 (m, 4H), 2.97 (s, 3H), 2.33 (s, 3H), 2.04 (s, 3H), 1.84 (s, 3H).
$^{13}$C NMR (CD$_3$OD): δ=172.9, 163.5, 161.5, 161.0, 156.7, 152.0, 151.9, 142.6, 141.5, 138.9, 138.6, 135.3, 131.2, 130.4, 130.3, 126.5, 123.0, 120.3, 56.4, 36.7, 36.6, 36.5, 21.2, 19.9, 19.7.

Example 18

Synthesis of N-(5-Isopropylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. Diethyl 2-isopropylmalonate (Aldrich) was sequentially converted via Methods OO and QQ into 4,6-dichloro-5-isopropylpyrimidine. L-4-(N,N-Dimethylcarbamyloxy)phenylalanine tert-butyl ester and 4,6-dichloro-5-isopropylpyrimidine were coupled via Method RR, and the product of this coupling was sequentially converted via Methods SS and ZZ to give the title compound.

Physical data were as follows:
$^1$H NMR (CD$_3$OD): δ=8.44 (bs, 1H), 7.94 (bs, 1H), 7.22 (d, 2H), 6.94 (d, 2H), 5.12 (dd, 1H), 3.46 (dd, 1H), 3.19 (dd, 1H), 3.07 (s, 3H), 2.95 (s, 3H), 3.00-2.88 (m, 1H), 1.25 (d, 3H), 1.13 (d, 3H).

¹³C NMR (CD₃OD): δ=175.60, 165.74, 163.78, 156.91, 152.38, 151.85, 141.88, 136.30, 131.43, 126.17, 122.87, 57.84, 37.48, 36.81, 36.64, 26.63, 21.09, 20.94.

Example 19

Synthesis of N-(2-(N-Methyl-N-butylamino)-5-(2-tolyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-butylamine (Aldrich) via Method CC to give a product that was coupled with o-tolyl boronic acid (Aldrich) via Method DD. The product of this coupling was converted via Method ZZ to give the title compound.

Physical data were as follows:
¹H NMR (CDCl₃): δ=12.5-11.4 (br, 1H), 7.6 (s, 0.5H), 7.58 (s, 0.5H), 7.3-6.8 (m, 8H), 6.3 (m, 1H), 4.7 (m, 1H), 3.7-2.9 (m, 4H), 3.08 (s, 3H), 3.01 (s, 6H), 2.13 (s, 1.5H), 1.91 (s, 1.5H), 1.57 (bs, 2H), 1.33 (m, 2H), 0.96 (t, 3H).
¹³C NMR (CDCl₃): δ=174.21, 174.06, 159.37, 159.22, 154.69, 153.52, 169.99, 141.87, 137.77, 137.54, 134.43, 130.78, 130.59, 130.10, 128.98, 126.51, 126.32, 121.17, 121.11, 110.20, 109.96, 56.82, 56.43, 50.03, 36.54, 36.32, 35.91, 29.27, 19.89, 19.52, 19.35, 13.84.

Example 20

Synthesis of N-(2-(N-Ethyl-N-propylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-ethyl-N-propylamine (Aldrich) via Method CC to give a product that was coupled with o-tolyl boronic acid (Aldrich) via Method DD. The product of this coupling was converted via Method ZZ to give the title compound.

Physical data were as follows:
¹H NMR (CDCl₃): δ=11.0-9.5 (br, 1H), 7.66 (s, 0.5H), 7.64 (s, 0.5H), 7.4-6.8 (m, 8H), 6.28 (m, 1H), 4.65 (m, 1H), 3.70-2.80 (m, 6H), 3.09 (s, 3H), 3.01 (s, 3H), 3.01 (s, 3H), 2.2 (s, 1.5H), 1.85 (s, 1.5H), 1.58 (bs, 2H), 1.05 (bs, 3H), 0.85 (bs, 3H).
¹³C NMR (CDCl₃): δ=174.26, 174.11, 159.36, 159.11, 154.70, 153.07, 149.96, 142.43, 137.80, 137.56, 134.54, 134.37, 130.84, 130.74, 130.57, 130.14, 128.86, 126.47, 126.29, 121.10, 121.06, 110.01, 109.71, 56.86, 56.49, 49.62, 63.20, 36.55, 36.32, 20.87, 19.61, 19.41, 12.63, 11.03.

Example 21

Synthesis of N-(2-(N,N-Diethylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N,N-diethylamine (Aldrich) via Method CC to give a product that was coupled with o-tolyl boronic acid (Aldrich) via Method DD. The product of this coupling was converted via Method ZZ to give the title compound.

Physical data were as follows:
¹H NMR (CDCl₃): δ=12.2 (br, 1H), 7.63 (s, 0.5H), 7.60 (s, 0.5H), 7.40-6.80 (m, 8H), 6.28 (m, 1H), 4.70 (m, 1H), 3.80-2.90 (m, 6H), 3.06 (s, 3H), 2.98 (s, 3H), 2.13 (s, 1.5H), 1.92 (s, 1.5H), 0.90 (s, 6H).
¹³C NMR (CDCl₃): δ=174.34, 174.15, 159.4, 159.1, 154.70, 152.66, 169.97, 142.06, 137.76, 137.55, 134.44, 134.27, 130.81, 130.57, 130.10, 128.95, 126.48, 126.32, 121.14, 121.08, 110.08, 109.80, 56.78, 56.37, 42.77, 36.53, 36.31, 19.57, 19.38, 12.77.

Example 22

Synthesis of N-(2-(N-Methyl-N-ethylamino)-5-(2-tolyl)pyrimidin-4-yl)-L-4-(N,N-dimethylcarbamyloxy)phenylalanine Tyrosine tert-butyl ester (Bachem) was sequentially converted-via. Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-ethylamine (Aldrich) via Method CC to give a product that was coupled with o-tolyl boronic acid (Aldrich) via Method DD. The product of this coupling was converted via Method ZZ to give the title compound.

Physical data were as follows:
¹H NMR (CDCl₃): δ=12.5 (br, 2H), 8.23 (s, 1H), 7.50 (s, 0.5H), 7.44 (s, 0.5H), 7.30-6.80 (m, 8H), 6.10 (m, 1H), 4.75 (m, 1H), 3.58 (bs, 2H), 3.30 (m, 1H), 3.00 (m, 1H), 3.08 (s, 3H), 3.00 (s, 3H), 2.93 (s, 3H), 2.08 (s, 1.5H), 1.92 (s, 1.5H), 1.50 (s, 3H).
¹³C NMR (CDCl₃): δ=174.63, 174.34, 165.72, 159.96, 159.72, 154.88, 152.62, 150.49, 150.45, 140.64, 137.90, 137.81, 133:83, 133.65, 131.03, 130.95, 130.85, 130.63, 130.10, 130.04, 129.76, 129.62, 126.88, 126.72, 121.70, 121.61, 110.69, 110.46, 56.65, 56.11, 45.16, 36.57, 36.35, 35.17, 19.38, 19.17, 11.96.

No Example 23

Example 24

Synthesis of N-(5-Benzyloxypyrimidin-4-yl)-L-phenylalanine

Methyl 2-benzyloxyacetate (Aldrich) was sequentially converted via Methods PP and QQ into 4-chloro-5-benzyloxypyrimidine. L-4-phenylalanine tert-butyl ester (Bachem) and 4-chloro-5-benzyloxypyrimidine were coupled via Method RR, and the product of this coupling was converted via Method ZZ to give the title compound.

Physical data were as follows:
¹H NMR (CD₃OD): δ=8.54 (s, formate), 8.03 (s, 1H), 7.67 (s, 1H), 7.37-7.31 (m, 5H), 7.17-7.12 (m, 5H), 5.11 (s, 2H), 4.78-4.75 (m, 1H), 3.35-3.11 (m, 214).

$^{13}$C NMR (CD$_3$OD): δ=159.07, 143.16, 132.35, 130.64, 124.52, 123.94, 123.83, 123.59, 123.11, 122.00, 99.47, 66.28, 50.32, 32.05.

Example 25

Synthesis of N-(5-Benzyloxypyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. Methyl 2-benzyloxyacetate (Aldrich) was sequentially converted via Methods PP and QQ into 4-chloro-5-benzyloxypyrimidine. L-4-(N,N-Dimethylcarbamyloxy)phenylalanine tert-butyl ester and 4-chloro-5-benzyloxypyrimidine were coupled via Method RR, and the product of this coupling was converted via Method ZZ to give the title compound.

Example 26

Synthesis of N-(5-(N-Methyl-N-4-toluenesulfonylamino)pyrimidin-4-yl)-L-phenylalanine 5-Nitrouracil (Aldrich) was converted via Method AAA into 2,4-dichloro-5-nitropyrimidine. L-4-Phenylalanine tert-butyl ester (Bachem) and 2,4-dichloro-5-nitropyrimidine were coupled via Method BBB, and the product of this coupling was sequentially converted via Methods CCC, DDD, EEE and ZZ to give the title compound.

Example 27

Synthesis of N-(5-(N-Methyl-N-3-pyridinesulfonylamino)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 5-Nitrouracil (Aldrich) was converted via Method AAA into 2,4-dichloro-5-nitropyrimidine. L-4-(N,N-Dimethylcarbamyloxy)-phenylalanine tert-butyl ester and 2,4-dichloro-5-nitropyrimidine were coupled via Method BBB, and the product of this coupling was sequentially converted via Methods CCC, DDD (using 3-chlorosulfonylpyridine), EEE and ZZ to give the title compound.

Physical data were as follows:
$^1$H NMR (CD$_3$OD): δ=8.90 (d, 1H), 8.85 (d, 1H), 8.36 (s, 1H), 8.15 (d, 1H), 7.64 (dd, 1H), 7.53 (bs, 1H), 7.27 (bs, 2H), 6.99 (d, 2H), 5.04-4.87 (m, 1H), 3.40-3.28 (m, 1H), 3.26-3.16 (m, 1H), 3.13 (bs, 3H), 3.09 (s, 3H), 2.97 (s, 3H).

Example 28

Synthesis of N-(5-Phenylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P, and the coupled product was reacted with phenyl boronic acid (Aldrich) via Method S. The product of this coupling was converted via Method HH to give the title compound.

Physical data were as follows:
$^1$H NMR (CD$_3$OD): δ=8.62 (s, 1H), 8.04 (s, 1H), 7.53-7.51 (m, 3H), 7.30-7.27 (m, 2H), 7.17-7.15 (m, 2H), 7.00-6.97 (m, 2H), 5.27-5.22 (m, 1H), 3.45-3.39 (m, 1H), 3.16-3.08 (m, 4H), 2.96 (s, 3H).
$^{13}$C NMR (CD$_3$OD): δ=173.8, 163.7, 157.5, 152.8, 152.3, 142.4, 135.9, 132.2, 132.1, 131.8, 130.7, 123.9, 122.4, 57.7, 37.7, 37.5.

Example 29

Synthesis of N-(3-(N-Methyl-N-4-toluenesulfonylamino)pyrazin-2-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 2,3-Dichloropyrazine (Lancaster) was converted via Method QQQ and RRR into 2-chloro-3-nitropyrazine. L-4-(N,N-Dimethylcarbamyloxy)phenylalanine tert-butyl ester and 2-chloro-3-nitropyrazine were coupled via Method BBB, and the product of this coupling was sequentially converted via Methods CCC, DDD, EEE and ZZ to give the title compound.

Physical data were as follows:
$^1$H NMR (CD$_3$OD): δ=8.07 (s, formate), 7.94 (d, 1H), 7.59 (d, 2H), 7.51 (d, 1H), 7.36 (d, 2H), 7.29 (d, 2H), 7.01 (d, 2H), 4.90 (m, 1H), 3.30-3.18 (m, 2H), 3.08 (s, 3H), 2.96 (s, 3H), 2.94 (s, 3H), 2.43 (s, 3H).
$^{13}$C NMR (CD$_3$OD): δ=177.07, 169.41, 158.64, 150.92, 147.23, 145.92, 139.97, 137.14, 133.12, 129.62, 128.90, 125.69, 124.67, 124.08, 116.86, 49.99, 31.67, 31.28, 30.77, 30.62, 15.46.

No Example 30

Example 31

Synthesis of N-(5-(2,2,2-Trifluoroethyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 1-Trifluoromethanesulfonyloxy-2,2,2-trifluoroethane was sequentially converted via Methods LL, OO and QQ into 4,6-dichloro-5-(2,2,2-trifluoroethyl)pyrimidine. L-4-(N,N-Dimethylcarbamyloxy)-phenylalanine tert-butyl ester and 4,6-dichloro-5-(2,2,2-trifluoroethyl)pyrimidine were coupled via Method RR, and the product of this coupling was sequentially converted via Methods SS and ZZ to give the title compound.

Physical data were as follows:
$^1$H NMR (CD$_3$OD): δ=8.41 (s, 1H), 8.09 (s, formate), 8.06 (s, 1H), 7.24 (d, 2H), 6.96 (d, 2H), 5.06 (m, 1H), 3.60-3.40 (m, 2H), 3.37-3.11 (m, 2H), 3.08 (s, 3H), 2.96 (s, 3H).
$^{13}$C NMR (CD$_3$OD): δ=169.35, 158.91, 156.43, 151.33, 150.97, 148.87, 145.76, 130.21, 125.27, 116.80, 50.80, 31.34, 30.75, 30.60, 26.65, 26.23.

Example 32

Synthesis of N-(5-(N-Methyl-N-3-pyridinesulfonylamino)pyrimidin-4-yl)-L-4-(4-methylpiperazin-1-ylcarbonyloxy)phenylalanine Isopropyl Ester L-Tyrosine (Aldrich) was sequentially converted via Methods LLL, UU, XX and YY into L-4-(4-methylpiperazin-1- ylcarbonyloxy)phenylalanine isopropyl ester. 5-Nitrouracil (Aldrich) was converted via Method AAA into 2,4-dichloro-5-nitropyrimidine. L-4-(4-Methylpiperazin-1-ylcarbonyloxy)phenylalanine isopropyl ester and 2,4-dichloro-5-nitropyrimidine were coupled via Method BBB, and the product of this coupling was sequentially converted via Methods CCC, DDD (using 3-chlorosulfonylpyridine) and EEE to give the title compound.

Example 33

Synthesis of N-(5-Benzylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. Diethyl 2-benzylmalonate (Aldrich) was sequentially converted via Methods OO and QQ into 4,6-dichloro-5-benzylpyrimidine. L-4-(N,N-Dimethylcarbamyloxy)phenylalanine tert-butyl ester and 4,6-dichloro-5-benzylpyrimidine were coupled via Method RR, and the product of this coupling was sequentially converted via Methods SS and ZZ to give the title compound.

Physical data were as follows:
$^1$H NMR (CD$_3$OD): δ=8.41 (s, 1H), 8.13 (s, formate), 7.80 (s, 1H) 7.34-7.19 (m, 3H), 7.17 (d, 2H), 7.00 (d, 2H), 6.85 (d, 2H), 5.01 (m, 1H), 3.82 (m, 2H), 3.09 (s, 3H), 3.09-2.97 (m, 2H), 2.97 (s, 3H).
$^{13}$C NMR (CD$_3$OD): δ=159.31, 156.23, 150.88, 148.07, 145.70, 141.38, 131.56, 129.81, 125.30, 124.21, 124.01, 122.37, 116.81, 51.35, 31.68, 30.78, 30.61, 28.28.

Example 34

Synthesis of N-(5-(N-Methyl-N-3-pyridinesulfonylamino)pyrimidin-4-yl)-L-4-(4-methylpiperazin-1-ylcarbonyloxy)phenylalanine tert-Butyl Ester L-Tyrosine tert-butyl ester (Bachem) was sequentially converted via Methods UU, XX and YY into L-4-(4-methylpiperazin-1-ylcarbonyloxy)phenylalanine tert-butyl ester. 5-Nitrouracil (Aldrich) was converted via Method AAA into 2,4-dichloro-5-nitropyrimidine. L-4-(4-Methylpiperazin-1-ylcarbonyloxy)phenylalanine tert-butyl ester and 2,4-dichloro-5-nitropyrimidine were coupled via Method BBB, and the product of this coupling was sequentially converted via Methods CCC, DDD (using 3-chlorosulfonylpyridine) and EEE to give the title compound.

Example 35

Synthesis of N-(5-(2-Trifluoromethylphenyl)pyrimidin-4-yl)-L-4-(N,N-dimethylcarbamyloxy)phenylalanine L-Tyrosine tert-butyl ester (Bachem) was sequentially converted via UU, VV and WW into L-4-(N,N-dimethylcarbamyloxy)phenylalanine tert-butyl ester. 4(3H)-Pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with 2-trifluoromethylphenyl boronic acid (Aldrich) via Method Q. The product of this coupling was converted via Method HH to give the title compound.

Physical data were as follows:
$^1$H NMR (CD$_3$OD): δ=8.51 (s, 1H), 7.84-7.49 (m, 2H), 7.71-7.63 (m, 2H), 7.37 (d, 1H), 7.11-6.97 (m, 4H), 6.88 (d, 1H), 4.99 (s, 1H), 3.37-3.19 (m, 1H), 3.14-3.02 (m, 4H), 2.97 (s, 3H).
$^{13}$C NMR (CD$_3$OD): δ=175.7, 175.5, 165.6, 161.9, 161.7, 158.6, 157.6, 157.5, 153.3, 153.1, 152.6, 152.5, 136.4, 136.2, 135.0, 134.9, 134.5, 133.1, 132.2, 131.9, 131.7, 128.9, 128.7, 127.8, 124.3, 123.6.

No Example 36

Example 37

Synthesis of N-(5-(2-N,N-Dimethylcarbamylethyl) pyrimidin-4-yl)-L-4-(N,N-dimethylcarbamyloxy) phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with dimethylacrylamide (Aldrich) via Method U. The product of this reaction which was sequentially converted via Methods V and HH to give the title compound.

Physical data were as follows:
$^1$H NMR (CD$_3$OD): δ=8.56 (s, 1H), 8.06 (s, 1H), 7.32 (d, 2H), 7.01 (d, 2H), 5.35-5.30 (m, 1H), 3.56-3.49 (m, 1H), 3.23-3.18 (m, 1H), 3.11 (s, 3H), 3.02 (s, 3H), 2.99 (s, 3H), 2.97 (s, 3H), 2.88 (t, 2H), 2.65 (t, 2H).
$^{13}$C NMR (CD$_3$OD): δ=174.5, 174.2, 152.7, 151.6, 142.6, 136.5, 132.0, 123.8, 121.0, 57.8, 38.4, 37.9, 37.5, 36.9, 32.2, 24.6.

Example 38

Synthesis of N-(5-(N-Methyl-N-3-(1-methylpyrazole)sulfonylamino)pyrimidin-4-yl)-L-4-(N,N-dimethylcarbamyloxy)phenylalanine Isopropyl Ester L-Tyrosine (Aldrich) was sequentially converted via Methods LLL, UU, VV and WW into L-4-(N,N-dimethylcarbamyloxy)phenylalanine isopropyl ester. 5-Nitrouracil (Aldrich) was converted via Method AAA into 2,4-dichloro-5-nitropyrimidine. L-4-(N,N-Dimethylcarbamyloxy)-phenylalanine isopropyl ester and 2,4-dichloro-5-nitropyrimidine were coupled via Method BBB, and the product of this coupling was sequentially converted via Methods CCC, DDD (using 1-methyl-3-chlorosulfonylpyrazole) and EEE to give the title compound.

Physical data were as follows:
$^1$H NMR (CDCl$_3$) δ=8.47 (s, 1H), 7.76 (s, 1H), 7.68 (bs, 2H), 7.19 (m, 2H), 7.04 (d, 2H), 6.17 (d, 1H), 5.03 (m, 2H), 3.95 (s, 3H), 3.31-3.12 (m, 2H), 3.08 (s, 3H), 3.06 (s, 3H), 2.99 (s, 3H), 1.24 (d, 3H), 1.21 (d, 3H).

Example 39

Synthesis of N-(6-Phenylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 4,6-dichloropyrimidine (Aldrich) were coupled via Method Y and the coupled product was reacted with phenyl boronic acid (Aldrich) via Method Z. The product of this coupling was converted via Method HH to give the title compound.

Physical data were as follows:
$^1$H NMR (CD$_3$OD): δ=8.65 (s, 1H), 7.82-7.79 (m, 2H), 7.77-7.62 (m, 3H), 7.31 (d, 2H), 7.06-7.01 (m, 4H), 5.32-5.28 (m, 1H); 3.50-3.44 (m, 1H), 3.20-3.06 (m, 4H), 2.99 (s, 3H).
$^{13}$C NMR (CD$_3$OD): δ=173.9, 165.7, 157.6, 154.9, 154.3, 152.8, 135.8, 134.6, 132.3, 132.2, 131.7, 129.2, 123.8, 104.6, 57.8, 38.8, 37.7, 37.5.

Example 40

Synthesis of N-(6-(2-Trifluoromethylphenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 4,6-dichloropyrimidine (Aldrich) were coupled via Method Y and the coupled product was reacted with 2-trifluoromethylphenyl boronic acid (Aldrich) via Method Z. The product of this coupling was converted via Method HH to give the title compound.

Physical data were as follows:
$^1$H NMR (CD$_3$OD): δ=8.46 (s, 1H), 7.95-7.82 (m, 1H), 7.73-7.67 (m, 2H), 7.50-7.48 (m, 1H), 7.29 (d, 2H), 7.03 (d, 2H), 6.65 (s, 1H), 5.05 (s, 1H), 3.39 (m, 1H), 3.16-3.12 (m, 4H), 3.00 (s, 3H).
$^{13}$C NMR (CD$_3$OD): δ=176.0, 164.3, 158.8, 157.7, 152.6, 136.6, 139.0, 132.9, 132.1, 131.4, 130.1, 129.7, 128.2, 128.2, 123.6, 38.8, 37.7, 37.5.

Example 41

Synthesis of N-(6-(2-Hydroxymethylphenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 4,6-dichloropyrimidine (Aldrich) were coupled via Method Y and the coupled product was reacted with 2-(hydroxymethyl) phenyl boronic acid, (Lancaster Synthesis) via Method Z. The product of this coupling was converted via Method HH to give the title compound.

Physical data were as follows:
$^1$H NMR (CD$_3$OD): δ=8.48 (s, 1H), 8.09 (s, 1H), 7.61-7.44 (m, 4H), 7.29 (d, 2H), 7.02 (d, 2H), 6.71 (s, 1H), 5.27 (s, 2H), 5.10-5.02 (m, 1H), 3.42-3.41 (m, 1H), 3.16-3.12 (m, 4H), 2.99 (s, 3H).
$^{13}$C NMR (CD$_3$OD): δ=175.7, 165.6, 164.7, 158.0, 157.6, 152.6, 141.6, 138.5, 136.7, 135.8, 132.2, 131.9, 131.7, 131.4, 131.3, 123.7, 64.9, 64.3, 38.9, 37.7, 37.5.

Example 42

Synthesis of N-(5-Cyclohexylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. Cyclohexanone (Aldrich) was sequentially converted via Methods MM, NN, OO and QQ into 4,6-dichloro-5-cyclohexylpyrimidine. L-4-(N,N-Dimethylcarbamyloxy)phenylalanine tert-butyl ester and 4,6-dichloro-5-cyclohexylpyrimidine were coupled via Method RR, and the product of this coupling was sequentially converted via Methods SS and ZZ to give the title compound.

Physical data were as follows:
$^1$H NMR (CD$_3$OD): δ=8.41 (bs, 1H), 7.89 (bs, 1H), 7.21 (d, 2H), 6.94 (d, 2H), 5.12 (dd, 1H), 3.47 (dd, 1H), 3.19 (dd, 1H), 3.06 (s, 3H), 2.95 (s, 3H), 3.0 (m, 1H), 2.88-2.57 (bs, 1H), 2.5 (bs, 1H), 1.95-1.67 (m, 1H).
$^{13}$C NMR (CD$_3$OD): δ=175.68, 165.82, 156.87, 152.10, 151.88, 141.96, 136.30, 131.44, 125.38, 122.89, 57.86, 37.44, 36.81, 36.64, 36.30, 32.65, 32.13, 27.29, 27.25, 26.95.

Example 43

Synthesis of N-(2-(N-Methyl-N-2-furanmethylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methylfurfurylamine (Salor) via Method CC to give a product that was coupled with o-tolyl boronic acid (Aldrich) via Method DD. The product of this coupling was converted via Method ZZ to give the title compound.

Physical data were as follows:
$^1$H NMR (CD$_3$OD): δ=7.43-7.35 (m, 2H), 7.35-7.2 (m, 2H), 7.2-7.0 (m, 4H), 7.0-6.9 (m, 2H), 6.42 (d, 1H), 6.39 (d, 1H), 4.85 (m, 1H), 3.3-3.1 (m, 7H), 3.09 (s, 3H), 2.98 (s, 3H), 2.16 (s, 3H), 1.89 (s, 3H).

Example 44

Synthesis of N-(2-(N-Methyl-N-4-chlorophenylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-4-chloroaniline (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CD$_3$OD): δ=8.17 (s, 1H), 7.56-7.34 (m, 8H), 7.1-6.97 (m, 4H), 3.50 (m, 2H), 3.13 (s, 3H), 2.1 (s, 3H), 2.17 (s, 3H), 1.94 (s, 3H).

Example 45

Synthesis of N-(5-(3-Thienyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with 3-thiophenyl boronic acid (Frontier Scientific, Inc.) via Method S. The product of this coupling was converted via Method KK to give the title compound.

Physical data were as follows:
$^1$H NMR (CD$_3$OD): δ=8.62 (s, 1H), 8.13 (s, 1H), 7.62 (m, 1H), 7.59 (m, 1H), 7.20 (d, 2H), 7.09 (d, 1H), 7.01 (d, 2H), 3.47-3.13 (m, 2H), 3.13 (s, 3H), 2.97 (s, 3H).
$^{13}$C NMR: δ=173.22, 162.83, 156.84, 152.17, 151.43, 141.46, 135.22, 131.54, 131.35, 129.96, 127.99, 127.90, 123.24, 117.13, 56.87, 36.82, 36.64.

Example 46

Synthesis of N-(5-(2-Thienyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O to 4-chloro-5-iodopyrimidine. L-4-(N,N-dimethylcarbamyloxy)phenylalanine tert-butyl ester and 4-chloro-5-iodopyrimidine were coupled via Method P, and the coupled product was reacted with 2-thiophenyl boronic acid (Frontier Scientific, Inc.) via Method S. The product of this coupling was converted via Method KK to give the title compound.

Physical data were as follows:
$^1$H NMR (CD$_3$OD): δ=8.10 (s, 1H), 7.67 (s, 1H), 7.19 (d, 1H), 6.73 (m, 4H), 6.49 (m, 2H), 4.80 (m, 1H), 2.89 (m, 1H), 2.70 (m, 1H), 2.60 (s, 3H), 2.45 (s, 3H).
$^{13}$C NMR (CD$_3$OD): δ=173.07, 162.72, 156.80, 152.13, 151.74, 142.30, 135.07, 131.58, 131.14, 130.69, 130.38, 129.92, 123.19, 115.18, 56.94, 36.87, 36.81, 36.62, 28.74.

Example 47

Synthesis of N-(2-(N-Methyl-N-2-hydroxyethylamino)-5-(2-fluorophenyl)pyrimidin-4-yl)-L-4-(N,N-dimethylcarbamyloxy)phenylalanine Tyrosine tert-butyl ester (Bachem) was sequentially converted via
Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with 2-(N-methylamino)ethanol (Aldrich) via Method CC to give a product that was coupled with 2-fluorophenyl boronic acid (Aldrich) via Method DD. The product of this coupling was converted via Method KK to give the title compound.

Example 48

Synthesis of N-(5-(Piperidin-1-yl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. Piperidine (Aldrich) was sequentially converted via Methods FFF, GGG and HHH into 4,6-dichloro-5-piperidin-1-ylpyrimidine. L-4-(N,N-Dimethylcarbamyloxy)phenylalanine tert-butyl ester and 4,6-dichloro-5-piperidin-1-ylpyrimidine were coupled via Method III, and the product of this coupling was sequentially converted via Methods JJJ and ZZ into the title compound.

Example 49

Synthesis of N-(5-(1-Propylbutyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4-Heptanone (Aldrich) was sequentially converted via Methods MM, NN, OO and QQ into 4,6-dichloro-5-(1-propylbutyl)pyrimidine. L-4-(N,N-Dimethylcarbamyloxy)phenylalanine tert-butyl ester and 4,6-dichloro-5-(1-propylbutyl)pyrimidine were coupled via Method RR, and the product of this coupling was sequentially converted via Methods SS and ZZ to give the title compound.

Example 50

Synthesis of N-(2-(N-Methyl-N-cyclobutylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methylcyclobutylamine (prepared by the Method of Giardina et al. J. Med. Chem. 1994, 37(21), 3482-3491) via Method CC to give a product that was coupled with o-tolyl boronic acid (Aldrich) via Method DD. The product of this coupling was converted via Method ZZ to give the title compound.

Example 51

Synthesis of N-(2-(N,N-Bis-(2-hydroxyethyl)amino)pyrimidin-4-yl)-L-4-(N,N-dimethylcarbamyloxy)phenylalanine A byproduct was isolated by chromatography of the crude product of Example 52, and the byproduct was converted via Method KK into the title compound.

Physical data were as follows:
$^1$H NMR (CD$_3$OD): δ=7.59 (d, 1H), 7.25 (d, 2H), 7.02 (d, 2H), 6.18 (d, 1H), 3.76 (brs, 8H), 2.97 (s, 8H).
$^{13}$C NMR (CD$_3$OD): δ=174.1, 163.7, 155, 152, 142.1, 135.2, 131.3, 123.7, 99, 60.5, 56.8, 53.2, 37.5, 36.8, 36.6.

Example 52

Synthesis of N-(2-(N,N-bis-(2-Hydroxyethyl)amino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with diethanolamine (Aldrich) via Method CC to give a product that was coupled with o-tolyl boronic acid (Aldrich) via Method DD. The product of this coupling was converted via Method KK to give the title compound.

Physical data were as follows:

$^1$H NMR (CD$_3$OD): δ=7.48-7.31 (m, 5H), 7.15-6.98 (m, 4H), 4.9 (m, 1H), 4.63 (m, 1H), 3.83 (d, 8H), 3.1 (s, 8H), 1.9 (d, 3H).

$^{13}$C NMR (CD$_3$OD): δ=173.8, 162.3, 154.6, 152.6, 140.9, 139.6, 139.4, 135.9, 135.8, 132.2, 132.0, 131.4, 131.2, 131.1, 128, 123.2, 123.1, 66.8, 60.6, 56:9, 56.4, 53.2, 52.8, 36.8, 36.6, 36.3; 19.5.

No Example 53

Example 54

Synthesis of N-(2-(N-Methyl-N-phenylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methylaniline (Aldrich) via Method CC to give a product that was coupled with o-tolyl boronic acid (Aldrich) via Method DD. The product of this coupling was converted via Method ZZ to give the title compound.

Physical data were as follows:

$^1$H NMR (CD$_3$OD): δ=7.57-6.99 (m, 14H), 4.99 (m, 1H), 3.49 (s, 3H), 3.11 (m, 5H), 2.98 (s, 3H), 2.16 (s, 3H).

$^{13}$C NMR (CD$_3$OD): δ=183.07, 173.72, 173.49, 162.55; 156.82, 153.97, 152.07, 142.25, 141.06, 140.91, 139.53, 139.40, 135.50, 135.39, 132.21, 132.16, 132.05, 131.52, 131.31, 130.53, 128.44, 128.11, 128.00, 123.13, 123.04, 113.18, 56.95, 56.49, 40.02, 39.96, 37.14, 36.83, 36.65, 19.56, 19.47.

Example 55

Synthesis of N-(2-(Isopropoxy)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was sequentially converted via Methods NNN, DD (using o-tolyl boronic acid, Aldrich) and ZZ to give the title compound.

Physical data were as follows:

$^1$H NMR (CDCl$_3$): δ=7.77 (bs, 1H), 7.40-6.8 (m, 9H), 6.43 (d, 0.5H) 6.27 (d, 0.5H), 6.78 (m, 1H), 6.16 (m, 1H), 3.09 (s, 3H), 3.00 (s, 3H), 3.40-2.80 (m, 4H), 2.20 (s, 1.5H), 1.94 (s, 1.5H), 1.23 (m, 6H).

$^{13}$C NMR (CDCl$_3$): δ=176.28, 176.15, 160.03, 159.78, 154.77, 153.65, 150.01, 169.97, 139.20, 137.81, 137.64, 134.39, 134.25, 130.71, 130.47, 130.12, 129.15, 126.69, 126.46, 121.24, 121.18, 109.56, 56.81, 56.34, 63.19, 36.90, 36.56, 36.32, 22.19, 21.99, 21.95, 19.51, 19.27.

Example 56

Synthesis of N-(2-(N-Methyl-N-3-methylbutylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl N-isoamylamine (Pfaltz-Bauer) via Method CC to give a product that was coupled with o-tolyl boronic acid (Aldrich) via Method DD. The product of this coupling was converted via Method ZZ to give the title compound.

Physical data were as follows:

$^1$H NMR (CDCl$_3$): δ=7.6 (s, 0:5 H), 7.56 (s, 0.5H), 7.30-6.80 (m, 8H) 6.30 (bm, 1H), 7.00-6.00 (br, 1H), 4.63 (m, 1H), 3.09 (s, 3H), 3.01 (s, 6H), 3.80-2.80 (m, 4H), 2.13 (s, 1.5H), 1.90 (s, 1.5H), 1.61 (m, 1H), 1.51 (bs, 2H), 0.96 (d, 6H).

$^{13}$C NMR (CDCl$_3$): δ=174.03, 173.87, 159.28, 159.04, 154.71, 153.67, 150.00, 142.10, 137.81, 137.53, 134.39, 134.22, 130.78, 130.58, 130.13, 128.96, 126.52, 126.30, 121.19, 121.13, 110.11, 109.91, 56.80, 56.40, 48.75, 36.55, 36:33, 35.80, 25.92, 22.54, 22.48, 19.53, 19.34.

Example 57

Synthesis of N-(2-(N-Methylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methylamine (Aldrich) via Method CC to give a product that was coupled with o-tolyl boronic acid (Aldrich) via Method DD. The product of this coupling was converted via Method ZZ to give the title compound.

Physical data were as follows:

$^1$H NMR (CDCl$_3$): δ=10.0-8.0 (br, 1H), 9.42 (bs, 1H), 8.24 (s, 1H), 7.4-6.8 (m, 10H), 5.93 (m, 1H), 4.85 (m, 1H), 3.2-2.8 (m, 1H), 3.37 (m, 1H), 3.12 (s, 1.5H), 3.11 (s, 1.5H), 3.03 (s, 1.5H), 3.02 (s, 1.5H), 2.95 (s, 3H), 2.13 (s, 1.5H), 1.83 (s, 1.5H).

Example 58

Synthesis of N-(2-(2-tolyl)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB: The product of this reaction was reacted with o-tolyl boronic acid (Aldrich) via Method KKK. The product of this coupling was converted via Method ZZ to give the title compound.

Physical data were as follows:
¹H NMR (CDCl₃): δ=8.14 (d, 1H), 7.68 (d, 1H), 7.4-6.8 (m, 12H), 5.42 (m, 1H), 4.94 (m, 1H), 3.11 (s, 3H), 3.02 (s, 3H), 3.4-2.8 (m, 2H), 2.49 (s, 3H), 2.11 (s, 1.5H), 1.91 (s, 1.5H).

Example 59

Synthesis of N-(2-(N-Methyl-N-2-hydroxyethylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with 2-(methylamino)-ethanol (Aldrich) via Method CC to give a product that was coupled with o-tolyl boronic acid (Aldrich) via Method DD. The product of this coupling was converted via Method ZZ to give the title compound.

Physical data were as follows:
¹H NMR (CD₃OD): δ=7.4-6.94 (m, 4H), 4.82 (m, 1H), 3.8 (brs, 4H), 3.23/3.26 (s, rotamers, 3H), 2.98/3.7 (s, rotamers, 6H), 1.93/2.14 (s, rotamers, 3H).

Example 60

Synthesis of N-(2-(N-Methyl-N-2-methylpropylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into. L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl isobutylamine (Aldrich) via Method CC to give a product that was coupled with o-tolyl boronic acid (Aldrich) via Method DD. The product of this coupling was converted via Method ZZ to give the title compound.

Physical data were as follows:
¹H NMR (CDCl₃): δ=10.5-9.8 (br, 1H), 7.63 (d, 1H), 7.3-6.8 (m, 8H), 6.35 (m, 1H), 4.65 (m, 1H), 3.6-2.8 (m, 4H), 3.08 (s, 3H), 3.01 (s, 6H), 2.13 (s, 1.5H), 2.06 (bs, 1H), 1.25 (s, 1.5H), 0.9 (s, 6H).
¹³C NMR (CDCl₃): δ=174.13, 173.97, 159.17, 158.9, 154.7, 153.99, 149.96, 142.00, 137.76, 137.53, 134.50, 134.33, 130.80, 130.58, 130.15, 128.95, 126.51, 126.30, 121.15, 121.11, 110.25, 109.99, 57.46, 56.90, 56.51, 36.89, 36.55, 36.32, 27.08, 19.87, 19.53, 19.38.

Example 61

Synthesis of N-(2-(N-Methyl-N-propylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-propylamine (Aldrich) via Method CC to give a product that was coupled with o-tolyl boronic acid (Aldrich) via Method DD. The product of this coupling was converted via Method ZZ to give the title compound.

Physical data were as follows:
¹H NMR (CDCl₃): δ=10.5-9.5 (br, 1H), 7.6 (d, 1H), 7.38-6.7 (m, 8H), 6.3 (m, 1H), 4.7 (m, 1H), 3.7-3.0 (m, 4H), 3.09 (s, 3H), 3.01 (s, 6H), 2.13 (s, 1.5H), 1.92 (s, 1.5H), 1.59 (bs, 2H), 0.89 (bs, 3H).
¹³C NMR (CDCl₃): δ=174.22, 174.06, 159.26, 159.0, 154.7, 153.76, 149.97, 142.22, 137.78, 137.53, 134.53, 134.36, 130.80, 130.73, 130.51, 130.12, 128.93, 126.50, 126.30, 121.16, 121.10, 110.13, 109.87, 56.90, 56.52, 51.72, 36.55, 36.33, 35.96, 20.45, 19.56, 19.37, 11.06.

Example 62

Synthesis of N-(2-(N,N-Dimethylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N,N-dimethylamine (Aldrich) via Method CC to give a product that was coupled with o-tolylboronic acid (Aldrich) via Method DD. The product of this coupling was converted via Method ZZ to give the title compound.

Physical data were as follows:
¹H NMR (CDCl₃): δ=11.0-9.5 (br, 1H), 7.62 (d, 1H), 7.3-6.8 (m, 8H), 6.22 (m, 1H), 4.72 (m, 1H), 3.5-3.0 (m, 2H), 3.8 (s, 6H), 3.01 (s, 3H), 2.12 (s, 1.5H), 1.94 (s, 1.5H).
¹³C NMR (CDCl₃): δ=174.49, 174.3, 159.4, 158.93, 154.72, 149.93, 140.30, 137.75; 137.60, 134.67, 134.50, 130.92, 130.80, 130.51, 130.11, 128.87, 126.48, 126.32, 121.15, 121.08, 109.87, 109.69, 56.86, 56.49, 37.51, 36.87, 36.55, 36.34, 19.50, 19.38.

Example 63

Synthesis of N-(2-(N-Methyl-N-cyclohexylamino)-5-(3-pyridyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-cyclohexylamine (Aldrich) via Method CC to give a product that was coupled with 3-pyridyl boronic acid 1,3-propanediol cyclic ester (Lancaster Synthesis) via Method DD. The product of this coupling was converted via Method HH to give the title compound.

Physical data were as follows:
¹H NMR (CD₃OD): δ=8.83-8.78 (m, 1H), 8.56 (brs, 1H), 8.09-7.95 (m, 2H), 7.76-7.73 (m, 1H), 7.22 (d, 2H), 7.06 (d, 2H), 4.85 (m, 1H), 3.45-3.38 (m, 1H), 3.18-3.11 (m, 41-1), 3.06 (s, 3H), 2.99 (sm, overlapping 4H), 1.92 (m, 2H), 1.76-1.57 (m, 8H).
¹³C NMR (CD₃OD): δ=173.7, 161.5, 161.4, 160.9, 157.0, 152.0, 146.0, 145.7, 145.6, 143.3, 136.0, 132.2, 131.3, 128.1, 123.4, 107.8, 57.8, 57.4, 36.8, 36.6, 36.1, 30.6, 30.0, 26.4, 26.2.

Example 64

Synthesis of N-(5-(2-Phenyl-2,2-difluoroethyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 1-Trifluoromethanesulfonyloxy-2,2-difluoro-2-phenylethane was sequentially converted via Methods LL, OO and QQ into 4,6-dichloro-5-(2,2-difluoro-2-phenylethyl)pyrimidine. L-4-(N,N-Dimethylcarbamyloxy)-phenylalanine tert-butyl ester and 4,6-dichloro-5-(2,2-difluoro-2-phenylethyl)pyrimidine were coupled via Method RR, and the product of this coupling was sequentially converted via Methods TT and ZZ to give the title compound.

Physical data were as follows:

$^1$H NMR (CD$_3$OD): δ=8.37 (s, 1H), 7.79 (s, 1H), 7.44 (s, 5H), 7.25 (d, 2H), 6.98 (d, 2H), 5.07 (dd, 1H), 3.62-3.32 (m, 3H), 3.14 (dd, 1H) 3.08 (s, 3H), 2.96 (s, 3H).

Example 65

Synthesis of N-(5-(2-Phenyl-2,2-difluoroethyl)-6-chloropyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 1-Trifluoromethanesulfonyloxy-2,2-difluoro-2-phenylethane was sequentially converted via Methods LL, OO and QQ into 4,6-dichloro-5-(2,2-difluoro-2-phenylethyl)pyrimidine. L-4-(N,N-Dimethylcarbamyloxy)-phenylalanine tert-butyl ester and 4,6-dichloro-5-(2,2-difluoro-2-phenylethyl)pyrimidine were, coupled via Method RR, and the product of this coupling was converted via Method ZZ to give the title compound.

Physical data were as follows:

$^1$H NMR (CD$_3$OD): δ=8.18 (s, 1H), 7.42-7.41 (m, 5H), 7.26 (d, 2H), 7.0 (d, 2H), 5.03 (dd, 1H), 3.72-3.45 (m, 2H), 3.34 (dd, 1H), 3.19 (dd, 1H), 3.08 (s, 3H), 2.96 (s, 3H).

Example 66

Synthesis of N-(5-(2-Phenylethyl)pyrimidin-4-yl)-L-4-(N,N-dimethylcarbamyloxy)phenylalanine 4(3H)-Pyrimidinone (Aldrich) was sequentially converted via Methods N and O into 4-chloro-5-iodopyrimidine. L-Phenylalanine tert-butyl ester hydrochloride (Bachem) and 4-chloro-5-iodopyrimidine were coupled via Method P. The product of this reaction was converted via Method W to a product that was sequentially converted via Methods X and HH to give the title compound.

Physical data were as follows:

$^1$H NMR (CD$_3$OD): δ=8.55 (d, 1H), 7.64 (d, 1H), 7.35-7.19 (m, 8H), 7.01-6.98 (m, 2H), 5.46-5.41 (m, 1H), 5.34-3.60 (m, 1H), 3.29-3.23 (m, 1H), 2.94-2.75 (m, 4H).

$^{13}$C NMR (CD$_3$OD): δ=174.3, 164.3, 151.5, 141.8, 141.7, 139.2, 131.0, 130.6, 130.5, 130.4, 128.9, 128.4, 120.6, 57.8, 38.4, 34.0, 30.7.

Example 67

Synthesis of N-(2-(N-Methyl-N-cyclohexylamino)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-cyclohexylamine. (Aldrich) via Method CC to give a product which was sequentially converted via Methods MMM and ZZ to give the title compound.

Physical data were as follows:

$^1$H NMR (CDCl$_3$): δ=11.20 (bs, 2H), 8.44 (s, 1H), 7.76 (bs, 1H), 7.50 (br, 1H), 7.18 (d, 2H), 6.96 (d, 2H), 5.91 (bs, 1H), 4.83 (bs, 1H), 4.53 (br, 1H), 3.20 (m, 2H), 3.08 (s, 3H), 2.98 (s, 6H), 2.00-1.00 (m, 10H).

$^{13}$C NMR (CDCl$_3$): δ=176.18, 171.50, 167.75, 162.44, 156.31, 154.49, 151.52, 135.83, 131.61, 122.85, 58.04, 56.87, 38.02, 37.79, 31.16, 31.00, 26.68.

Example 68

Synthesis of N-(5-Propylpyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P, and the product of this coupling was sequentially converted via Methods II, JJ and KK to give the title compound.

Physical data were as follows:

$^1$H NMR (CD$_3$OD): δ=8.51 (s, 1H), 7.97 (s, 1H), 7.26 (d, 2H), 6.97 (d, 2H), 5.36 (m, 1H), 3.51 (m, 1H), 3.23 (m, 1H), 3.16 (s, 3H), 2.95 (s, 3H), 2.47 (m, 2H), 1.57 (m, 2H), 0.99 (m, 3H).

$^{13}$C NMR (CD$_3$OD): δ=173.48, 163.61, 151.97, 150.75, 140.68, 135.74, 133.14, 131.30, 123.02, 120.85, 56.96, 36.99, 36.76, 36.58, 29.87, 21.02, 13.67.

Example 69

Synthesis of N-(5-(2-Methoxyphenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O to 4-chloro-5-iodopyrimidine L-4-(N,N-Dimethylcarbamyloxy)phenylalanine tert-butyl ester and 4-chloro-5-iodopyrimidine were coupled via Method P and the coupled product was reacted with 2-methoxyphenyl boronic acid (Lancaster Synthesis) via Method Q. The product of this coupling was converted via Method HH to give the title compound.

Physical data were as follows:

$^1$H NMR (CD$_3$OD): δ=8.64 (s, 1H), 8.05 (s, 1H), 7.61-7.55 (m, 1H), 7.27-7.13 (m, 5H), 6.99 (d, 2H), 5.36-5.32 (m, 1H), 3.73 (s, 3H), 3.46-3.40 (m, 1H), 4.20-3.13 (m, 4H), 3.02 (s, 3H).

$^{13}$C NMR (CD$_3$OD): δ=173.8, 163.5, 159.5, 157.5, 152.8, 152.1, 143.0, 135.9, 134.2, 133.9, 132.2, 123.8, 123.4, 120.5, 120.0, 113.7, 57.5, 57.1, 37.9, 37.7, 37.5.

Example 70

Synthesis of N-(5-(2-Fluorophenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with 2-fluorophenyl boronic acid (Lancaster Synthesis) via Method Q. The product of this coupling was converted via Method HH to give the title compound.

Example 71

Synthesis of N-(2-(N-Methyl-N-isopropylamino)-5-(2-tolyl)pyrimidin-4-yl)-L-4-(N,N-dimethylcarbamyloxy)phenylalanine Tyrosine tert-butyl ester (Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-isopropylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=10.5-9.5 (br, 1H), 7.59 (d, 1H), 7.30-6.70 (m, 8H), 6.3 (m, 1H), 4.92 (bs, 1H), 4.7 (m, 1H), 3.50-3.0 (m, 2H), 3.08 (s, 3H), 3.00 (s, 3H), 2.83 (s, 3H), 2.13 (s, 1.5H), 1.93 (s, 1.5H) 1.15 (d, 6H).
$^{13}$C NMR (CDCl$_3$): δ=174.31, 174.15, 159.21, 158.95, 154.70, 153.41, 149.92, 141.98, 137.79, 137.56, 134.59, 134.41, 130.59, 130.17, 128.95, 126.51, 126.32, 121.15, 110.26, 110.02, 56.87, 56.50, 46.86, 36.82, 36.55, 36.31, 28.18, 19.50, 19.39.

Example 72

Synthesis of N-(2-(N-Isopropylamino)-5-(2-tolyl)pyrimidin-4-yl)-L-4-(N,N-dimethylcarbamyloxy)phenylalanine Tyrosine tert-butyl ester-(Bachem) was sequentially converted via Methods UU, VV and WW into L-4-(N,N-dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with isopropylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=9.57 (s, 1H), 8.31 (s, 1H), 7.40-6.80 (m, 8H), 6.19 (m, 1H), 4.79 (m, 1H), 4.15 (m, 1H), 3.4-3.0 (m, 2H), 3.10 (s, 3H), 3.01 (s, 3H), 2.16 (s, 1.5H), 1.41 (s, 1.5H), 1.24 (s, 6H).
$^{13}$C NMR (CDCl$_3$): δ=176.07, 175.8, 166.23, 160.23, 159.99, 154.79, 153.50, 158.06, 139.38, 137.86, 137.66, 134.10, 133.93, 130.77, 130.61, 130.26, 130.01, 129.25, 126.71, 126.50, 121.46, 121.36, 109.59, 109.37, 56.77, 56.22, 43.31, 36.57, 36.34, 22.12, 21.96, 19.47, 19.22.

No Examples 73-77

Example 78

Synthesis of N-(5-(2-Phenylethyl)pyrimidin-4-yl)-L-4-(N,N-dimethylcarbamyloxy)phenylalanine Isopropyl Ester L-Tyrosine was sequentially converted via Methods LLL, UU, VV and WW into L-4-(N,N-dimethylcarbamyloxy)phenylalanine isopropyl ester. 4(3H)-Pyrimidinone (Aldrich) was sequentially converted via Methods N and O to 4-chloro-5-iodopyrimidine. L-4-(N,N-Dimethylcarbamyloxy)phenylalanine isopropyl ester and 4-chloro-5-iodopyrimidine were coupled via Method P, and the coupled product was converted via Method OOO to a product, which was converted via Method X to give the title compound.

Physical data were as follows:
$^1$H NMR (CDCl$_3$): δ=8.50 (s, 1H), 7.91 (s, 1H), 7.31-7.20 (m, 3H), 7.42-7.00 (m, 6H), 5.19-5.17 (m, 1H), 5.08-5.02 (m, 2H), 3.23-3.17 (m, 2H), 3.06 (s, 3H), 2.99 (s, 3H), 2.83-2.78 (m, 2H), 2.65-2.60 (m, 2H), 1.75-1.23 (m, 6H).
$^{13}$C NMR (CDCl$_3$): δ=171.8, 159.2, 156.7, 153.5, 150.7, 140.5, 130.3, 128.7, 128.5, 126.4, 121.8, 117.1, 69.4, 54.2, 36.9, 36.6, 36.5, 33.6, 29.8, 21.7, 21.6.

Example 79

Synthesis of N-(3-(N-Methyl-N-4-toluenesulfonylamino)pyrazin-2-yl)-L-phenylalanine Isopropyl Ester L-Phenylalanine (Aldrich) was converted via Method LLL to L-phenylalanine isopropyl ester hydrochloride. 2,3-Dichloropyrazine (Lancaster) was converted via Method QQQ and RRR into 2-chloro-3-nitropyrazine. L-Phenylalanine isopropyl ester hydrochloride and 2-chloro-3-nitropyrazine were coupled via Method BBB, and the product of this coupling was sequentially converted via Methods CCC, DDD and EEE to give the title compound.

Physical data were as follows:
$^1$H NMR (CDCl$_3$): δ=7.91 (d, 1H), 7.59 (d, 2H), 7.51 (d, 1H), 7.31-7.23 (m, 7H), 6.08 (d, 1H), 5.01-4.97 (m, 1H), 4.92-4.89 (m, 1H) 3.24 (d, 2H), 2.97 (s, 3H), 2.43 (s, 3H), 1.21-1.12 (m, 6H).
$^{13}$C NMR (CDCl$_3$): δ=167.32, 147.440, 139.85, 137.38, 133.25, 131.98, 128.68, 126.17, 125.17, 125.06, 124.41, 124.11, 122.58, 64.38, 50.65, 33.49, 32.41, 17.16, 17.08, 17.03.

Example 80

Synthesis of N-(5-(2-Phenylethyl)pyrimidin-4-yl)-L-phenylalanine Isopropyl Ester L-Phenylalanine isopropyl ester hydrochloride was prepared by Method LLL. 4(3H)-Pyrimidinone (Aldrich) was sequentially converted via Methods N and O to 4-chloro-5-iodopyrimidine. L-Phenylalanine isopropyl ester hydrochloride and 4-chloro-5-iodopyrimidine were coupled via Method P and the coupled product sequentially converted via Methods OOO and X to give the title compound.

Physical data were as follows:
$^1$H NMR (CDCl$_3$): δ=8.51 (s, 1H), 7.92 (s, 1H), 7.30-7.15 (m, 5H), 7.14-7.06 (m, 4H), 5.16 (m, 1H), 5.09-5.01 (m, 2H), 3.31-3.16 (m, 2H), 2.79-2.74 (m, 2H), 2.62-2.57 (m, 2H), 1.15-1.20 (m, 6H).
$^{13}$C NMR (CDCl$_3$): δ=171.7, 159.1, 156.7, 153.5, 140.5, 136.1, 129.4, 128.6, 128.5, 128.3, 127.1, 126.4, 117.0, 69.3, 54.2, 37.6, 33.7, 30.0, 21.7, 21.6.

No Example 81

Example 82

Synthesis of N-(5-(N-Methyl-N-3-pyridinesulfonylamino)pyrimidin-4-yl)-L-4-(4-methylpiperazin-1-ylcarbonyloxy)phenylalanine L-Tyrosine tert-butyl ester (Bachem) was sequentially converted via Methods UU, XX and YY into L-4-(4-methylpiperazin-1-ylcarbonyloxy)-phenylalanine tert-butyl ester. 5-Nitrouracil (Aldrich) was converted via Method AAA into 2,4-dichloro-5-nitropyrimidine. L-4-(4-Methylpiperazin-1-ylcarbonyloxy)phenylalanine tert-butyl ester and 2,4-dichloro-5-nitropyrimidine were coupled via Method BBB, and the product of this coupling was sequentially converted via Methods CCC, DDD (using 3-chlorosulfonylpyridine), EEE and ZZ to give the title compound.

No Examples 83-84

Example 85

Synthesis of N-(2-(N-Methyl-N-cyclohexylamino)-5-(2-tolyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N dimethylcarbamyloxy)-phenylalanine tert-butyl ester. L-4-(N,N-Dimethylcarbamyloxy)-phenylalanine tert-butyl ester and 5-bromo-2,4-dichloropyrimidine (Aldrich) were coupled via Method BB. The product of this reaction was reacted with N-methyl-N-cyclohexylamine (Aldrich) via Method CC to give a product that was coupled with o-tolyl boronic acid (Aldrich) via Method DD. The product of this coupling was converted via Method ZZ to give the title compound.

Physical data were as follows:
$^1$H NMR (CDCl$_3$): δ=10.0-9.08 (br, 1H), 7.55 (s, 0.5H), 7.52 (s, 0.5H), 7.20-6.31 (m, 8H), 6.36 (br, 1H), 4.69 (m, 2H), 3.40 (m, 1H), 3.15 (m, 1H), 3.06 (brs, 3H), 2.98 (brs, 3H), 2.84 (brs, 3H), 2.11 (s, 1.5H), 2.00-1.00 (brm, 11.5H).
$^{13}$C NMR (CDCl$_3$): δ=164.10, 159.20, 159.00, 154.79, 153.50, 150.03, 137.68, 137.48, 134.48, 130.66, 130.22, 129.01, 126.62, 126.40, 121.16, 110.20, 57.00, 56.58, 55.50, 36.62, 36.39, 29.91, 29.52, 25.41, 19.60, 19.65.

No Examples 86-87

Example 88

Synthesis of N-(5-(2-Tolyl)pyrimidin-4-yl)-L-4-(N,N-dimethylcarbamyloxy)phenylalanine Isopropyl Ester L-Tyrosine (Aldrich) was sequentially converted via Methods LLL, UU, VV and WW into. L-4-(N,N-dimethylcarbamyloxy)phenylalanine isopropyl ester. 4(3H)-Pyrimidinone (Aldrich) was sequentially converted via Methods N and O into 4-chloro-5-iodopyrimidine. L-4-(N,N-dimethylcarbamyloxy)-phenylalanine isopropyl ester and 4-chloro-5-iodopyrimidine were coupled via Method P. The product of this coupling was reacted with o-tolyl boronic acid via Method Q to afford the title compound.

Physical data were as follows:
$^1$H NMR (CDCl$_3$): δ=8.58 (s, 1H), 7.99 (s, 1H), 7.76-7.33 (m, 3H), 7.13 (m, 0.5H), 7.03-6.95 (m, 4H), 4.97-4.87 (m, 3H), 3.08-2.99 (m, 8H), 2.09 (s, 2H), 1.92 (s, 1.5H), 1.24-1.12 (m, 6H).
$^{13}$C NMR (CDCl$_3$): δ=171.4, 171.2, 158.8, 158.5, 157.5, 154.7, 153.6, 153.5, 150.5, 137.1, 137.0, 132.9, 132.3, 132.5, 130.8, 130.7, 130.0, 129.8, 129.7, 128.9, 126.6, 126.5, 121.6, 119.5, 119.4, 69.0, 54.5, 54.0, 36.9, 36.8, 36.6, 36.4, 21.65 21.60, 19.3, 19.2.

Example 89

Synthesis of N-(5-(3-Nitrophenyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P, and the coupled product was reacted with 3-nitrophenyl boronic acid (Aldrich) via Method T. The product of this coupling was converted via Method HH to give the title compound.

Physical data were as follows:
$^1$H NMR (CD$_3$OD): δ=8.67 (s, 1H), 8.41-8.38 (m, 1H), 8.28-8.27 (m, 1H), 8.17 (s, 1H), 7.82-7.77 (m, 1H), 7.67-7.65 (m, 1H), 7.20 (d, 2H), 7.02 (d, 2H), 5.33-5.28 (m, 1H), 3.47-3.411 (m, 1H), 3.12-3.04 (m, 4H), 2.97 (s, 3H).
$^{13}$C NMR (CD$_3$OD): δ=173.7, 163.6, 157.6, 152.8, 152.7, 151.2, 143.8, 137.4, 136.3, 134.2, 133.1, 132.2, 126.7, 126.3, 124.0, 120.3, 58.0, 37.7, 37.6, 37.5.

No Example 90

Example 91

Synthesis of N-(5-(3-Pyridyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O to 4-chloro-5-iodopyrimidine. L-4-(N,N-Dimethylcarbamyloxy)phenylalanine tert-butyl ester and 4-chloro-5-iodopyrimidine were coupled via Method P, and the coupled product was reacted with 3-pyridyl boronic acid 1,3-propanediol cyclic ester (Lancaster Synthesis) via Method Q. The product of this coupling was converted via Method HH to give the title compound.

Example 92

Synthesis of N-(5-(2-Phenylethyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P. The product of this reaction was sequentially converted via Methods W, X, and HH to give the title compound.

Physical data were as follows:

$^1$H NMR (CD$_3$OD): δ=8.52 (s, 1H), 7.67 (s, 1H), 7.34-7.19 (m, 5H), 7.08-6.99 (m, 4H), 5.50-5.42 (m, 1H), 5.59-5.53 (m, 1H), 3.26-3.21 (m, 1H), 3.09 (s, 2H), 2.99 (s, 3H), 2.94-2.85 (m, 4H).

$^{13}$C NMR (CD$_3$OD): δ=174.2, 164.2, 157.5, 152.7, 151.4, 141.8, 141.7, 136.5, 132.0, 130.5, 130.4, 128.4, 123.8, 120.5, 57.8, 37.9, 37.6, 37.5, 34.1, 30.6.

Example 93

Synthesis of N-(2-N,N-Dimethylamino-5-(N-methyl-N-4-toluenesulfonylamino)pyrimidin-4-yl)-L-phenylalanine 5-Nitrouracil (Aldrich) was converted via Method AAA into 2,4-dichloro-5-nitropyrimidine. L-Phenylalanine tert-butyl ester (Bachem) and 2,4-dichloro-5-nitropyrimidine were coupled via Method BBB, and the product of this coupling was sequentially converted via Methods SSS (using dimethylamine), CCC, DDD, EEE and ZZ to give the title compound.

Physical data were as follows:

$^1$H NMR (CD$_3$OD): δ=8.15 (s, formate), 7.65 (m, 2H), 7.41 (d, 2H), 7.40-7.19 (m, 5H), 7.02-6.92 (m, 1H), 4.90 (m, 1H), 3.40-3.10 (m, 2H), 3.09-2.92 (m, 9H), 2.43 (s, 3H).

$^{13}$C NMR (CD$_3$OD): δ=177.07, 159.64, 154.70, 152.25, 144.10, 141.97, 141.33, 140.25, 132.57, 129.02, 125.21, 124.82, 123.57, 123.42, 121.88, 107.64, 51.08, 33.71, 32.72, 31.76, 15.49.

Example 94

Synthesis of N-(5-(2-Tolyl)pyrimidin-4-yl)-L-4-(N,N-dimethylcarbamyloxy)phenylalanine L-Tyrosine tert-butyl ester (Bachem) was sequentially converted via Methods UU, VV and WW into L-4-(N,N-dimethylcarbamyloxy)-phenylalanine tert-butyl ester. 4(3H)-Pyrimidinone (Aldrich) was sequentially converted via Methods N and O into 4-chloro-5-iodopyrimidine. L-4-(N,N-Dimethylcarbamyloxy)phenylalanine tert-butyl ester and 4-chloro-5-iodopyrimidine were coupled via Method P and the coupled product was reacted with o-tolyl boronic acid (Aldrich) via Method Q. The product of this coupling was converted via Method HH to give the title compound.

Physical data were as follows:

$^1$H NMR (CD$_3$OD): δ=8.75-8.65 (d, 1H), 8.05-8.03 (d, 1H), 7.51-7.35 (m, 3H), 7.26-7.11 (m, 3H), 7.02-6.97 (m, 2H), 5.38-5.27 (m, 2H), 3.50-3.39 (m, 1H), 3.21-3.07 (m, 4H), 3.02 (s, 3H), 2.21-1.93 (s, 3H).

$^{13}$C NMR (CD$_3$OD): δ=173.8, 173.6, 164.0, 163.8, 157.5, 152.7, 152.6, 143.0, 142.8, 139.7, 139.5, 136.1, 135.9, 133.2, 133.0, 132.4, 132.2, 132.1, 131.9, 131.1, 129.0, 128.9, 123.8, 123.7, 122.2, 122.0, 57.6, 57.4, 37.8, 37.7, 37.5, 37.4, 20.3, 20.2.

Additionally, using the procedures described herein and the appropriate starting materials, the following additional compounds can be prepared:

N-(2-(N-methyl-N-cyclohexylamino)-5-(2-methoxyphenyl)pyrimidin-4-yl)-L-4-(2,6-dimethoxyphenyl)phenylalanine (Example 95), N-(2-(N-methyl-N-isopropylamino)-5-(2-fluorophenyl)pyrimidin-4-yl)-L-4-(2,6-dimethoxyphenyl)phenylalanine (Example 96), N-(2-(N-methyl-N-isopropylamino)-5-(2-fluorophenyl)pyrimidin-4-yl)-L-4-(2-methoxyphenyl)phenylalanine (Example 97), N-(2-(N-methyl-N-cyclohexylamino)-5-(2,6-difluorophenyl)pyrimidin-4-yl)-L-4-(2,6-difluorophenyl)phenylalanine (Example 98), N-(2-(N-methyl-N-cyclohexylamino)-5-(2-hydroxymethylphenyl)pyrimidin-4-yl)-L-4-(2,6-dimethoxyphenyl)phenylalanine (Example 99), N-(2-(N,N-bis-(2-hydroxyethyl)amino)-5-(2,4,6-trimethylphenyl)pyrimidin-4-yl)-L-4-(2,6-dimethoxyphenyl)phenylalanine (Example 100), N-(2-(N-methyl-N-cyclohexylamino)-5-(2-trifluoromethylphenyl)pyrimidin-4-yl)-L-4-(2-cyanophenyl)phenylalanine (Example 101), N-(2-(N-methyl-N-cyclohexylamino)-5-(3-thienyl)pyrimidin-4-yl)-L-4-(2,6-dimethoxyphenyl)phenylalanine (Example 102), N-(2-(N-methyl-N-cyclohexylamino)-5-(2-thienyl)pyrimidin-4-yl)-L-4-(4-trifluoromethylphenyl)phenylalanine (Example 103), N-(2-(N-methyl-N-cyclohexylamino)-5-(3-pyridyl)pyrimidin-4-yl)-L-4-(2,6-dimethoxyphenyl)phenylalanine (Example 104), N-(2-(N-methyl-N-cyclohexylamino)-5-(3-nitrophenyl)pyrimidin-4-yl)-L-4-(2,6-dimethoxyphenyl)phenylalanine (Example 105), N-(2-(N-methyl-N-cyclohexylamino)-5-(2,6-dichlorophenyl)pyrimidin-4-yl)-L-4-(2,6-dimethoxyphenyl)phenylalanine (Example 106), N-(2-(N-methyl-N-cyclohexylamino)-5-(4-pyridyl)pyrimidin-4-yl)-L-4-(3-hydroxymethylphenyl)phenylalanine (Example 107), N-(2-(N-ethyl-N-isopropylamino)-5-(2,6-dimethoxyphenyl)pyrimidin-4-yl)-L-4-(2,6-dimethoxyphenyl)phenylalanine (Example 108), N-(2-(N-methyl-N-cyclohexylamino)-5-(2,3-dichlorophenyl)pyrimidin-4-yl)-L-4-(2,6-dimethoxyphenyl)phenylalanine (Example 109), N-(2-(N-methyl-N-ethylamino)-5-(2,4,6-trimethylphenyl)pyrimidin-4-yl)-L-4-(2-cyanophenyl)phenylalanine (Example 110), N-(2-(N-methyl-N-isopropylamino)-5-(2,4,6-trimethylphenyl)pyrimidin-4-yl)-L-4-(3-pyridyl)phenylalanine (Example 111), N-(2-(N,N-bis-(2-hydroxyethyl)amino)-5-(2,4,6-trimethylphenyl)pyrimidin-4-yl)-L-4-(2-cyanophenyl)phenylalanine (Example 112), N-(2-(N-methyl-N-(1-methylpiperidin-4-yl)amino)-5-(2-cyanophenyl)pyrimidin-4-yl)-L-4-(2,6-difluorophenyl)phenylalanine (Example 113), N-(2-(N-ethyl-N-isopropylamino)-5-(2,4,6-trimethylphenyl)pyrimidin-4-yl)-L-4-(o-tolyl)phenylalanine (Example 114), N-(2-(N-methyl-N-4-chlorophenylamino)-5-(2,4,6-trimethylphenyl)pyrimidin-4-yl)-L-4-(2,6-dimethoxyphenyl)phenylalanine (Example 115), N-(5-(N-methyl-N-2-(phenyl)ethylamino)pyrimidin-4-yl)-L-4-(N,N-dimethylcarbamyloxy)phenylalanine (Example 116),
N-(5-(N-methyl-N-hexylamino)pyrimidin-4-yl)-L-4-(N,N-dimethylcarbamyloxy)phenylalanine (Example 117),
N-(5-(N-methyl-N-isopropylamino)pyrimidin-4-yl)-L-4-(N,N-dimethylcarbamyloxy)phenylalanine (Example 118),
N-(5-(N-methyl-N-isopropylamino)pyrimidin-4-yl)-L-4-(N,N-dimethylcarbamyloxy)phenylalanine (Example 119),
N-(5-(N-methyl-N-tert-butylamino)pyrimidin-4-yl)-L-4-(N,N-dimethylcarbamyloxy)phenylalanine (Example 120),
N-(5-(N-ethyl-N-isopropylamino)pyrimidin-4-yl)-L-4-(N,N-dimethylcarbamyloxy)phenylalanine (Example 121),
N-(5-(N-methyl-N-2-(4-pyridyl)ethyl-pyrimidin-4-yl)-L-4-(N,N-dimethylcarbamyloxy)phenylalanine (Example 122),
N-(5-(N-methyl-N-2-(phenyl)ethylamino)pyrimidin-4-yl)-L-4-(4-(2,6-dimethoxyphenyl)phenylalanine (Example 123),
N-(5-(N-methyl-N-hexylamino)pyrimidin-4-yl)-L-4-(2,6-dimethoxyphenyl)phenylalanine (Example 124),
N-(5-(N-methyl-N-isopropylamino)pyrimidin-4-yl)-L-4-(2,6-dimethoxyphenyl)phenylalanine (Example 125),
N-(5-(N-methyl-N-isopropylamino)pyrimidin-4-yl)-L-4-(2,6-dimethoxyphenyl)phenylalanine (Example 126),
N-(5-(N-methyl-N-tert-butylamino)pyrimidin-4-yl)-L-4-(2,6-dimethoxyphenyl)phenylalanine (Example 127),
N-(5-(N-ethyl-N-isopropylamino)pyrimidin-4-yl)-L-4-(2,6-dimethoxyphenyl)phenylalanine (Example 128),
N-(5-(N-methyl-N-2-(4-pyridyl)ethyl-pyrimidin-4-yl)-L-4-(2,6-dimethoxyphenyl)phenylalanine (Example 129)
N-(2-(N-methyl-N-cyclohexylamino)-5-ethylpyrimidin-4-yl)-L-4-(N,N-dimethylcarbamyloxy)phenylalanine (Example 130).

Example 131

Synthesis of N-(4-(N,N-Di-n-hexylamino)-1,1-dioxo-1,2,5-thiadiazol-3-yl)-L-tyrosine Step A: Preparation of 3,4-Diethyloxy-1-oxo-1,2,5-thiadiazole and 3,4-Diethyloxy-1,1-dioxo-1,2,5-thiadiazole The title intermediates were prepared according to the procedures described in R. Y. Wen et al, *J Org. Chem.*, (1975) 40, 2743; and R. Y. Wen et al, *Org Prep Proceed.*, (1969) 1, 255.

Step B: Preparation of 4-(N,N-Di-n-hexylamino)-3-ethoxy-1,1-dioxo-1,2,5-thiadiazole Dihexylamine (90 mg, 0.48 mmol) was added to a solution of 3,4-diethyloxy-1,1-dioxo-1,2,5-thiadiazole (100 mg, 0.48 mmol) in ethanol (5 mL) and the reaction stirred overnight at room temperature. The solvent was removed under reduced pressure and the residue absorbed onto silica gel; and purified by flash column chromatography (silica, hexane:EtOAc 3:1) to yield the title intermediate (120 mg, 72%).
Physical data were as follows:
MS (EI, m/e) 345.

Step C: Preparation of N-(4-(N,N-Di-n-hexylamino)-1,1-dioxo-1,2,5-thiadiazol-3-yl)-L-tyrosine tert-Butyl Ester A solution of 4-(N,N-di-n-hexylamino)-3-ethoxy-1,1-dioxo-1,2,5-thiadiazole (400 mg, 1.02 mmol) and L-tyrosine t-butyl ester (261 mg, 1.1 mmol) in EtOH (10 mL) was stirred at room temperature for 36 hrs. The solvent was removed under reduced pressure residue purified by flash column chromatography (silica, hexane:EtOAc 3:1 then 1:1) to give the title compound as a white waxy solid (400 mg, 73%).
Physical data were as follows:
Anal. Calc'd for $C_{27}H_{44}N_4O_5S \cdot 0.55 EtOAc$: C, 59.93; H, 8.34; N, 9.57. Found: C, 59.84; H, 8.44; N, 9.62.

Step D: Preparation of N-(4-(N,N-Di-n-hexylamino)-1,1-dioxo-1,2,5-thiadiazol-3-yl)-L-tyrosine The compound from Step C (100 mg, 0.19 mmol) was dissolved in formic acid and the mixture stirred at room temperature for 36 hrs. Excess formic acid was removed under reduced pressure to yield the title compound as a white solid (90 mg, 98%).
Physical data were as follows:
Anal. Calc'd for $C_{23}H_{36}N_4O_5S$: C, 57.48; H, 7.55; N, 11.66. Found: C, 57.04; H, 7.23; N, 11.38.

Example 132

Synthesis of N-(4-(N,N-Di-n-hexylamino)-1,1-dioxo-1,2,5-thiadiazol-3-yl)-L-4-(N,N-dimethylcarbamyloxy)phenylalanine Step A: Preparation of N-(4-(N,N-Di-n-hexylamino)-1,1-dioxo-1,2,5-thiadiazol-3-yl)-L-4-(N,N-dimethylcarbamyloxy)-phenylalanine tert-Butyl Ester N-(4-(N,N-Di-n-hexylamino)-1,1-dioxo-1,2,5-thiadiazol-3-yl)-L-tyrosine tert-butyl ester (180 mg, 0.34 mmol.) was dissolved in pyridine (5 ml). Dimethylcarbamoyl chloride (108 mg, 1 mmol) was added dropwise and the mixture stirred at room temperature overnight. Pyridine was removed under high vacuum (low water bath temperature), the residue absorbed onto silica gel and purified by flash column chromatography (silica, hexane:EtOAc 2:1) to yield the title compound (140 mg, 68%).

Step B: Preparation of N-(4-(N,N-Di-n-hexylamino)-1,1-dioxo-1,2,5-thiadiazol-3-yl)-L-4-(N,N-dimethylcarbamyloxy)-phenylalanine The compound from Step A (140 mg, 0.23 mmol) was dissolved in formic acid and the mixture stirred at room temperature overnight. Excess formic acid was removed under reduced pressure to yield the title compound as a white solid (110 mg, 87%).
Physical data were as follows:
Anal. Calc'd for $C_{26}H_{41}N_5O_6S$: C, 56.6; H, 7.49; N, 12.69. Found: C, 56.67; H, 7.4; N, 12.46.

Example 133

Synthesis of N-(4-(N,N-Di-n-hexylamino)-1,1-dioxo-1,2,5-thiadiazol-3-yl)-L-4-(4-methylpiperazin-1-ylcarbonyloxy)phenylalanine Step A: Preparation of N-(4-(N,N-Di-n-hexylamino)-1,1-dioxo-1,2,5-thiadiazol-3-yl)-L-4-(4-methylpiperazin-1-ylcarbonyloxy)phenylalanine tert-Butyl Ester A solution of N-(4-(N,N-di-n-hexylamino)-1,1-dioxo-1,2,5-thiadiazol-3-yl)-L-tyrosine tert-butyl ester (500 mg, 0.93 mmol), and p-nitrophenyl chloroformate (179 mg, 0.89 mmol) in dichloromethane (20 mL) was cooled to 0° C. under an argon atmosphere. Triethylamine (235 mg, 2.32 mmol) was added dropwise and the mixture stirred at 0° C. for 30 mins, then allowed to warm to room temperature for a further 40 mins. The mixture was recooled to 0° C. and N-methylpiperazine (90 mg, 0.89 mmol) added. The mixture was allowed to warm to room temperature and stirred for three hours. The mixture was diluted with diethyl ether (150 mL) and the organic solution washed with 10% potassium carbonate solution until no further yellow color was produced in the aqueous phase. The organic layer was separated, dried ($MgSO_4$) and the solvent removed under reduced pressure. The residue was purified by flash column chromatography (silica, EtOAc:MeOH:$Et_3$N 94:5:1) to give the title compound as a pale yellow foam (310 mg, 50%).

Physical data were as follows:

Anal. Calc'd for $C_{33}H_{54}N_6O_6S$: C, 59.79; H, 8.21; N, 12.68. Found: C, 59.47; H, 8.25; N, 12.49.

Step B: Preparation of N-(4-(N,N-Di-n-hexylamino)-1,1-dioxo-1,2,5-thiadiazol-3-yl)-L-4-(4-methylpiperazin-1-ylcarbonyloxy)phenylalanine The compound from Step A (200 mg, 0.3 mmol) was dissolved in formic acid (5 mL) and the mixture stirred at room temperature for 48 hrs. Excess formic acid was removed under reduced pressure and the residue recrystallized from EtOAc/MeOH to yield the title compound as an off-white solid (120 mg, 67%).

Physical data were as follows:

Anal. Calc'd for $C_{29}H_{46}N_6O_6S$. $0.75H_2O$: C, 56.15; H, 7.72; N, 13.55. Found: C, 56.1; H, 7.44; N, 13.46.

Example 134

Synthesis of N-[4-(2-(3-Methylphenylaminocarbonylamino)eth-1-ylamino)-1,1-dioxo-1,2,5-thiadiazol-3-yl]-L-4-(N,N-dimethylcarbamyloxy)phenylalanine Step A: Preparation of N-(4-Ethoxy-1,1-dioxo-1,2,5-thiadiazol-3-yl)-L-tyrosine tert-Butyl Ester A solution of 3,4-diethyloxy-1,1-dioxo-1,2,5-thiadiazole (400 mg, 1.94 mmol) and L-tyrosine t-butyl ester (1.25 g, 5.2 mmol) in ethanol (25 mL) was stirred at room temperature overnight. Solvent was removed under reduced pressure and the product used in further transformations without further purification (Yield 790 mg).

Step B: Preparation of 2-(3-Methylphenylaminocarbonylamino)eth-1-ylamine

N-Boc-Ethylene diamine (800 mg, 5 mmol) and m-tolyl isocyanate (665 mg, 5 mmol) were dissolved in acetonitrile and the mixture stirred at room temperature for 4 hrs. Solvent was removed under reduced pressure and the residue absorbed onto silica gel; prior to purification by flash column chromatography (silica, hexane:EtOAc 1:1) to yield the desired compound as a white solid (300 mg, 21%) (MS (+ESI, m/e) 294 (M+H)$^+$). The N-Boc protected compound (300 mg, 1.02 mmol) was dissolved in formic acid (10 ml) and the mixture stirred at room temperature overnight. Excess acid was removed to yield the formate salt of the title compound as a white foam (210 mg).

Step C: Preparation of N-[4-(2-(3-Methylphenylaminocarbonylamino)eth-1-ylamino)-1,1-dioxo-1,2,5-thiadiazol-3-yl]-L-tyrosine tert-Butyl Ester To a solution of N-(4-ethoxy-1,1-dioxo-1,2,5-thiadiazol-3-yl)-L-tyrosine tert-butyl ester from Step A (150 mg, 0.38 mmol) and the formate salt of 2-(3-methylphenylaminocarbonylamino)eth-1-ylamine from Step B (210 mg, 0.89 mmol) in ethanol (10 mL) was added triethylamine (133 mg, 1.44 mmol). The reaction was stirred at room temperature overnight. Solvent was removed under reduced pressure and the residue purified by flash column chromatography (silica, 5% MeOH in EtOAc) to give the title compound (130 mg, 91%).

Physical data were as follows:

MS (+ESI, m/e) 545 (M+H)$^+$.

Step D: Preparation of N-[4-(2-(3-Methylphenylaminocarbonylamino)eth-1-ylamino)-1,1-dioxo-1,2,5-thiadiazol-3-yl]-L-4-(N,N-dimethylcarbamyloxy)phenylalanine tert-Butyl Ester The intermediate from Step C (130 mg, 0.24 mmol) was dissolved in pyridine (5 mL). Dimethylcarbamoyl chloride (77 mg, 0.72 mmol) was added dropwise and the mixture heated at 50° C. under an argon atmosphere overnight. Pyridine was removed under reduced pressure, the residue absorbed onto silica gel and purified by flash column chromatography (silica, hexane:EtOAc 1:2, then 5% MeOH in EtOAc) to yield the title compound (140 mg, 93%).

Physical data were as follows:

MS (+ESI, m/e) 616 (M+H)$^+$.

Step E: Preparation of N-[4-(2-(3-Methylphenylaminocarbonylamino)eth-1-ylamino)-1,1-dioxo-1,2,5-thiadiazol-3-yl]-L-4-(N,N-dimethylcarbamyloxy)phenylalanine The compound from Step D (120 mg, 0.19 mmol) was dissolved in formic acid (10 mL) and the mixture stirred at room temperature for 36 hrs. Excess acid was removed to yield the title compound as a pale yellow foam (100 mg, 93%).

Physical data were as follows:

MS (+ESI, m/e) 560 (M+H)$^+$.

Example 135

Synthesis of N-(4-(N,N-Dimethylamino)-1-oxo-1,2,5-thiadiazol-3-yl)-L-4-(N,N-dimethylcarbamyloxy)phenylalanine tert-Butyl Ester Step A: Preparation of —N-(4-Ethoxy-1-oxo-1,2,5-thiadiazol-3-yl)-L-tyrosine tert-Butyl Ester A solution of 3,4-diethoxy-1-oxo-1,2,5-thiadiazole (1 g, 0.52 mmol) and L-tyrosine t-butyl ester (1.25 g, 0.52 mmol) in ethanol (25 mL) was stirred at room temperature for 60 hr. Solvent was removed under reduced pressure and the residue purified by flash column chromatography (silica, hexane:EtOAc 1:1 to give the title intermediate (1.75 g, 88%).

Physical data were as follows:

MS (+ESI, m/e) 382 (M+H)$^+$.

Step B: Preparation of N-(4-Ethoxy-1-oxo-1,2,5-thiadiazol-3-yl)-L-4-(N,N-dimethylcarbamyloxy)phenylalanine tert-Butyl Ester The intermediate from Step A (400 mg, 1.05 mmol) was dissolved in pyridine (10 mL) and dimethylcarbamoyl chloride (338 mg, 3.15 mmol) was added. The reaction was stirred at room temperature under an inert atmosphere overnight. TLC indicated large amounts of unreacted starting material so the mixture was heated at 50° C. for a further 48 hrs. Excess pyridine was removed under reduced pressure and the residue purified by flash column chromatography (silica, hexane: EtOAc 1:1 to give the title intermediate (280 mg, 59%).

Physical data were as follows:
MS (+ESI, m/e)'453 (M+H).

Step C: Preparation of N-(4-(N,N-Dimethylamino)-1-oxo-1,2,5-thiadiazol-3-yl)-L-4-(N,N-dimethylcarbamyloxy)phenylalanine tert-Butyl Ester A 2M solution of dimethylamine in THF (5 mL, 10 mmol) was added to a solution of the compound from Step B (180 mg, 0.35 mmol) in ethanol (10 mL). The reaction was stirred at room temperature overnight and solvent removed under reduced pressure. Residue was purified by flash column chromatography (silica, EtOAc:MeOH:Et$_3$N 90:10:1) to give the title compound as a white foam (140 mg, 88%).

Physical data were as follows:
Anal. Calc'd for $C_{220}H_{29}N_5O_5S$: C, 53.2; H, 6.47; N, 15.51. Found: C, 52.94; H, 6.18; N, 15.34.

Example 136

Synthesis of N-(5-(2,2,2-Trifluoroethyl)pyrimidin-4-yl)-L-4-(2,6-dimethoxyphenyl)phenylalanine Substituting L-4-(2,6-dimethoxyphenyl)phenylalanine methyl ester from Method TTT for L-4-(N,N-dimethylcarbamyloxy)phenylalanine tert-butyl ester and following the procedure described for the preparation of Example 31 yielded the title compound.

Physical data were as follows:
$^1$H NMR (CD$_3$OD): δ 8.41 (s, 1H), 8.05 (s, 1H), 7.24 (t, 1H), 7.2 (d, 2H), 7.1 (d, 2H), 6.67 (d, 2H), 5.1 (dd, 1H), 3.65 (s, 61-1), 161-3.42 (m, 2H), 3.36 (dd, 1H), 3.2 (dd, 1H).
$^{13}$C NMR (CD$_3$OD): δ 175.8, 162.3, 159.2, 157.9, 155.8, 136.9, 134.4, 132.2, 130.0, 129.5, 127.4, 120.9, 109.6, 105.7, 56.8, 56.2, 37.9, 32.6.

Example 137

Synthesis of N-(2-(N-Cyclohexyl-N-methyl)-5-(2-tolyl)pyrimidin-4-yl)-L-4-(2,6-dimethoxyphenyl)phenylalanine Substituting L-4-(2,6-dimethoxyphenyl)phenylalanine methyl ester from Method TTT for L-4-(N,N-dimethylcarbamyloxy)phenylalanine tert-butyl ester and following the procedure described for the preparation of Example 14 yielded the title compound.

Physical data were as follows:
$^1$H NMR (CD$_3$OD): δ 7.37-7.19 (m, 5.5H), 7.09-7.02 (m, 4H), 6.94 (d, 0.5H), 6.68 (d, 2H), 4.79-4.74 (m, 0.5H), 4.69-4.65 (m. 0.5H), 3.6.7 (s, 3H), 3.65 (s, 3H), 3.44-3.33 (m, 1H), 3.02-2.95 (m, 4H), 2.19 (s, 1.5H), 1.85-1.71 (m, 6.5H), 1:57 (m, 4H), 1.29-1.2 (br s, 1H).

Example 138

Synthesis of N-(5-(2-Fluorophenyl)pyrimidin-4-yl)-L-4-(2,6-dimethoxyphenyl)phenylalanine Substituting L-4-(2,6-dimethoxyphenyl)phenylalanine methyl ester from Method TTT for L-4-(N,N-dimethylcarbamyloxy)phenylalanine tert-butyl ester and following the procedure described for the preparation of Example 70 yielded the title compound.

Physical data were as follows:
$^1$H NMR (CD$_3$OD): δ 8.50 (s, 1H), 8.01 (s, 1H), 7.3-7.0 (m, 9H), 6.69 (d, 2H), 5.0 (m, 1H), 3.65 (s, 6H), 3.20-3.05 (m, 2H).
$^{13}$C NMR (CD$_3$OD): δ 153.2, 151.6, 147.1, 130.2, 128.6, 126.7, 126.6, 126.5, 126.4, 126.3, 123.9, 123.5, 123.2, 120.5, 120.4, 111.7, 111.4, 99.6, 59.3, 31.7.

Example 139

Synthesis of N-(2-(N-Methyl-N-propyl)-5-(2-tolyl)pyrimidin-4-yl)-L-4-(2,6-dimethoxyphenyl)phenylalanine Substituting L-4-(2,6-dimethoxyphenyl)phenylalanine methyl ester from Method TTT for L-4-(N,N-dimethylcarbamyloxy)phenylalanine tert-butyl ester and following the procedure described for the preparation of Example 61 yielded the title compound.

Physical data were as follows:
$^1$H NMR (CD$_3$OD): δ 10.30-8:80 (br, 1H), 7.68 (s, 0.5H), 7.63 (s, 0.5H), 7.40-6.60 (m, 1H), 6.15 (m, 1H), 4.70 (m, 1H), 3.68 (s, 3H), 3.66 (s, 3H), 3.80-3.00 (m, 4H), 3.07 (s, 3H), 2.12 (s, 1.5H), 2.08 (s, 1.5H), 1.61 (bs, 2H), 0.87 (bs, 3H).

Example 140

Synthesis of N-(3-Chloropyrazin-2-yl)-L-4-[1-(tert-butoxycarbonyl)piperidin-4-ylcarbonylamino]phenylalanine Ethyl Ester Step A: Preparation of N-(3-Chloropyrazin-2-yl)-L-4-nitrophenylalanine 4-Nitrophenylalanine (50 mm, ±10.59 mg) were stirred in absolute ethanol containing 1.0 eq (1.26 g) of sodium metal. The reaction mixture was stripped to a brown solid and the sodium salt was taken up in 200 mL of butanol containing 1.0 eq (7.45 g) 2,3-dichloropyrazine. The reaction mixture was refluxed overnight and the solvent was then removed under reduced pressure. The residue was taken up in ethyl acetate and washed with water (1×), brine (1×), dried over Na$_2$SO$_4$, filtered and stripped to give 15.5 g of the title intermediate as a brown oil.

Physical data were as follows:
Analytical: MS: (+)FAB [M+H]@M/Z 323 with 1 Cl.

Step B: Preparation of N-(3-Chloropyrazin-2-yl)-L-4-nitrophenylalanine Ethyl Ester The intermediate from Step A was suspended in 300 mL of absolute ethanol. The reaction flask was placed in an ice bath and cooled to 0° C. and HCl (g) was bubbled into reaction for 15 minutes. The gas tube was replaced with a drying tube and the reaction mixture was warmed to room temperature and stirred overnight. Ethanol was stripped off under reduced pressure to afford a dark brown residue which was taken up in ethyl acetate and washed with sat. NaHCO$_3$ (2×), H$_2$O (1×), brine (1×), dried over Na$_2$SO$_4$, filtered and stripped to afford 15 g of a dark brown oil. This oil (8.0 g) was chromatographed on a silica 60 column packed in methylene chloride to provide 1.5 g (20% yield) of the title intermediate.

Physical data were as follows:
Analytical: MS: EI M+@M/Z 350 1 Cl present.

Step C: Preparation of N-(3-Chloropyrazin-2-yl)-L-4-aminophenylalanine Ethyl Ester The intermediate from Step B (0.75 g, 0.021 mol) was placed in a Paar hydrogenation bottle with 50 mL ethanol and 0.40 g of Pd/C catalyst. The bottle was placed on Paar shaker under 50 psi of $H_2$ for 3 hrs. The reaction mixture was then filtered through a sintered glass funnel (F) and the filtered catalyst was washed with ethanol. The combined filtrates were stripped to a yellow oil and the oil was taken up in ethyl acetate. A yellow precipitate formed and was filtered off. The filtrate was washed with $NaHCO_3$ solution (1×), $H_2O$ (1×), brine (1×), dried over. $Na_2SO_4$, filtered and stripped to afford the title, intermediate as a yellow oil (0.340 g, 55% yield):

Step D: Preparation of N-(3-Chloropyrazin-2-yl)-L-4-[1-(tert-butoxycarbonyl)piperidin-4-ylcarbonylamino]phenylalanine Ethyl Ester N-Boc-piperidine 4-carboxylic acid (0.253 g, 1.0 eq., 0.0011 mol) was stirred in 30 mL methylene chloride and reaction mixture was cooled to 0° C. in ice bath. HOBt (0.224 g, 1.5 eq) was added and the mixture was stirred for 10 minutes then the intermediate from Step C (1 eq., 0.32 g) was added. The reaction mixture was stirred for 5 minutes and then 1,3-dicyclohexylcarbodiimide (0.25 g, 1.1 eq) was added. The reaction mixture was warmed to room temperature and stirred overnight. The reaction was then filtered and the filtrate was stripped to give a yellow solid. The solid was taken up in ethyl acetate and filtered. The ethyl acetate solution was washed with 10% citric acid (1×), $H_2O$ (1×), brine (1×), dried over $Na_2SO_4$, filtered and stripped to afford a yellow oil (0.630 g; MS: EI M+@M/Z 531 (1 chloro)). The yellow oil was chromatographed on a silica 60 column eluting with 3:1 hexane/ethyl acetate to afford 0.097 g of the title compound. This compound may also be used as an intermediate for other compounds of this invention.

Physical data were as follows:
Analytical: CHN: Theory (0.5$H_2O$): C, 57.71; H, 6.72; N, 12.94 Found: C, 57.79; H, 6.32; N, 12.78. MS: M+@M/Z 531 (1 Chloro).

Example A

In Vitro Assay For Determining Binding of Candidate Compounds to VLA-4

An in vitro assay was used to assess binding of candidate compounds to $\alpha_4\beta_1$ integrin. Compounds which bind in this assay can be used to assess VCAM-1 levels in biological samples by conventional assays (e.g., competitive assays). This assay is sensitive to $IC_{50}$ values as low as about 1 nM.

The activity of $\alpha_4\beta_1$ integrin was measured by the interaction of soluble VCAM-1 with Jurkat cells (e.g., American Type Culture Collection Nos. TIB 152, TIB 153, and CRL 8163), a human T-cell line which expresses high levels of $\alpha_4\beta_1$ integrin. VCAM-1 interacts with the cell surface in an $\alpha_4\beta_3$, integrin-dependent fashion (Yednock, et al. J. Biol. Chem., 1995, 270:28740).

Recombinant soluble VCAM-1 was expressed as a chimeric fusion protein containing the seven extracellular domains of VCAM-1 on the N-terminus and the human $IgG_1$ heavy chain constant region on the C-terminus. The VCAM-1 fusion protein was made and purified by the manner described by Yednock, supra.

Jurkat cells were grown in RPMI 1640 supplemented with 10% fetal bovine serum, penicillin, streptomycin and glutamine as described by Yednock, supra.

Jurkat cells were incubated with 1.5 mM $MnCl_2$ and 5 μg/mL 15/7 antibody for 30 minutes on ice. $Mn^{+2}$ activates the receptor to enhance ligand binding, and 15/7 is a monoclonal antibody that recognizes an activated/ligand occupied conformation of $\alpha_4\beta_1$ integrin and locks the molecule into this conformation thereby stabilizing the VCAM-1/$\alpha_4\beta_1$ integrin interaction. Yednock, et al., supra. Antibodies similar to the 15/7 antibody have been prepared by other investigators (Luque, et al, 1996, J. Biol. Chem. 271:11067) and may be used in this assay.

Cells were then incubated for 30 minutes at room temperature with candidate compounds, in various concentrations ranging from 66 μM to 0.01 μM using a standard 5-point serial dilution. 15 μL soluble recombinant VCAM-1 fusion protein was then added to Jurkat cells and incubated for 30 minutes on ice. (Yednock et al., supra.).

Cells were then washed two times and resuspended in PE-conjugated goat F(ab'), anti-mouse IgG Fc (Immunotech, Westbrook, Me.) at 1:200 and incubated on ice, in the dark, for 30 minutes. Cells were washed twice and analyzed with a standard fluorescence activated cell sorter ("FACS") analysis as described in Yednock, et al., supra.

Compounds having an $IC_{50}$ of less than about 15 μM possess binding affinity to $\alpha_4\beta_1$.

When tested in this assay, each of the compound prepared in the above examples has or is expected to have an $IC_{50}$ of 15 μM or less (or is expected to be active in vivo).

Example B

In Vitro Saturation Assay for Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 μg/ml of the 15/7 antibody (described in the above example).

The Jurkat cells are diluted two-fold into either normal plasma samples containing known candidate compound amounts in various concentrations ranging from 66 μM to 0.01 μM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any non-specific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related $\alpha_4\beta_1$ (Palmer et al, 1993, J. Cell Bio., 123:1289). Such binding is predictive of in vivo utility for inflammatory conditions mediated by $\alpha_9\beta_1$ integrin, including by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228) transfected with cDNA encoding $\alpha_9$ integrin (Yokosaki et al., 1994, J. Biol. Chem., 269:26691), in place of the Jurkat cells, to measure the binding of the $\alpha_9\beta_1$ integrin. As a control, SW 480 cells which express other $\alpha$ and $\beta_1$ subunits may be used.

Accordingly, another aspect of this invention is directed to a method for treating a disease in a mammalian patient, which disease is mediated by $\alpha_9\beta_1$, and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 µg/kg per day.

Example C

In Vivo Evaluation

The standard multiple sclerosis model, Experimental Autoimmune (or Allergic) Encephalomyelitis ("EAE"), was used to determine the effect of candidate compounds to reduce motor impairment in rats or guinea pigs. Reduction in motor impairment is based on blocking adhesion between leukocytes and the endothelium and correlates with anti-inflammatory activity in the candidate compound. This model has been previously described by Keszthelyi et al., Neurology, 1996, 47:1053-1059, and measures the delay of onset of disease.

Brains and spinal cords of adult Hartley guinea pigs were homogenized in an equal volume of phosphate-buffered saline. An equal volume of Freund's complete adjuvant (100 mg *mycobacterium tuberculosis* plus 10 ml Freund's incomplete adjuvant) was added to the homogenate. The mixture was emulsified by circulating it repeatedly through a 20 ml syringe with a peristaltic pump for about 20 minutes.

Female Lewis rats (2-3 months old, 170-220 g) or Hartley guinea pigs (20 day old, 180-200 g) were anesthetized with isoflurane and three injections of the emulsion, 0.1 ml each, were made in each flank. Motor impairment onset is seen in approximately 9 days.

Candidate compound treatment began on Day 8, just before onset of symptoms. Compounds were administered subcutaneously ("SC"), orally ("PO") or intraperitoneally ("IP"). Doses were given in a range of 10 mg/kg to 200 mg/kg, bid, for five days, with typical dosing of 10 to 100 mg/kg SC, 10 to 50 mg/kg PO, and 10 to 100 mg/kg IP.

Antibody GG513 against $\alpha_4\beta_1$ integrin (Keszthelyi et al., Neurology, 1996, 47:1053-1059), which delays the onset of symptoms, was used as a positive control and was injected subcutaneously at 3 mg/kg on Day 8 and 11.

Body weight and motor impairment were measured daily. Motor impairment was rated with the following clinical score:

0 no change
1 tail weakness or paralysis
2 hindlimb weakness
3 hindlimb paralysis
4 moribund or dead A candidate compound was considered active if it delayed the onset of symptoms, e.g., produced clinical scores no greater than 2 or slowed body weight loss as compared to the control.

Example D

Asthma Model

Inflammatory conditions mediated by $\alpha_4\beta_1$ integrin include, for example, airway hyper-responsiveness and occlusion that occurs with chronic asthma. The following describes an asthma model which can be used to study the in vivo effects of the compounds of this invention for use in treating asthma.

Following the procedures described by Abraham et al, J. Clin. Invest, 93:776-787 (1994), and Abraham et al, Am J. Respir Crit. Care Med, 156:696-703 (1997), both of which are incorporated by reference in their entirety. Compounds of this invention are formulated into an aerosol and administered to sheep which are hypersensitive to *Ascaris suum* antigen. Compounds which decrease the early antigen-induced bronchial response and/or block the late-phase airway response, e.g., have a protective effect against antigen-induced late responses and airway hyper-responsiveness ("AHR"), are considered to be active in this model.

Allergic sheep which are shown to develop both early and late bronchial responses to inhaled *Ascaris suum* antigen are used to study the airway effects of the candidate compounds. Following topical anesthesia of the nasal passages with 2% lidocaine, a balloon catheter is advanced through one nostril into the lower esophagus. The animals are then intubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provides an aerosol with a mass median aerodynamic diameter of 3.2 µm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at $V_T$ of 500 ml and a rate of 20 breaths/minute. A 0.5% sodium bicarbonate solution only is used as a control.

To assess bronchial responsiveness, cumulative concentration-response curves to carbachol can be generated according to Abraham (1994). Bronchial biopsies can be taken prior to and following the initiation of treatment and 24 hours after antigen challenge. Bronchial biopsies can be preformed according to Abraham (1994).

An in vitro adhesion study of alveolar macrophages can also be performed according to Abraham (1994), and a percentage of adherent cells is calculated.

Aerosol Formulation

A solution of the candidate compound in 0.5% sodium bicarbonate/saline (w/v) at a concentration of 30.0 mg/mL is prepared using the following procedure:

A. Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:
1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

B. Preparation of 30.0 mg/mL Candidate Compound: 10.0 mL

| Ingredient | Gram/10.0 mL | Final Concentration |
|---|---|---|
| Candidate Compound | 0.300 g | 30.0 mg/mL |
| 0.5% Sodium Bicarbonate/Saline Stock Solution | q.s. ad 10.0 mL | q.s ad 100% |

Procedure:
1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix thoroughly.

Using a conventional oral formulation, compounds of this invention would be active in this model.

Example E

Allograft Model

Allograft rejection, associated with infiltration of inflammatory cells, is the leading obstacle to long-term allograft survival. Cell surface adhesion molecules facilitate alloantigen recognition in vitro and may be critical for lymphocyte traffic in vivo. The following describes a model which can be used to study the in vivo effects of the compounds of this invention in the control of allograft rejection.

The following procedures are described in Coito et al., *Transplantation* (1998) 65(6):699-706 and in Korom et al., *Transplantation* (1998) 65(6):854-859, both of which are incorporated by reference in their entirety.

Following the procedures described in Coito and Korom, male adult rats weighing approximately 200-250 g are used in this model. Lewis rats are used as the recipients of cardiac allografts from Lewis X Brown Norway rats. Hearts are transplanted into the abdominal great vessels using standard microvascular techniques.

A candidate compound is administered to the transplant recipient in a suitable pharmaceutical carrier for a 7-day course of treatment starting the day of the engraftment. Doses range from 0.3 to 30 mg/kg/day. Control recipients receive the pharmaceutical carrier only. The rats are euthanized and their cardiac allografts are analyzed as described in Coito and Korom.

Using conventional formulations, compounds of this invention would be active in this model.

What is claimed is:

1. A method for treating a condition in a patient said condition selected from the group consisting of asthma, inflammatory bowel disease, ulcerative colitis, Crohn's disease, multiple sclerosis, rheumatoid arthritis, graft versus host disease, and organ or graft rejection, which method comprises administering a pharmaceutical composition comprising a pharmaceutically acceptable carrier and a therapeutically effective amount of compound of formula IIa:

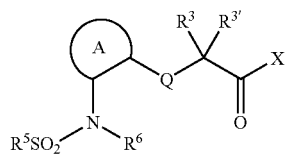

or a pharmaceutically acceptable salt thereof,
wherein
ring A forms a pyrimidine ring, optionally substituted with 1 or 2 substituents selected from the group consisting of $R^{101}$, $R^{102}$, $R^{103}$, $R^{104}$, $R^{105}$, $R^{106}$, $R^{107}$, $R^{108}$, $R^{109}$, $R^{110}$, alkoxy, substituted alkoxy, amino, substituted amino and halogen,
$R^3$ is —$(CH_2)_x$—Ar—$R^9$, wherein
Ar is $R^{107}$ or $R^{109}$;
x is an integer from 0 to 4; and
$R^9$ is selected from the group consisting of acyl, acylamino, acyloxy, aminoacyl, aminocarbonylamino, aminothiocarbonylamino, aminocarbonyloxy, oxycarbonylamino, thioamidino, thiocarbonylamino, aminosulfonylamino, aminosulfonyloxy, aminosulfonyl, oxysulfonylamino and oxysulfonyl;
$R^{3'}$ is hydrogen;
Q is —$NR^4$—, wherein $R^4$ is hydrogen or $R^{101}$;
$R^5$ is selected from the group consisting of $R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{115}$ and $R^{116}$;
$R^6$ is selected from the group consisting of hydrogen, $R^{110}$, $R^{102}$, $R^{103}$, $R^{104}$, $R^{105}$, $R^{106}$, $R^{107}$, $R^{108}$, $R^{109}$, $R^{110}$, $R^{115}$ and $R^{116}$; and
X is selected from the group consisting of hydroxyl, alkoxy, substituted alkoxy, alkenoxy, substituted alkenoxy, cycloalkoxy, substituted cycloalkoxy, cycloalkenoxy, substituted cycloalkenoxy, aryloxy, substituted aryloxy, heteroaryloxy, substituted heteroaryloxy, heterocyclyloxy, substituted heterocyclyloxy and —NR"R", wherein each R" is independently selected from the group consisting of hydrogen, $R^{101}$, $R^{102}$, $R^{103}$, $R^{104}$, $R^{105}$, $R^{106}$, $R^{107}$, $R^{108}$, $R^{109}$, $R^{110}$, $R^{111}$ and $R^{112}$
wherein
$R^{101}$ is alkyl of from 1 to 10 carbon atoms;

$R^{102}$ is substituted alkyl of from 1 to 10 carbon atoms, having from 1 to 5 substituents selected from the group consisting of
  (1) $R^{200}$;
  (2) unsymmetric di-substituted amines having different substituents selected from the group consisting of $R^{101}$, $R^{102}$, $R^{107}$, $R^{108}$, $R^{109}$, $R^{110}$, $R^{105}$ and $R^{106}$;
  (3) amino groups blocked by blocking groups selected from the group consisting of tert-butyloxycarbonyl (Boc), carbobenzyloxy (Cbz) and formyl; and
  (4) $R^{300}$;
$R^{103}$ is cycloalkyl of from 3 to 8 carbon atoms;
$R^{104}$ is substituted cycloalkyl of from 3 to 8 carbon atoms, having from 1 to 5 substituents selected from the group consisting of
  (1) $R^{200}$;
  (2) oxo (=O);
  (3) thioxo (=S);
  (4) unsymmetric di-substituted amines having different substituents selected from the group consisting of $R^{101}$, $R^{102}$, $R^{107}$, $R^{108}$, $R^{109}$, $R^{110}$, $R^{105}$ and $R^{106}$;
  (5) amino groups blocked by blocking groups selected from tert-butyloxycarbonyl (Boc), carbobenzyloxy (Cbz) and formyl; and
  (6) $R^{300}$;
$R^{105}$ is heterocyclic referring to a saturated or unsaturated group having from 1 to 10 carbon atoms and from 1 to 4 heteroatoms selected from nitrogen, sulfur and oxygen, and having a single ring or multiple fused rings, wherein in fused ring systems one or more of the rings can be aryl ($R^{107}$) or heteroaryl ($R^{109}$);
$R^{106}$ is substituted heterocyclic of from 1 to 10 carbon atoms and from 1 to 4 heteroatoms, substituted with from 1 to 3 substituents selected from the group consisting of
  (1) $R^{200}$;
  (2) oxo (=O);
  (3) thioxo (=S);
  (4) unsymmetric di-substituted amines having different substituents selected from the group consisting of $R^{110}$, $R^{102}$, $R^{107}$, $R^{108}$, $R^{109}$, $R^{110}$, $R^{105}$ and $R^{106}$;
  (5) amino groups blocked by blocking groups selected from tert-butyloxycarbonyl (Boc), carbobenzyloxy (Cbz) and formyl; and
  (6) $R^{300}$;
$R^{107}$ is aryl, wherein aryl is an unsaturated aromatic carbocyclic group of from 6 to 14 carbon atoms having a single ring or multiple condensed rings, wherein the condensed rings may or may not be aromatic;
$R^{108}$ is substituted aryl, wherein substituted aryl is aryl substituted with from 1 to 3 substituents selected from the group consisting of
  (1) $R^{201}$;
  (2) unsymmetric di-substituted amines having different substituents selected from the group consisting of $R^{101}$, $R^{102}$, $R^{105}$, $R^{106}$, $R^{107}$, $R^{108}$, $R^{109}$ and $R^{110}$;
  (3) amino groups blocked by blocking groups selected from tert-butyloxycarbonyl (Boc), carbobenzyloxy (Cbz) and formyl; and
  (4) —SO$_2$ NRR;
$R^{109}$ is heteroaryl of from 2 to 10 carbon atoms and 1 to 4 heteroatoms selected from oxygen, nitrogen and sulfur within the ring or oxides thereof, having a single ring or multiple condensed rings;
$R^{110}$ is substituted heteroaryl of from 2 to 10 carbon atoms and 1 to 4 heteroatoms selected from oxygen, nitrogen and sulfur, substituted with from 1 to 3 substituents selected from the group consisting of
  (1) $R^{201}$;
  (2) unsymmetric di-substituted amines having different substituents selected from the group consisting of $R^{101}$, $R^{102}$, $R^{107}$, $R^{108}$, $R^{109}$, $R^{110}$, $R^{105}$ and $R^{106}$;
  (3) amino groups blocked by blocking groups selected from tert-butyloxycarbonyl (Boc), carbobenzyloxy (Cbz) and formyl; and
  (4) —SO$_2$ NRR;
$R^{111}$ is alkenyl of from 2 to 10 carbon atoms and from 1 to 2 sites of alkenyl unsaturation;
$R^{112}$ is substituted alkenyl, wherein substituted alkenyl is alkenyl substituted with from 1 to 5 substituents selected from the group consisting of
  (1) $R^{200}$;
  (2) unsymmetric di-substituted amines having different substituents selected from the group consisting of $R^{101}$, $R^{102}$, $R^{107}$, $R^{108}$, $R^{109}$, $R^{110}$, $R^{105}$ and $R^{106}$;
  (3) amino groups blocked by blocking groups selected from tert-butyloxycarbonyl (Boc), carbobenzyloxy (Cbz) and formyl; and
  (4) $R^{300}$;
$R^{113}$ is alkynyl of from 2 to 10 carbon atoms and from 1 to 2 sites of alkynyl unsaturation;
$R^{114}$ is substituted alkynyl, wherein substituted alkynyl is alkynyl substituted with from 1 to 5 substituents selected from the group consisting of
  (1) $R^{200}$;
  (2) unsymmetric di-substituted amines having different substituents selected from the group consisting of $R^{101}$, $R^{102}$, $R^{107}$, $R^{108}$, $R^{109}$, $R^{110}$, $R^{105}$ and $R^{106}$;
  (3) amino groups blocked by blocking groups selected from tert-butyloxycarbonyl (Boc), carbobenzyloxy (Cbz) and formyl; and
  (4) $R^{300}$;
$R^{115}$ is cycloalkenyl, wherein cycloalkenyl is a cyclic alkenyl group of from 3 to 8 carbon atoms having single or multiple unsaturation, and which is not aromatic;
$R^{116}$ is substituted cycloalkenyl of from 3 to 8 carbon atoms, having from 1 to 5 substituents selected from the group consisting of
  (1) $R^{200}$;
  (2) oxo (=O);
  (3) thioxo (=S); and
  (4) unsymmetric di-substituted amines having different substituents selected from the group consisting of $R^{101}$, $R^{102}$, $R^{107}$, $R^{108}$, $R^{109}$, $R^{110}$, $R^{105}$ and $R^{106}$;
  (5) amino groups blocked by blocking groups slected from tert-butyloxycarbonyl (Boc), carbobenzyloxy (Cbz) and formyl; and
  (6) $R^{300}$;
wherein
$R^{200}$ is a member selected from
  (1) alkoxy;
  (2) substituted alkoxy;
  (3) acyl;
  (4) acylamino;
  (5) thiocarbonylamino;
  (6) acyloxy;
  (7) amino;
  (8) amidino;
  (9) alkylamidino wherein alkyl is $R^{101}$;
  (10) thioamidino;
  (11) aminoacyl;
  (12) aminocarbonylamino;
  (13) aminothiocarbonylamino;

(14) aminocarbonyloxy;
(15) $R^{107}$;
(16) $R^{108}$;
(17) aryloxy;
(18) substituted aryloxy;
(19) aryloxyaryl;
(20) substituted aryloxyaryl;
(21) halogen;
(22) hydroxyl;
(23) cyano;
(24) nitro;
(25) carboxyl;
(26) carboxylalkyl wherein alkyl is $R^{101}$;
(27) carboxyl-substituted alkyl wherein substituted alkyl is $R^{102}$;
(28) carboxyl-cycloalkyl wherein cycloalkyl is $R^{103}$;
(29) carboxyl-substituted cycloalkyl wherein substituted cycloalkyl is $R^{104}$;
(30) carboxylaryl wherein aryl is $R^{107}$;
(31) carboxyl-substituted aryl wherein substituted aryl is $R^{108}$;
(32) carboxylheteroaryl wherein heteroaryl is $R^{109}$;
(33) carboxyl-substituted heteroaryl wherein substituted heteroaryl is $R^{110}$;
(34) carboxylheterocyclic wherein heterocyclic is $R^{105}$;
(35) carboxyl-substituted heterocyclic wherein substituted heterocyclic is $R^{106}$;
(36) $R^{103}$;
(37) $R^{104}$;
(38) guanidino;
(39) guanidinosulfone;
(40) thiol having the formula —SH;
(41) thioalkyl;
(42) substituted thioalkyl;
(43) thioaryl;
(44) substituted thioaryl;
(45) thiocycloalkyl;
(46) substituted thiocycloalkyl;
(47) thioheteroaryl;
(48) substituted thioheteroaryl;
(49) thioheterocyclic;
(50) substituted thioheterocyclic;
(51) $R^{109}$;
(52) $R^{110}$;
(53) $R^{105}$;
(54) $R^{106}$;
(55) cycloalkoxy;
(56) substituted cycloalkoxy;
(57) heteroaryloxy;
(58) substituted heteroaryloxy;
(59) heterocyclyloxy;
(60) substituted heterocyclyloxy;
(61) oxycarbonylamino;
(62) oxythiocarbonylamino;
(63) —OS(O)$_2$-alkyl, wherein alkyl is $R^{101}$;
(64) —OS(O)$_2$-substituted alkyl wherein substituted alkyl is $R^{102}$;
(65) —OS(O)$_2$-aryl, wherein aryl is $R^{107}$;
(66) —OS(O)$_2$-substituted aryl wherein substituted aryl is $R^{108}$;
(67) —OS(O)$_2$-heteroaryl wherein heteroaryl is $R^{109}$;
(68) —OS(O)$_2$-substituted heteroaryl wherein substituted heteroaryl is $R^{110}$;
(69) —OS(O)$_2$-heterocyclic wherein heterocyclic is $R^{105}$;
(70) —OS(O)$_2$-substituted heterocyclic wherein substituted heterocyclic is $R^{106}$;
(71) —OSO$_2$—NRR where R is hydrogen or $R^{101}$;
(72) —NRS(O)$_2$-alkyl, wherein alkyl is $R^{101}$;
(73) —NRS(O)$_2$-substituted alkyl wherein substituted alkyl is $R^{102}$;
(74) —NRS(O)$_2$-aryl, wherein aryl is $R^{107}$;
(75) —NRS(O)$_2$-substituted aryl wherein substituted aryl is $R^{108}$;
(76) —NRS(O)$_2$-heteroaryl wherein heteroaryl is $R^{109}$;
(77) —NRS(O)$_2$-substituted heteroaryl wherein substituted heteroaryl is $R^{110}$;
(78) —NRS(O)$_2$-heterocyclic wherein heterocyclic is $R^{105}$;
(79) —NRS(O)$_2$-substituted heterocyclic wherein substituted heterocyclic is $R^{106}$;
(80) —NRS(O)$_2$—NR-alkyl, wherein alkyl is $R^{101}$;
(81) —NRS(O)$_2$—NR-substituted alkyl wherein substituted alkyl is $R^{102}$;
(82) —NRS(O)$_2$—NR-aryl, wherein aryl is $R^{107}$;
(83) —NRS(O)$_2$—NR-substituted aryl wherein substituted aryl is $R^{108}$;
(84) —NRS(O)$_2$—NR-heteroaryl wherein heteroaryl is $R^{109}$;
(85) —NRS(O)$_2$—NR-substituted heteroaryl wherein substituted heteroaryl is $R^{110}$;
(86) —NRS(O)$_2$—NR-heterocyclic wherein heterocyclic is $R^{105}$;
(87) —NRS(O)$_2$—NR-substituted heterocyclic wherein substituted heterocyclic is $R^{106}$,
(88) mono- and di-alkylamino, wherein alkyl is $R^{101}$;
(89) mono- and di-(substituted alkyl)amino, wherein substituted alkyl is $R^{102}$;
(90) mono- and di-arylamino wherein aryl is $R^{107}$;
(91) mono- and di-substituted arylamino wherein substituted aryl is $R^{108}$;
(92) mono- and di-heteroarylamino wherein heteroaryl is $R^{109}$;
(93) mono- and di-substituted heteroarylamino wherein substituted heteroaryl is $R^{110}$;
(94) mono- and di-heterocyclic amino wherein heterocyclic is $R^{105}$; and
(95) mono- and di-substituted heterocyclic amino wherein substituted heterocyclic is $R^{106}$;

$R^{201}$ is a member selected from
(1) hydroxyl;
(2) acyl;
(3) acylamino;
(4) thiocarbonylamino;
(5) acyloxy;
(6) $R^{101}$;
(7) $R^{102}$;
(8) alkoxy;
(9) substituted alkoxy;
(10) $R^{111}$;
(11) $R^{112}$;
(12) $R^{113}$;
(13) $R^{114}$;
(14) amidino;
(15) alkylamidino, wherein alkyl is $R^{101}$;
(16) thioamidino;
(17) amino;
(18) aminoacyl;
(19) aminocarbonyloxy;
(20) aminocarbonylamino;
(21) aminothiocarbonylamino;
(22) $R^{107}$;
(23) $R^{108}$;
(24) aryloxy;

(25) substituted aryloxy;
(26) cycloalkoxy;
(27) substituted cycloalkoxy;
(28) heteroaryloxy;
(29) substituted heteroaryloxy;
(30) heterocyclyloxy;
(31) substituted heterocyclyloxy;
(32) carboxyl;
(33) carboxylalkyl wherein alkyl is $R^{101}$;
(34) carboxyl-substituted alkyl wherein substituted alkyl is $R^{102}$;
(35) carboxyl-cycloalkyl wherein cycloalkyl is $R^{103}$;
(36) carboxyl-substituted cycloalkyl wherein substituted cycloalkyl is $R^{104}$;
(37) carboxylaryl wherein aryl is $R^{107}$;
(38) carboxyl-substituted aryl wherein substituted aryl is $R^{108}$;
(39) carboxylheteroaryl wherein heteroaryl is $R^{109}$;
(40) carboxyl-substituted heteroaryl wherein substituted heteroaryl is $R^{110}$;
(41) carboxylheterocyclic wherein heterocyclic is $R^{105}$;
(42) carboxyl-substituted heterocyclic wherein substituted heterocyclic is $R^{106}$;
(43) carboxylamido;
(44) cyano;
(45) thiol having the formula —SH;
(46) thioalkyl;
(47) substituted thioalkyl;
(48) thioaryl;
(49) substituted thioaryl;
(50) thioheteroaryl;
(51) substituted thioheteroaryl;
(52) thiocycloalkyl;
(53) substituted thiocycloalkyl;
(54) thioheterocyclic;
(55) substituted thioheterocyclic;
(56) $R^{103}$;
(57) $R^{104}$;
(58) guanidino;
(59) guanidinosulfone;
(60) halogen;
(61) nitro;
(62) $R^{109}$;
(63) $R^{110}$;
(64) $R^{105}$;
(65) $R^{106}$;
(66) cycloalkoxy;
(67) substituted cycloalkoxy;
(68) heteroaryloxy;
(69) substituted heteroaryloxy;
(70) heterocyclyloxy;
(71) substituted heterocyclyloxy;
(72) oxycarbonylamino;
(73) oxythiocarbonylamino;
(74) —S(O)$_2$-alkyl wherein alkyl is $R^{101}$;
(75) —S(O)$_2$-substituted alkyl wherein substituted alkyl is $R^{102}$;
(76) —S(O)$_2$-cycloalkyl wherein cycloalkyl is $R^{103}$;
(77) —S(O)$_2$-substituted cycloalkyl wherein substituted cycloalkyl is $R^{104}$;
(78) —S(O)$_2$-alkenyl wherein alkenyl is $R^{111}$;
(79) —S(O)$_2$-substituted alkenyl wherein substituted alkenyl is $R^{112}$;
(80) —S(O)$_2$-aryl wherein aryl is $R^{107}$;
(81) —S(O)$_2$-substituted aryl wherein substituted aryl is $R^{108}$;
(82) —S(O)$_2$-heteroaryl wherein heteroaryl is $R^{109}$;
(83) —S(O)$_2$-substituted heteroaryl wherein substituted heteroaryl is $R^{110}$;
(84) —S(O)$_2$-heterocyclic wherein heterocyclic is $R^{105}$;
(85) —S(O)$_2$-substituted heterocyclic wherein substituted heterocyclic is $R^{106}$;
(86) —OS(O)$_2$-alkyl wherein alkyl is $R^{101}$;
(87) —OS(O)$_2$-substituted alkyl wherein substituted alkyl is $R^{102}$;
(88) —OS(O)$_2$-aryl wherein aryl is $R^{107}$;
(89) —OS(O)$_2$-substituted aryl wherein substituted aryl is $R^{108}$;
(90) —OS(O)$_2$-heteroaryl wherein heteroaryl is $R^{109}$;
(91) —OS(O)$_2$-substituted heteroaryl wherein substituted heteroaryl is $R^{110}$;
(92) —OS(O)$_2$-heterocyclic wherein heterocyclic is $R^{105}$;
(93) —OS(O)$_2$-substituted heterocyclic wherein substituted heterocyclic is $R^{106}$;
(94) —OSO$_2$—NRR where R is hydrogen or $R^{101}$;
(95) —NRS(O)$_2$-alkyl wherein alkyl is $R^{101}$;
(96) —NRS(O)$_2$-substituted alkyl wherein substituted alkyl is $R^{102}$;
(97) —NRS(O)$_2$-aryl wherein aryl is $R^{107}$;
(98) —NRS(O)$_2$-substituted aryl wherein substituted aryl is $R^{108}$;
(99) —NRS(O)$_2$-heteroaryl wherein heteroaryl is $R^{109}$;
(100) —NRS(O)$_2$-substituted heteroaryl wherein substituted heteroaryl is $R^{110}$;
(101) —NRS(O)$_2$-heterocyclic wherein heterocyclic is $R^{105}$;
(102) —NRS(O)$_2$-substituted heterocyclic wherein substituted heterocyclic is $R^{106}$;
(103) —NRS(O)$_2$—NR-alkyl wherein alkyl is $R^{101}$;
(104) —NRS(O)$_2$—NR-substituted alkyl wherein substituted alkyl is $R^{102}$;
(105) —NRS(O)$_2$—NR-aryl wherein aryl is $R^{107}$;
(106) —NRS(O)$_2$—NR-substituted aryl wherein substituted aryl is $R^{108}$;
(107) —NRS(O)$_2$—NR-heteroaryl wherein heteroaryl is $R^{109}$;
(108) —NRS(O)$_2$—NR-substituted heteroaryl wherein substituted heteroaryl is $R^{110}$;
(109) —NRS(O)$_2$—NR-heterocyclic wherein heterocyclic is $R^{105}$;
(110) —NRS(O)$_2$—NR-substituted heterocyclic wherein substituted heterocyclic is $R^{106}$,
(111) mono- and di-alkylamino, wherein alkyl is $R^{101}$;
(112) mono- and di-(substituted alkyl)amino, wherein substituted alkyl is $R^{102}$;
(113) mono- and di-arylamino wherein aryl is $R^{107}$;
(114) mono- and di-substituted arylamino wherein substituted aryl is $R^{108}$;
(115) mono- and di-heteroarylamino wherein heteroaryl is $R^{109}$;
(116) mono- and di-substituted heteroarylamino wherein substituted heteroaryl is $R^{110}$;
(117) mono- and di-heterocyclic amino wherein heterocyclic is $R^{105}$;
(118) mono- and di-substituted heterocyclic amino wherein substituted heterocyclic is $R^{106}$;

$R^{300}$ is a member selected from
(i) —SO$_2$-alkyl wherein alkyl is $R^{101}$;
(ii) —SO$_2$-substituted alkyl wherein substituted alkyl is $R^{102}$;
(iii) —SO$_2$-alkenyl wherein alkenyl is $R^{111}$;
(iv) —SO$_2$-substituted alkenyl wherein substituted alkenyl is $R^{112}$;

(v) —SO$_2$-cycloalkyl wherein cycloalkyl is R$^{103}$;
(vi) —SO$_2$-substituted cycloalkyl wherein substituted cycloalkyl is R$^{104}$;
(vii) —SO$_2$-aryl wherein aryl is R$^{107}$;
(viii) —SO$_2$-substituted aryl wherein substituted aryl is R$^{108}$;
(ix) —SO$_2$-heteroaryl wherein heteroaryl is R$^{109}$;
(x) —SO$_2$-substituted heteroaryl wherein substituted heteroaryl is R$^{110}$;
(xi) —SO$_2$-heterocyclic wherein heterocyclic is R$^{105}$;
(xii) —SO$_2$-substituted heterocyclic wherein substituted heterocyclic is R$^{106}$; and
(xiii) —SO$_2$ NRR;

alkoxy has the formula "alkyl-O—", wherein alkyl is R$^{101}$;
substituted alkoxy has the formula "substituted alkyl-O—", wherein substituted alkyl is R$^{102}$;
cycloalkoxy has the formula "—O-cycloalkyl", wherein cycloalkyl is R$^{103}$;
substituted cycloalkoxy has the formula "—O-substituted cycloalkyl", wherein substituted cycloalkyl is R$^{104}$;
alkenoxy has the formula "alkenyl-O—", wherein alkenyl is R$^{111}$;
substituted alkenoxy has the formula "substituted alkenyl-O—", wherein substituted alkenyl is R$^{112}$;
cycloalkenoxy has the formula "cycloalkenyl-O—", wherein cycloalkenyl is R$^{115}$;
substituted cycloalkenoxy has the formula "substituted cycloalkenyl-O—", wherein substituted cycloalkenyl is R$^{116}$;
aryloxy has the formula "aryl-O—", wherein aryl is R$^{107}$;
substituted aryloxy has the formula "substituted aryl-O—", wherein substituted aryl is R$^{108}$;
heteroaryloxy has the formula "—O-heteroaryl", wherein heteroaryl is R$^{109}$;
substituted heteroaryloxy has the formula "—O-substituted heteroaryl", wherein substituted heteroaryl is R$^{110}$;
heterocyclyloxy has the formula "—O-heterocyclic", wherein heterocyclic is R$^{105}$;
substituted heterocyclyloxy has the formula "—O-substituted heterocyclic", wherein substituted heterocyclic is R$^{106}$;
aryloxyaryl has the formula "aryl-O-aryl", wherein each aryl is R$^{107}$;
substituted aryloxyaryl has the formula "aryl-O-aryl", wherein each aryl is R$^{107}$, substituted on one or both aryl rings with from 1 to 3 substituents selected from the group consisting of
(1) R$^{201}$;
(2) unsymmetric di-substituted amines having different substituents selected from the group consisting of R$^{110}$, R$^{102}$, R$^{107}$, R$^{108}$, R$^{109}$, R$^{110}$, R$^{105}$ and R$^{106}$;
(3) amino groups blocked by blocking groups selected from tert-butyloxycarbonyl (Boc), carbobenzyloxy (Cbz) and formyl; and
(4) —SO$_2$ NRR;

acyl is R$^c$—C(O)—;
acylamino is selected from the group —C(O)NRR$^c$R$^c$, wherein each R$^c$ is optionally joined to form together with the nitrogen atom a heterocyclic or substituted heterocyclic ring, wherein heterocyclic is R$^{105}$ and substituted heterocyclic is R$^{106}$;
thiocarbonylamino is selected from the group —C(S)NR-CR$^c$R$^c$, wherein each R$^c$ is optionally joined to form together with the nitrogen atom a heterocyclic or substituted heterocyclic ring, wherein heterocyclic is R$^{105}$ and substituted heterocyclic R$^{106}$;
acyloxy is selected from R$^b$—C(O)O—;
oxysulfonyl has the formula R$^b$—SO$_2$O—;
amino has the formula —NH$_2$;
substituted amino has the formula —NR$^d$R$^d$, where each R$^d$ is independently selected from the group consisting of hydrogen, R$^{101}$, R$^{102}$, R$^{113}$, R$^{104}$, R$^{105}$, R$^{106}$, R$^{107}$, R$^{108}$, R$^{109}$, R$^{110}$, R$^{111}$, R$^{112}$, R$^{113}$, R$^{114}$ and —SO$_2$—R$^e$, wherein R$^e$ is a member selected from R$^{101}$, R$^{102}$, R$^{103}$, R$^{104}$, R$^{105}$, R$^{106}$, R$^{107}$, R$^{108}$, R$^{109}$, R$^{110}$, R$^{111}$ and R$^{112}$; or the R$^d$ groups can be joined together with the nitrogen atom to form a heterocyclic or a substituted heterocyclic ring, wherein heterocyclic is R$^{105}$ and substituted heterocyclic is R$^{106}$, provided that both R$^d$ groups are not hydrogen;
amidino has the formula H$_2$NC(=NH)—;
alkyl amidino is "alkylHNC(=NH)—", wherein alkyl is R$^{101}$;
thioamidino has the formula RSC(=NH)—;
aminoacyl has the formula —NRC(O)R$^b$;
aminosulfonyl having the formula —NRSO$_2$ R$^b$;
aminocarbonyloxy having the formula —NRC(O)O—R$^b$;
aminosulfonyloxy has the formula —NRSO$_2$ O—R$^b$;
oxycarbonylamino has the formula —OC(O)NH$_2$, —OC(O)NRR or —OC(O)NRR$^b$, wherein each R is optionally joined to form together with the nitrogen atom a heterocyclic or substituted heterocyclic ring, wherein heterocyclic is R$^{105}$ and substituted heterocyclic is R$^{106}$;
oxythiocarbonylamino has the formula —OC(S)NH$_2$, —OC(S)NRR or —OC(S)NRR$^b$, wherein each R is optionally joined to form together with the nitrogen atom a heterocyclic or substituted heterocyclic ring, wherein heterocyclic is R$^{105}$ and substituted heterocyclic is R$^{106}$
aminocarbonylamino has the formula —NR$^f$C(O)NR$^f$R$^f$ or —NR$^f$C(O)NR$^f$R$^b$, wherein each R$^f$ is optionally joined to form together with the nitrogen atom a heterocyclic or substituted heterocyclic ring, wherein heterocyclic is R$^{105}$ and substituted heterocyclic is R$^{106}$
aminothiocarbonylamino has the formula —NR$^f$C(S)NR$^f$R$^f$ or —NR$^f$C(S)NR$^f$R$^b$, wherein each R$^f$ is optionally joined to form together with the nitrogen atom a heterocyclic or substituted heterocyclic ring, wherein heterocyclic is R$^{105}$ and substituted heterocyclic is R$^{106}$;
aminosulfonylamino has the formula —NR$^f$SO$_2$ NR$^f$R$^f$ or —NR$^f$SO$_2$ NR$^f$R$^b$, wherein each R$^f$ is optionally joined to form together with the nitrogen atom a heterocyclic or substituted heterocyclic ring, wherein heterocyclic is R$^{105}$ and substituted heterocyclic is R$^{106}$
oxysulfonylamino has the formula —OSO$_2$ NH$_2$, —OSO$_2$ NRR or —OSO$_2$ NRR$^b$, wherein each R is optionally joined to form together with the nitrogen atom a heterocyclic or substituted heterocyclic ring, wherein heterocyclic is R$^{105}$ and substituted heterocyclic is R$^{106}$
halogen is fluoro, chloro, bromo or iodo;
guanidino has the formula —NR$^f$C(=NR$^f$)NR$^f$R$^f$ or —NR$^f$C(=NR$^f$)NR$^f$R$^b$;
guanidinosulfone has the formula —NRC(=NR)NRSO$_2$—R$^b$;
thioalkyl having the formula "—S-alkyl", wherein alkyl is R$^{101}$;
substituted thioalkyl has the formula "—S-substituted alkyl", wherein substituted alkyl is R$^{102}$;
thiocycloalkyl has the formula "—S-cycloalkyl", wherein cycloalkyl is R$^{103}$;
substituted thiocycloalkyl has the formula "—S-substituted cycloalkyl", wherein substituted cycloalkyl is R$^{104}$;

thioaryl has the formula "—S-aryl", wherein aryl is $R^{107}$;

substituted thioaryl has the formula "—S-substituted aryl", wherein substituted aryl is $R^{108}$;

thioheteroaryl has the formula "—S-heteroaryl", wherein heteroaryl is $R^{109}$;

substituted thioheteroaryl has the formula "—S-substituted heteroaryl", wherein substituted heteroaryl is $R^{110}$;

thioheterocyclic has the formula "—S-heterocyclic", wherein heterocyclic is $R^{105}$; and substituted thioheterocyclic has the formula "—S-substituted heterocyclic", wherein substituted heterocyclic is $R^{106}$;

wherein each R is independently hydrogen or $R^{101}$ each $R^b$ is a member independently selected from $R^{101}$, $R^{102}$, $R^{103}$, $R^{104}$, $R^{105}$, $R^{106}$, $R^{107}$, $R^{108}$ $R^{109}$, $R^{110}$, $R^{111}$, $R^{112}$, $R^{113}$ and $R^{114}$;

each $R^c$ is a member independently selected from H, $R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{113}$ and $R^{114}$; and each $R^f$ is independently hydrogen, $R^{101}$ or a blocking group selected from tert-butyloxycarbonyl (Boc), carbobenzyloxy (Cbz) and formyl.

2. The method of claim 1, wherein the condition is inflammatory bowel disease.

3. The method of claim 2, wherein the condition is Crohn's disease.

4. The method of claim 2, wherein the condition is ulcerative colitis.

5. The method of claim 1, wherein the condition is multiple sclerosis.

6. The method of claim 1, wherein the patient is human.

7. The method of claim 1, wherein ring A is substituted with substituted amino.

8. The method of claim 7, wherein the substituted amino is dialkyl amino.

9. The method of claim 1, wherein $R^3$ is —$CH_2$—Ar—$R^9$, where Ar is $R^{107}$.

10. The method of claim 1, wherein X is hydroxyl.

11. The method of claim 1, wherein the compound has the formula:

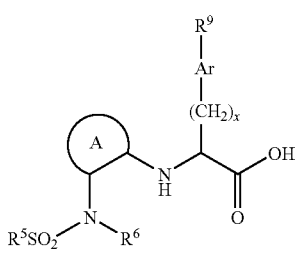

or a pharmaceutically acceptable salt or ester thereof, wherein ring A forms a pyrimidine ring substituted with substituted amino; and x is an integer from 1 to 4.

12. The method of claim 11, wherein the substituted amino on ring A is disubstituted with alkyl.

13. The method of claim 1, wherein the compound has the structure according to Formula B:

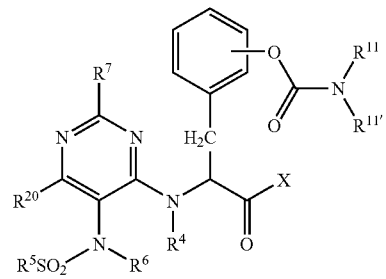

or a pharmaceutically acceptable salt thereof, wherein $R^7$ is selected from the group consisting of hydrogen, $R^{101}$, $R^{102}$, $R^{103}$, $R^{104}$, $R^{105}$, $R^{106}$, $R^{107}$, $R^{108}$, $R^{109}$, $R^{110}$, halogen and substituted amino;

$R^{11}$ and $R^{11'}$ are independently selected from the group consisting of $R^{101}$, $R^{102}$, $R^{103}$, $R^{104}$, $R^{105}$, $R^{106}$, $R^{115}$ and $R^{116}$, or $R^{11}$ and $R^{11'}$ are joined to form a heterocyclic or a substituted heterocyclic ring, wherein heterocyclic is $R^{105}$ and substituted heterocyclic is $R^{106}$; and $R^{20}$ is selected from the group consisting of hydrogen, $R^{101}$, $R^{102}$, $R^{103}$, $R^{104}$, $R^{105}$, $R^{106}$, $R^{107}$, $R^{108}$, $R^{109}$, $R^{110}$, alkoxy, substituted alkoxy and halogen, wherein $R^{101}$, $R^{102}$, $R^{103}$, $R^{104}$, $R^{105}$, $R^{106}$, $R^{107}$, $R^{108}$, $R^{109}$, $R^{110}$, $R^{115}$ and $R^{116}$ are defined as in claim 1.

14. A method for treating a condition in a patient said condition selected from the group consisting of asthma, inflammatory bowel disease, ulcerative colitis, Crohn's disease, multiple sclerosis, rheumatoid arthritis, graft versus host disease, and organ or graft rejection, which method comprises administering a pharmaceutical composition comprising a pharmaceutically acceptable carrier and a therapeutically effective amount of compound of formula:

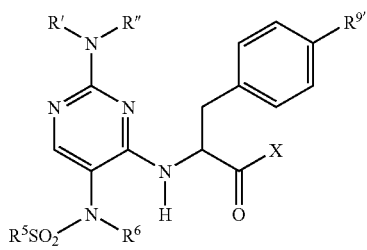

or a pharmaceutically acceptable salt thereof, wherein $R^5$ is selected from the group consisting of $R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{115}$ and $R^{116}$;

$R^6$ is selected from the group consisting of hydrogen, $R^{101}$, $R^{102}$, $R^{103}$, $R^{104}$, $R^{105}$, $R^{106}$, $R^{107}$, $R^{108}$, $R^{109}$, $R^{110}$, $R^{115}$ and $R^{116}$;

R' and R" are independently selected from the group consisting of hydrogen and $R^{101}$, or R' and R", together with the nitrogen to which they are bound, join to form a heterocyclic group, wherein heterocyclic is $R^{105}$;

X is selected from the group consisting of hydroxyl, alkoxy and substituted alkoxy; and $R^{9'}$ is selected from the group consisting of hydrogen, acylamino, aminoacyl, oxycarbonylamino, aminocarbonyloxy and $R^{105}$, wherein
- $R^{101}$ is alkyl of from 1 to 10 carbon atoms;
- $R^{102}$ is substituted alkyl of from 1 to 10 carbon atoms, having from 1 to 5 substituents selected from the group consisting of
  - (1) $R^{200}$;
  - (2) unsymmetric di-substituted amines having different substituents selected from the group consisting of $R^{101}, R^{102}, R^{107}, R^{108}, R^{109}, R^{110}, R^{105}$ and $R^{106}$;
  - (3) amino groups blocked by blocking groups selected from the group consisting of tert-butyloxycarbonyl (Boc), carbobenzyloxy (Cbz) and formyl; and
  - (4) $R^{300}$;
- $R^{103}$ is cycloalkyl of from 3 to 8 carbon atoms;
- $R^{104}$ is substituted cycloalkyl of from 3 to 8 carbon atoms, having from 1 to 5 substituents selected from the group consisting of
  - (1) $R^{200}$;
  - (2) oxo (=O);
  - (3) thioxo (=S);
  - (4) unsymmetric di-substituted amines having different substituents selected from the group consisting of $R^{101}, R^{102}, R^{107}, R^{108}, R^{109}, R^{111}, R^{105}$ and $R^{106}$;
  - (5) amino groups blocked by blocking groups selected from tert-butyloxycarbonyl (Boc), carbobenzyloxy (Cbz) and formyl; and
  - (6) $R^{300}$;
- $R^{105}$ is heterocyclic referring to a saturated or unsaturated group having from 1 to 10 carbon atoms and from 1 to 4 heteroatoms selected from nitrogen, sulfur and oxygen, and having a single ring or multiple fused rings, wherein in fused ring systems one or more of the rings can be aryl ($R^{107}$) or heteroaryl ($R^{109}$);
- $R^{106}$ is substituted heterocyclic of from 1 to 10 carbon atoms and from 1 to 4 heteroatoms, substituted with from 1 to 3 substituents selected from the group consisting of
  - (1) $R^{200}$;
  - (2) oxo (=O);
  - (3) thioxo (=S);
  - (4) unsymmetric di-substituted amines having different substituents selected from the group consisting of $R^{101}, R^{102}, R^{107}, R^{108}, R^{109}, R^{110}, R^{105}$ and $R^{106}$;
  - (5) amino groups blocked by blocking groups selected from tert-butyloxycarbonyl (Boc), carbobenzyloxy (Cbz) and formyl; and
  - (6) $R^{300}$;
- $R^{107}$ is aryl, wherein aryl is an unsaturated aromatic carbocyclic group of from 6 to 14 carbon atoms having a single ring or multiple condensed rings, wherein the condensed rings may or may not be aromatic;
- $R^{108}$ is substituted aryl, wherein substituted aryl is aryl substituted with from 1 to 3 substituents selected from the group consisting of
  - (1) $R^{201}$;
  - (2) unsymmetric di-substituted amines having different substituents selected from the group consisting of $R^{101}, R^{102}, R^{105}, R^{106}, R^{107}, R^{108}, R^{109}$ and $R^{110}$;
  - (3) amino groups blocked by blocking groups selected from tert-butyloxycarbonyl (Boc), carbobenzyloxy (Cbz) and formyl; and
  - (4) —SO$_2$ NRR;
- $R^{109}$ is heteroaryl of from 2 to 10 carbon atoms and 1 to 4 heteroatoms selected from oxygen, nitrogen and sulfur within the ring or oxides thereof, having a single ring or multiple condensed rings;
- $R^{110}$ is substituted heteroaryl of from 2 to 10 carbon atoms and 1 to 4 heteroatoms selected from oxygen, nitrogen and sulfur, substituted with from 1 to 3 substituents selected from the group consisting of
  - (1) $R^{201}$;
  - (2) unsymmetric di-substituted amines having different substituents selected from the group consisting of $R^{101}, R^{102}, R^{107}, R^{108}, R^{109}, R^{110}, R^{105}$ and $R^{106}$;
  - (3) amino groups blocked by blocking groups selected from tert-butyloxycarbonyl (Boc), carbobenzyloxy (Cbz) and formyl; and
  - (4) —SO$_2$ NRR;
- $R^{111}$ is alkenyl of from 2 to 10 carbon atoms and from 1 to 2 sites of alkenyl unsaturation;
- $R^{112}$ is substituted alkenyl, wherein substituted alkenyl is alkenyl substituted with from 1 to 5 substituents selected from the group consisting of
  - (1) $R^{200}$;
  - (2) unsymmetric di-substituted amines having different substituents selected from the group consisting of $R^{101}, R^{102}, R^{107}, R^{108}, R^{109}, R^{110}, R^{105}$ and $R^{106}$;
  - (3) amino groups blocked by blocking groups selected from tert-butyloxycarbonyl (Boc), carbobenzyloxy (Cbz) and formyl; and
  - (4) $R^{300}$;
- $R^{113}$ is alkynyl of from 2 to 10 carbon atoms and from 1 to 2 sites of alkynyl unsaturation;
- $R^{114}$ is substituted alkynyl, wherein substituted alkynyl is alkynyl substituted with from 1 to 5 substituents selected from the group consisting of
  - (1) $R^{200}$;
  - (2) unsymmetric di-substituted amines having different substituents selected from the group consisting of $R^{101}, R^{102}, R^{107}, R^{108}, R^{109}, R^{110}, R^{105}$ and $R^{106}$;
  - (3) amino groups blocked by blocking groups selected from tert-butyloxycarbonyl (Boc), carbobenzyloxy (Cbz) and formyl; and
  - (4) $R^{300}$
- $R^{115}$ is cycloalkenyl, wherein cycloalkenyl is a cyclic alkenyl group of from 3 to 8 carbon atoms having single or multiple unsaturation, and which is not aromatic;
- $R^{116}$ is substituted cycloalkenyl of from 3 to 8 carbon atoms, having from 1 to 5 substituents selected from the group consisting of
  - (1) $R^{200}$;
  - (2) oxo (=O);
  - (3) thioxo (=S); and
  - (4) unsymmetric di-substituted amines having different substituents selected from the group consisting of $R^{101}, R^{102}, R^{107}, R^{108}, R^{109}, R^{110}, R^{105}$ and $R^{106}$;
  - (5) amino groups blocked by blocking groups slected from tert-butyloxycarbonyl (Boc), carbobenzyloxy (Cbz) and formyl; and
  - (6) $R^{300}$;

wherein
- $R^{200}$ is a member selected from
  - (1) alkoxy;
  - (2) substituted alkoxy;
  - (3) acyl;
  - (4) acylamino;
  - (5) thiocarbonylamino;
  - (6) acyloxy;
  - (7) amino;
  - (8) amidino;
  - (9) alkylamidino wherein alkyl is $R^{101}$;
  - (10) thioamidino;
  - (11) aminoacyl;

(12) aminocarbonylamino;
(13) aminothiocarbonylamino;
(14) aminocarbonyloxy;
(15) $RO^{107}$;
(16) $R^{108}$;
(17) aryloxy;
(18) substituted aryloxy;
(19) aryloxyaryl;
(20) substituted aryloxyaryl;
(21) halogen;
(22) hydroxyl;
(23) cyano;
(24) nitro;
(25) carboxyl;
(26) carboxylalkyl wherein alkyl is $R^{101}$;
(27) carboxyl-substituted alkyl wherein substituted alkyl is $R^{102}$;
(28) carboxyl-cycloalkyl wherein cycloalkyl is $R^{103}$;
(29) carboxyl-substituted cycloalkyl wherein substituted cycloalkyl is $R^{104}$;
(30) carboxylaryl wherein aryl is $R^{107}$;
(31) carboxyl-substituted aryl wherein substituted aryl is $R^{108}$;
(32) carboxylheteroaryl wherein heteroaryl is $R^{109}$;
(33) carboxyl-substituted heteroaryl wherein substituted heteroaryl is $R^{110}$;
(34) carboxylheterocyclic wherein heterocyclic is $R^{105}$;
(35) carboxyl-substituted heterocyclic wherein substituted heterocyclic is $R^{106}$;
(36) $R^{103}$;
(37) $R^{104}$;
(38) guanidino;
(39) guanidinosulfone;
(40) thiol having the formula —SH;
(41) thioalkyl;
(42) substituted thioalkyl;
(43) thioaryl;
(44) substituted thioaryl;
(45) thiocycloalkyl;
(46) substituted thiocycloalkyl;
(47) thioheteroaryl;
(48) substituted thioheteroaryl;
(49) thioheterocyclic;
(50) substituted thioheterocyclic;
(51) $R^{109}$;
(52) $R^{110}$;
(53) $R^{105}$;
(54) $R^{106}$;
(55) cycloalkoxy;
(56) substituted cycloalkoxy;
(57) heteroaryloxy;
(58) substituted heteroaryloxy;
(59) heterocyclyloxy;
(60) substituted heterocyclyloxy;
(61) oxycarbonylamino;
(62) oxythiocarbonylamino;
(63) —OS(O)$_2$-alkyl, wherein alkyl is $R^{101}$;
(64) —OS(O)$_2$-substituted alkyl wherein substituted alkyl is $R^{102}$;
(65) —OS(O)$_2$-aryl, wherein aryl is $R^{107}$;
(66) —OS(O)$_2$-substituted aryl wherein substituted aryl is $R^{108}$;
(67) —OS(O)$_2$-heteroaryl wherein heteroaryl is $R^{109}$;
(68) —OS(O)$_2$-substituted heteroaryl wherein substituted heteroaryl is $R^{110}$;
(69) —OS(O)$_2$-heterocyclic wherein heterocyclic is $R^{105}$;
(70) —OS(O)$_2$-substituted heterocyclic wherein substituted heterocyclic is $R^{106}$;
(71) —OSO$_2$—NRR where R is hydrogen or $R^{101}$;
(72) —NRS(O)$_2$-alkyl, wherein alkyl is $R^{101}$;
(73) —NRS(O)$_2$-substituted alkyl wherein substituted alkyl is $R^{102}$;
(74) —NRS(O)$_2$-aryl, wherein aryl is $R^{107}$;
(75) —NRS(O)$_2$-substituted aryl wherein substituted aryl is $R^{108}$;
(76) —NRS(O)$_2$-heteroaryl wherein heteroaryl is $R^{109}$;
(77) —NRS(O)$_2$-substituted heteroaryl wherein substituted heteroaryl is $R^{110}$;
(78) —NRS(O)$_2$-heterocyclic wherein heterocyclic is $R^{105}$;
(79) —NRS(O)$_2$-substituted heterocyclic wherein substituted heterocyclic is $R^{106}$;
(80) —NRS(O)$_2$—NR-alkyl, wherein alkyl is $R^{101}$;
(81) —NRS(O)$_2$—NR-substituted alkyl wherein substituted alkyl is $R^{102}$;
(82) —NRS(O)$_2$—NR-aryl, wherein aryl is $R^{107}$;
(83) —NRS(O)$_2$—NR-substituted aryl wherein substituted aryl is $R^{108}$;
(84) —NRS(O)$_2$—NR-heteroaryl wherein heteroaryl is $R^{109}$;
(85) —NRS(O)$_2$—NR-substituted heteroaryl wherein substituted heteroaryl is $R^{110}$;
(86) —NRS(O)$_2$—NR-heterocyclic wherein heterocyclic is $R^{105}$;
(87) —NRS(O)$_2$—NR-substituted heterocyclic wherein substituted heterocyclic is $R^{106}$
(88) mono- and di-alkylamino, wherein alkyl is $R^{101}$;
(89) mono- and di-(substituted alkyl)amino, wherein substituted alkyl is $R^{102}$;
(90) mono- and di-arylamino wherein aryl is $R^{107}$;
(91) mono- and di-substituted arylamino wherein substituted aryl is $R^{108}$;
(92) mono- and di-heteroarylamino wherein heteroaryl is $R^{109}$;
(93) mono- and di-substituted heteroarylamino wherein substituted heteroaryl is $R^{110}$;
(94) mono- and di-heterocyclic amino wherein heterocyclic is $R^{105}$; and
(95) mono- and di-substituted heterocyclic amino wherein substituted heterocyclic is $R^{106}$ $R^{201}$ is a member selected from
(1) hydroxyl;
(2) acyl;
(3) acylamino;
(4) thiocarbonylamino;
(5) acyloxy;
(6) $R^{101}$;
(7) $R^{102}$;
(8) alkoxy;
(9) substituted alkoxy;
(10) $R^{111}$;
(11) $R^{112}$;
(12) $R^{113}$;
(13) $R^{114}$;
(14) amidino;
(15) alkylamidino, wherein alkyl is $R^{101}$;
(16) thioamidino;
(17) amino;
(18) aminoacyl;
(19) aminocarbonyloxy;
(20) aminocarbonylamino;
(21) aminothiocarbonylamino;
(22) $R^{107}$;

(23) $R^{108}$;
(24) aryloxy;
(25) substituted aryloxy;
(26) cycloalkoxy;
(27) substituted cycloalkoxy;
(28) heteroaryloxy;
(29) substituted heteroaryloxy;
(30) heterocyclyloxy;
(31) substituted heterocyclyloxy;
(32) carboxyl;
(33) carboxylalkyl wherein alkyl is $R^{101}$;
(34) carboxyl-substituted alkyl wherein substituted alkyl is $R^{102}$;
(35) carboxy-cycloalkyl wherein cycloalkyl is $R^{103}$;
(36) carboxyl-substituted cycloalkyl wherein substituted cycloalkyl is $R^{104}$;
(37) carboxylaryl wherein aryl is $R^{107}$;
(38) carboxyl-substituted aryl wherein substituted aryl is $R^{108}$;
(39) carboxylheteroaryl wherein heteroaryl is $R^{109}$;
(40) carboxyl-substituted heteroaryl wherein substituted heteroaryl is $R^{110}$;
(41) carboxylheterocyclic wherein heterocyclic is $R^{105}$;
(42) carboxyl-substituted heterocyclic wherein substituted heterocyclic is $R^{106}$;
(43) carboxylamido;
(44) cyano;
(45) thiol having the formula —SH;
(46) thioalkyl;
(47) substituted thioalkyl;
(48) thioaryl;
(49) substituted thioaryl
(50) thioheteroaryl;
(51) substituted thioheteroaryl;
(52) thiocycloalkyl;
(53) substituted thiocycloalkyl;
(54) thioheterocyclic;
(55) substituted thioheterocyclic;
(56) $R^{103}$;
(57) $R^{104}$;
(58) guanidino;
(59) guanidinosulfone;
(60) halogen;
(61) nitro;
(62) $R^{109}$;
(63) $R^{110}$;
(64) $R^{105}$;
(65) $R^{106}$;
(66) cycloalkoxy;
(67) substituted cycloalkoxy;
(68) heteroaryloxy;
(69) substituted heteroaryloxy;
(70) heterocyclyloxy;
(71) substituted heterocyclyloxy;
(72) oxycarbonylamino;
(73) oxythiocarbonylamino;
(74) —S(O)$_2$-alkyl wherein alkyl is $R^{101}$;
(75) —S(O)$_2$-substituted alkyl wherein substituted alkyl is $R^{102}$;
(76) —S(O)$_2$-cycloalkyl wherein cycloalkyl is $R^{103}$;
(77) —S(O)$_2$-substituted cycloalkyl wherein substituted cycloalkyl is $R^{104}$;
(78) —S(O)$_2$-alkenyl wherein alkenyl is $R^{111}$;
(79) —S(O)$_2$-substituted alkenyl wherein substituted alkenyl is $R^{112}$;
(80) —S(O)$_2$-aryl wherein aryl is $R^{107}$;
(81) —S(O)$_2$-substituted aryl wherein substituted aryl is $R^{108}$;
(82) —S(O)$_2$-heteroaryl wherein heteroaryl is $R^{109}$;
(83) —S(O)$_2$-substituted heteroaryl wherein substituted heteroaryl is $R^{110}$;
(84) —S(O)$_2$-heterocyclic wherein heterocyclic is $R^{105}$;
(85) —S(O)$_2$-substituted heterocyclic wherein substituted heterocyclic is $R^{106}$;
(86) —OS(O)$_2$-alkyl wherein alkyl is $R^{101}$;
(87) —OS(O)$_2$-substituted alkyl wherein substituted alkyl is $R^{102}$;
(88) —OS(O)$_2$-aryl wherein aryl is $R^{107}$;
(89) —OS(O)$_2$-substituted aryl wherein substituted aryl is $R^{108}$;
(90) —OS(O)$_2$-heteroaryl wherein heteroaryl is $R^{109}$;
(91) —OS(O)$_2$-substituted heteroaryl wherein substituted heteroaryl is $R^{110}$;
(92) —OS(O)$_2$-heterocyclic wherein heterocyclic is $R^{105}$;
(93) —OS(O)$_2$-substituted heterocyclic wherein substituted heterocyclic is $R^{106}$;
(94) —OSO$_2$—NRR where R is hydrogen or $R^{101}$;
(95) —NRS(O)$_2$-alkyl wherein alkyl is $R^{101}$;
(96) —NRS(O)$_2$-substituted alkyl wherein substituted alkyl is $R^{102}$;
(97) —NRS(O)$_2$-aryl wherein aryl is $R^{107}$;
(98) —NRS(O)$_2$-substituted aryl wherein substituted aryl is $R^{108}$;
(99) —NRS(O)$_2$-heteroaryl wherein heteroaryl is $R^{109}$;
(100) —NRS(O)$_2$-substituted heteroaryl wherein substituted heteroaryl is $R^{110}$;
(101) —NRS(O)$_2$-heterocyclic wherein heterocyclic is $R^{105}$;
(102) —NRS(O)$_2$-substituted heterocyclic wherein substituted heterocyclic is $R^{106}$;
(103) —NRS(O)$_2$—NR-alkyl wherein alkyl is $R^{101}$;
(104) —NRS(O)$_2$—NR-substituted alkyl wherein substituted alkyl is $R^{102}$;
(105) —NRS(O)$_2$—NR-aryl wherein aryl is $R^{107}$;
(106) —NRS(O)$_2$—NR-substituted aryl wherein substituted aryl is $R^{108}$;
(107) —NRS(O)$_2$—NR-heteroaryl wherein heteroaryl is $R^{109}$;
(108) —NRS(O)$_2$—NR-substituted heteroaryl wherein substituted heteroaryl is $R^{110}$;
(109) —NRS(O)$_2$—NR-heterocyclic wherein heterocyclic is $R^{105}$;
(110) —NRS(O)$_2$—NR-substituted heterocyclic wherein substituted heterocyclic is $R^{106}$,
(111) mono- and di-alkylamino, wherein alkyl is $R^{101}$;
(112) mono- and di-(substituted alkyl)amino, wherein substituted alkyl is $R^{102}$;
(113) mono- and di-arylamino wherein aryl is $R^{107}$;
(114) mono- and di-substituted arylamino wherein substituted aryl is $R^{108}$;
(115) mono- and di-heteroarylamino wherein heteroaryl is $R^{109}$;
(116) mono- and di-substituted heteroarylamino wherein substituted heteroaryl is $R^{110}$;
(117) mono- and di-heterocyclic amino wherein heterocyclic is $R^{105}$;
(118) mono- and di-substituted heterocyclic amino wherein substituted heterocyclic is $R^{106}$;
$R^{300}$ is a member selected from
(i) —SO$_2$-alkyl wherein alkyl is $R^{101}$;
(ii) —SO$_2$-substituted alkyl wherein substituted alkyl is $R^{102}$;

(iii) —$SO_2$-alkenyl wherein alkenyl is $R^{111}$;
(iv) —$SO_2$-substituted alkenyl wherein substituted alkenyl is $R^{112}$;
(v) —$SO_2$-cycloalkyl wherein cycloalkyl is $R^{103}$;
(vi) —$SO_2$-substituted cycloalkyl wherein substituted cycloalkyl is $R^{104}$;
(vii) —$SO_2$-aryl wherein aryl is $R^{107}$;
(viii) —$SO_2$-substituted aryl wherein substituted aryl is $R^{108}$;
(ix) —$SO_2$-heteroaryl wherein heteroaryl is $R^{109}$;
(x) —$SO_2$-substituted heteroaryl wherein substituted heteroaryl is $R^{110}$;
(xi) —$SO_2$-heterocyclic wherein heterocyclic is $R^{105}$;
(xii) —$SO_2$-substituted heterocyclic wherein substituted heterocyclic is $R^{106}$; and
(xiii) —$SO_2$ NRR;

alkoxy has the formula "alkyl-O—", wherein alkyl is $R^{101}$;
substituted alkoxy has the formula "substituted alkyl-O—", wherein substituted alkyl is $R^{102}$;
cycloalkoxy has the formula "—O-cycloalkyl", wherein cycloalkyl is $R^{103}$;
substituted cycloalkoxy has the formula "—O-substituted cycloalkyl", wherein substituted cycloalkyl is $R^{104}$;
alkenoxy has the formula "alkenyl-O—", wherein alkenyl is $R^{111}$;
substituted alkenoxy has the formula "substituted alkenyl-O—", wherein substituted alkenyl is $R^{112}$
cycloalkenoxy has the formula "cycloalkenyl-O—", wherein cycloalkenyl is $R^{115}$;
substituted cycloalkenoxy has the formula "substituted cycloalkenyl-O—", wherein substituted cycloalkenyl is $R^{116}$;
aryloxy has the formula "aryl-O—", wherein aryl is $R^{107}$;
substituted aryloxy has the formula "substituted aryl-O—", wherein substituted aryl is $R^{108}$;
heteroaryloxy has the formula "—O-heteroaryl", wherein heteroaryl is $R^{109}$;
substituted heteroaryloxy has the formula "—O-substituted heteroaryl", wherein substituted heteroaryl is $R^{110}$;
heterocyclyloxy has the formula "—O-heterocyclic", wherein heterocyclic is $R^{105}$;
substituted heterocyclyloxy has the formula "—O-substituted heterocyclic", wherein substituted heterocyclic is $R^{106}$;
aryloxyaryl has the formula "aryl-O-aryl", wherein each aryl is $R^{107}$;
substituted aryloxyaryl has the formula "aryl-O-aryl", wherein each aryl is $R^{107}$, substituted on one or both aryl rings with from 1 to 3 substituents selected from the group consisting of
(1) $R^{201}$;
(2) unsymmetric di-substituted amines having different substituents selected from the group consisting of $R^{101}$, $R^{102}$, $R^{107}$, $R^{108}$, $R^{109}$, $R^{110}$, $R^{105}$ and $R^{106}$;
(3) amino groups blocked by blocking groups selected from tert-butyloxycarbonyl (Boc), carbobenzyloxy (Cbz) and formyl; and
(4) —$SO_2$ NRR;
acyl is $R^c$—C(O)—;
acylamino is selected from the group —C(O)$NRR^cR^c$, wherein each $R^c$ is optionally joined to form together with the nitrogen atom a heterocyclic or substituted heterocyclic ring, wherein heterocyclic is $R^{105}$ and substituted heterocyclic is $R^{106}$;
thiocarbonylamino is selected from the group —C(S)NR-$CR^cR^c$, wherein each $R^c$ is optionally joined to form together with the nitrogen atom a heterocyclic or substituted heterocyclic ring, wherein heterocyclic is $R^{15}$ and substituted heterocyclic $R^{106}$;
acyloxy is selected from $R^b$—C(O)O—;
oxysulfonyl has the formula $R^b$—$SO_2$O—;
amino has the formula —$NH_2$;
substituted amino has the formula —$NR^d R^d$, where each $R^d$ is independently selected from the group consisting of hydrogen, $R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{113}$, $R^{114}$ and —$SO_2$—$R^e$, wherein $R^e$ is a member selected from $R^{101}$, $R^{102}$, $R^{103}$, $R^{104}$, $R^{105}$, $R^{106}$, $R^{107}$, $R^{108}$, $R^{109}$, $R^{110}$, $R^{111}$ and $R^{112}$; or the $R^d$ groups can be joined together with the nitrogen atom to form a heterocyclic or a substituted heterocyclic ring, wherein heterocyclic is $R^{105}$ and substituted heterocyclic is $R^{106}$
provided that both $R^d$ groups are not hydrogen;
amidino has the formula $H_2NC(=NH)$—;
alkyl amidino is "alkylHNC(=NH)—", wherein alkyl is $R^{101}$;
thioamidino has the formula RSC(=NH)—;
aminoacyl has the formula —NRC(O)$R^b$;
aminosulfonyl having the formula —$NRSO_2$ $R^b$;
aminocarbonyloxy having the formula —NRC(O)O—$R^b$;
aminosulfonyloxy has the formula —$NRSO_2O$—$R^b$;
oxycarbonylamino has the formula —OC(O)$NH_2$, —OC(O)NRR or —OC(O)$NRR^b$, wherein each R is optionally joined to form together with the nitrogen atom a heterocyclic or substituted heterocyclic ring, wherein heterocyclic is $R^{105}$ and substituted heterocyclic is $R^{106}$;
oxythiocarbonylamino has the formula —OC(S)$NH_2$, —OC(S)NRR or —OC(S)$NRR^b$, wherein each R is optionally joined to form together with the nitrogen atom a heterocyclic or substituted heterocyclic ring, wherein heterocyclic is $R^{105}$ and substituted heterocyclic is $R^{106}$;
aminocarbonylamino has the formula —$NR^fC(O)NR^fR^f$ or —$NR^fC(O)NR^fR^b$, wherein each $R^f$ is optionally joined to form together with the nitrogen atom a heterocyclic or substituted heterocyclic ring, wherein heterocyclic is $R^{105}$ and substituted heterocyclic is $R^{106}$;
aminothiocarbonylamino has the formula —$NR^fC(S)NR^f$ $R^f$ or —$NR^fC(S)NR^fR^b$, wherein each $R^f$ is optionally joined to form together with the nitrogen atom a heterocyclic or substituted heterocyclic ring, wherein heterocyclic is $R^{105}$ and substituted heterocyclic is $R^{106}$;
aminosulfonylamino has the formula —$NR^fSO_2$ $NR^fR^f$ or —$NR^fSO_2$ $NR^fR^b$, wherein each $R^f$ is optionally joined to form together with the nitrogen atom a heterocyclic or substituted heterocyclic ring, wherein heterocyclic is $R^{105}$ and substituted heterocyclic is $R^{106}$;
oxysulfonylamino has the formula —$OSO_2$ $NH_2$, —$OSO_2$ NRR or —$OSO_2$ $NRR^b$, wherein each R is optionally joined to form together with the nitrogen atom a heterocyclic or substituted heterocyclic ring, wherein heterocyclic is $R^{105}$ and substituted heterocyclic is $R^{106}$;
halogen is fluoro, chloro, bromo or iodo; guanidino has the formula —$NR^fC(=NR^f)NRR^f$ or —$NR^fC(=NR^f)NR^f$ $R^b$;
guanidinosulfone has the formula —NRC(=NR)$NRSO_2$—$R^b$;
thioalkyl having the formula "—S-alkyl", wherein alkyl is $R^{101}$;
substituted thioalkyl has the formula "—S-substituted alkyl", wherein substituted alkyl is $R^{102}$;
thiocycloalkyl has the formula "—S-cycloalkyl", wherein cycloalkyl is $R^{103}$;

substituted thiocycloalkyl has the formula "—S-substituted cycloalkyl", wherein substituted cycloalkyl is $R^{104}$;

thioaryl has the formula "—S-aryl", wherein aryl is $R^{107}$;

substituted thioaryl has the formula "—S-substituted aryl", wherein substituted aryl is $R^{108}$;

thioheteroaryl has the formula "—S-heteroaryl", wherein heteroaryl is $R^{109}$;

substituted thioheteroaryl has the formula "—S-substituted heteroaryl", wherein substituted heteroaryl is $R^{110}$;

thioheterocyclic has the formula "—S-heterocyclic", wherein heterocyclic is $R^{105}$; and substituted thioheterocyclic has the formula "—S-substituted heterocyclic", wherein substituted heterocyclic is $R^{106}$;

wherein each R is independently hydrogen or $R^{101}$;

each $R^b$ is a member independently selected from $R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{113}$ and $R^{114}$;

each $R^c$ is a member independently selected from H, $R^{101}$, $R^{102}$, $R^{103}$, $R^{104}$, $R^{105}$, $R^{106}$, $R^{107}$, $R^{108}$, $R^{109}$, $R^{110}$, $R^{111}$, $R^{112}$, $R^{113}$ and $R^{114}$; and each $R^f$ is independently hydrogen, $R^{101}$ or a blocking group selected from tert-butyloxycarbonyl (Boc), carbobenzyloxy (Cbz) and formyl.

15. The method of claim 14, wherein the condition is inflammatory bowel disease.

16. The method of claim 15, wherein the condition is Crohn's disease.

17. The method of claim 15, wherein the condition is ulcerative colitis.

18. The method of claim 14, wherein the condition is multiple sclerosis.

19. The method of claim 14, wherein the patient is human.

* * * * *